US012540332B2

(12) United States Patent
Crawford et al.

(10) Patent No.: US 12,540,332 B2
(45) Date of Patent: Feb. 3, 2026

(54) METHODS AND COMPOSITIONS FOR REDUCING POD SHATTER IN CANOLA

(71) Applicant: Pairwise Plants Services, Inc., Durham, NC (US)

(72) Inventors: Brian Charles Wilding Crawford, Cary, NC (US); Nathaniel Graham, Durham, NC (US); Lolita George Mathew, Cary, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 418 days.

(21) Appl. No.: 17/933,883

(22) Filed: Sep. 21, 2022

(65) Prior Publication Data

US 2023/0087522 A1 Mar. 23, 2023

Related U.S. Application Data

(60) Provisional application No. 63/246,512, filed on Sep. 21, 2021.

(51) Int. Cl.
*C12N 15/82* (2006.01)
*C12N 15/11* (2006.01)

(52) U.S. Cl.
CPC .......... *C12N 15/8266* (2013.01); *C12N 15/11* (2013.01); *C12N 15/8213* (2013.01); *C12N 2310/20* (2017.05)

(58) Field of Classification Search
CPC ...... C07K 14/415; C07K 14/21; C12N 15/11; C12N 15/8213; C12N 15/8266; C12N 2310/20; C12N 9/22; C12N 15/8261; C12N 15/8273; C12N 15/8262; C12N 2800/80; C12N 15/8247; C12N 15/8269; C12N 15/8227; C12N 15/8271; C12N 9/1014; C12N 15/8205; C12N 15/8243; C12N 15/827; C12N 15/8282; C12N 9/12; C12N 9/24; C12N 9/2402; Y02A 40/146; C12Q 1/6895; C12Q 2600/156; C12Q 2600/13; A01H 5/10; A01H 6/202; A01H 6/20; A01H 6/4678; A01H 6/4684; A01H 6/46; C12Y 114/19; C12Y 114/19006; C12Y 207/11; C12Y 207/11001; C12Y 302/01015
See application file for complete search history.

(56) References Cited

U.S. PATENT DOCUMENTS

| | | | | |
|---|---|---|---|---|
| 7,135,621 | B2 | 11/2006 | Yanofsky et al. | |
| 8,809,635 | B2 | 8/2014 | Laga et al. | |
| 2018/0160639 | A1 | 6/2018 | Singh et al. | |
| 2019/0053458 | A1* | 2/2019 | Marks | A01H 6/20 |
| 2021/0024947 | A1* | 1/2021 | Gocal | C07K 14/415 |

FOREIGN PATENT DOCUMENTS

| | | | |
|---|---|---|---|
| WO | 2019140009 | A1 | 7/2019 |

OTHER PUBLICATIONS

Roewer et al., EST database, Accession No. DX892725, published in database on Feb. 14, 2014. (Year: 2014).*
Liu et al., NCBI database, NCBI Accession No. MT637186, published online Jul. 1, 2020. (Year: 2020).*
Srivastava (NCBI Accession No. JQ973085, version JQ973085.1, published online Sep. 13, 2013) (Year: 2013).*
Liljegren et al. "Control of Fruit Patterning in Arabidopsis by Indehiscent" Cell 116(6):843-853 (2004).
Liljegren et al. "Shatterproof MADS-box genes control seed dispersal in *Arabidopsis*" Nature 404:766-770 (2000).
Notification of Transmittal of the International Search Report and the Written Opinion of the International Searching Authority, or the Declaration, in corresponding PCT Application No. PCT/US2022/076746 (9 pages) (Jan. 23, 2023).
Zaman et al. "Characterization of Shatterproof Homoeologs and CRISPR-Cas9-Mediated Genome Editing Enhances Pod-Shattering Resistance in *Brassica napus* L" The CRISPR Journal 4(3) (2021).

* cited by examiner

*Primary Examiner* — Charles Logsdon
*Assistant Examiner* — Jessica Nicole Stockdale
(74) *Attorney, Agent, or Firm* — Myers Bigel, P.A.

(57) ABSTRACT

This invention relates to compositions and methods for modifying SHATTERPROOF MADS-BOX(SHP) genes in canola plants, optionally to reduce pod shattering. The invention further relates to canola plants having reduced pod shatter produced using the methods and compositions of the invention.

7 Claims, No Drawings

Specification includes a Sequence Listing.

METHODS AND COMPOSITIONS FOR REDUCING POD SHATTER IN CANOLA

STATEMENT OF PRIORITY

This application claims the benefit, under 35 U.S.C. § 119 (e), of U.S. Provisional Application No. 63/246,512 filed on Sep. 21, 2021, the entire contents of which is incorporated by reference herein.

STATEMENT REGARDING ELECTRONIC FILING OF A SEQUENCE LISTING

A Sequence Listing in XML text format, entitled 1499-73_ST26.xml, 556,402 bytes in size, generated on Sep. 7, 2022 and filed herewith, is hereby incorporated by reference into the specification for its disclosures.

FIELD OF THE INVENTION

This invention relates to compositions and methods for modifying SHATTERPROOF MADS-BOX(SHP) genes in canola plants, optionally to reduce pod shattering. The invention further relates to canola plants having reduced pod shatter produced using the methods and compositions of the invention.

BACKGROUND OF THE INVENTION

Canola oil is a vegetable oil derived from a variety of rapeseed that is low in erucic acid, as opposed to colza oil. Both edible and industrial forms of oil are produced from the seed of any of several cultivars of the plant family Brassicaceae, namely cultivars of *Brassica napus* L., *Brassica rapa* subsp. Oleifera (syn. *B. campestris* L.) and/or *Brassica juncea*, which are also referred to as "canola". Canola seed pods contain the black seeds that are pressed to extract the oil.

The canola seedpod is a fruit that encloses and protects the seeds as they are maturing, then dries and opens to disperse the seeds at maturity. There are three major regions in the canola fruit: the valves, the replum, and the valve margins. The valves are the seedpod walls that encircle the developing seeds and connect to the replum, which forms the middle ridge that attaches the fruit to the plant. The valve margins (VM) form at the boundary between the valves and the replum and are specialized for seed dispersal. When the fruit matures and dries, the valves detach from the replum along the margins in a process called dehiscence or pod shatter.

Three specialized cell types contribute to the opening of the fruit: the two layers of the margin—the separation layer (or dehiscence zone) and the lignified margin layer—as well as the lignified valve layer (endocarp b). The valves detach through cell-cell separation within the dehiscence zone that occurs following the secretion of hydrolytic enzymes. Lignification of the lignified margin layer and the internal lignified valve layer leads to stress that contributes mechanically to fruit opening. As the fruit dries, differential shrinkage of the remaining thin-walled valve cells relative to the rigid lignified margin and valve layers is thought to create internal tension, causing the shattering that is characteristic of fruit dehiscence.

The timing of dehiscence affects seed yields from canola. The fruit of canola develop throughout the growing season. The earliest fruit are fully developed while later fruit are still developing. The highly differentiated cells in the valve margins weaken the strength of the fruit, leading to seed dispersal at maturity. However, pod shattering is a highly undesirable trait for commercial seed production in canola and can cause significant yield losses of up to 70% in canola. Generally, canola is 'windrowed' to reduce seed loss due to shattering but this practice is not completely effective and is labor intensive. Seed losses accelerate further in the presence of high wind velocity and extremely high temperatures during the time of harvesting.

The aim of the present invention is to develop canola varieties having resistance to pod shattering so the standing crop can be directly harvested with combines without significant seed loss by providing new compositions and methods for reducing pod shattering in canola.

SUMMARY OF THE INVENTION

One aspect of the invention provides a canola plant or plant part thereof comprising at least one mutation in an endogenous SHATTERPROOF MADS-BOX (SHP) gene encoding a Shatterproof MADS-box transcription factor (SHP) polypeptide, optionally wherein the at least one mutation may be a non-natural mutation.

A second aspect of the invention provides a canola plant cell, comprising an editing system the editing system comprising: (a) a CRISPR-Cas effector protein; and (b) a guide nucleic acid comprising a spacer sequence with complementarity to an endogenous target gene encoding a Shatterproof MADS-box transcription factor (SHP) polypeptide in the canola plant cell.

A third aspect of the invention provides a canola plant cell comprising at least one mutation within an endogenous SHP gene, wherein the at least one non-natural mutation is a base substitution, a base insertion or a base deletion that is introduced using an editing system that comprises a nucleic acid binding domain that binds to a target site in the endogenous SHP gene, optionally wherein the at least one mutation may be a non-natural mutation.

A fourth aspect of the invention provides a method of producing/breeding a transgene-free edited canola plant, comprising: crossing a canola plant of the invention with a transgene free plant, thereby introducing the at least one mutation into the canola plant that is transgene-free; and selecting a progeny canola plant that comprises the at least one mutation and is transgene-free, thereby producing a transgene free edited canola plant, optionally wherein the at least one mutation may be a non-natural mutation.

A fifth aspect of the invention provides a method of providing a plurality of canola plants having one or more improved yield traits, the method comprising planting two or more canola plants of the invention in a growing area, thereby providing the plurality of canola plants having a phenotype of reduced pod shattering and/or reduced lignification (reduced lignin content) in the pod valve margin as compared to a plurality of control canola plants devoid of the at least one mutation, optionally wherein the at least one mutation may be a non-natural mutation.

In a sixth aspect, a method of creating a mutation in an endogenous SHATTERPROOF MADS-BOX (SHP) gene in a canola plant is provided, the method comprising: (a) targeting a gene editing system to a portion of the endogenous SHP gene that (i) comprises a sequence having at least 90% sequence identity to any one of SEQ ID NOs:72-96, 103-144, 151-173, 180-202, 209-236, 243-288 or 324-338; and/or (ii) encodes a sequence having at least 80% identity to any one NOs:97-99, 145-147, 174-176, 203-205, 237-239 or 289-291, and (b) selecting a canola plant that comprises a modification located in a region of the endogenous SHP gene having at least 80% sequence identity to any one of SEQ ID NOs:72-96, 103-144, 151-173, 180-202, 209-236, 243-288 or 324-338, optionally located in a region of the endogenous SHP gene having at least 80% sequence identity to any one of SEQ ID NOs:75-82, 85-92, 107-112, 116-120, 124-127, 129, 135, 136, 139, 140, 156, 157, 159-161, 164-166, 181-184, 187-190, 195, 196, 212-219, 222-224, 229, 230, 246-248, 251-253, 255-257, 261-264, 267, 268, 271, 272, 275, 276, 279, 280, 283, or 285.

In a seventh aspect, a method is provided for generating variation in a Shatterproof MADS-box transcription factor (SHP) polypeptide in a canola plant cell, comprising: introducing an editing system into a canola plant cell, wherein the editing system is targeted to a region of SHATTERPROOF MADS-BOX (SHP) gene; and contacting the region of the SHP gene with the editing system, thereby introducing a mutation into the SHP gene and generating variation in the SHP polypeptide in the canola plant cell.

A eighth aspect provides a method for editing a specific site in the genome of a canola plant cell, the method comprising: cleaving, in a site-specific manner, a target site within an endogenous SHATTERPROOF MADS-BOX (SHP) gene in the canola plant cell, the endogenous SHP gene: (a) comprising a nucleotide sequence having at least 80% sequence identity to any one of SEQ ID NOs:69, 70, 100, 101, 148, 149, 177, 178, 206, 207, 240 or 241, (b) comprising a region having at least 80% sequence identity to any one of SEQ ID NOs:72-96, 103-144, 151-173, 180-202, 209-236, 243-288 or 324-338, (c) encoding an amino acid sequence having at least 80% sequence identity to any one of SEQ ID NOs:71, 102, 150, 179, 208, or 242, (d) encoding a region having at least 80% sequence identity to an amino acid sequence of any one of SEQ ID NOs:97-99, 145-147, 174-176, 203-205, 237-239 or 289-291, thereby generating an edit in the endogenous SHP gene of the canola plant cell and producing a canola plant cell comprising the edit in the endogenous SHP gene.

A ninth aspect provides a method for making a canola plant, the method comprising (a) contacting a population of canola plant cells comprising an endogenous SHATTERPROOF MADS-BOX (SHP) gene with a nuclease linked to a nucleic acid binding domain (e.g., editing system) that binds to a sequence (i) having at least 80% sequence identity to a nucleotide sequence of any one of SEQ ID NOs:69, 70, 100, 101, 148, 149, 177, 178, 206, 207, 240 or 241, (ii) comprising a region having at least 80% identity to any one of SEQ ID NOs:72-96, 103-144, 151-173, 180-202, 209-236, 243-288 or 324-338; (iii) encoding an amino acid sequence having at least 80% sequence identity to any one of SEQ ID NOs:71, 102, 150, 179, 208, or 242, and/or (iv) encoding a region having at least 80% sequence identity to any one of SEQ ID NOs:97-99, 145-147, 174-176, 203-205, 237-239 or 289-291; (b) selecting a canola plant cell from the population of canola plant cells in which an endogenous SHP gene has been mutated, thereby producing a canola plant cell comprising a mutation in the endogenous SHP gene; and (c) growing the selected canola plant cell into a canola plant comprising a mutation in the endogenous SHP gene.

A tenth aspect provides a method for reducing pod shattering and/or reducing lignification (reduced lignin content) in the pod valve margin in a canola plant, comprising (a) contacting a canola plant cell comprising an endogenous SHATTERPROOF MADS-BOX (SHP) gene with a nuclease targeting the endogenous SHP gene, wherein the nuclease is linked to a nucleic acid binding domain (e.g., editing system) that binds to a target site in the endogenous SHP gene, wherein the endogenous SHP gene: (i) comprises a nucleotide sequence having at least 80% sequence identity to any one of SEQ ID NOs:69, 70, 100, 101, 148, 149, 177, 178, 206, 207, 240 or 241; (ii) comprises a region having at least 80% sequence identity to a nucleotide sequence of any one of SEQ ID NOs:72-96, 103-144, 151-173, 180-202, 209-236, 243-288 or 324-338; (iii) encodes a SHP polypeptide having at least 80% sequence identity to any one of SEQ ID NOs:71, 102, 150, 179, 208, or 242; and/or (iv) encodes a region of a SHP polypeptide having at least 80% sequence identity to any one of SEQ ID NOs:97-99, 145-147, 174-176, 203-205, 237-239 or 289-291 to produce a canola plant cell comprising a mutation in the endogenous SHP gene; and (b) growing the canola plant cell comprising a mutation in the endogenous SHP gene into a canola plant comprising the mutation in the endogenous SHP gene thereby producing a canola plant having a mutated endogenous SHP gene and reduced pod shattering and/or reduced lignification (reduced lignin content) in the pod valve margin.

A eleventh aspect provides a method of producing a canola plant or part thereof comprising at least one cell having a mutated endogenous SHATTERPROOF MADS-BOX(SHP) gene, the method comprising contacting a target site in an endogenous SHP gene in the canola plant or plant part with a nuclease comprising a cleavage domain and a nucleic acid binding domain, wherein the nucleic acid binding domain binds to a target site in the endogenous SHP gene, wherein the endogenous SHP gene (a) comprises a nucleotide sequence having at least 80% sequence identity to any one of SEQ ID NOs:69, 70, 100, 101, 148, 149, 177, 178, 206, 207, 240 or 241; (b) comprises a region having at least 80% sequence identity to a nucleotide sequence of any one of SEQ ID NOs:72-96, 103-144, 151-173, 180-202, 209-236, 243-288 or 324-338; (c) encodes a SHP polypeptide having at least 80% sequence identity to any one of SEQ ID NOs:71, 102, 150, 179, 208, or 242; and/or (d) encodes a region of a SHP polypeptide having at least 80% sequence identity to any one of SEQ ID NOs:97-99, 145-147, 174-176, 203-205, 237-239 or 289-291, thereby producing the canola plant or part thereof comprising at least one cell having a mutation in the endogenous SHP gene.

A twelfth aspect of the invention provides a method for producing a canola plant or part thereof comprising a mutated endogenous SHATTERPROOF MADS-BOX (SHP) gene and exhibiting reduced pod shattering and/or reduced lignification (reduced lignin content) in the pod valve margin, the method comprising contacting a target site in an endogenous SHP gene in the canola plant or plant part with a nuclease comprising a cleavage domain and a nucleic acid binding domain, wherein the nucleic acid binding domain binds to a target site in the endogenous SHP gene, wherein the endogenous SHP gene: (a) comprises a nucleotide sequence having at least 80% sequence identity to any one of SEQ ID NOs:69, 70, 100, 101, 148, 149, 177, 178, 206, 207, 240 or 241; (b) comprises a region having at least 80% sequence identity to a nucleotide sequence of any one of SEQ ID NOs:72-96, 103-144, 151-173, 180-202, 209-236, 243-288 or 324-338; (c) encodes a SHP polypeptide having at least 80% sequence identity to any one of SEQ ID NOs:71, 102, 150, 179, 208, or 242; and/or (d) encodes a region of a SHP polypeptide having at least 80% sequence identity to any one of SEQ ID NOs:97-99, 145-147, 174-176, 203-205, 237-239 or 289-291, thereby producing the canola plant or part thereof comprising an endogenous SHP gene having a mutation and exhibiting reduced pod shattering and/or reduced lignification (reduced lignin content) in the pod valve margin.

An thirteenth aspect provides a guide nucleic acid that binds to a target site in a SHATTERPROOF MADS-BOX (SHP) gene, wherein the target site is in a region of the SHP gene having at least 80% sequence identity to any one of SEQ ID NOs:72-96, 103-144, 151-173, 180-202, 209-236, 243-288 or 324-338, optionally a region of the SHP gene having at least 80% sequence identity to any one of SEQ ID NOs:75-82, 85-92, 107-112, 116-120, 124-127, 129, 135, 136, 139, 140, 156, 157, 159-161, 164-166, 181-184, 187-190, 195, 196, 212-219, 222-224, 229, 230, 246-248, 251-253, 255-257, 261-264, 267, 268, 271, 272, 275, 276, 279, 280, 283, or 285.

In a fourteenth aspect, a system is provided that comprises a guide nucleic acid of the invention and a CRISPR-Cas effector protein that associates with the guide nucleic acid.

A fifteenth aspect provides a gene editing system comprising a CRISPR-Cas effector protein in association with a guide nucleic acid, wherein the guide nucleic acid comprises a spacer sequence that binds to an endogenous SHATTERPROOF MADS-BOX (SHP) gene.

In a sixteenth aspect, a complex comprising a guide nucleic acid and a CRISPR-Cas effector protein comprising a cleavage domain is provided, wherein the guide nucleic acid binds to a target site in endogenous SHATTERPROOF MADS-BOX (SHP) gene, wherein the endogenous SHP gene: (a) comprises a nucleotide sequence having at least 80% sequence identity to any one of SEQ ID NOs:69, 70, 100, 101, 148, 149, 177, 178, 206, 207, 240 or 241; (b) comprises a region having at least 80% sequence identity to a nucleotide sequence of any one of SEQ ID NOs:72-96, 103-144, 151-173, 180-202, 209-236, 243-288 or 324-338; (c) encodes a SHP polypeptide having at least 80% sequence identity to any one of SEQ ID NOs:71, 102, 150, 179, 208, or 242; and/or (d) encodes a region of a SHP polypeptide having at least 80% sequence identity to any one of SEQ ID NOs:97-99, 145-147, 174-176, 203-205, 237-239 or 289-291, and the cleavage domain cleaves a target strand in the SHP gene.

In a seventeenth aspect, an expression cassette is provided, the expression cassette comprising (a) a polynucleotide encoding CRISPR-Cas effector protein comprising a cleavage domain and (b) a guide nucleic acid that binds to a target site in an endogenous SHATTERPROOF MADS-BOX (SHP) gene, wherein the guide nucleic acid comprises a spacer sequence that is complementary to and binds to (i) a portion of a nucleic acid having at least 80% sequence identity to any one of SEQ ID NOs:69, 70, 100, 101, 148, 149, 177, 178, 206, 207, 240 or 241; (ii) a portion of a nucleic acid having at least 80% sequence identity to any one of SEQ ID NOs:72-96, 103-144, 151-173, 180-202, 209-236, 243-288 or 324-338; (iii) a portion of a nucleic acid encoding an amino acid sequence having at least 80% sequence identity to any one of SEQ ID NOs:71, 102, 150, 179, 208, or 242; and/or (iv) a portion of a nucleic acid encoding an amino acid sequence having at least 80% identity to any one SEQ ID NOs:97-99, 145-147, 174-176, 203-205, 237-239 or 289-291.

In another aspect, plants are provided that comprise in their genome one or more mutated SHATTERPROOF MADS-BOX(SHP) genes produced by the methods of the invention, optionally wherein the at least one mutation may be a non-natural mutation, optionally wherein the mutated SHP gene comprises a nucleotide sequence having at least 90% sequence identity to any one of SEQ ID NOs:298, 300, 302, 304, 306, 308, 310, 312, 314, 316, 318, 319, 321, 322, or 323 and/or encodes a SHP polypeptide having at least 90% sequence identity to any one of SEQ ID NOs:299, 301, 303, 305, 307, 309, 311, 313, 315, or 317.

A further aspect of the invention provides a canola plant or plant part thereof comprising at least one mutation in at least one endogenous SHATTERPROOF MADS-BOX (SHP) gene having a gene identification number (gene ID) of BnaA04g01810D (SHP3), BnaA07g18050D (SHP2), BnaA05g02990D (SHP4), BnaA09g55330D (SHP1), BnaC04g23360D (SHP3), and/or BnaC06g16910D (SHP2), optionally wherein the at least one mutation may be a non-natural mutation.

In a further aspect, a guide nucleic acid is provided that binds to target nucleic acid in a SHATTERPROOF MADS-BOX (SHP) gene having a gene identification number (gene ID) of BnaA04g01810D (SHP3), BnaA07g18050D (SHP2), BnaA05g02990D (SHP4), BnaA09g55330D (SHP1), BnaC04g23360D (SHP3), and/or BnaC06g16910D (SHP2). Further provided are polypeptides, polynucleotides, nucleic acid constructs, expression cassettes and vectors for making a canola plant of this invention.

These and other aspects of the invention are set forth in more detail in the description of the invention below.

BRIEF DESCRIPTION OF THE SEQUENCES

SEQ ID NOs:1-17 are exemplary Cas12a amino acid sequences useful with this invention.

SEQ ID NOs:18-20 are exemplary Cas12a nucleotide sequences useful with this invention.

SEQ ID NO:21-22 are exemplary regulatory sequences encoding a promoter and intron.

SEQ ID NOs:23-29 are exemplary cytosine deaminase sequences useful with this invention.

SEQ ID NOs:30-40 are exemplary adenine deaminase amino acid sequences useful with this invention.

SEQ ID NO:41 is an exemplary uracil-DNA glycosylase inhibitor (UGI) sequences useful with this invention.

SEQ ID NOs:42-44 provide example peptide tags and affinity polypeptides useful with this invention.

SEQ ID NOs:45-55 provide example RNA recruiting motifs and corresponding affinity polypeptides useful with this invention.

SEQ ID NOs:56-57 are exemplary Cas9 polypeptide sequences useful with this invention.

SEQ ID NOs:58-68 are exemplary Cas9 polynucleotide sequences useful with this invention.

SEQ ID NO:69 (BnaA04g01810D) is an example SHP3 (SHP3A) genomic sequence from canola.

SEQ ID NO:70 is an example SHP3 (SHP3A) coding sequence from canola.

SEQ ID NO:71 is an example SHP3 (SHP3A) polypeptide sequence from canola.

SEQ ID NOs:72-96 are example portions or regions of SHP3 genomic and coding sequences from canola (BnaA04g01810D, SHP3A).

SEQ ID NOs:97-99 are an example portions or regions of an SHP3 polypeptide from canola (SHP3A).

SEQ ID NO:100 (BnaA07g18050D) is an example SHP2 (SHP2A) genomic sequence from canola.

SEQ ID NO:101 is an example SHP2 (SHP2A) coding sequence from canola.

SEQ ID NO:102 is an example SHP2 (SHP2A) polypeptide sequence from canola.

SEQ ID NOs:103-144 are example portions or regions of SHP2 genomic and coding sequences from canola (BnaA07g18050D, SHP2A).

SEQ ID NOs:145-147 are an example portions or regions of an SHP2 polypeptide from canola (SHP2A).

SEQ ID NO:148 (BnaA05g02990D) is an example SHP4 (SHP4A) genomic sequence from canola.

SEQ ID NO:149 is an example SHP4 (SHP4A) coding sequence from canola.

SEQ ID NO:150 is an example SHP4 (SHP4A) polypeptide sequence from canola.

SEQ ID NOs:151-173 and 324-338 are example portions or regions of SHP4 genomic and coding sequences from canola (BnaA05g02990D, SHP4A).

SEQ ID NOs:174-176 are an example portions or regions of an SHP4 polypeptide from canola (SHP4A).

SEQ ID NO:177 (BnaA09g55330D) is an example SHP1 (SHP1A) genomic sequence from canola.

SEQ ID NO:178 is an example SHP1 (SHP1A) coding sequence from canola.

SEQ ID NO:179 is an example SHP1 polypeptide sequence from canola (SHP1A).

SEQ ID NOs:180-202 are example portions or regions of a canola SHP1 genomic and coding sequences (BnaA09g55330D, SHP1A).

SEQ ID NOs:203-205 are an example portions or regions of an SHP1 polypeptide from canola (SHP1A).

SEQ ID NO:206 (BnaC04g23360D) is an example SHP3 (SHP3C) genomic sequence from canola.

SEQ ID NO:207 is an example SHP3 (SHP3C) coding sequence from canola.

SEQ ID NO:208 is an example SHP3 (SHP3C) polypeptide sequence from canola.

SEQ ID NOs:209-236 are example portions or regions of SHP3 genomic and coding sequences from canola (BnaC04g23360D, SHP3C).

SEQ ID NOs:237-239 are an example portions or regions of an SHP3 polypeptide from canola (SHP3C).

SEQ ID NO:240 (BnaC06g16910D) is an example SHP2 (SHP2C) genomic sequence from canola.

SEQ ID NO:241 is an example SHP2 (SHP2C) coding sequence from canola.

SEQ ID NO:242 is an example SHP2 (SHP2C) polypeptide sequence from canola.

SEQ ID NOs:243-288 are example portions or regions of SHP2 genomic and coding sequences from canola (BnaC06g16910D, SHP2C).

SEQ ID NOs:289-291 are an example portions or regions of an SHP2 polypeptide from canola (SHP2C).

SEQ ID NOs:292-297 and 342-346 are example spacer sequences for nucleic acid guides useful with this invention.

SEQ ID NOs:298, 300, 302, 306, 312, 314, and 321 are example mutated SHP2 (SHP2A) genomic sequences (BnaA07g18050D, SEQ ID NO:100) produced using the methods of the invention.

SEQ ID NOs:299, 301, 303, 307, 313 and 315 are example mutated SHP2 (SHP2A) polypeptide sequences encoded by the mutated SHP2 genomic sequences of SEQ ID NOs:298, 300, 302, 312 and 314, respectively.

SEQ ID NOs:304, 308, 310, 316, 318 and 319 are example mutated SHP2 (SHP2C) genomic sequences (BnaC06g16910D, SEQ ID NO:240) produced using the methods of the invention.

SEQ ID NOs:305, 309, 311, and 317 are example mutated SHP2 (SHP2C) polypeptide sequences encoded by the mutated SHP2 genomic sequences of SEQ ID NOs:304, 308, 310 and 316, respectively.

SEQ ID NO:320 is an example deleted portion from an SHP2C gene ((BnaC06g16910D, SEQ ID NO:240).

SEQ ID NO:322 and SEQ ID NO:323 are example mutated SHP4 (SHP4A) genomic sequences (BnaA05g02990D, SEQ ID NO:148) produced using the methods of the invention.

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, +5%, +1%, +0.5%, or even ±0.1% of the specified value as well as the specified value. For example, "about X" where X is the measurable value, is meant to include X as well as variations of ±10%, +5%, +1%, +0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500% or more as compared to a control. For example, a canola plant comprising a mutation in a SHATTERPROOF MADS-BOX (SHP) gene as described herein can exhibit an increase in harvestable seed, wherein the increase in harvestable seed is an increase of at least 10% over that produced by a control plant (e.g., an increase of at least about 10% to about 70% in harvestable seed, e.g., about 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70%, or any range or value therein).

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount. As an example, a canola plant comprising a mutation in a SHATTERPROOF MADS-BOX (SHP) gene as described herein can exhibit a reduction in pod shattering of at least 10% when compared to a control canola plant devoid of the at least one mutation (e.g., a reduction in pod shattering of at least about 10% to about 100%, e.g., about 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range or value therein).

A control canola plant is typically the same plant as the edited plant, but the control plant has not been similarly edited and therefore is devoid of the mutation. A control plant maybe an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a canola plant of the invention and a control canola plant is made under the same growth conditions, e.g., the same environmental conditions (soil, hydration, light, heat, nutrients, and the like).

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A "heterologous" or a "recombinant" nucleotide sequence is a nucleotide sequence not naturally associated with a host cell into which it is introduced, including non-naturally occurring multiple copies of a naturally occurring nucleotide sequence. A "heterologous" nucleotide/polypeptide may originate from a foreign species, or, if from the same species, is substantially modified from its native form in composition and/or genomic locus by deliberate human intervention.

A "native" or "wild type" nucleic acid, nucleotide sequence, polypeptide or amino acid sequence refers to a naturally occurring or endogenous nucleic acid, nucleotide sequence, polypeptide or amino acid sequence. In some contexts, a "wild type" nucleic acid is a nucleic acid that is not edited as described herein and can differ from an "endogenous" gene that may be edited as described herein (e.g., a mutated endogenous gene). In some contexts, a "wild type" nucleic acid (e.g., unedited) may be heterologous to the organism in which the wild type nucleic acid is found (e.g., a transgenic organism). As an example, a "wild type endogenous SHATTERPROOF MADS-BOX (SHP) gene" is a SHP gene that is naturally occurring in or endogenous to the reference organism, e.g., a canola plant, and may be subject to modification as described herein, after which, such a modified endogenous gene is no longer wild type. In some embodiments, an endogenous SHP gene may be an endogenous SHP1 gene, an endogenous SHP2 gene, an endogenous SHP3 gene, and/or an endogenous SHP4 gene, optionally wherein the endogenous SHP gene has a gene identification number (gene ID) of BnaA04g01810D (SHP3A), BnaA07g18050D (SHP2A), BnaA05g02990D (SHP4A), BnaA09g55330D (SHP1A), BnaC04g23360D (SHP3C), and/or BnaC06g16910D (SHP2C) (BrassicaEDB—a Gene Expression Database for *Brassica* Crops (brassica.biodb.org/analysis) or plants.ensembl.org).

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is nonfunctional.

A "recessive mutation" is a mutation in a gene that produces a phenotype when homozygous but the phenotype is not observable when the locus is heterozygous.

A "dominant mutation" is a mutation in a gene that produces a mutant phenotype in the presence of a nonmutated copy of the gene. A dominant mutation may be a loss or a gain of function mutation, a hypomorphic mutation, a hypermorphic mutation or a weak loss of function or a weak gain of function.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in Techniques et Utilisations Des Marqueurs Moleculaires Les Colloques, Vol. 72, pp. 45-56 (1995); and Openshaw et al., *Marker-assisted Selection in Backcross Breeding*, in Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one (e.g., one or more) progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms “cultivar” and “variety” refer to a group of similar plants that by structural or genetic features and/or performance can be distinguished from other varieties within the same species.

As used herein, the terms “exotic,” “exotic line” and “exotic germplasm” refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term “hybrid” in the context of plant breeding refers to a plant that is the offspring of genetically dissimilar parents produced by crossing plants of different lines or breeds or species, including but not limited to the cross between two inbred lines.

As used herein, the term “inbred” refers to a substantially homozygous plant or variety. The term may refer to a plant or plant variety that is substantially homozygous throughout the entire genome or that is substantially homozygous with respect to a portion of the genome that is of particular interest.

A “haplotype” is the genotype of an individual at a plurality of genetic loci, i.e., a combination of alleles. Typically, the genetic loci that define a haplotype are physically and genetically linked, i.e., on the same chromosome segment. The term “haplotype” can refer to polymorphisms at a particular locus, such as a single marker locus, or polymorphisms at multiple loci along a chromosomal segment.

A canola plant in which at least one (e.g., one or more, e.g., 1, 2, 3, or 4, or more) endogenous SHP gene (e.g., an endogenous SHP1 gene, an endogenous SHP2 gene, an endogenous SHP3 gene, and/or an endogenous SHP4 gene) is modified as described herein (e.g., comprises a modification as described herein) may have reduced pod shattering as compared to a canola plant that does not comprise (is devoid of) the modification in the at least one endogenous SHP gene. In some embodiments, a canola plant in which at least one endogenous SHP gene is modified as described herein may exhibit reduced lignification (reduced lignin content) in the pod valve margin of the canola plant comprising the at least one endogenous SHP gene modified as described herein. In some embodiments, a canola plant in which at least one endogenous SHP gene is modified as described herein may exhibit an increase in harvestable seed as compared to a canola plant that does not comprise (is devoid of) the modification in the at least one endogenous SHP gene.

As used herein, “reduced pod shattering” means a reduction in pod shattering of at least 10% when compared to a control canola plant devoid of the at least one mutation (e.g., a reduction in pod shattering of at least about 10% to about 100%, e.g., a reduction of about 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range or value therein). Reduced pod shattering may result in an increase in harvestable seed.

As used herein, “reduced lignification in the pod valve margin” means a reduction in detectable lignin content by at least 10% at the pod valve margin when compared to pod valve margins in a control canola plant devoid of the at least one mutation (e.g., a reduction in lignification in the pod valve margin of at least about 10% to about 100%, e.g., a reduction of about 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range or value therein), wherein a reduction of 100% means no detectable lignin (e.g., no lignin staining in the pod valve margin). Reduced lignification in the pod valve margin can result in reduced pod shatter.

As used herein, an “increase in harvestable seed” means an increase in harvestable seed of at least 10% when compared to a control canola plant devoid of the at least one mutation (e.g., an increase of at least about 10% to about 70% in harvestable seed, e.g., about 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70%, or any range or value therein).

As used herein a “control plant” means a canola plant that does not contain an edited SHP gene or gene as described herein that imparts an altered phenotype of reduced pod shattering and/or increased harvestable seed and/or reduced lignification (reduced lignin content) in the pod valve margin. A control canola plant is used to identify and select a canola plant edited as described herein and that has an enhanced trait or altered phenotype as compared to the control canola plant. A suitable control plant can be a plant of the parental line used to generate a plant comprising a mutated SHP gene(s), for example, a wild type plant devoid of an edit in an endogenous SHP gene as described herein. A suitable control plant can also be a plant that contains recombinant nucleic acids that impart other traits, for example, a transgenic plant having enhanced herbicide tolerance. A suitable canola control plant can in some cases be a progeny of a heterozygous or hemizygous transgenic canola plant line that is devoid of the mutated SHP gene as described herein, known as a negative segregant, or a negative isogenic line.

An enhanced trait (e.g., improved yield trait) may include, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield (e.g., increase in harvestable seed), increased nitrogen use efficiency, and/or increased water use efficiency as compared to a control plant. An altered phenotype may be, for example, plant height, biomass, canopy area, anthocyanin content, chlorophyll content, water applied, water content, and water use efficiency.

In some embodiments, a plant of this invention may comprise one or more improved yield traits including, but not limited to, In some embodiments, the one or more improved yield traits includes higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods, including an increased number of pods per node and/or an increased number of pods per plant, increased number of seeds per pod, increased number of seeds, increased seed size, and/or increased seed weight (e.g., increase in 100-seed weight) as compared to a control plant devoid of the at least one mutation. In some embodiments, a plant of this invention may comprise one or more improved yield traits including, but not limited to, optionally an increase in yield (bu/acre), seed size (including kernel size), seed weight (including kernel weight), increased kernel row number (optionally wherein ear length is not substantially reduced), increased number of pods, increased number of seeds per pod and an increase in ear length as compared to a control plant or part thereof.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. However, any technique can be used to measure the amount of, the comparative level of, or the difference in any selected chemical compound or macromolecule in the transgenic plants.

As used herein an "enhanced trait" means a characteristic of a canola plant resulting from mutations in a SHP gene(s) as described herein. Such traits include, but are not limited to, an enhanced agronomic trait characterized by enhanced plant morphology, physiology, growth and development, yield, nutritional enhancement, disease or pest resistance, or environmental or chemical tolerance. In some embodiments, an enhanced trait/altered phenotype may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, and/or increased yield. In some embodiments, a trait is increased yield under nonstress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a canola plant comprising a mutation in an endogenous SHP gene as described herein relative to a canola plant not comprising the mutation, such as a wild-type plant, or a negative segregant. In some cases, the trait modification can be evaluated quantitatively. For example, the trait modification can entail an increase or decrease in an observed trait characteristic or phenotype as compared to a control plant. It is known that there can be natural variations in a modified trait. Therefore, the trait modification observed can entail a change of the normal distribution and magnitude of the trait characteristics or phenotype in the plants as compared to a control plant.

The present disclosure relates to a canola plant with improved economically relevant characteristics, more specifically reduced pod shattering, reduced lignification (reduced lignin content) in the pod valve margin, and/or increased harvestable seed yield. More specifically the present disclosure relates to a canola plant comprising a mutation(s) in an SHP gene(s) as described herein, wherein the canola plant has reduced pod shattering, reduced lignification (reduced lignin content) in the pod valve margin, and/or increased harvestable seed yield as compared to a control plant devoid of said mutation(s). In some embodiments, a canola plant of the present disclosure exhibits an improved trait that is related to yield, including but not limited to increased nitrogen use efficiency, increased nitrogen stress tolerance, increased water use efficiency and/or increased drought tolerance, as defined and discussed infra.

Yield can be defined as the measurable produce of economic value from a crop. Yield can be defined in the scope of quantity and/or quality. Yield can be directly dependent on several factors, for example, the number and size of organs (e.g., number of flowers), plant architecture (such as the number of branches, plant biomass, e.g., increased root biomass, steeper root angle and/or longer roots, and the like), flowering time and duration, grain fill period. Root architecture and development, photosynthetic efficiency, nutrient uptake, stress tolerance, early vigor, delayed senescence and functional stay green phenotypes may be factors in determining yield. Optimizing the above-mentioned factors can therefore contribute to increasing crop yield.

Reference herein to an increase/improvement in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. In some embodiments, performance of the methods of the disclosure results in canola plants having increased harvestable seed (and thus increased seed yield), optionally reduced lignification (decreased lignin content) in the pod valve margin, relative to suitable control canola plants due to reduced seed loss resulting from reduced pod shattering. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination.

"Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor, for example, can be a combination of the ability of seeds to germinate and emerge after planting and the ability of the young plants to grow and develop after emergence. Plants having early vigor also show increased seedling survival and better establishment of the crop, which often results in highly uniform fields with the majority of the plants reaching the various stages of development at substantially the same time, which often results in increased yield. Therefore, early vigor can be determined by measuring various factors, such as kernel weight, percentage germination, percentage emergence, seedling growth, seedling height, root length, root and shoot biomass, canopy size and color and others.

Further, increased yield can also manifest as increased total seed yield, which may result from one or more of an increase in seed biomass (seed weight) due to an increase in the seed weight on a per plant and/or on an individual seed basis an increased number of, for example, flowers/panicles per plant; an increased number of pods; an increased number of nodes; an increased number of flowers ("florets") per panicle/plant; increased seed fill rate; an increased number of filled seeds; increased seed size (length, width, area, perimeter, and/or weight), which can also influence the composition of seeds; and/or increased seed volume, which can also influence the composition of seeds. In one embodiment, increased yield can be increased seed yield, for example, increased seed weight; increased number of filled seeds; and/or increased harvest index.

Increased yield can also result in modified architecture, or can occur because of modified plant architecture.

Increased yield can also manifest as increased harvest index, which is expressed as a ratio of the yield of harvestable parts, such as seeds, over the total biomass The disclosure also extends to harvestable parts of a plant such as, but not limited to, seeds, leaves, fruits, flowers, bolls, pods, siliques, nuts, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Typically, plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 20, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, or 900 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a "portion" of a wild type CRISPR-Cas repeat sequence (e.g., a wild type CRISPR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a nucleic acid fragment may comprise, consist essentially of or consist of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 320, 330, 340, 350, 360, 370, 380, 390, 395, 400, 410, 415, 420, 425, 430, 435, 440, 445, 450, 500, 550, 600, 650, 700, 750, 800, 850, 900, 950, 1000, 1100, 1150, 1200, 1250, 1300, 1350, 1400, 1450, 1500, 1550, 1600, 1650, 1700, 1750, 1800, 1900, 2000, 3000, 4000 or 5000 or more consecutive nucleotides, or any range or value therein, of a nucleic acid encoding a SHP polypeptide, optionally a fragment of a SHP gene may be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 115, 120, 125, 130, 135, 140, 145, 150 consecutive nucleotides to about 155, 160, 165, 170, 175, 180, 185, 190, 195, 200, 205, 210, 215, 220, 225, 230, 240, 245, 250, 255, 260, 265, 270, 275, 280, 285, 290, 295, 300, 305, 310, 315, 320, 325, 330, 340, 345, 350, 355, 360, 365, 370, 375, 380, 385, 390, 395, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740 or 750 or more consecutive nucleotides in length, or any range or value therein (e.g., a fragment or portion of any one SEQ ID NOs:69, 70, 100, 101, 148, 149, 177, 178, 206, 207, 240 or 241 (e.g., SEQ ID NOs:72-96, 103-144, 151-173, 180-202, 209-236, 243-288 or 324-338).

In some embodiments, a "sequence-specific nucleic acid binding domain" may bind to one or more fragments or portions of nucleotide sequences (e.g., DNA, RNA) encoding, for example, a Shatterproof MADS-box transcription factor (SHP) polypeptide as described herein.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, a polypeptide fragment may comprise, consist essentially of, or consist of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 260, 270, 280, or 290 or more consecutive amino acids of a reference polypeptide. In some embodiments, a polypeptide fragment may comprise, consist essentially of or consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, or 150, or more consecutive amino acid residues, or any range or value therein, of a SHP (e.g., a fragment or a portion of any one of the polypeptides of SEQ ID NOs:71, 102, 150, 179, 208, or 242 (e.g., SEQ ID NOs:100-102, 148-150, 177-179, 206-208, 240-242 or 292-294)). In some embodiments, an SHP polypeptide fragment may comprise, consist essentially of or consist of about 13, 59, 63, 64, 68, 69, 71, 72, 76, or 77 consecutive amino acid residues (see, e.g., SEQ ID NOs:97-99, 145-147, 174-176, 203-205, 237-239 or 289-291).

In some embodiments, a fragment of a SHP polypeptide can be a truncated SHP polypeptide resulting from a mutation of the SHP genomic sequence encoding the SHP polypeptide as described herein. For example, a fragment of a SHP polypeptide can be the N-terminus of an SHP polypeptide or a portion thereof (see, e.g., about the first 170-190 consecutive amino acid residues (e.g., the first 170, 171, 172, 173, 174, 175, 176, 177, 178, 179, 180, 181, 182, 183, 184, 185, 186, 187, 188, 189, 190 consecutive amino acid residues, e.g., the first 172 to 185 (e.g., 172, 173, 174, 175, 176, 178, 179, 180, 181, 182, 183, 184, 185, 186, 187, 188, or 189) consecutive amino acid residues, and any range or value therein) (e.g., SEQ ID NOs:71, 102, 150, 179, 208, or 242). In some embodiments, a fragment of an SHP polypeptide may be the result of a mutation generated in at least one endogenous gene encoding an SHP polypeptide (e.g., an endogenous SHP1 gene, an endogenous SHP2 gene, an endogenous SHP3 gene, and/or an endogenous SHP4 gene) as described herein (e.g., a deletion, insertion and the like, in one or more of the endogenous SHP genes in a canola plant). In some embodiments, SHP polypeptides edited as described herein are N-terminal truncated polypeptides missing the first about 170-190 consecutive amino acids, see, e.g., SEQ ID NOs:299, 301, 303, 305, 307, 309, 311, or 317. In some embodiments, a truncated SHP polypeptide (N-terminal fragment) may comprise at least one amino acid substitution at the C-terminal end of the truncated polypeptide that are not present in the polypeptide encoded by the endogenous SHP gene (e.g., a substitution of 1, 2, 3, 4, 5, 6, 7, 8, 9, 10, 11, 12, 13, 14, 15, 16, 17, 18, 19, or 20 amino acid residues at the C-terminus, optionally 1 amino acid residue to about 2, 3, 4, 5, 6, 7, 8, 9, or 10 amino acid residues) (see, e.g., SEQ ID NO:313 or SEQ ID NO:315).

In some embodiments, a fragment of a SHP polypeptide may be from the C-terminus of the SHP polypeptide. For example, a fragment of a SHP polypeptide can be about the last 76 or 77 consecutive amino acid residues of an SHP polypeptide or a portion thereof (see, e.g., SEQ ID NOs: 97-99, 145-147, 174-176, 203-205, 237-239 or 289-291). In some embodiments, a fragment of a SHP polypeptide can comprise the portion of the SHP polypeptide encoded by the second to last exon and/or the last exon of an SHP gene. In some embodiments, a fragment of a SHP polypeptide can comprise the portion of the SHP polypeptide encoded by all but the second to last exon and/or the last exon of an SHP gene.

In some embodiments, such a deletion when comprised in a canola plant can result in the canola plant exhibiting reduced pod shatter and/or reduced lignification (reduced lignin content) in the pod valve margin, as compared to a canola plant not comprising (devoid of) said deletion. An SHP gene may be edited in one or more than one location (and using one or more different editing tools), thereby providing a SHP gene comprising one or more than one mutation. In some embodiments, an SHP polypeptide mutated as described herein may comprise one or more than one edit that may result in a polypeptide having a deletion of one or more amino acid residues (e.g., a deletion of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, or more consecutive amino acid residue, and any range or value therein (e.g., a truncated polypeptide), optionally a deletion of about 100 to about 600 consecutive amino acid residues (e.g., about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, or 600, and any range or value therein).

In some embodiments, a "portion" or "region" in reference to a nucleic acid means at least 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 210, 220, 230, 240, 250, 260, 270, 280, 285, 290, 300, 310, 320, 330, 340, 350, 360, 370, 380, 390, 395, 400, 405, 410, 415, 420, 425, 430, 435, 440, 445, 450, 500, 600, 700, 800, 900, 1000, 1100, 1200, 1300, 1400, 1500, 1600, 1700, 1800, 1900, 2000, 2500, 3000, 3500, 4000, 4500, or 5000 or more consecutive nucleotides from a gene (e.g., consecutive nucleotides from an SHP gene), optionally a "portion" or "region" of a SHP gene may be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, or 150 consecutive nucleotides to about 155, 160, 165, 170, 175, 180, 185, 190, 195, 200, 205, 210, 215, 220, 225, 230, 240, 245, 250, 255, 260, 265, 270, 275, 280, 285, 290, 295, 300, 305, 310, 315, 320, 325, 330, 340, 345, 350, 355, 360, 365, 370, 375, 380, 385, 390, 395, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740 or 750 or more consecutive nucleotides in length, or any range or value therein (e.g., a portion or region of any one of SEQ ID NOs:69, 70, 100, 101, 148, 149, 177, 178, 206, 207, 240 or 241 (e.g., SEQ ID NOs:75-82, 85-92, 107-112, 116-120, 124-127, 129, 135, 136, 139, 140, 156, 157, 159-161, 164-166, 181-184, 187-190, 195, 196, 212-219, 222-224, 229, 230, 246-248, 251-253, 255-257, 261-264, 267, 268, 271, 272, 275, 276, 279, 280, 283, or 285).

In some embodiments, a "portion" or "region" of a SHP polypeptide sequence may be about 5 to about 200 or more consecutive amino acid residues in length (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 176, 177, 178, 179, 180, 181, 812, 183, 184, 185, 186, 187, 188, 189, 190, 195, or 200, or more consecutive amino acid residues in length (e.g., a portion of any one of SEQ ID NOs:71, 102, 150, 179, 208, or 242, optionally SEQ ID NOs:97-99, 145-147, 174-176, 203-205, 237-239 or 289-291) (e.g., a C-terminal portion of a SHP polypeptide, e.g., SEQ ID NOs:299, 301, 303, 305, 307, 309, or 317).

As used herein with respect to nucleic acids, the term "functional fragment" refers to nucleic acid that encodes a functional fragment of a polypeptide. A "functional fragment" with respect to a polypeptide is a fragment of a polypeptide that retains one or more of the activities of the native reference polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, inversions and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. A frameshift mutation can occur when deletions or insertions of one or more base pairs are introduced into a gene, optionally resulting in an out-of-frame mutation or an in-frame mutation. Frameshift mutations in a gene can result in the production of a polypeptide that is longer, shorter or the same length as the wild type polypeptide depending on when the first stop codon occurs following the mutated region of the gene. As an example, an out-of-frame mutation that produces a premature stop codon can produce a polypeptide that is shorter that the wild type polypeptide, or, in some embodiments, the polypeptide may be absent/undetectable. A DNA inversion is the result of a rotation of a genetic fragment within a region of a chromosome.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity"

can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide.

As used herein, the phrase "substantially identical," or "substantial identity" in the context of two nucleic acid molecules, nucleotide sequences, or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more in length, or any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40, 50, 60, 70, or 80 nucleotides or more).

In some embodiments of the invention, the substantial identity exists over a region of consecutive amino acid residues of a polypeptide of the invention that is about 3 amino acid residues to about 20 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8 consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 300, 350 or more amino acids in length or more consecutive amino acid residues). In some embodiments, two or more SHP polypeptides may be identical or substantially identical (e.g., at least 70% to 99.9% identical; e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% identical or any range or value therein) over at least 8 consecutive amino acids to about 350 consecutive amino acids. In some embodiments, two or more SHP polypeptides may be identical or substantially identical over at least 8, 9, 10, 11, 12, 13, 14, or 15 consecutive amino acids to about 20, 21, 22, 23, 24, 25, 26, 27, 28, 29, 30, 31, 32, 33, 34, 35, 36, 37, 38, 39, or 40 consecutive amino acids).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2×(or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific nucleic acid binding domain (e.g., a sequence-specific nucleic acid binding domain (e.g., DNA binding domain) from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a nucleic acid binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) Proc. Natl. Acad. Sci. USA 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (Mol. Gen. Genet. 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as 0-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. Genome 60(6):485-495 (2017)), LAT52 and LAT59 from tomato (Twell et al. Development 109(3):705-713 (1990)), Zm13 (U.S. Pat. No. 10,421,972), $PLA_2$-δ promoter from *Arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine symthetase (S AMS) (Vander Mijnsbrugge et al. (1996) *Plant and Cell Physiology,* 37(8):1108-1115), corn light harvesting complex promoter (Bansal et al. (1992) Proc. Natl. Acad. Sci. USA 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) Mol. Gen. Genet. 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *Petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) Mol. Gen. Genet. 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter, or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one (e.g., one or more) of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific nucleic acid binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific nucleic acid binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g., expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally, included are shuttle vectors by which is meant a DNA vehicle capable, naturally or by design, of replication in two different host organisms, which may be selected from actinomycetes and related species, bacteria and eukaryotic (e.g., higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific nucleic acid binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific nucleic acid binding protein, the reverse transcriptase and/or the deaminase are expressed and the sequence-specific nucleic acid binding protein binds to the target nucleic acid, and the reverse transcriptase and/or deaminase may be fused to either the sequence-specific nucleic acid binding protein or recruited to the sequence-specific nucleic acid binding protein (via, for example, a peptide tag fused to the sequence-specific nucleic acid binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in Methods in *Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

The present invention is directed to the modification of expression and protein production by genes that contribute to pod shattering in order to control seed dehiscence and improve yield and labor costs. The functionally redundant MADS-domain factors SHATTERPROOF1 (SHP1) and SHATTERPROOF2 (SHP2) are required for both separation layer differentiation and to promote lignification of the lignified margin layer in *Arabidopsis. Consequently, when shp*1 shp2 mutant fruit are mature, they fail to open, and the seeds are trapped inside. Accordingly, the present invention provides methods and compositions for modifying SHATTERPROOF MADS-BOX (SHP) genes in canola plants (e.g., an endogenous SHP1 gene, an endogenous SHP2 gene, an endogenous SHP3 gene, and/or an endogenous SHP4 gene) to provide canola plants that exhibit reduced pod shattering and/or reduced lignification (reduced lignin content) in the pod valve margin. In canola, SHP genes include SHP1 (BnaA09g55330D), SHP2 (BnaA07g18050D, BnaC06g16910D), SHP3 (BnaA04g01810D, BnaC04g23360D), and/or SHP4 (BnaA05g02990D) (Gene IDs from BrassicaEDB—a Gene Expression Database for *Brassica* Crops (brassica.biodb.org/analysis)), each of which may be targeted in a plant. Thus, an editing strategy useful for this invention can include generating a mutation in one or more than one SHP gene in a canola plant, e.g., a canola plant may comprise 1, 2, 3, 4, 5, and/or 6 or more SHP genes comprising a modification as described herein. In some embodiments, one or more than one mutation (optionally, a non-natural mutation) may be generated in a SHP gene of a plant. Mutations that may be useful for producing canola plants having reduced pod shattering and/or reduced lignification (reduced lignin content) in the pod valve margin include, for example, substitutions, deletions, and/or insertions. In some aspects, a mutation generated by the editing technology can be a point mutation. In some embodiments, a mutation in one or more than one SHP gene as described herein results in knockdown of expression of the one or more than one SHP gene. In some embodiments, a mutation in one or more than one SHP gene as described herein results in production of a modified SHP polypeptide, optionally wherein the modified SHP polypeptide comprises a C-terminal truncation, optionally a truncation of about the last 65-80 consecutive amino acid residues (about 65, 66, 67, 68, 69, 70, 71, 72, 73, 74, 75, 76, 77, 78, 79, or 80 consecutive amino acid residues) of the SHP polypeptide produced by the unmodified endogenous SHP gene.

In some embodiments, the invention provides a canola plant or plant part thereof comprising at least one mutation in at least one (e.g., one or more than one SHP gene) endogenous SHATTERPROOF MADS-BOX(SHP) gene encoding a Shatterproof MADS-box transcription factor (SHP) polypeptide, optionally wherein the at least one mutation may be a non-natural mutation. In some embodiments, an endogenous SHP gene is an endogenous SHP1 gene, an endogenous SHP2 gene, an endogenous SHP3 gene, and/or an endogenous SHP4 gene, wherein the encoded SHP polypeptide is an SHP1 polypeptide, an SHP2 polypeptide, an SHP3 polypeptide, or an SHP4 polypeptide, respectively. An endogenous SHP gene may have the gene identification number (gene ID) of BnaA04g01810D (SHP3), BnaA07g18050D (SHP2), BnaA05g02990D (SHP4), BnaA09g55330D (SHP1), BnaC04g23360D (SHP3), and/or BnaC06g16910D (SHP2). In some embodiments, the at least one mutation in the canola plant may be a hypomorphic mutation, a dominant negative mutation, or a dominant negative hypomorphic mutation. In some embodiments, a mutation may be a knock-down mutation. As used herein, a knock-down mutation results in a reduction in activity of at least 5% (e.g., a reduction in activity of about 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, and any range or value therein).

In some embodiments, a canola plant cell is provided, the canola plant cell comprising an editing system, the editing system comprising: (a) a CRISPR-Cas effector protein; and (b) a guide nucleic acid (e.g., gRNA, gDNA, crRNA, crDNA, sgRNA, sgDNA) comprising a spacer sequence with complementarity to an endogenous target gene encoding a Shatterproof MADS-box transcription factor (SHP) polypeptide in the canola plant cell. The editing system may be used to generate a mutation in the endogenous target gene encoding a SHP polypeptide. In some embodiments, the endogenous target gene is an endogenous SHATTERPROOF MADS-BOX (SHP) gene (e.g., one or more than one endogenous SHP gene), optionally an endogenous SHP1 gene, an endogenous SHP2 gene, an endogenous SHP3 gene, and/or an endogenous SHP4 gene, and the SHP polypeptide is an SHP1 polypeptide, an SHP2 polypeptide, an SHP3 polypeptide, or an SHP4 polypeptide, respectively. In some embodiments, the mutation is a non-natural mutation. In some embodiments, the endogenous target gene: (a) comprises a nucleotide sequence having at least 80% sequence identity to any one of SEQ ID NOs:69, 70, 100, 101, 148, 149, 177, 178, 206, 207, 240 or 241; (b) comprises a region having at least 80% sequence identity to a nucleotide sequence of any one of SEQ ID NOs:72-96, 103-144, 151-173, 180-202, 209-236, 243-288 or 324-338; (c) encodes a SHP polypeptide having at least 80% sequence identity to any one of SEQ ID NOs:71, 102, 150, 179, 208, or 242; and/or (d) encodes a region of a SHP polypeptide having at least 80% sequence identity to any one of SEQ ID NOs:97-99, 145-147, 174-176, 203-205, 237-239 or 289-291. In some embodiments, a guide nucleic acid of an editing system may comprise the nucleotide sequence (a spacer sequence, e.g., one or more spacers) of any one of SEQ ID NOs:292-297 (e.g., SEQ ID NO:292 (PWsp236), SEQ ID NO:293 (PWsp237), SEQ ID NO:294 (PWsp238), SEQ ID NO:295 (PWsp239), SEQ ID NO:296 (PWsp240), and/or SEQ ID NO:297 (PWsp241)) and/or SEQ ID NOs: 342-346 (e.g., SEQ ID NO:342 (PWsp291), SEQ ID NO:343 (PWsp292), SEQ ID NO:344 (PWsp293), SEQ ID NO:345 (PWsp294), and/or SEQ ID NO:346 (PWsp294), or reverse complement thereof.

A mutation in an SHP gene of a canola plant, plant part thereof, or a canola plant cell useful for this invention may be any type of mutation, including a base substitution, a base deletion, and/or a base insertion. In some embodiments, the mutation may be a non-natural mutation. In some embodiments, the mutation may comprise a base substitution to an A, a T, a G, or a C. In some embodiments, the mutation may be a deletion (optionally, an out-of-frame deletion or an in-frame deletion) (e.g., of at least one base pair (e.g., 1 base pair to about 100 base pairs; e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 consecutive base pairs; e.g., 1 to about 50 consecutive base pairs, 1 to about 30 consecutive base pairs, 1 to about 15 consecutive base pairs) or an insertion of at least one base pair (e.g., 1 base pair to about 15 base pairs; e.g., 1, 2, 3, 4, 5, 6, 7, 8, 9, 10, 11, 12, 13, 14, or 15 consecutive base pairs), optionally wherein the deletion is an out-of-frame deletion. For example, a deletion in an SHP gene may be about 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, or 45 consecutive base pairs, optionally about 7, 8, 10, 20, or 45 consecutive base pairs. In some embodiments, a non-natural mutation may be an insertion of at least one base pair (e.g., 1 base pair to about 100 consecutive base pairs; e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 consecutive base. In some embodiments, an insertion of 1 to about 100 base pairs is an out-of-frame insertion.

A mutation in an SHP gene may be located in the 3' region of the SHP gene (e.g., a SHP1 gene, a SHP2 gene, a SHP3 gene, and/or a SHP4gene), optionally a non-natural mutation, optionally in the 3' region of the SHP gene that encodes the C-terminal region of the encoded SHP polypeptide (e.g., the 3' coding regions (exons)). For example, a mutation in an SHP gene may be located (a) in the second to the last exon, (b) in the second to the last exon and the intron that is 3' to the second to the last exon and 5' to the last exon, and/or (c) in the last exon. In some embodiments, the mutation may be an out-of-frame deletion, an in-frame deletion, or an out-of-frame insertion. In some embodiments, the out-of-frame deletion, in-frame deletion, or out-of-frame insertion may result in a deletion of the last exon of the gene. In some embodiments, the out-of-frame deletion, in-frame deletion, or out-of-frame insertion results in a gene that encodes a truncated polypeptide, optionally a polypeptide having a C-terminal truncation resulting from a premature stop codon generated by the deletion or insertion. In some embodiments, the C-terminal truncation is a deletion of about 65 to about 80 consecutive amino acid residues (about 65, 66, 67, 68, 69, 70, 71, 72, 73, 74, 75, 76, 77, 78, 79, or 80 consecutive amino acid residues) from the C-terminus of the SHP polypeptide (e.g., about the last 65 to 80 consecutive amino acid residues).

As used herein, a "non-natural mutation" refers to a mutation that is generated though human intervention and differs from mutations found in the same gene that have occurred in nature (e.g., occurred naturally)).

In some embodiments, a mutation useful with this invention may be a hypomorphic mutation, a dominant negative mutation, or a dominant negative hypomorphic mutation.

The types of editing tools that may be used to generate these and other mutations in canola SHP genes include any base editors or cutters, which are guided to a target site using spacers having at least 80% (e.g., 80, 81, 82, 83, 84, 85, 86, 87, 88, 89, 90, 91, 92, 93, 94, 95, 96, 97, 98, 99, or 100%, or any range or value therein), complementarity to a portion or a region of a SHP gene (e.g., one or more than one SHP gene, e.g., an SHP1 gene, an SHP2 gene, an SHP3 gene, and/or an SHP4 gene) as described herein.

In some embodiments, a mutation of a SHP gene is within a portion or region of the endogenous SHP gene having at least 80% sequence identity to any one of the nucleotide sequences of SEQ ID NOs:72-96, 103-144, 151-173, 180-202, 209-236, 243-288 or 324-338, optionally a portion or region of the endogenous SHP gene having at least 80% sequence identity to any one of the nucleotide sequences of SEQ ID NOs:75-82, 85-92, 107-112, 116-120, 124-127, 129, 135, 136, 139, 140, 156, 157, 159-161, 164-166, 181-184, 187-190, 195, 196, 212-219, 222-224, 229, 230, 246-248, 251-253, 255-257, 261-264, 267, 268, 271, 272, 275, 276, 279, 280, 283, 285, or 324-338.

An endogenous SHP gene useful with this invention (e.g., an endogenous target gene) encodes a Shatterproof MADS-box transcription factor (SHP) polypeptide, and includes an endogenous SHP1 gene, an endogenous SHP2 gene, an endogenous SHP3 gene, or an endogenous SHP4 gene, which encode an SHP1 polypeptide, an SHP2 polypeptide, an SHP3 polypeptide, or an SHP4 polypeptide, respectively. In some embodiments, an endogenous SHP gene (e.g., endogenous target gene) (1) may comprise a nucleic acid sequence having at least 80% sequence identity to any one of SEQ ID NOs:69, 70, 100, 101, 148, 149, 177, 178, 206, 207, 240 or 241, (2) may comprise a region of a SHP gene having at least 80% sequence identity to any one of SEQ ID NOs:72-96, 103-144, 151-173, 180-202, 209-236, 243-288 or 324-338, (3) may encode a polypeptide having at least 80% sequence identity to any one of SEQ ID NOs:71, 102, 150, 179, 208, or 242, and/or (4) may encode a region of a SHP polypeptide having at least 80% sequence identity to any one of SEQ ID NOs:97-99, 145-147, 174-176, 203-205, 237-239 or 289-291.

In some embodiments, a canola plant comprising at least one (e.g., one or more, e.g., 1, 2, 3, 4, 5, or more) mutation in an endogenous SHP gene (in at least one endogenous SHP gene, e.g., in one or more SHP genes, e.g., SHP1, SHP2, SHP3, SHP4) exhibits reduced pod shattering (and/or reduced lignification (reduced lignin content) in the pod valve margin and/or increased harvestable seed) as compared to a canola plant devoid of the at least one mutation (e.g., an isogenic plant (e.g., wild type unedited plant or a null segregant).

In some embodiments, a canola plant may be regenerated from a canola plant part and/or plant cell of the invention comprising a mutation in one or more than one endogenous SHP gene (an endogenous SHP1 gene, an endogenous SHP2 gene, an endogenous SHP3 gene, and/or an endogenous SHP4 gene) as described herein, wherein the regenerated canola plant comprises the mutation in the one or more than one endogenous SHP gene and a phenotype of reduced pod shattering and/or reduced lignification (reduced lignin content) in the pod valve margin as compared to a control canola plant devoid of the same mutation in the one or more than one SHP gene.

In some embodiments, a canola plant cell is provided, the canola plant cell comprising at least one (e.g., one or more) mutation (optionally a non-natural mutation) within an endogenous SHATTERPROOF MADS-BOX(SHP) gene, wherein the at least one mutation is a substitution, insertion, or deletion that is introduced using an editing system that comprises a nucleic acid binding domain that binds to a target site in the endogenous SHP gene. In some embodiments, the substitution, insertion, or deletion results in, for example, a premature stop codon. In some embodiments, the substitution, insertion, or deletion results in, for example, a truncated SHP protein, optionally an SHP polypeptide having a C-terminal truncation. In some embodiments, the at least one mutation is a point mutation, optionally resulting in a premature stop codon, optionally a truncated SHP protein. In some embodiments, the at least one mutation within the SHP gene is an insertion and/or a deletion, optionally the at least one mutation is an out-of-frame insertion or out-of-frame deletion. In some embodiments, the endogenous SHP gene is an endogenous SHP1 gene, an endogenous SHP2 gene, an endogenous SHP3 gene, or an endogenous SHP4 gene.

In some embodiments, a target site in an SHP gene of a canola plant cell may be within a region or portion of the endogenous SHP gene, the region having at least 80% sequence identity to any one of the nucleotide sequences of SEQ ID NOs:72-96, 103-144, 151-173, 180-202, 209-236, 243-288 or 324-338, optionally at least 80% sequence identity to any one of SEQ ID NOs:75-82, 85-92, 107-112, 116-120, 124-127, 129, 135, 136, 139, 140, 156, 157, 159-161, 164-166, 181-184, 187-190, 195, 196, 212-219, 222-224, 229, 230, 246-248, 251-253, 255-257, 261-264, 267, 268, 271, 272, 275, 276, 279, 280, 283, or 285. In some embodiments, the target site in the SHP gene is within a region of the endogenous SHP gene that encodes an amino acid sequence having at least 80% sequence identity to any one of SEQ ID NOs:97-99, 145-147, 174-176, 203-205, 237-239 or 289-291.

In some embodiments, a mutation may be made following cleavage by an editing system that comprises a nuclease and a nucleic acid binding domain that binds to a target site within: (a) a sequence having least 80% sequence identity to a sequence encoding of any one of SEQ ID NOs:69, 70, 100, 101, 148, 149, 177, 178, 206, 207, 240 or 241, optionally within the 3' region of a sequence having least 80% sequence identity to a sequence encoding of any one of SEQ ID NOs:69, 70, 100, 101, 148, 149, 177, 178, 206, 207, 240 or 241, optionally located (i) in the second to the last exon, (ii) in the second to the last exon and the intron that is 3' to the second to the last exon and 5' to the last exon, and/or (iii) in the last exon of a sequence having least 80% sequence identity to a sequence encoding of any one of SEQ ID NOs:69, 100, 148, 177, 206, or 240, or (b) a sequence having at least 80% sequence identity to a sequence encoding any one of SEQ ID NOs:72-96, 103-144, 151-173, 180-202, 209-236, 243-288 or 324-338, optionally at least 80% sequence identity to any one of SEQ ID NOs:75-82, 85-92, 107-112, 116-120, 124-127, 129, 135, 136, 139, 140, 156, 157, 159-161, 164-166, 181-184, 187-190, 195, 196, 212-219, 222-224, 229, 230, 246-248, 251-253, 255-257, 261-264, 267, 268, 271, 272, 275, 276, 279, 280, 283, or 285, and the at least one mutation within an SHP gene is made following cleavage by the nuclease, optionally wherein the at least one mutation is a non-natural mutation.

In some embodiments, the at least one mutation may result in a hypomorphic mutation, a dominant negative mutation, or a dominant negative hypomorphic mutation.

In some embodiments, the canola plant cell may be regenerated into a canola plant that comprises the at least one mutation, optionally wherein the canola plant regenerated from the canola plant cell exhibits a phenotype of reduced pod shattering and/or reduced lignification (reduced lignin content) in the pod valve margin as compared to a control plant devoid of the at least one mutation. In some embodiments, a canola plant comprising the at least one mutation in an endogenous SHP gene is not regenerated.

In some embodiments, a method of producing/breeding a transgene-free edited canola plant is provided, the method comprising: crossing a canola plant of the present invention (e.g., a canola plant comprising one or more mutations (optionally, one or more non-natural mutations) in one or more SHP genes and having reduced pod shattering and/or reduced lignification (reduced lignin content) in the pod valve margin) with a transgene free plant, thereby introducing the mutation into the canola plant that is transgene-free; and selecting a progeny canola plant that comprises the mutation and is transgene-free, thereby producing a transgene free edited canola plant.

Also provided herein is a method of providing a plurality of canola plants having reduced pod shattering and/or reduced lignification (reduced lignin content) in the pod valve margin, the method comprising planting two or more canola plants of the invention (e.g., 2, 3, 4, 5, 6, 7, 8, 9, 10, 20, 30, 40, 50, 100, 200, 300, 400, 500, 1000, 2000, 3000, 400, 5000, or 10,000 or more canola plants comprising one or more mutations (optionally, one or more non-natural mutations) in one or more SHP genes and having reduced pod shattering and/or reduced lignification (reduced lignin content) in the pod valve margin) in a growing area (e.g., a field (e.g., a cultivated field, an agricultural field), a growth chamber, a greenhouse, a recreational area, a lawn, and/or a roadside and the like), thereby providing a plurality of canola plants having reduced pod shattering and/or reduced lignification (reduced lignin content) in the pod valve margin as compared to a plurality of control canola plants devoid of the mutation.

In some embodiments, a method for editing a specific site in the genome of a canola plant cell is provided, the method comprising: cleaving, in a site-specific manner, a target site within an endogenous SHATTERPROOF MADS-BOX (SHP) gene in the canola plant cell, the endogenous SHP gene: ((a) comprising a nucleotide sequence having at least 80% sequence identity to any one of SEQ ID NOs:69, 70, 100, 101, 148, 149, 177, 178, 206, 207, 240 or 241, (b) comprising a region having at least 80% sequence identity to any one of SEQ ID NOs:72-96, 103-144, 151-173, 180-202, 209-236, 243-288 or 324-338, (c) encoding an amino acid sequence having at least 80% sequence identity to any one of SEQ ID NOs:71, 102, 150, 179, 208, or 242, (d) encoding a region having at least 80% sequence identity to an amino acid sequence of any one of SEQ ID NOs:97-99, 145-147, 174-176, 203-205, 237-239 or 289-291, thereby generating an edit in the endogenous SHP gene of the canola plant cell and producing a canola plant cell comprising the edit in the endogenous SHP gene. In some embodiments, the endogenous SHP gene is an endogenous SHP1 gene, an endogenous SHP2 gene, an endogenous SHP3 gene, or an endogenous SHP4 gene, optionally wherein an edit is generated in two or more endogenous SHP genes (e.g., two or more of SHP1, SHP2, SHP3, and/or SHP4).

In some embodiments, the edit in the endogenous SHP gene in a canola plant results in a mutation including, but not limited to, a base deletion, a base substitution, or a base insertion, optionally wherein the at least one mutation is a mutation. In some embodiments, the at least one mutation may be located in the 3' region of an SHP gene, for example, located in the second to the last exon, in the second to the last exon and the 3' adjacent intron, and/or in the last exon of an SHP genomic sequence. In some embodiments, the edit may result in at least one mutation that is an insertion of at least one base pair (e.g., 1 base pair to about 100 base pairs), optionally wherein the insertion is an out-of-frame insertion. In some embodiments, the edit may result in at least one mutation that is a deletion, optionally wherein the deletion is about 1 to about 100 consecutive base pairs in length, e.g., about 1-50 consecutive base pairs, about 1-30 consecutive base pairs or about 1-15 consecutive base pairs in length, optionally about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, or 50 consecutive base pairs. A deletion or insertion useful with this invention may be an out-of-frame insertion or an out-of-frame deletion. In some embodiments, an out-of-frame insertion or out-of-frame deletion may result in a premature stop codon and truncated protein. In some embodiments, the edit in a SHP gene results in a truncated SHP polypeptide, optionally a C-terminal truncation of the SHP polypeptide, optionally wherein the C-terminal truncation is a deletion of about 65 to about 80 consecutive amino acid residues (about 65, 66, 67, 68, 69, 70, 71, 72, 73, 74, 75, 76, 77, 78, 79, or 80 consecutive amino acid residues) from the C-terminus of the SHP polypeptide (e.g., about the last 65 to 80 consecutive amino acid residues; at least all of the consecutive amino acid residues encoded by the last exon of the SHP genomic sequence, optionally all of the amino acid residues encoded by the last exon of the SHP genomic sequence and at least a portion of the amino acid residues encoded by the second to the last exon of the SHP genomic sequence).

In some embodiments, a method of editing may further comprise regenerating a canola plant from the canola plant cell comprising the edit in the endogenous SHP gene, thereby producing a canola plant comprising the edit in its endogenous SHP gene (optionally in the 3' end of the SHP gene, optionally in the second to the last exon, the second to the last exon and the 3' adjacent intron, and/or in the last exon) and having a phenotype of reduce pod shattering when compared to a control canola plant that is devoid of the edit.

In some embodiments, a method for making a canola plant is provided, the method comprising (a) contacting a population of canola plant cells comprising an endogenous SHATTERPROOF MADS-BOX (SHP) gene with a nuclease linked to a nucleic acid binding domain (e.g., editing system) that binds to a sequence (i) having at least 80% sequence identity to a nucleotide sequence of any one SEQ ID NOs:69, 70, 100, 101, 148, 149, 177, 178, 206, 207, 240 or 241, (ii) comprising a region having at least 80% identity to any one of SEQ ID NOs:72-96, 103-144, 151-173, 180-202, 209-236, 243-288 or 324-338; (iii) encoding an amino acid sequence having at least 80% sequence identity to any one of SEQ ID NOs:71, 102, 150, 179, 208, or 242, and/or (iv) encoding a region having at least 80% sequence identity to any one of SEQ ID NOs:97-99, 145-147, 174-176, 203-205, 237-239 or 289-291; (b) selecting a canola plant cell from the population of canola plant cells in which an endogenous SHP gene has been mutated, thereby producing a canola plant cell comprising a mutation in the endogenous SHP gene; and (c) growing the selected canola plant cell into a canola plant comprising a mutation in the endogenous SHP gene.

In some embodiments, a method for reducing pod shattering and/or reducing lignification (reduced lignin content) in the pod valve margin in a canola plant is provided, the method comprising (a) contacting a canola plant cell comprising an endogenous SHATTERPROOF MADS-BOX (SHP) gene with a nuclease targeting the endogenous SHP gene, wherein the nuclease is linked to a nucleic acid binding domain (e.g., editing system) that binds to a target site in the endogenous SHP gene, wherein the endogenous SHP gene: (i) comprises a nucleotide sequence having at least 80% sequence identity to any one of SEQ ID NOs:69, 70, 100, 101, 148, 149, 177, 178, 206, 207, 240 or 241; (ii) comprises a region having at least 80% sequence identity to a nucleotide sequence of any one of SEQ ID NOs:72-96, 103-144, 151-173, 180-202, 209-236, 243-288 or 324-338; (iii) encodes a SHP polypeptide having at least 80% sequence identity to any one of SEQ ID NOs:71, 102, 150, 179, 208, or 242; and/or (iv) encodes a region of a SHP polypeptide having at least 80% sequence identity to any one of SEQ ID NOs:97-99, 145-147, 174-176, 203-205, 237-239 or 289-291 to produce a canola plant cell comprising a mutation in the endogenous SHP gene; and (b) growing the canola plant cell comprising a mutation in the endogenous SHP gene into a canola plant comprising the mutation in the endogenous SHP gene thereby producing a canola plant having a mutated endogenous SHP gene and reduced pod shattering and/or reduced lignification (reduced lignin content) in the pod valve margin.

In some embodiments, a method for producing a canola plant or part thereof comprising at least one cell having a mutated endogenous SHATTERPROOF MADS-BOX (SHP) gene (e.g., one or more mutated endogenous SHP gene), the method comprising contacting a target site in an endogenous SHP gene in the canola plant or plant part with a nuclease comprising a cleavage domain and a nucleic acid binding domain, wherein the nucleic acid binding domain binds to a target site in the endogenous SHP gene, wherein the endogenous SHP gene (a) comprises a nucleotide sequence having at least 80% sequence identity to any one of SEQ ID NOs:69, 70, 100, 101, 148, 149, 177, 178, 206, 207, 240 or 241; (b) comprises a region having at least 80% sequence identity to a nucleotide sequence of any one of SEQ ID NOs:72-96, 103-144, 151-173, 180-202, 209-236, 243-288 or 324-338; (c) encodes a SHP polypeptide having at least 80% sequence identity to any one of SEQ ID NOs:71, 102, 150, 179, 208, or 242; and/or (d) encodes a region of a SHP polypeptide having at least 80% sequence identity to any one of SEQ ID NOs:97-99, 145-147, 174-176, 203-205, 237-239 or 289-291, thereby producing the canola plant or part thereof comprising at least one cell having a mutation in the endogenous SHP gene (e.g., a mutation in one or more endogenous SHP genes).

Also provided herein is a method for producing a canola plant or part thereof comprising a mutated endogenous SHATTERPROOF MADS-BOX (SHP) gene and exhibiting reduced pod shattering and/or reduced lignification (reduced lignin content) in the pod valve margin, the method comprising contacting a target site in an endogenous SHP gene in the canola plant or plant part with a nuclease comprising a cleavage domain and a nucleic acid binding domain, wherein the nucleic acid binding domain binds to a target site in the endogenous SHP gene, wherein the endogenous SHP gene: (a) comprises a nucleotide sequence having at least 80% sequence identity to any one of SEQ ID NOs:69, 70, 100, 101, 148, 149, 177, 178, 206, 207, 240 or 241; (b) comprises a region having at least 80% sequence identity to a nucleotide sequence of any one of SEQ ID NOs:72-96, 103-144, 151-173, 180-202, 209-236, 243-288 or 324-338; (c) encodes a SHP polypeptide having at least 80% sequence identity to any one of SEQ ID NOs:71, 102, 150, 179, 208, or 242; and/or (d) encodes a region of a SHP polypeptide having at least 80% sequence identity to any one of SEQ ID NOs:97-99, 145-147, 174-176, 203-205, 237-239 or 289-291, thereby producing the canola plant or part thereof comprising an endogenous SHP gene having a mutation (e.g., at least one endogenous SHP gene having a mutation) and exhibiting reduced pod shattering and/or reduced lignification (reduced lignin content) in the pod valve margin.

In some embodiments, a nuclease may cleave an endogenous SHP gene, thereby introducing the mutation into the endogenous SHP gene. A nuclease useful with the invention may be any nuclease that can be utilized to edit/modify a target nucleic acid. Such nucleases include, but are not limited to a zinc finger nuclease, transcription activator-like effector nucleases (TALEN), endonuclease (e.g., Fok1) and/or a CRISPR-Cas effector protein. Likewise, any nucleic acid binding domain useful with the invention may be any DNA binding domain or RNA binding domain that can be utilized to edit/modify a target nucleic acid. Such nucleic acid binding domains include, but are not limited to, a zinc finger, transcription activator-like DNA binding domain (TAL), an argonaute and/or a CRISPR-Cas effector DNA binding domain.

In some embodiments, a nucleic acid binding domain (e.g., DNA binding domain) is comprised in a nucleic acid binding polypeptide. A "nucleic acid binding protein" or "nucleic acid binding polypeptide" as used herein refers to a polypeptide that binds and/or is capable of binding a nucleic acid in a site- and/or sequence-specific manner. In some embodiments, a nucleic acid binding polypeptide may be a sequence-specific nucleic acid binding polypeptide (e.g., a sequence-specific DNA binding domain) such as, but not limited to, a sequence-specific binding polypeptide and/or domain from, for example, a polynucleotide-guided endonuclease, a CRISPR-Cas effector protein (e.g., a CRISPR-Cas endonuclease), a zinc finger nuclease, a transcription activator-like effector nuclease (TALEN) and/or an Argonaute protein. In some embodiments, a nucleic acid binding polypeptide comprises a cleavage polypeptide (e.g., a nuclease polypeptide and/or domain) such as, but not limited to, an endonuclease (e.g., Fok1), a polynucleotide-guided endonuclease, a CRISPR-Cas endonuclease, a zinc finger nuclease, and/or a transcription activator-like effector nuclease (TALEN). In some embodiments, the nucleic acid binding polypeptide associates with and/or is capable of associating with (e.g., forms a complex with) one or more nucleic acid molecule(s) (e.g., forms a complex with a guide nucleic acid as described herein) that can direct or guide the nucleic acid binding polypeptide to a specific target nucleotide sequence (e.g., a gene locus of a genome) that is complementary to the one or more nucleic acid molecule(s) (or a portion or region thereof), thereby causing the nucleic acid binding polypeptide to bind to the nucleotide sequence at the specific target site. In some embodiments, the nucleic acid binding polypeptide is a CRISPR-Cas effector protein as described herein. In some embodiments, reference is made to specifically to a CRISPR-Cas effector protein for simplicity, but a nucleic acid binding polypeptide as described herein may be used. In some embodiments, a polynucleotide and/or a nucleic acid construct of the invention can be an "expression cassette" or can be comprised within an expression cassette.

In some embodiments, a method of editing an endogenous SHATTERPROOF MADS-BOX (SHP) gene (e.g., SHP1, SHP2, SHP3, and/or SHP4) in a canola plant or plant part is provided, the method comprising contacting a target site in an endogenous SHP gene in the canola plant or plant part with a cytosine base editing system comprising a cytosine deaminase and a nucleic acid binding domain that binds to a target site in the endogenous SHP gene, wherein the endogenous SHP gene: (a) comprises a nucleotide sequence having at least 80% sequence identity to any one of SEQ ID NOs:69, 70, 100, 101, 148, 149, 177, 178, 206, 207, 240 or 241; (b) comprises a region having at least 80% sequence identity to a nucleotide sequence of any one of SEQ ID NOs:72-96, 103-144, 151-173, 180-202, 209-236, 243-288 or 324-338; (c) encodes a SHP polypeptide having at least 80% sequence identity to any one of SEQ ID NOs:71, 102, 150, 179, 208, or 242; and/or (d) encodes a region of a SHP polypeptide having at least 80% sequence identity to any one of SEQ ID NOs:97-99, 145-147, 174-176, 203-205, 237-239 or 289-291, thereby editing the endogenous SHP gene in the canola plant or part thereof and producing a canola plant or part thereof comprising at least one cell having a mutation in the endogenous SHP gene.

In some embodiments, a method of editing an endogenous SHATTERPROOF MADS-BOX (SHP) gene (e.g., SHP1, SHP2, SHP3, and/or SHP4) in a canola plant or plant part is provided, the method comprising contacting a target site in an SHP gene in the canola plant or plant part with an adenosine base editing system comprising an adenosine deaminase and a nucleic acid binding domain that binds to a target site in the SHP gene, wherein the SHP gene (a) comprises a nucleotide sequence having at least 80% sequence identity to any one of SEQ ID NOs:69, 70, 100, 101, 148, 149, 177, 178, 206, 207, 240 or 241; (b) comprises a region having at least 80% sequence identity to a nucleotide sequence of any one of SEQ ID NOs:72-96, 103-144, 151-173, 180-202, 209-236, 243-288 or 324-338; (c) encodes a SHP polypeptide having at least 80% sequence identity to any one of SEQ ID NOs:71, 102, 150, 179, 208, or 242; and/or (d) encodes a region of a SHP polypeptide having at least 80% sequence identity to any one of SEQ ID NOs:97-99, 145-147, 174-176, 203-205, 237-239 or 289-291, thereby editing the endogenous SHP gene in the canola plant or part thereof and producing a canola plant or part thereof comprising at least one cell having a mutation in the endogenous SHP gene.

In some embodiments, a method of creating a mutation in a SHATTERPROOF MADS-BOX (SHP) gene (e.g., SHP1, SHP2, SHP3, and/or SHP4) in a canola plant is provided, comprising (a) targeting a gene editing system to a portion of the endogenous SHP gene that (i) comprises a sequence having at least 80% sequence identity to any one of SEQ ID NOs:72-96, 103-144, 151-173, 180-202, 209-236, 243-288 or 324-338; and/or (ii) encodes a sequence having at least 80% identity to any one SEQ ID NOs:72-96, 103-144, 151-173, 180-202, 209-236, 243-288 or 324-338, and (b) selecting a canola plant that comprises a modified nucleic acid sequence in a region having at least 80% sequence identity to any one of SEQ ID NOs:75-82, 85-92, 107-112, 116-120, 124-127, 129, 135, 136, 139, 140, 156, 157, 159-161, 164-166, 181-184, 187-190, 195, 196, 212-219, 222-224, 229, 230, 246-248, 251-253, 255-257, 261-264, 267, 268, 271, 272, 275, 276, 279, 280, 283, or 285. In some embodiments, the modification is a deletion or an insertion.

In some embodiments, the modification is an out-of-frame deletion or out-of-frame insertion resulting in a truncated Shatterproof MADS-box transcription factor (SHP) polypeptide.

In some embodiments, a mutation provided by methods of the invention may a non-natural mutation. In some embodiments, the mutation may be a substitution, an insertion and/or a deletion, optionally wherein the insertion or deletion is an out-of-frame insertion or an out-of-frame deletion. In some embodiments, a mutation may be a hypomorphic mutation, a dominant negative mutation, or a dominant negative hypomorphic mutation. In some embodiments, a mutation may comprise a base substitution to an A, a T, a G, or a C. In some embodiments, the mutation may be a deletion (e.g., out-of-frame deletion) of about 1 base pair to about 100 consecutive base pairs, optionally, 1 to about 50 consecutive base pairs, 1 to about 30 consecutive base pairs, 1 to about 15 consecutive base pairs. In some embodiments, the mutation may be an insertion (e.g., an out-of-frame insertion) of at least one base pair (e.g., 1 base pair to about 100 consecutive base pairs). A mutation in a SHP gene may be located in the 3' region of the SHP gene, optionally wherein the mutation may be within a portion or region of the endogenous SHP gene that encodes the SHP polypeptide (e.g., the coding regions (exons), e.g., second to last exon and/or last exon). In some embodiments, the mutation in a SHP gene may be located in the intron located between the second to last exon and the last exon of the SHP gene. In some embodiments, the mutation may be located in a region of a SHP gene that bridges between the second to last exon and the intron located between the second to last exon and the last exon of the SHP gene (e.g., the intron located immediately 3' to the second to the last exon). A mutation in an SHP gene can result in a polypeptide having a deletion of the amino acids encoded by the last exon, optionally a deletion of the amino acids encoded by the last exon and at least one amino acid (e.g., 1, 2, 3, 4, 5, 6, 7, 8, 9, 10, 11, 12, or 13 amino acids) encoded by the second to the last exon of the SHP gene. In some embodiments, a mutation of a SHP gene that is an out-of-frame deletion or an out-of-frame insertion may result in a premature stop codon and a truncated SHP polypeptide. In some embodiments, the out-of-frame deletion or out-of-frame insertion may be a hypomorphic mutation, a dominant negative mutation, or a dominant negative hypomorphic mutation.

In some embodiments, a method of detecting a mutant SHATTERPROOF MADS-BOX (SHP) gene (e.g., SHP1, SHP2, SHP3, and/or SHP4) in a canola plant is provided, the method comprising detecting in the genome of a canola plant an endogenous SHP gene encoding a truncated SHP polypeptide, optionally wherein the mutation is located in the 3' region (optionally, second to last exon and/or last exon and/or the intron located between the second to last exon and the last exon) of the SHP gene, the 3' region having at least 80% sequence identity to any one of the nucleotide sequences of SEQ ID NOs:72-96, 103-144, 151-173, 180-202, 209-236, 243-288 or 324-338, optionally having at least 80% sequence identity to any one of SEQ ID NOs:75-82, 85-92, 107-112, 116-120, 124-127, 129, 135, 136, 139, 140, 156, 157, 159-161, 164-166, 181-184, 187-190, 195, 196, 212-219, 222-224, 229, 230, 246-248, 251-253, 255-257, 261-264, 267, 268, 271, 272, 275, 276, 279, 280, 283, or 285. In some embodiments, the mutation that is detected is an out-of-frame deletion or an out-of-frame insertion.

In some embodiments, the present invention provides a method of producing a canola plant comprising a mutation in an endogenous SHATTERPROOF MADS-BOX(SHP) gene (e.g., SHP1, SHP2, SHP3, and/or SHP4) and at least one polynucleotide of interest, the method comprising crossing a canola plant of the invention comprising at least one mutation in an endogenous SHP gene (a first canola plant) with a second canola plant that comprises the at least one polynucleotide of interest to produce progeny canola plants; and selecting progeny canola plants comprising at least one mutation in the SHP gene and the at least one polynucleotide of interest, thereby producing the canola plant comprising a mutation in an endogenous SHP gene and at least one polynucleotide of interest.

The present invention further provides a method of producing a canola plant comprising a mutation in an endogenous SHATTERPROOF MADS-BOX (SHP) gene (e.g., SHP1, SHP2, SHP3, and/or SHP4) and at least one polynucleotide of interest, the method comprising introducing at least one polynucleotide of interest into a canola plant of the present invention comprising at least one mutation in a SHP gene, thereby producing a canola plant comprising at least one mutation in a SHP gene and at least one polynucleotide of interest.

In some embodiments, also provided is a method of producing a canola plant comprising a mutation in an endogenous SHATTERPROOF MADS-BOX (SHP) gene (e.g., SHP1, SHP2, SHP3, and/or SHP4) and exhibiting a phenotype of reduced pod shattering and/or reduced lignification (reduced lignin content) in the pod valve margin, the method comprising crossing a first canola plant, which is a canola plant of the present invention comprising at least one mutation in a SHP gene, with a second canola plant that exhibits a phenotype of reduced pod shattering and/or reduced lignification (reduced lignin content) in the pod valve margin; and selecting progeny canola plants comprising the mutation in the SHP gene and a phenotype of reduced pod shattering and/or reduced lignification (reduced lignin content) in the pod valve margin, thereby producing the canola plant comprising a mutation in an endogenous SHP gene and exhibiting a phenotype of reduced pod shattering and/or reduced lignification (reduced lignin content) in the pod valve margin as compared to a control plant.

Further provided is a method of controlling weeds in a container (e.g., pot, or seed tray and the like), a growth chamber, a greenhouse, a field, a recreational area, a lawn, or on a roadside, the method comprising applying an herbicide to one or more (a plurality) canola plants of the invention (e.g., a canola plant comprising at least one mutation in a SHATTERPROOF MADS-BOX (SHP) gene (e.g., SHP1, SHP2, SHP3, and/or SHP4) as described herein) growing in a container, a growth chamber, a greenhouse, a field, a recreational area, a lawn, or on a roadside, thereby controlling the weeds in the container, the growth chamber, the greenhouse, the field, the recreational area, the lawn, or on the roadside in which the one or more canola plants are growing.

In some embodiments, a method of reducing insect predation on a canola plant is provided, the method comprising applying an insecticide to one or more canola plants of the invention, optionally, wherein the one or more canola plants are growing in a container, a growth chamber, a greenhouse, a field, a recreational area, a lawn, or on a roadside, thereby reducing insect predation on the one or more canola plants.

In some embodiments, a method of reducing fungal disease on a canola plant is provided, the method comprising applying a fungicide to one or more canola plants of the invention, optionally, wherein the one or more canola plants are growing in a container, a growth chamber, a greenhouse, a field, a recreational area, a lawn, or on a roadside, thereby reducing fungal disease on the one or more canola plants.

Example endogenous SHP genes and encoded SHP polypeptides useful with this invention, as well as target regions for editing and example edited SHP genes and encoded polypeptides are provided in Table 1.

TABLE 1

| Endogenous SHP gene | Gene ID No. | Genomic SEQ ID NOs | Coding and polypeptide SEQ ID NOs | Genomic Regions | Poly-peptide regions | SEQ ID NOs for example edited genes and mutated protein |
|---|---|---|---|---|---|---|
| SHP1A | BnaA09g55330D | 177 | 178, 179 | 180-202 | 203-205 | |
| SHP2A | BnaA07g18050D | 100 | 101, 102 | 103-144 | 145-147 | Gene: 298, 300, 302, 306, 312, 314, 321<br>Protein: 299, 301, 303, 307, 313, 315 |
| SHP2C | BnaC06g16910D | 240 | 241, 242 | 243-288 | 289-291 | Gene: 304, 308, 310, 316, 318, 319<br>Protein: 305, 309, 311, 317<br>Deleted portion of gene: 320 |
| SHP3A | BnaA04g01810D | 69 | 70, 71 | 72-96 | 97-99 | |
| SHP3C | BnaC04g23360D | 206 | 207, 208 | 209-236 | 237-239 | |
| SHP4A | BnaA05g02990D | 148 | 149, 150 | 151-173, 324-338 | 174-176 | Gene: 322, 323 |

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, nematode resistance, disease resistance, increased yield, increased nutrient use efficiency or abiotic stress resistance.

Thus, plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the CryIA, CryIAb, CryIAc, CryIIA, CryIIIA, CryIIIB2, Cry9c Cry2Ab, Cry3Bb and CryIF proteins or toxic fragments thereof and also hybrids or combinations thereof, especially the CryIF protein or hybrids derived from a CryIF protein (e.g. hybrid CryIA-CryIF proteins or toxic fragments thereof), the CryIA-type proteins or toxic fragments thereof, preferably the CryIAc protein or hybrids derived from the CryIAc protein (e.g. hybrid CryIAb-CryIAc proteins) or the CryIAb or Bt2 protein or toxic fragments thereof, the Cry2Ae, Cry2Af or Cry2Ag proteins or toxic fragments thereof, the CryIA.105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci US A. 28; 93(11):5389-94, the Cry proteins as described in WO2001/47952, the insecticidal proteins from Xenorhabdus (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g., WO2007/024782), a mutated *Arabidopsis* ALS/AHAS gene (e.g., U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV- GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US-A 2005-216969); Event 3006-210-23 (cotton, insect control—herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIB No. 41603, described in WO2010/080829); Event BLR1 (oilseed rape, restoration of male sterility, deposited as NCIB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCMIB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control-herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MSl 1 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYH-TOH2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control—herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VIP1034 (corn, insect control—herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYH-TOH2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDT09Y (corn, ATCC Accession N° PTA-13025, WO2013/012775A1).

The genes/events (e.g., polynucleotides of interest), which impart the desired traits in question, may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEND™, INTACTA RR2 PRO®, VISTIVE GOLD®, and/or XTENDFLEX™ trade names.

A SHATTERPROOF MADS-BOX (SHP) gene (e.g., SHP1, SHP2, SHP3, and/or SHP4) useful with this invention includes any canola SHP gene in which a mutation as described herein can confer reduced pod shattering and/or reduced lignification (reduced lignin content) in the pod valve margin in a canola plant or part thereof comprising the mutation. In some embodiments, an endogenous SHP gene (a) comprises a nucleotide sequence having at least 80% sequence identity to any one of SEQ ID NOs:69, 70, 100, 101, 148, 149, 177, 178, 206, 207, 240 or 241; (b) comprises a region having at least 80% sequence identity to a nucleotide sequence of any one of SEQ ID NOs:72-96, 103-144, 151-173, 180-202, 209-236, 243-288 or 324-338; (c) encodes a SHP polypeptide having at least 80% sequence identity to any one of SEQ ID NOs:71, 102, 150, 179, 208, or 242; and/or (d) encodes a region of a SHP polypeptide having at least 80% sequence identity to any one of SEQ ID NOs:97-99, 145-147, 174-176, 203-205, 237-239 or 289-291.

In some embodiments, the at least one mutation in an endogenous SHP gene in a canola plant may be a base substitution, a base deletion and/or a base insertion, optionally wherein the at least one mutation may be a non-natural mutation. In some embodiments, the at least one mutation in an endogenous SHP gene in a canola plant may result in a canola plant having the phenotype of reduced pod shattering and/or reduced lignification (reduced lignin content) in the pod valve margin as compared to a control plant devoid of the edit/mutation. A canola plant of the invention having the phenotype of reduced pod shattering and/or reduced lignification (reduced lignin content) in the pod valve margin may also exhibit/provide an increase in harvestable seed.

In some embodiments, a mutation in an endogenous SHP gene may be a base substitution, a base deletion and/or a base insertion of at least 1 base pair. In some embodiments, a base deletion may be 1 nucleotide to about 100 nucleotides (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 base pairs, or any range or value therein, e.g., 1 to about 50 base pairs, 1 to about 30 base pairs, 1 to about 15 base pairs, or any range or value therein), optionally where the mutation is at about 2 to about 100 consecutive nucleotides (e.g., 1 to about 50 consecutive base pairs, 1 to about 30 consecutive base pairs, 1 to about 15 consecutive base pairs). In some embodiments, a mutation in an endogenous SHP gene may be a base insertion of 1 to about 100 consecutive nucleotides of the SHP nucleic acid. In some embodiments, a mutation in an endogenous SHP gene may be an out-of-frame insertion or an out-of-frame deletion that results in an SHP protein having a C-terminal truncation. In some embodiments, the at least one mutation may be a base substitution, optionally a substitution to an A, a T, a G, or a C. A mutation useful with this invention may be a point mutation. In some embodiments, the mutation may be a non-natural mutation.

In some embodiments, a mutation in an endogenous SHP gene may be made following cleavage by an editing system that comprises a nuclease and a nucleic acid binding domain that binds to a target site within a target nucleic acid (e.g., an endogenous SHP gene, e.g., SHP1, SHP2, SHP3, and/or SHP4), the target nucleic acid comprising a sequence having at least 80% sequence identity to any one of the nucleotide sequences of SEQ ID NOs:69, 70, 100, 101, 148, 149, 177, 178, 206, 207, 240 or 241, and/or encoding an amino acid sequence having at least 80% sequence identity to any one of SEQ ID NOs:71, 102, 150, 179, 208, or 242, optionally wherein the target site is located in a region of the SHP gene: the region comprising a sequence having at least 80% identity to any one of SEQ ID NOs:72-96, 103-144, 151-173, 180-202, 209-236, 243-288 or 324-338 and/or encoding a sequence having at least 80% sequence identity to an amino acid sequence of any one of SEQ ID NOs:97-99, 145-147, 174-176, 203-205, 237-239 or 289-291.

Further provided are guide nucleic acids (e.g., gRNA, gDNA, crRNA, crDNA) that bind to a target site in a SHATTERPROOF MADS-BOX (SHP) gene (e.g., SHP1, SHP2, SHP3, and/or SHP4)), wherein the target site is in a region of the SHP gene having at least 80% sequence identity to any one of the nucleotide sequences of SEQ ID NOs:72-96, 103-144, 151-173, 180-202, 209-236, 243-288 or 324-338, optionally any one of SEQ ID NOs:75-82, 85-92, 107-112, 116-120, 124-127, 129, 135, 136, 139, 140, 156, 157, 159-161, 164-166, 181-184, 187-190, 195, 196, 212-219, 222-224, 229, 230, 246-248, 251-253, 255-257, 261-264, 267, 268, 271, 272, 275, 276, 279, 280, 283, or 285. In some embodiments, the guide nucleic acid comprises a spacer comprising any one of the nucleotide sequences of SEQ ID NOs:292-297 and/or SEQ ID NOs:342-346.

In some embodiments, a canola plant or plant part thereof is provided that comprises at least one mutation in at least one endogenous SHATTERPROOF MADS-BOX(SHP) gene having a gene identification number (gene ID) of BnaA04g01810D (SHP3), BnaA07g18050D (SHP2), BnaA05g02990D (SHP4), BnaA09g55330D (SHP1), BnaC04g23360D (SHP3), and/or BnaC06g16910D (SHP2).

In some embodiments, a guide nucleic acid is provided that binds to a target nucleic acid in a SHATTERPROOF MADS-BOX (SHP) gene having a gene identification number (gene ID) of BnaA04g01810D (SHP3), BnaA07g18050D (SHP2), BnaA05g02990D (SHP4), BnaA09g55330D (SHP1), BnaC04g23360D (SHP3), and/or BnaC06g16910D (SHP2).

In some embodiments, a system is provided comprising a guide nucleic acid comprising a spacer (e.g., one or more spacers) having the nucleotide sequence of any one of SEQ ID NOs:292-297 and/or SEQ ID NOs:342-346, and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site in a gene.

The invention further provides a gene editing system comprising a CRISPR-Cas effector protein in association with a guide nucleic acid and the guide nucleic acid comprises a spacer sequence that binds to a SHATTERPROOF MADS-BOX(SHP) gene, optionally wherein the SHP gene (a) comprises a nucleotide sequence having at least 80% sequence identity to any one of SEQ ID NOs:69, 70, 100, 101, 148, 149, 177, 178, 206, 207, 240 or 241; (b) comprises a region having at least 80% sequence identity to a nucleotide sequence of any one of SEQ ID NOs:72-96, 103-144, 151-173, 180-202, 209-236, 243-288 or 324-338; (c) encodes a SHP polypeptide having at least 80% sequence identity to any one of SEQ ID NOs:71, 102, 150, 179, 208, or 242; and/or (d) encodes a region of a SHP polypeptide having at least 80% sequence identity to any one of SEQ ID NOs:97-99, 145-147, 174-176, 203-205, 237-239 or 289-291. In some embodiments, a spacer sequence of the guide nucleic acid may comprise the nucleotide sequence of any of SEQ ID NOs:292-297 and/or SEQ ID NOs:342-346. In some embodiments, the gene editing system may further comprise a tracr nucleic acid that associates with the guide nucleic acid and a CRISPR-Cas effector protein, optionally wherein the tracr nucleic acid and the guide nucleic acid are covalently linked.

The present invention further provides a complex comprising a CRISPR-Cas effector protein comprising a cleavage domain and a guide nucleic acid, wherein the guide nucleic acid binds to a target site in an endogenous SHATTERPROOF MADS-BOX (SHP) gene in canola, wherein the endogenous SHP gene: (a) comprises a nucleotide sequence having at least 80% sequence identity to any one of SEQ ID NOs:69, 70, 100, 101, 148, 149, 177, 178, 206, 207, 240 or 241; (b) comprises a region having at least 80% sequence identity to a nucleotide sequence of any one of SEQ ID NOs:72-96, 103-144, 151-173, 180-202, 209-236, 243-288 or 324-338; (c) encodes a SHP polypeptide having at least 80% sequence identity to any one of SEQ ID NOs:71, 102, 150, 179, 208, or 242; and/or (d) encodes a region of a SHP polypeptide having at least 80% sequence identity to any one of SEQ ID NOs:97-99, 145-147, 174-176, 203-205, 237-239 or 289-291, and the cleavage domain cleaves a target strand in the SHP gene.

In some embodiments, an expression cassette(s) is/are provided that comprise (a) a polynucleotide encoding CRISPR-Cas effector protein comprising a cleavage domain and (b) a guide nucleic acid that binds to a target site in an endogenous SHATTERPROOF MADS-BOX (SHP) gene in canola, wherein the guide nucleic acid comprises a spacer sequence that is complementary to and binds to (i) a portion of a nucleic acid having at least 80% sequence identity to any one of SEQ ID NOs:69, 70, 100, 101, 148, 149, 177, 178, 206, 207, 240 or 241; (ii) a portion of a nucleic acid having at least 80% sequence identity to any one of SEQ ID NOs:72-96, 103-144, 151-173, 180-202, 209-236, 243-288 or 324-338, optionally SEQ ID NOs:75-82, 85-92, 107-112, 116-120, 124-127, 129, 135, 136, 139, 140, 156, 157, 159-161, 164-166, 181-184, 187-190, 195, 196, 212-219, 222-224, 229, 230, 246-248, 251-253, 255-257, 261-264, 267, 268, 271, 272, 275, 276, 279, 280, 283, or 285; (iii) a portion of a nucleic acid encoding an amino acid sequence having at least 80% sequence identity to any one of SEQ ID NOs:71, 102, 150, 179, 208, or 242; and/or (iv) a portion of a nucleic acid encoding an amino acid sequence having at least 80% identity to any one of SEQ ID NOs:97-99, 145-147, 174-176, 203-205, 237-239 or 289-291.

Also provided are nucleic acids encoding a Shatterproof MADS-box transcription factor (SHP) polypeptide (e.g., SHP1, SHP2, SHP3, SHP4), optionally wherein when present in a canola plant or plant part the mutated SHP polypeptide/mutated SHP gene results in the canola plant comprising a phenotype of reduced pod shattering and/or reduced lignification (reduced lignin content) in the pod valve margin as compared to a control canola plant or plant part devoid of the mutation.

Nucleic acid constructs of the invention (e.g., a construct comprising a sequence specific nucleic acid binding domain (e.g., sequence specific DNA binding domain), a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids (e.g., endogenous SHP genes, e.g., endogenous SHP1 gene, endogenous SHP2 gene, endogenous SHP3 gene, endogenous SHP4 gene) and/or their expression.

Any canola plant comprising an endogenous SHP gene that is capable of conferring reduced pod shattering and/or reduced lignification (reduced lignin content) in the pod valve margin when modified as described herein, may be modified (e.g., mutated, e.g., base edited, cleaved, nicked, etc.) as described herein (e.g., using the polypeptides, polynucleotides, RNPs, nucleic acid constructs, expression cassettes, and/or vectors of the invention) to reduce pod shattering and/or reduced lignification (reduced lignin content) in the pod valve margin in the canola plant.

An editing system useful with this invention can be any site-specific (sequence-specific) genome editing system now known or later developed, which system can introduce mutations in a target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing SHATTERPROOF MADS-BOX (SHP) gene may comprise contacting a target nucleic acid (e.g., a nucleic acid encoding a Shatterproof MADS-box transcription factor (SHP) polypeptide, e.g., a SHP1 polypeptide, a SHP2 polypeptide, a SHP3 polypeptide, a SHP4 polypeptide) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific nucleic acid binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing a SHATTERPROOF MADS-BOX(SHP) gene may comprise contacting a target nucleic acid (e.g., a nucleic acid encoding a SHP polypeptide) with a sequence-specific nucleic acid binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific nucleic acid binding fusion protein to the target nucleic acid and the sequence-specific nucleic acid binding fusion protein is capable of recruiting the deaminase fusion protein to the target nucleic acid via the peptide tag-affinity polypeptide interaction, thereby editing a locus within the target nucleic acid. In some embodiments, the sequence-specific nucleic acid binding fusion protein may be fused to the affinity polypeptide that binds the peptide tag and the deaminase may be fused to the peptide tag, thereby recruiting the deaminase to the sequence-specific nucleic acid binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific nucleic acid binding fusion proteins, deaminase fusion proteins and guides may be provided as ribonucleoproteins (RNPs).

In some embodiments, methods such as prime editing may be used to generate a mutation in an endogenous SHP gene in a canola plant or part thereof. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantages of the various methods of recruiting proteins for use in the editing to the target site, such methods including both non-covalent and covalent interactions between the proteins and nucleic acids used in the selected process of genome editing.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a sequence-specific nucleic acid binding domain may be a CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g., Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophilus*), *Lactobacillus* spp., *Bifidobacterium* spp., *Kandleria* spp., *Leuconostoc* spp., Oenococcus spp., *Pediococcus* spp., Weissella spp., and/or Olsenella spp. Example Cas9 sequences include, but are not limited to, the amino acid sequences of SEQ ID NO:56 and SEQ ID NO:57 or the nucleotide sequences of SEQ ID NOs:58-68.

In some embodiments, the CRISPR-Cas effector protein may be a Cas9 polypeptide derived from *Streptococcus pyogenes* and recognizes the PAM sequence motif NGG, NAG, NGA (Mali et al, Science 2013; 339(6121): 823-826). In some embodiments, the CRISPR-Cas effector protein may be a Cas9 polypeptide derived from *Streptococcus thermophiles* and recognizes the PAM sequence motif NGGNG and/or NNAGAAW (W=A or T) (See, e.g., Horvath et al, Science, 2010; 327(5962): 167-170, and Deveau et al, J Bacteriol 2008; 190(4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190(4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S.*

*aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from *Leptotrichia shahii*, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease, see, e.g., amino acid sequences of SEQ ID NOs:1-17, nucleic acid sequences of SEQ ID NOs:18-20. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37: 1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, a cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO:28 or SEQ ID NO:29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO:25 or SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of SEQ ID NO:23, SEQ ID NO:24, SEQ ID NO:25, SEQ ID NO:26, SEQ ID NO:27, SEQ ID NO:28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:30. In some embodiments, a mutated/evolved *E. coli* TadA* comprises the amino acid sequence of SEQ ID NOs:31-40 (e.g., SEQ ID NOs: 31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific nucleic acid binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt function; and/or generation of point mutations in genomic DNA to disrupt splice junctions.

The nucleic acid constructs of the invention encoding a base editor comprising a sequence-specific nucleic acid binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof, a repeat of a Type V C2c1 CRISPR Cas system, or a fragment thereof, a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made, and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids* Res. 35 (Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g., protospacer) (e.g., a portion of consecutive nucleotides of a sequence that (a) comprises a sequence having at least 80% sequence identity to a nucleotide sequence of any one of SEQ ID NOs:69, 70, 100, 101, 148, 149, 177, 178, 206, 207, 240 or 241; (b) comprises a region having at least 80% identity to any one of SEQ ID NOs: 72-96, 103-144, 151-173, 180-202, 209-236, 243-288 or 324-338, optionally SEQ ID NOs:75-82, 85-92, 107-112, 116-120, 124-127, 129, 135, 136, 139, 140, 156, 157, 159-161, 164-166, 181-184, 187-190, 195, 196, 212-219, 222-224, 229, 230, 246-248, 251-253, 255-257, 261-264, 267, 268, 271, 272, 275, 276, 279, 280, 283, or 285; (c) encodes an amino acid sequence having at least 80% sequence identity to any one of SEQ ID NOs:71, 102, 150, 179, 208, or 242; and/or (d) encodes an amino acid sequence comprising a region having at least 80% identity to any one of SEQ ID NOs:97-99, 145-147, 174-176, 203-205, 237-239 or 289-291. In some embodiments, a spacer sequence (e.g., one or more spacers) may include, but is not limited to, the nucleotide sequences of any one of SEQ ID NOs:292-297 and/or SEQ ID NOs:342-346. The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (see, for example, a spacer sequence of a Type V CRISPR-Cas system), or the 3' region of a spacer sequence of a guide nucleic acid may be identical to a target DNA, while the 5' region of the spacer may be substantially complementary to the target DNA (see, for example, a spacer sequence of a Type II CRISPR-Cas system), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

```
      5′-NNNNNNNNNNNNNNNNNNNN-3′ RNA Spacer
         ||||||||||||||||||||
   3′AAANNNNNNNNNNNNNNNNNNNN-5′ Target strand
     ||||
  5′-TTTNNNNNNNNNNNNNNNNNNNN-3′ Non-Target strand
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains (e.g., sequence-specific DNA binding domains), CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5): 910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins. Example peptide tag sequences and their affinity polypeptides include, but are not limited to, the amino acid sequences of SEQ ID NOs:42-44.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases). Example RNA recruiting motifs and their affinity polypeptides include, but are not limited to, the sequences of SEQ ID NOs:45-55.

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide Pumilio/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together, e.g., dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The nucleic acid constructs of the invention (e.g., a construct comprising a sequence specific DNA binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, ribonucleoproteins (RNPs), nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Any canola plant comprising an endogenous SHATTERPROOF MADS-BOX (SHP) gene may be modified as described herein to improve one or more yield traits. Non-limiting examples of canola plant species that may be modified as described herein may include, but are not limited to, *Brassica napus, Brassica rapa, Brassica juncea* and/or *Brassica rapa* subsp. *oleifera* (syn. *B. campestris* L.).

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1. Modification of SHATTERPROOF MADS-BOX (SHP) Genes in Canola

A strategy to generate edits in the canola SHP genes of BnaA07g18050D (SEQ ID NO:100) (SHP2) and BnaC06g16910D (SHP2) (SEQ ID NO:240) was developed to decrease activity of the MADS domain transcription factor encoded by the SHP genes. To generate a range of alleles with edits in the C-terminal region of the target SHP genes, multiple CRISPR guide nucleic acids comprising spacers (SEQ ID NOs:292-297) (see Table 2) having complementarity to targets within the SHP genes were designed and placed into a construct.

Lines carrying edits in the SHP genes were screened and those that showed about 10% of the sequencing reads having edits in the targeted gene were advanced to the next generation.

TABLE 2

Spacers for guide nucleic acids

| Spacer (SEQ ID NO:) | Target gene |
|---|---|
| PWsp236 (292) | BnaA07g18050D (SHP2) (SEQ ID NO: 100), BnaC06g16910D (SHP2) (SEQ ID NO:240) |
| PWsp237 (293) | BnaC06g16910D (SHP2) (SEQ ID NO:240) |
| PWsp238 (294) | BnaC06g16910D (SHP2) (SEQ ID NO:240), BnaA07g18050D (SHP2) (SEQ ID NO: 100) |
| PWsp239 (295) | BnaC06g16910D (SHP2) (SEQ ID NO:240) |
| PWsp240 (296) | BnaC06g16910D (SHP2) (SEQ ID NO:240), BnaA07g18050D (SHP2) (SEQ ID NO: 100) |
| PWsp241 (297) | BnaC06g16910D (SHP2) (SEQ ID NO:240), BnaA07g18050D (SHP2) (SEQ ID NO: 100) |

Example 2

Edited plants were sequenced with NGS sequencing techniques to further characterize the edit alleles generated. A range of alleles for the target genes were generated as further described in Table 3.

TABLE 3

Edited alleles

| E1 plant | Edit |
|---|---|
| CE69293 | The BnaA07g18050D allele (SEQ ID NO: 100) (SHP2) in CE69293 is heterozygous and the edited copy contains two deletions, one of 8 bp and the other of 10 bp, which results in a frame shift mutation leading to the insertion of 6 novel amino acids at position 180 in the protein sequence before reaching a premature stop codon |

TABLE 3-continued

| Edited alleles | |
|---|---|
| E1 plant | Edit |
| CE69294 | The BnaA07g18050D allele (SEQ ID NO: 100) (SHP2) in CE69294 is homozygous for a 10 bp deletion. The deletion results in a frame shift mutation such that 9 novel amino acids are added to the terminal end of the translated protein and an early stop codon is generated. The resulting protein is missing the amino acids encoded by the last exon of the gene and is also missing a portion of the amino acids encoded by the second to last exon. |
| CE69295 | The BnaA07g18050D allele (SEQ ID NO: 100) (SHP2) in CE69295 is homozygous for a 45 bp deletion. The deletion removes the intron-exon boundary of the final exon of the gene and generates an altered protein which does not contain the amino acids encoded by the last exon. The BnaC06g16910D (SHP2) (SEQ ID NO: 240) allele in CE69295 is homozygous for a 7 bp deletion. The deletion of the 7 bp results in a frame shift mutation such that a portion of the second to last exon is not translated into the protein and none of the last exon is included in the protein. The edit also results in the addition of 10 novel amino acids to the C-terminal end of the protein before reaching a stop codon. |
| CE69307 | The BnaA07g18050D allele (SEQ ID NO: 100) (SHP2) of CE69307 is homozygous for a 20 bp deletion. The deletion results in an immediate stop codon which truncates the resulting protein such that a portion of the amino acids encoded by the second to last exon are missing and all of the amino acids from the last exon are missing. The BnaC06g16910D (SHP2) (SEQ ID NO: 240) allele in CE69307 is homozygous for a 7 bp deletion which results in a frame shift leading to a stop codon at position 180 in the amino acid sequence. This frame shift results in a portion of the amino acids in the second to last exon, and all of the amino acids encoded by the last exon are missing from the edited allele. |

Example 3. Evaluation of Lignin Content of Edited Plants

Plants carrying edits as provided above in Table 3, above, were evaluated by staining for lignin content in the pod valve margin. The results are provided in Table 4 for two of the edited plants.

TABLE 4

| Lignin staining | |
|---|---|
| Plant line | Lignin staining |
| CE69293 | +++ |
| CE69294 | + |
| Wild type | +++++ |

Example 4: Edited Alleles

Canola lines were generated as described in Example 1 and several lines were recovered which contained a range of edited alleles of the SUP genes BnaA7g18050D (SEQ ID NO:100) and BnaC06g16910D (SEQ ID NO:240). The SHP genes were sequenced by next generation sequencing and the edited alleles identified are further described in Table 5 and Table 6.

TABLE 5

| Edited alleles of BnaA07g18050D | | |
|---|---|---|
| Allele name (SEQ ID NO) | Description | Notes |
| Allele C<br>SEQ ID NO: 321 | 7 bp deletion (AGATATC) starting at position 6240 of SEQ ID NO: 100 | Out of frame deletion |

TABLE 5-continued

Edited alleles of BnaA07g18050D

| Allele name (SEQ ID NO) | Description | Notes |
|---|---|---|
| Allele D SEQ ID NO: 312 | 11 bp deletion (CAACTTGTCTA SEQ ID NO: 339) starting at position 6422 of SEQ ID NO: 100 | Out-of-frame deletion which removes the last 3 amino acids of the wild type polypeptide sequence (SEQ ID NO: 102) and replaces them with new amino acids (SEQ ID NO: 313) (encoded by SEQ ID NO: 312) |
| Allele F SEQ ID NO: 314 | 12 bp deletion (AACTTGTCTAAG SEQ ID NO: 340) starting at position 6423 of SEQ ID NO: 100 | Out-of-frame deletion which removes the last 3 amino acids of the wild type polypeptide sequence (SEQ ID NO: 102) and replaces them with new amino acids (SEQ ID NO: 315) (encoded by SEQ ID NO: 314) |

TABLE 6

Edited alleles of BnaC06g16910D

| Allele name (SEQ ID NO) | Description | Notes |
|---|---|---|
| Allele A SEQ ID NO: 318 | 420 bp deleted starting at position 3349 of SEQ ID NO: 240 | Deletes 42 amino acids from C terminal end of the protein |
| Allele B SEQ ID NO: 310 | 10 bp deletion (TTCAACTTGT SEQ ID NO: 341) starting at position 3387 of SEQ ID NO: 240 | Removes the last four amino acids from SEQ ID NO: 242 and replaces them with the amino acids PKF (SEQ ID NO: 311) |
| Allele E SEQ ID NO: 319 | 70 bp deletion (SEQ ID NO: 320) starting at position 3391 of SEQ ID NO: 240 | Deletes the last 3 amino acids from SEQ ID NO: 242 (SEQ ID NO: 313) |
| Allele G SEQ ID NO: 316 | 8 bp deletion (TACCTGCG) starting at position 3105 of SEQ ID NO: 240; and 6 bp deletion (CCTCTT) starting at position 3383 of SEQ ID NO: 240 | Replaces the last 68 amino acids of SEQ ID NO: 242 with an S residue (SEQ ID NO: 317) |

Example 5. Phenotype Analysis

Pod shatter was evaluated by harvesting canola pods when fully mature. The harvested pods were fully dried in a seed dryer (e.g., 48-72 hours). Ten canola pods were selected at random for evaluation and placed into an empty plastic pipette tip box along with 2-9 mm steel balls. The box with the pods and steel balls was placed into a Geno/Grinder automated plant tissue homogenizer set to a speed of 600 for 45 seconds. The contents of the box were inspected, and the number of unbroken pods recorded. The foregoing was repeated five more times for each sample evaluated and a statistical analysis of the results is provided below in Table 7.

TABLE 7

Pod shatter results

| Genotype (number of plants) | Mean for number of unbroken pods (standard deviation) |
|---|---|
| Wild type control (24) | 3.9 (1.2) |
| Wild type control expressing GUS (24) | 5.0 (1.4) |
| Null segregant control (27) | 5.1 (2.0) |

TABLE 7-continued

Pod shatter results

| Genotype (number of plants) | Mean for number of unbroken pods (standard deviation) |
|---|---|
| Allele A (16) | 3.1 (1.5) |
| Allele B homozygous (36) | 6.1 (1.7) * |
| Allele C (27) | 3.0 (1.8) |
| Allele D homozygous Allele E (27) | 5.4 (1.6) * |
| Allele F homozygous Allele G homozygous (12) | 7.1 (1.3) * |
| Allele F homozygous Allele B homozygous (28) | 5.7 (1.9) * |

* indicates significance to the $p < 0.05$ when compared to wild type

The canola lines with edited Allele A of BnaC06g16910D and no other SHP gene edit; as well as canola lines with edited Allele C of BnaA07g18050D and no other SHP gene edit were not significantly different from the wild type control in the number of unshattered pods.

The canola lines with the combination of the edited Allele F/Allele G genotype showed an increase in the number of unshattered pods that was significantly different from the wild type control. The canola lines with edited Allele B and no other SHP gene edit also exhibited significantly less shattering when compared to the wild type control. Additionally, the canola lines with the combination of the edited Allele D and edited Allele E, and the canola lines having the combination of the edited Allele F and edited Allele B were significantly improved when compared to the wild type control lines; but were not significantly different from the null segregant control suggesting that there may be a transformation affect that is contributing to the observed phenotype.

A strong statistical evidence of decreased pod shatter in the canola lines was observed with the combination of edited Allele F/Allele G (p-value <0.003). Additionally, the genotype having the edited SHP Allele B alone also showed a strong decrease in pod shatter when compared to the wild type control line and showed a moderate decrease in pod shatter when compared to the null segregant control (p-values <0.07). The genotypes having the edited SHP allele combination of Allele D/Allele E and the genotype having the combination of Allele F/Allele B were both found to be significantly improved for the presence of intact pods (reduced pod shattering) when compared to the wild type control line but not when compared to the null segregant control (p-values >0.58).

Example 6. Modification of SHATTERPROOF MADS-BOX (SHP) Genes in Canola

A strategy to generate edits in the canola SHP gene of BnaA05g02990D (SEQ ID NO:148) (SHP4, SHP4A) was developed to decrease activity of the MADS domain transcription factor encoded by the SHP gene. To generate a range of alleles with edits in the C-terminal region of the target SHP gene, multiple CRISPR guide nucleic acids comprising spacers (SEQ ID NOs:342-346) (see Table 8) having complementarity to targets within the SHP gene were designed and placed into a construct.

TABLE 8

Spacer sequences for guides for canola SHP gene having the gene ID number of BnaA05g02990D (SHP4A, SEQ ID NO: 148)

| Spacer name | SEQ ID NO | sequence |
|---|---|---|
| PWsp291 | 342 | TATAATTCTACAGATTAATGAAA |
| PWsp292 | 343 | CGAGTCATCTTCTCATCAGTCGG |
| PWsp293 | 344 | CTTAAACAAGTTGGAGAGGTGGT |

TABLE 8-continued

Spacer sequences for guides for canola SHP gene having the gene ID number of BnaA05g02990D (SHP4A, SEQ ID NO: 148)

| Spacer name | SEQ ID NO | sequence |
|---|---|---|
| PWsp294 | 345 | ACCATAATTGTAACATGAATAGA |
| PWsp295 | 346 | AGAGGGACCTAAGTTACATATGT |

Lines carrying edits in the SHP4 gene were screened and those that showed about 10% of the sequencing reads having edits in the targeted gene were advanced to the next generation. Edited plants were sequenced with NGS sequencing techniques to further characterize the edit alleles generated.

Two edited alleles of the BnaA05g02990D gene were identified. Allele H of Bna05g02990D contains a 2 bp deletion (AC) at position 3472 of SEQ ID NO:148 giving rise to the edited genomic sequence of SEQ ID NO:322. The deletion in Allele H does not affect the coding region of BnaA05g02990D (SEQ ID NO:148) but alters the 3' UTR of the gene.

Allele I of Bna05g02990D contains a 7 bp deletion (CTATTCA) at position 3401 of SEQ ID NO:148 giving rise to the edited genomic sequence of SEQ ID NO:323. The deletion in Allele I does not affect the coding region of BnaA05g02990D (SEQ ID NO:148) but alters the 3' UTR of the gene.

Plants carrying the edited alleles Allele H and/or Allele I were evaluated by staining for lignin content in the pod valve margin. The results are provided in Table 9.

TABLE 9

| Genotype | Lignin Staining |
|---|---|
| Null segregant | +++++ |
| Heterozygous Allele I | +++++ |
| Homozygous Allele I | +++++ |
| Homozygous Allele H | +++ |

A considerable amount of variation was observed in the intensity of lignin staining within each genotype, likely due to the difference in developmental stages of collected pods. Pods from SHP4a Allele I (both Hom and Het) stained just as strongly as the null segregant samples. The pods from SHP4a—Homozygous Allele H did not stain as strongly as the null segregant. This data suggest there's a moderate reduction in lignin deposition associated with at least Allele H.

The foregoing is illustrative of the present invention and is not to be construed as limiting thereof. The invention is defined by the following claims, with equivalents of the claims to be included therein.

That which is claimed is:

1. A method for producing a canola plant or plant part thereof comprising at least one cell having a mutated endogenous SHATTERPROOF MADS-BOX(SHP) gene, the method comprising:

contacting a target site in an endogenous SHP gene in the canola plant or plant part thereof with a guide nucleic acid and a nuclease comprising a cleavage domain and a nucleic acid binding domain, wherein the guide nucleic acid binds to the target site and the target site is in a region of the endogenous SHP gene having at least 95% sequence identity to any one of SEQ ID NOs:103, 112, 243, or 261, wherein the nucleic acid binding domain binds to the target site in the endogenous SHP gene, and wherein the endogenous SHP gene (a) comprises a nucleotide sequence having at least 95% sequence identity to any one of SEQ ID NOs:69, 70, 100, 101, 148, 149, 177, 178, 206, 207, 240 or 241;

(b) comprises a region having at least 95% sequence identity to a nucleotide sequence of any one of SEQ ID NOs:72-96, -103-144, 151-173, 180-202, 209-236, 243-288 or -324-338;

(c) encodes a SHP polypeptide having at least 95% sequence identity to any one of SEQ ID NOs:71, 102, 150, 179, 208, or 242; and/or (d) encodes a region of a SHP polypeptide having at least 95% sequence identity to any one of SEQ ID NOs:97-99, 145-147, 174-176, 203-205, 237-239 or 289-291, thereby producing the canola plant or plant part thereof comprising the at least one cell having a mutation in the endogenous SHP gene to provide the mutated endogenous SHP gene.

2. The method of claim 1, wherein the mutation is an out-of-frame insertion or an out-of-frame deletion that results in a premature stop codon.

3. The method of claim 1, wherein the mutated endogenous SHP gene comprises a nucleotide sequence having at least 90% sequence identity to any one of SEQ ID NOs:298, 300, 302, 304, 306, 308, 310, 312, 314, 316, 318, 319, 321, 322, or 323.

4. A guide nucleic acid that binds to a target site in a *Brassica napus* SHATTERPROOF MADS-BOX (SHP) gene, wherein the target site is in a region of the *Brassica napus* SHP gene having at least 95% sequence identity to any one of SEQ ID NOs: 103, 112, 243, or 261.

5. The guide nucleic acid of claim 4, wherein the guide nucleic acid comprises a spacer comprising a nucleotide sequence of any one of SEQ ID NOs:292-297.

6. The method of claim 1, wherein the mutation results in a mutated SHP polypeptide that comprises an amino acid sequence having at least 90% sequence identity to any one of SEQ ID NOs:299, 301, 303, 305, 307, 309, 311, 313, 315, or 317.

7. A *Brassica napus* plant or plant part thereof comprising a mutation in an endogenous SHATTERPROOF MADS-BOX (SHP) gene that encodes a SHP polypeptide, wherein the mutation is introduced using the guide nucleic acid of claim 4.

* * * * *

SEQUENCE LISTING

```
Sequence total quantity: 346
SEQ ID NO: 1            moltype = AA  length = 1228
FEATURE                 Location/Qualifiers
REGION                  1..1228
                        note = Lachnospiraceae bacterium
source                  1..1228
                        mol_type = protein
                        organism = unidentified
SEQUENCE: 1
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
```

-continued

IGGFVTESGE KIKGLNEYIN LYNQKTKQKL PKFKPLYKQV LSDRESLSFY GEGYTSDEEV 300
LEVFRNTLNK NSEIFSSIKK LEKLFKNFDE YSSAGIFVKN GPAISTISKD IFGEWNVIRD 360
KWNAEYDDIH LKKKAVVTEK YEDDRRKSFK KIGSFSLEQL QEYADADLSV VEKLKEIIIQ 420
KVDEIYKVYG SSEKLFDADF VLEKSLKKND AVVAIMKDLL DSVKSFENYI KAFFGEGKET 480
NRDESFYGDF VLAYDILLKV DHIYDAIRNY VTQKPYSKDK FKLYFQNPQF MGGWDKDKET 540
DYRATILRYG SKYYLAIMDK KYAKCLQKID KDDVNGNYEK INYKLLPGPN KMLPKVFFSK 600
KWMAYYNPSE DIQKIYKNGT FKKGDMFNLN DCHKLIDFFK DSISRYPKWS NAYDFNFSET 660
EKYKDIAGFY REVEEQGYKV SFESASKKEV DKLVEEGKLY MFQIYNKDFS DKSHGTPNLH 720
TMYFKLLFDE NNHGQIRLSG GAELFMRRAS LKKEELVVHP ANSPIANKNP DNPKKTTTLS 780
YDVYKDKRFS EDQYELHIPI AINKCPKNIF KINTEVRVLL KHDDNPYVIG IDRGERNLLY 840
IVVVDGKGNI VEQYSLNEII NNFNGIRIKT DYHSLLDKKE KERFEARQNW TSIENIKELK 900
AGYISQVVHK ICELVEKYDA VIALEDLNSG FKNSRVKVEK QVYQKFEKML IDKLNYMVDK 960
KSNPCATGGA LKGYQITNKF ESFKSMSTQN GFIFYIPAWL TSKIDPSTGF VNLLKTKYTS 1020
IADSKKFISS FDRIMYVPEE DLFEFALDYK NFSRTDADYI KKWKLYSYGN RIRIFRNPKK 1080
NNVFDWEEVC LTSAYKELFN KYGINYQQGD IRALLCEQSD KAFYSSFMAL MSLMLQMRNS 1140
ITGRTDVDFL ISPVKNSDGI FYDSRNYEAQ ENAILPKNAD ANGAYNIARK VLWAIGQFKK 1200
AEDEKLDKVK IAISNKEWLE YAQTSVKH 1228

SEQ ID NO: 2 moltype = AA length = 1307
FEATURE Location/Qualifiers
source 1..1307
mol_type = protein
organism = Acidaminococcus sp.
SEQUENCE: 2
MTQFEGFTNL YQVSKTLRFE LIPQGKTLKH IQEQGFIEED KARNDHYKEL KPIIDRIYKT 60
YADQCLQLVQ LDWENLSAAI DSYRKEKTEE TRNALIEEQA TYRNAIHDYF IGRTDNLTDA 120
INKRHAEIYK GLFKAELFNG KVLKQLGTVT TTEHENALLR SFDKFTTYFS GFYENRKNVF 180
SAEDISTAIP HRIVQDNFPK FKENCHIFTR LITAVPSLRE HFENVKKAIG IFVSTSIEEV 240
FSFPFYNQLL TQTQIDLYNQ LLGGISREAG TEKIKGLNEV LNLAIQKNDE TAHIIASLPH 300
RFIPLFKQIL SDRNTLSFIL EEFKSDEEVI QSFCKYKTLL RNENVLETAE ALFNELNSID 360
LTHIFISHKK LETISSALCD HWDTLRNALY ERRISELTGK ITKSAKEKVQ RSLKHEDINL 420
QEIISAAGKE LSEAFKQKTS EILSHAHAAL DQPLPTTLKK QEEKEILKSQ LDSLLGLYHL 480
LDWFAVDESN EVDPEFSARL TGIKLEMEPS LSFYNKARNY ATKKPYSVEK FKLNFQMPTL 540
ASGWDVNKEK NNGAILFVKN GLYYLGIMPK QKGRYKALSF EPTEKTSEGF DKMYYDYFPD 600
AAKMIPKCST QLKAVTAHFQ THTTPILLSN NFIEPLEITK EIYDLNNPEK EPKKFQTAYA 660
KKTGDQKGYR EALCKWIDFT RDFLSKYTKT TSIDLSSLRP SSQYKDLGEY YAELNPLLYH 720
ISFQRIAEKE IMDAVETGKL YLFQIYNKDF AKGHHGKPNL HTLYWTGLFS PENLAKTSIK 780
LNGQAELFYR PKSRMKRMAH RLGEKMLNKK LKDQKTPIPD TLYQELYDYV NHRLSHDLSD 840
EARALLPNVI TKEVSHEIIK DRRFTSDKFF FHVPITLNYQ AANSPSKFNQ RVNAYLKEHP 900
ETPIIGIDRG ERNLIYITVI DSTGKILEQR SLNTIQQFDY QKKLDNREKE RVAARQAWSV 960
VGTIKDLKQG YLSQVIHEIV DLMIHYQAVV VLENLNFGFK SKRTGIAEKA VYQQFEKMLI 1020
DKLNCLVLKD YPAEKVGGVL NPYQLTDQFT SFAKMGTQSG FLFYVPAPYT SKIDPLTGFV 1080
DPFVWKTIKN HESRKHFLEG FDFLHYDVKT GDFILHFKMN RNLSFQRGLP GFMPAWDIVF 1140
EKNETQFDAK GTPFIAGKRI VPVIENHRFT GRYRDLYPAN ELIALLEEKG IVFRDGSNIL 1200
PKLLENDDSH AIDTMVALIR SVLQMRNSNA ATGEDYINSP VRDLNGVCFD SRFQNPEWPM 1260
DADANGAYHI ALKGQLLLNH LKESKDLKLQ NGISNQDWLA YIQELRN 1307

SEQ ID NO: 3 moltype = AA length = 1241
FEATURE Location/Qualifiers
source 1..1241
mol_type = protein
organism = Butyrivibrio proteoclasticus
SEQUENCE: 3
MLLYENYTKR NQITKSLRLE LRPQGKTLRN IKELNLLEQD KAIYALLERL KPVIDEGIKD 60
IARDTLKNCE LSFEKLYEHF LSGDKKAYAK ESERLKKEIV KTLIKNLPEG IGKISEINSA 120
KYLNGVLYDF IDKTHKDSEE KQNILSDILE TKGYLALFSK FLTSRITTLE QSMPKRVIEN 180
FEIYAANIPK MQDALERGAV SFAIEYESIC SVDYYNQILS QEDIDSYNRL ISGIMDEDGA 240
KEKGINQTIS EKNIKIKSEH LEEKPFRILK QLHKQILEER EKAFTIDHID SDEEVVQVTK 300
EAFEQTKEQW ENIKKINGFY AKDPGDITLF IVVGPNQTHV LSQLIYGEHD RIRLLLEEYE 360
KNTLEVLPRR TKSEDARYDK FVNAVPKKVA KESHTFDGLQ KMTGDDRLFI LYRDELARNY 420
MRIKEAYGTF ERDILKSRRG IKGNRDVQES LVSFYDELTK FRSALRIINS GNDEKADPIF 480
YNTFDGIFEK ANRTYKAENL CRNYVTKSPA DDARIMASCL GTPARLRTHW WNGEENFAIN 540
DVAMIRRGDE YYYFVLTPDV KPVDLKTKDE TDAQIFVQRK GAKSFLGLPK ALFKCILEPY 600
FESPEHKNDK NCVIEEYVSK PLTIDRRAYD IFKNGTFKKT NIGIDGLTEE KFKDDCRYLI 660
DVYKEFIAVY TRYSCFNMSG LKRADEYNDI GEFFSDVDTR LCTMEWIPVS FERINDMVDK 720
KEGLLFLVRS MFLYNRPRKP YERTFIQLFS DSNMEHTSML LNSRAMIQYR AASLPRRVTH 780
KKGSILVALR DSNGEHIPMH IREAIYKMKN NFDISSEDFI MAKAYLAEHD VAIKKANEDI 840
IRNRRYTEDK FFLSLSYTKN ADISARTLDY INDKVEEDTQ DSRMAVIVTR NLKDLTYVAV 900
VDEKNNVLEE KSLNEIDGVN YRELLKERTK IKYHDKTRLW QYDVSSKGLK EAYVELAVTQ 960
ISKLATKYNA VVVVESMSST FKDKFSFLDE QIFKAFEARL CARMSDLSFN TIKEGEAGSI 1020
SNPIQVSNNN GNSYQDGVIY FLNNAYTRTL CPDTGFVDVF DKTRLITMQS KRQFFAKMKD 1080
IRIDDGEMLF TFNLEEYPTK RLLDRKEWTV KIAGDGSYFD KDKGEYVYVN DIVREQIIPA 1140
LLEDKAVFDG NMAEKFLDKT AISGKSVELI YKWFANALYG IITKKDGEKI YRSPITGTEI 1200
DVSKNTTYNF GKKFMFKQEY RGDGDFLDAF LNYMQAQDIA V 1241

SEQ ID NO: 4 moltype = AA length = 1238
FEATURE Location/Qualifiers

-continued

```
source               1..1238
                     mol_type = protein
                     organism = Candidatus Methanoplasma termitum
SEQUENCE: 4
MNNYDEFTKL YPIQKTIRFE LKPQGRTMEH LETFNFFEED RDRAEKYKIL KEAIDEYHKK  60
FIDEHLTNMS LDWNSLKQIS EKYYKSREEK DKKVFLSEQK RMRQEIVSEF KKDDRFKDLF  120
SKKLFSELLK EEIYKKGNHQ EIDALKSFDK FSGYFIGLHE NRKNMYSDGD EITAISNRIV  180
NENFPKFLDN LQKYQEARKK YPEWIIKAES ALVAHNIKMD IVFSLEYFNK VLNQEGIQRY  240
NLALGGYVTK SGEKMMGLND ALNLAHQSEK SSKGRIHMTP LFKQILSEKE SFSYIPDVFT  300
EDSQLLPSIG GFFAQIENDK DGNIFDRALE LISSYAEYDT ERIYIRQADI NRVSNVIFGE  360
WGTLGGLMRE YKADSINDIN LERTCKKVDK WLDSKEFALS DVLEAIDRTG NNDAFNEYIS  420
KMRTAREKID AARKEMKFIS EKISGDEESI HIIKTLLDSV QQFLHFFNLF KARQDIPLDG  480
AFYAEFDEVH SKLFAIVPLY NKVRNYLTKN NLNTKKIKLN FKNPTLANGW DQNKVYDYAS  540
LIFLRDGNYY LGIINPKRKK NIKFEQGSGN GPFYRKMVYK QIPGPNKNLR PVFLTSTKGK  600
KEYKPSKEII EGYEADKHIR GDKFDLDFCH KLIDFFKESI EKHKDWSKFN FYFSPTESYG  660
DISEFYLDVE KQGYRMHFEN ISAETIDEYV EKGDLFLFQI YNKDFVKAAT GKKDMHTIYW  720
NAAFSPENLQ DVVVKLNGEA ELFYRDKSDI KEIVHREGEI LVNRTYNGRT PVPDKIHKKL  780
TDYHNGRTKD LGEAKEYLDK VRYFKAHYDI TKDRRYLNDK IYFHVPLTLN FKANGKKNLN  840
KMVIEKFLSD EKAHIIGIDR GERNLLYYSI IDRSGKIIDQ QSLNVIDGFD YREKLNQREI  900
EMKDARQSWN AIGKIKDLKE GYLSKAVHEI TKMAIQYNAI VVMEELNYGF KRGRFKVEKQ  960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KYDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                        1238

SEQ ID NO: 5         moltype = AA  length = 1281
FEATURE              Location/Qualifiers
source               1..1281
                     mol_type = protein
                     organism = Eubacterium eligens
SEQUENCE: 5
MNGNRSIVYR EFVGVIPVAK TLRNELRPVG HTQEHIIQNG LIQEDELRQE KSTELKNIMD  60
DYYREYIDKS LSGVTDLDFT LLFELMNLVQ SSPSKDNKKA LEKEQSKMRE QICTHLQSDS  120
NYKNIFNAKL LKEILPDFIK NYNQYDVKDK AGKLETLALF NGFSTYFTDF FEKRKNVFTK  180
EAVSTSIAYR IVHENSLIFL ANMTSYKKIS EKALDEIEVI EKNNQDKMGD WELNQIFNPD  240
FYNMVLIQSG IDFYNEICGV VNAHMNLYCQ QTKNNYNLFK MRKLHKQILA YTSTSFEVPK  300
MFEDDMSVYN AVNAFIDETE KGNIIGKLKD IVNKYDELDE KRIYISKDFY ETLSCFMSGN  360
WNLITGCVEN FYDENIHAKG KSKEEKVKKA VKEDKYKSIN DVNDLVEKYI DEKERNEFKN  420
SNAKQYIREI SNIITDTETA HLEYDDHISL IESEEKADEM KKRLDMYMNM YHWAKAFIVD  480
EVLDRDEMFY SDIDDIYNIL ENIVPLYNRV RNYVTQKPYN SKKIKLNFQS PTLANGWSQS  540
KEFDNNAIIL IRDNKYYLAI FNAKNKPDKK IIQGNSDKKN DNDYKKMVYN LLPGANKMLP  600
KVFLSKKGIE TFKPSDYIIS GYNAHKHIKT SENFDISFCR DLIDYFKNSI EKHAEWRKYE  660
FKFSATDSYS DISEFYREVE MQGYRIDWTY ISEADINKLD EEGKIYLFQI YNKDFAENST  720
GKENLHTMYF KNIFSEENLD KIIKLNGQAE LFYRRASVKN PVKHKKDSVL VNKTYKNQLD  780
NGDVVRIPIP DDIYNEIYKM YNGYIKESDL SEAAKEYLDK VEVRTAQKDI VKDYRYTVDK  840
YFIHTPITIN YKVTARNNVN DMVVKYIAQN DDIHVIGIDR GERNLIYISV IDSHGNIVKQ  900
KSYNILNNYD YKKKLVEKEK TREYARKNWK SIGNIKELKE GYISGVVHEI AMLIVEYNAI  960
IAMEDLNYGF KRGRFKVERQ VYQKFESMLI NKLNYFASKE KSVDEPGGLL KGYQLTYVPD  1020
NIKNLGKQCG VIFYVPAAFT SKIDPSTGFI SAFNFKSIST NASRKQFFMQ FDEIRYCAEK  1080
DMFSFGFDYN NFDTYNITMG KTQWTVYTNG ERLQSEFNNA RRTGKTKSIN LTETIKLLLE  1140
DNEINYADGH DIRIDMEKMD EDKKSEFFAQ LLSLYKLTVQ MRNSYTEAEE QENGISYDKI  1200
ISPVINDEGE FFDSDNYKES DDKECKMPKD ADANGAYCIA LKGLYEVLKI KSEWTEDGFD  1260
RNCLKLPHAE WLDFIQNKRY E                                          1281

SEQ ID NO: 6         moltype = AA  length = 1300
FEATURE              Location/Qualifiers
source               1..1300
                     mol_type = protein
                     organism = Francisella novicida
SEQUENCE: 6
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKVNY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
```

-continued

```
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 7            moltype = AA  length = 1206
FEATURE                 Location/Qualifiers
source                  1..1206
                        mol_type = protein
                        note = Lachnospiraceae sp.
                        organism = unidentified
SEQUENCE: 7
MYYESLTKQY PVSKTIRNEL IPIGKTLDNI RQNNILESDV KRKQNYEHVK GILDEYHKQL  60
INEALDNCTL PSLKIAAEIY LKNQKEVSDR EDFNKTQDLL RKEVVEKLKA HENFTKIGKK  120
DILDLLEKLP SISEDDYNAL ESFRNFYTYF TSYNKVRENL YSDKEKSSTV AYRLINENFP  180
KFLDNVKSYR FVKTAGILAD GLGEEEQDSL FIVETFNKTL TQDGIDTYNS QVGKINSSIN  240
LYNQKNQKAN GFRKIPKMKM LYKQILSDRE ESFIDEFQSD EVLIDNVESY GSVLIESLKS  300
SKVSAFFDAL RESKGKNVYV KNDLAKTAMS VIVFENWRTF DDLLNQEYDL ANENKKKDDK  360
YFEKRQKELK KNKSYSLEHL CNLSEDSCNL IENYIHQISD DIENIIINNE TFLRIVINEH  420
DRSRKLAKNR KAVKAIKDFL DSIKVLEREL KLINSSGQEL EKDLIVYSAH EELLVELKQV  480
DSLYNMTRNY LTKKPFSTEK VKLNFNRSTL LNGWDRNKET DNLGVLLLKD GKYYLGIMNT  540
SANKAFVNPP VAKTEKVFKK VDYKLLPVPN QMLPKVFFAK SNIDFYNPSS EIYSNYKKGT  600
HKKGNMFSLE DCHNLIDFFK ESISKHEDWS KFGFKFDTQA SYNDISEFYR EVEKQGYKLT  660
YTDIDETYIN DLIERNELYL FQIYNKDFSM YSKGKLNLHT LYFMMLFDQR NIDDVVYKLN  720
GEAEVFYRPA SISEDELIIH KAGEEIKNKN PNRARTKETS TFSYDIVKDK RYSKDKFTLH  780
IPITMNFGVD EVKRFNDAVN SAIRIDENVN VIGIDRGERN LLYVVVIDSK GNILEQISLN  840
SIINKEYDIE TDYHALLDER EGGRDKARKD WNTVENIRDL KAGLYLQVVN VVAKLVLKYN  900
AIICLEDLNF GFKRGRQKVE KQVYQKFEKM LIDKLNYLVI DKSREQTSPK ELGGALNALQ  960
LTSKFKSFKE LGKQSGVIYY VPAYLTSKID PTTGFANLFY MKCENVEKSK RFFDGFDFIR  1020
FNALENVFEF GFDYRSFTQR ACGINSKWTV CTNGERIIKY RNPDKNNMFD EKVVVVTDEM  1080
KNLFEQYKIP YEDGRNVKDM IISNEEAEFY RRLYRLLQQT LQMRNSTSDG TRDYIISPVK  1140
NKREAYFNSE LSDGSVPKDA DANGAYNIAR KGLWVLEQIR QKSEGEKINL AMTNAEWLEY  1200
AQTHLL                                                            1206

SEQ ID NO: 8            moltype = AA  length = 1233
FEATURE                 Location/Qualifiers
source                  1..1233
                        mol_type = protein
                        note = Lachnospiraceae sp.
                        organism = unidentified
SEQUENCE: 8
MDYGNGQFER RAPLTKTITL RLKPIGETRE TIREQKLLEQ DAAFRKLVET VTPIVDDCIR  60
KIADNALCHF GTEYDFSCLG NAISKNDSKA IKKETEKVEK LLAKVLTENL PDGLRKVNDI  120
NSAAFIQDTL TSFVQDDADK RVLIQELKGK TVLMQRFLTT RITALTVWLP DRVFENFNIF  180
IENAEKMRIL LDSPLNEKIM KFDPDAEQYA SLEFYGQCLS QKDIDSYNLI ISGIYADDEV  240
KNPGINEIVK EYNQQIRGDK DESPLPKLKK LHKQILMPVE KAFFVRVLSN DSDARSILEK  300
ILKDTEMLPS KIIEAMKEAD AGDIAVYGSR LHELSHVIYG DHGKLSQIIY DKESKRISEL  360
METLSPKERK ESKKRLEGLE EHIRKSTYTF DELNRYAEKN VMAAYIAAVE ESCAEIMRKE  420
KDLRTLLSKE DVKIRGNRHN TLIVKNYFNA WTVFRNLIRI LRRKSEAEID SDFYDVLDDS  480
VEVLSLTYKG ENLCRSYITK KIGSDLKPEI ATYGSALRPN SRWWSPGEKF NVKFHTIVRR  540
DGRLYYFILP KGAKPVELED MDGDIECLQM RKIPNPTIFL PKLVFKDPEA FFRDNPEADE  600
FVFLSGMKAP VTITRETYEA YRYKLYTVGK LRDGEVSEEE YKRALLQVLT AYKEFLENRM  660
IYADLNFGFK DLEEYKDSSE FIKQVETHNT FMCWAKVSSS QLDDLVKSGN GLLFEIWSER  720
LESYYKYGNE KVLRGYEGVL LSILKDENLV SMRTLLNSRP MLVYRPKESS KPMVVHRDGS  780
RVVDRFDKDG KYIPPEVHDE LYRFFNNLLI KEKLGEKARK ILDNKKVKVK VLESERVKWS  840
KFYDEQFAVT FSVKKNADCL DTTKDLNAEV MEQYSESNRL ILIRNTTDIL YYLVLDKNGK  900
VLKQRSLNII NDGARDVDWK ERFRQVTKDR NEGYNEWDYS RTSNDLKEVY LNYALKEIAE  960
AVIEYNAILI IEKMSNAFKD KYSFLDDVTF KGFETKKLAK LSDLHFRGIK DGEPCSFTNP  1020
LQLCQNDSNK ILQDGVIFMV PNSMTRSLDP DTGFIFAIND HNIRTKKAKL NFLSKFDQLK  1080
VSSEGCLIMK YSGDSLPTHN TDNRVWNCCC NHPITNYDRE TKKVEFIEEP VEELSRVLEE  1140
NGIETDTELN KLNERENVPG KVVDAIYSLV LNYLRGTVSG VAGQRAVYYS PVTGKKYDIS  1200
FIQAMNLNRK CDYYRIGSKE RGEWTDFVAQ LIN                               1233

SEQ ID NO: 9            moltype = AA  length = 1227
FEATURE                 Location/Qualifiers
source                  1..1227
                        mol_type = protein
                        note = Lachnospiraceae sp.
                        organism = unidentified
SEQUENCE: 9
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
```

-continued

```
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI ANINKCPKNI FKINTEVRVL LKHDDNPYVI GIDRGERNLL  840
YIVVVDGKGN IVEQYSLNEI INNFNGIRIK TDYHSLLDKK EKERFEARQN WTSIENIKEL  900
KAGYISQVVH KICELVEKYD AVIALEDLNS GFKNSRVKVE KQVYQKFEKM LIDKLNYMVD  960
KKSNPCATGG ALKGYQITNK FESFKSMSTQ NGFIFYIPAW LTSKIDPSTG FVNLLKTKYT  1020
SIADKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IASNKEWLEY AQTSVKH                                    1227

SEQ ID NO: 10          moltype = AA  length = 1264
FEATURE                Location/Qualifiers
source                 1..1264
                       mol_type = protein
                       organism = Leptospira inadai
SEQUENCE: 10
MEDYSGFVNI YSIQKTLRFE LKPVGKTLEH IEKKGFLKKD KIRAEDYKAV KKIIDKYHRA  60
YIEEVFDSVL HQKKKKDKTR FSTQFIKEIK EFSELYYKTE KNIPDKERLE ALSEKLRKML  120
VGAFKGEFSE EVAEKYNKNL FSKELIRNEI EKFCETDEER KQVSNFKSFT TYFTGFHSNR  180
QNIYSDEKKS TAIGYRIIHQ NLPKFLDNLK IIESIQRRFK DFPWSDLKKN LKKIDKNIKL  240
TEYFSIDGFV NVLNQKGIDA YNTILGGKSE ESGEKIQGLN EYINLYRQKN NIDRKNPLNV  300
KILFKQILGD RETKSFIPEA FPDDQSVLNS ITEFAKYLKL DKKKKSIIAE LKKFLSSFNR  360
YELDGIYLAN DNSLASISTF LFDDWSFIKK SVSFKYDESV GDPKKKIKSP LKYEKEKEKW  420
LKQKYYTISF LNDAIESYSK SQDEKRVKIR LEAYFAEFKS KDDAKKQFDL LERIEEAYAI  480
VEPLLGAEYP RDRNLKADKK EVGKIKDFLD SIKSLQFFLK PLLSAEIFDE KDLGFYNQLE  540
GYYEEIDISG HLYNKVRNYL TGKIYSKEKF KLNFENSTLL KGWDENREVA NLCVIFREDQ  600
KYYLGVMDKE NNTILSDIPK VKPNELFYEK MVYKLIPTPH MQLPRIIFSS DNLSIYNPSK  660
SILKIREAKS FKEGKNFKLK DCHKFIDFYK ESISKNEDWS RFDFKFSKTS SYENISEFYR  720
EVERQGYNLD FKKVSKFYID SLVEDGKLYL FQIYNKDFSI FSKGKPNLHT IYFRSLFSKE  780
NLKDVCLKLN GEAEMFFRKK SINYDEKKKR EGHHPELFEK LKYPILKDKR YSEDKFQFHL  840
PISLNFKSKE RLNFNLKVNE FLKRNKDINI IGIDRGERNL LYLVMINQKG EILKQTLLDS  900
MQSGKGRPEI NYKEKLQEKE IERDKARKSW GTVENIKELK EGYLSIVIHQ ISKLMVENNA  960
IVVLEDLNIG FKRGRQKVER QVYQKFEKML IDKLNFLVFK ENKPTEPGGV LKAYQLTDEF  1020
QSFEKLSKQT GFLFYVPSWN TSKIDPRTGF IDFLHPAYEN IEKAKQWINK FDSIRFNSKM  1080
DWFEFTADTR KFSENLMLGK NRVWVICTTN VERYFTSKTA NSSIQYNSIQ ITEKLKELFV  1140
DIPFSNGQDL KPEILRKNDA VFFKSLLFYI KTTLSLRQNN GKKGEEEKDF ILSPVVDSKG  1200
RFFNSLEASD DEPKDADANG AYHIALKGLM NLLVLNETKE ENLSRPKWKI KNKDWLEFVW  1260
ERNR                                                             1264

SEQ ID NO: 11          moltype = AA  length = 1373
FEATURE                Location/Qualifiers
source                 1..1373
                       mol_type = protein
                       organism = Moraxella bovoculi
SEQUENCE: 11
MLFQDFTHLY PLSKTVRFEL FIDRTLEHIH AKNFLSQDET MADMHQKVKV ILDDYHRDFI  60
ADMMGEVKLT KLAEFYDVYL KFRKNPKDDE LQKAQLKDLQ AVLRKEIVKP IGNGGKYKAG  120
YDRLFGAKLF KDGKELGDLA KFVIAQEGES SPKLAHLAHF EKFSTYFTGF HDNRKNMYSD  180
EDKHTAIAYR LIHENLPRFI DNLQILTTIK QKHSALYDQI INELTASGLD VSLASHLDGY  240
HKLLTQEGIT AYNTLLGGIS GEAGSPKIQG INELINSHHN QHCHKSERIA KLRPLHKQIL  300
SDGMSVSFLP SKFADDSEMC QAVNEFYRHY ADVFAKVQSL FDGFDDHQKD GIYVEHKNLN  360
ELSKQAFGDF ALLGRVLDGY YVDVVNPEFN ERFAKAKTDN AKAKLTKEKD KFIKGVHSLA  420
SLEQAIEHYT ARHDDESVQA GKLGQYFKHG LAGVDNPIQK IHNNHSTIKG FLERERPAGE  480
RALPKIKSGK NPEMTQLRQL KELLDNALNV AHFAKLLTTK TTLDNQDGNF YGEFGVLYDE  540
LAKIPTLYNK VRDYLSQKPF STEKYKLNFG NPTLLNGWDL NKEKDNFGVI LQKDGCYYLA  600
LLDKAHKKVF DNAPNTGKSI YQKMIYKYLE VRKQFPKVFF SKEAIAINYH PSKELVEIKD  660
KGRQRSDDER LKLYRFILEC LKIHPKYDKK FEGAIGDIQL FKKDKKGREV PISEKDLFKD  720
INGIFSSKPK LEMEDFFIGE FKRYNPSQDL VDQYNIYKKI DSNDNRKKEN FYNNHPKFKK  780
DLVRYYYESM CKHEEWEESF EFSKKLQDIG CYVDVNELFT EIETRRLNYK ISFCNINADY  840
IDELVEQGQL YLFQIYNKDF SPKAHGKPNL HTLYFKALFS EDNLADPIYK LNGEAQIFYR  900
KASLDMNETT IHRAGEVLEN KNPDNPKKRQ FVYDIIKDKR YTQKDFMLHV PITMNFGVQG  960
MTIKEFNKKV NQSIQQYDEV NVIGIDRGER HLLYLTVINS KGEILEQCSL NDITTASANG  1020
TQMTTPYHKI LDKREIERLN ARVGWGEIET IKELKSGYLS HVVHQISQLM LKYNAIVVLE  1080
DLNFGFKRGR FKVEKQIYQN FENALIKKLN HLVLKDKADD EIGSYKNALQ LTNNFTDLKS  1140
IGKQTGFLFY VPAWNTSKID PETGFVDLLK PRYENIQASQ AFFGKFDKIC YNADKDYFEF  1200
HIDYAKFTDK AKNSRQIWTI CSHGDKRYVY DKTANQNKGA AKGINVNDIL KSLFARHHIN  1260
EKQPNLVMDI CQNNDKEFHK SLMYLLKTLL ALRYSNASSD EDFILSPVAN DEGVFFNSAL  1320
ADDTQPQNAD ANGAYHIALK GLWLLNELKN SDDLNKVKLA IDNQTWLNFA QNR        1373

SEQ ID NO: 12          moltype = AA  length = 1352
FEATURE                Location/Qualifiers
source                 1..1352
                       mol_type = protein
                       note = Parcubacteria bacterium
                       organism = unidentified
```

-continued

```
SEQUENCE: 12
MENIFDQFIG KYSLSKTLRF ELKPVGKTED FLKINKVFEK DQTIDDSYNQ AKFYFDSLHQ  60
KFIDAALASD KTSELSFQNF ADVLEKQNKI ILDKKREMGA LRKRDKNAVG IDRLQKEIND  120
AEDIIQKEKE KIYKDVRTLF DNEAESWKTY YQEREVDGKK ITESKADLKQ KGADFLTAAG  180
ILKVLKYEFP EEKEKEFQAK NQPSLFVEEK ENPGQKRYIF DSFDKFAGYL TKFQQTKKNL  240
YAADGTSTAV ATRIADNFII FHQNTKVFRD KYKNNHTDLG FDEENIFEIE RYKNCLLQRE  300
IEHIKNENSY NKIIGRINKK IKEYRDQKAK DTKLTKSDFP FFKNLDKQIL GEVEKEKQLI  360
EKTREKTEED VLIERFKEFI ENNEERFTAA KKLMNAFCNG EFESEYEGIY LKNKAINTIS  420
RRWFVSDRDF ELKLPQQKSK NKSEKNEPKV KKFISIAEIK NAVEELDGDI FKAVFYDKKI  480
IAQGGSKLEQ FLVIWKYEFE YLFRDIEREN GEKLLGYDSC LKIAKQLGIF PQEKEAREKA  540
TAVIKNYADA GLGIFQMMKY FSLDDKDRKN TPGQLSTNFY AEYDGYYKDF EFIKYYNEFR  600
NFITKKPFDE DKIKLNFENG ALLKGWDENK EYDFMGVILK KEGRLYLGIM HKNHRKLFQS  660
MGNAKGDNAN RYQKMIYKQI ADASKDVPRL LLTSKKAMEK FKPSQEILRI KKEKTFKRES  720
KNFSLRDLHA LIEYYRNCIP QYSNWSFYDF QFQDTGKYQN IKEFTDDVQK YGYKISFRDI  780
DDEYINQALN EGKMYLFEVV NKDIYNTKNG SKNLHTLYFE HILSAENLND PVFKLSGMAE  840
IFQRQPSVNE REKITTQKNQ CILDKGDRAY KYRRYTEKKI MFHMSLVLNT GKGEIKQVQF  900
NKIINQRISS SDNEMRVNVI GIDRGEKNLL YYSVVKQNGE IIEQASLNEI NGVNYRDKLI  960
EREKERLKNR QSWKPVVKIK DLKKGYISHV IHKICQLIEK YSAIVVLEDL NMRFKQIRGG  1020
IERSVYQQFE KALIDKLGYL VFKDNRDLRA PGGVLNGYQL SAPFVSFEKM RKQTGILFYT  1080
QAEYTSKTDP ITGFRKNVYI SNSASLDKIK EAVKKFDAIG WDGKEQSYFF KYNPYNLADE  1140
KYKNSTVSKE WAIFASAPRI RRQKGEDGYW KYDRVKVNEE FEKLLKVWNF VNPKATDIKQ  1200
EIIKKIKAGD LQGEKELDGR LRNFWHSFIY LFNLVLELRN SFSLQIKIKA GEVIAVDEGV  1260
DFIASPVKPF FTTPNPYIPS NLCWLAVENA DANGAYNIAR KGVMILKKIR EHAKKDPEFK  1320
KLPNLFISNA EWDEAARDWG KYAGTTALNL DH                                1352

SEQ ID NO: 13           moltype = AA  length = 1260
FEATURE                 Location/Qualifiers
source                  1..1260
                        mol_type = protein
                        organism = Porphyromonas crevioricanis
SEQUENCE: 13
MDSLKDFTNL YPVSKTLRFE LKPVGKTLEN IEKAGILKED EHRAESYRRV KKIIDTYHKV  60
FIDSSLENMA KMGIENEIKA MLQSFCELYK KDHRTEGEDK ALDKIRAVLR GLIVGAFTGV  120
CGRRENTVQN EKYESLFKEK LIKEILPDFV LSTEAESLPF SVEEATRSLK EFDSFTSYFA  180
GFYENRKNIY STKPQSTAIA YRLIHENLPK FIDNILVFQK IKEPIAKELE HIRADFSAGG  240
YIKKDERLED IFSLNYYIHV LSQAGIEKYN ALIGKIVTEG DGEMKGLNEH INLYNQQRGR  300
EDRLPLFRPL YKQILSDREQ LSYLPESFEK DEELLRALKE FYDHIAEDIL GRTQQLMTSI  360
SEYDLSRIYV RNDSQLTDIS KKMLGDWNAI YMARERAYDH EQAPKRITAK YERDRIKALK  420
GEESISLANL NSCIAFLDNV RDCRVDTYLS TLGQKEGPHG LSNLVENVFA SYHEAEQLLS  480
FPYPEENNLI QDKDNVVLIK NLLDNISDLQ RFLKPLWGMG DEPDKDERFY GEYNYIRGAL  540
DQVIPLYNKV RNYLTRKPYS TRKVKLNFGN SQLLSGWDRN KEKDNSCVIL RKGQNFYLAI  600
MNNRHKRSFE NKMLPEYKEG EPYFEKMDYK FLPDPNKMLP KVFLSKKGIE IYKPSPKLLE  660
QYGHGTHKKG DTFSMDDLHE LIDFFKHSIE AHEDWKQFGF KFSDTATYEN VSSFYREVED  720
QGYKLSFRKV SESYVYSLID QGKLYLFQIY NKDFSPCSKG TPNLHTLYWR MLFDERNLAD  780
VIYKLDGKAE IFFREKSLKN DHPTHPAGKP IKKKSRQKKG EESLFEYDLV KDRRYTMDKF  840
QFHVPITMNF KCSAGSKVND MVNAHIREAK DMHVIGIDRG ERNLLYICVI DSRGTILDQI  900
SLNTINDIDY HDLLESRDKD RQQEHRNWQT IEGIKELKQG YLSQAVHRIA ELMVAYKAVV  960
ALEDLNMGFK RGRQKVESSV YQQFEKQLID KLNYLVDKKK RPEDIGGLLR AYQFTAPFKS  1020
FKEMGKQNGF LFYIPAWNTS NIDPTTGFVN LFHVQYENVD KAKSFFQKFD SISYNPKKDW  1080
FEFAFDYKNF TKKAEGSRSM WILCTHGSRI KNFRNSQKNG QWDSEEFALT EAFKSLFVRY  1140
EIDYTADLKT AIVDEKQKDF FVDLLKLFKL TVQMRNSWKE KDLDYLISPV AGADGRFFDT  1200
REGNKSLPKD ADANGAYNIA LKGLWALRQI RQTSEGGKLK LAISNKEWLQ FVQERSYEKD  1260

SEQ ID NO: 14           moltype = AA  length = 664
FEATURE                 Location/Qualifiers
source                  1..664
                        mol_type = protein
                        organism = Prevotella disiens
SEQUENCE: 14
NSYKEDKKRL NKVIIAYIEQ IKQTNIKKSI IESISKYPNI SDDDKVTPSS LLEKIKKVSI  60
DSYNGILSFK SFQSVNKEVI DNLLKTISPL KNKAEFLDLI NKDYQIFTEV QAVIDEICKQ  120
KTFIYFPISN VELEKEMGDK DKPLCLFQIS NKDLSFAKTF SANLRKKRGA ENLHTMLFKA  180
LMEGNQDNLD LGSGAIFYRA KSLDGNKPTH PANEAIKCRN VANKDKVSLF TYDIYKNRRY  240
MENKFLFHLS IVQNYKAAND SAQLNSSATE YIRKADDLHI IGIDRGERNL LYYSVIDMKG  300
NIVEQDSLNI IRNNDLETDY HDLLDKREKE RKANRQNWEA VEGIKDLKKG YLSQAVHQIA  360
QLMLKYNAII ALEDLGQMFV TRGQKIEKAV YQQFEKSLVD KLSYLVDKKR PYNELGGILK  420
AYQLASSITK NNSDKQNGFL FYVPAWNTSK IDPVTGFTDL LRPKAMTIKE AQDFFGAFDN  480
ISYNDKGYFE FETNYDKFKI RMKSAQTRWT ICTFGNRIKR KKDKNYWNYE EVELTEEFKK  540
LFKDSNIDYE NCNLKEEIQN KDNRKFFDDL IKLLQLTLQM RNSDDKGNDY IISPVANAEG  600
QFFDSRNGDK KLPLDADANG AYNIARKGLW NIRQIKQTKN KDDLNLSISS TEWLDFVREK  660
PYLK                                                               664

SEQ ID NO: 15           moltype = AA  length = 1484
FEATURE                 Location/Qualifiers
SITE                    1073
                        note = misc_feature - Xaa can be any naturally occurring
                         amino acid
```

-continued

```
source                 1..1484
                       mol_type = protein
                       note = Peregrinibacteria bacterium
                       organism = unidentified
SEQUENCE: 15
MSNFFKNFTN LYELSKTLRF ELKPVGDTLT NMKDHLEYDE KLQTFLKDQN IDDAYQALKP  60
QFDEIHEEFI TDSLESKKAK EIDFSEYLDL FQEKKELNDS EKKLRNKIGE TFNKAGEKWK  120
KEKYPQYEWK KGSKIANGAD ILSCQDMLQF IKYKNPEDEK IKNYIDDTLK GFFTYFGGFN  180
QNRANYYETK KEASTAVATR IVHENLPKFC DNVIQFKHII KRKKDGTVEK TERKTEYLNA  240
YQYLKNNNKI TQIKDAETEK MIESTPIAEK IFDVYYFSSC LSQKQIEEYN RIIGHYNLLI  300
NLYNQAKRSE GKHLSANEKK YKDLPKFKTL YKQIGCGKKK DLFYTIKCDT EEEANKSRNE  360
GKESHSVEEI INKAQEAINK YFKSNNDCEN INTVPDFINY ILTKENYEGV YWSKAAMNTI  420
SDKYFANYHD LQDRLKEAKV FQKADKKSED DIKIPEAIEL SGLFGVLDSL ADWQTTLFKS  480
SILSNEKLKI ITDSQTPSEA LLKMIFNDIE KNMESFLKET NDIITLKKYK GNKEGTEKIK  540
QWFDYTLAIN RMLKYFLVKE NKIKGNSLDT NISEALKTLI YSDDAEWFKW YDALRNYLTQ  600
KPQDEAKENK LKLNFDNPSL AGGWDVNKEC SNFCVILKDK NEKKYLAMIK KGENTLFQKE  660
WTEGRGKNLT KKSNPLFEIN NCEILSKMEY DFWADVSKMI PKCSTQLKAV VNHFKQSDNE  720
FIFPIGYKVT SGEKFREECK ISKQDFELNN KVFNKNELSV TAMRYDLSST QEKQYIKAFQ  780
KEYWELLFKQ EKRDTKLTNN EIFNEWINFC NKKYSELLSW ERKYKDALTN WINFCKYFLS  840
KYPKTTLFNY SFKESENYNS LDEFYRDVDI CSYKLNINTT INKSILDRLV EEGKLYLFEI  900
KNQDSNDGKS IGHKNNLHTI YWNAIFENFD NRPKLNGEAE IFYRKAISKD KLGIVKGKKT  960
KNGTWIIKNY RFSKEKFILH VPITLNFCSN NEYVNDIVNT KFYNFSNLHF LGIDRGEKHL  1020
AYYSLVNKNG EIVDQGTLNL PFTDKDGNQR SIKKEKYFYN KQEDKWEAKE VDXWNYNDLL  1080
DAMASNRDMA RKNWQRIGTI KEAKNGYVSL VIRKIADLAV NNERPAFIVL EDLNTGFKRS  1140
RQKIDKSVYQ KFELALAKKL NFLVDKNAKR DEIGSPTKAL QLTPPVNNYG DIENKKQAGI  1200
MLYTRANYTS QTDPATGWRK TIYLKAGPEE TTYKKDGKIK NKSVKDQIIE TFTDIGFDGK  1260
DYYFEYDKGE FVDEKTGEIK PKKWRLYSGE NGKSLDRFRG EREKDKYEWK IDKIDIVKIL  1320
DDLFVNFDKN ISLLKQLKEG VELTRNNEHG TGESLRFAIN LIQQIRNTGN NERDNDFILS  1380
PVRDENGKHF DSREYWDKET KGEKISMPSS GDANGAFNIA RKGIIMNAHI LANSDSKDLS  1440
LFVSDEEWDL HLNNKTEWKK QLNIFSSRKA MAKRKKKRPA ATKK                 1484

SEQ ID NO: 16          moltype = AA  length = 1245
FEATURE                Location/Qualifiers
source                 1..1245
                       mol_type = protein
                       organism = Porphyromonas macacae
SEQUENCE: 16
MKTQHFFEDF TSLYSLSKTI RFELKPIGKT LENIKKNGLI RRDEQRLDDY EKLKKVIDEY  60
HEDFIANILS SFSFSEEILQ SYIQNLSISE ARAKIEKTMR DTLAKAFSED ERYKSIFKKE  120
LVKKDIPVWC PAYKSLCKKF DNFTTSLVPF HENRKNLYTS NEITASIPYR IVHVNLPKFI  180
QNIEALCELQ KKMGADLYLE MMENLRNVWP SFVKTPDDLC NLKTYNHLMV QSSISEYNRF  240
VGGYSTEDGT KHQGINEWIN IYRQRNKEMR LPGLVFLHKQ ILAKVDSSSF ISDTLENDDQ  300
VFCVLRQFRK LFWNTVSSKE DDAASLKDLF CGLSGYDPEA IYVSDAHLAT ISKNIFDRWN  360
YISDAIRRKT EVLMPRKKES VERYAEKISK QIKKRQSYSL AELDDLLAHY SEESLPAGFS  420
LLSYFTSLGG QKYLVSDGEV ILYEEGSNIW DEVLIAFRDL QVILDKDFTE KKLGKDEEAV  480
SVIKKALDSA LRLRKFFDLL SGTGAEIRRD SSFYALYTDR MDKLKGLLKM YDKVRNYLTK  540
KPYSIEKFKL HFDNPSLLSG WDKNKELNNL SVIFRQNGYY YLGIMTPKGK NLFKTLPKLG  600
AEEMFYEKME YKQIAEPMLM LPKVFFPKKT KPAFAPDQSV VDIYNKKTFK TGQKGFNKKD  660
LYRLIDFYKE ALTVHEWKLF NFSFSPTEQY RNIGEFFDEV REQAYKVSMV NVPASYIDEA  720
VENGKLYLFQ IYNKDFSPYS KGIPNLHTLY WKALFSEQNQ SRVYKLCGGG ELFYRKASLH  780
MQDTTVHPKG ISIHKKNLNK KGETSLFNYD LVKDKRFTED KFFFHVPISI NYKNKKITNV  840
NQMVRDYIAQ NDDLQHGIDR GERNLLYISR IDTRGNLLEQ FSLNVIESDK GDLRTDYQKI  900
LGDREQERLR RRQEWKSIES IKDLKDGYMS QVVHKICNMV VEHKAIVVLE NLNLSFMKGR  960
KKVEKSVYEK FERMLVDKLN YLVVDKKNLS NEPGGLYAAY QLTNPLFSFE ELHRYPQSGI  1020
LFFVDPWNTS LTDPSTGFVN LLGRINYTNV GDARKFFDRF NAIRYDGKGN ILFDLDLSRF  1080
DVRVETQRKL WTLTTFGSRI AKSKKSGKWM VERIENLSLC FLELFEQFNI GYRVEKDLKK  1140
AILSQDRKEF YVRLIYLFNL MMQIRNSDGE EDYILSPALN EKNLQFDSRL IEAKDLPVDA  1200
DANGAYNVAR KGLMVVQRIK RGDHESIHRI GRAQWLRYVQ EGIVE                1245

SEQ ID NO: 17          moltype = AA  length = 1250
FEATURE                Location/Qualifiers
source                 1..1250
                       mol_type = protein
                       organism = Smithella sp.
SEQUENCE: 17
MQTLFENFTN QYPVSKTLRF ELIPQGKTKD FIEQKGLLKK DEDRAEKYKK VKNIIDEYHK  60
DFIEKSLNGL KLDGLEKYKT LYLKQEKDDK DKKAFDKEKE NLRKQIANAF RNNEKFKTLF  120
AKELIKNDLM SFACEEDKKN VKEFEAFTTY FTGFHQNRAN MYVADEKRTA IASRLIHENL  180
PKFIDNIKIF EKMKKEAPEL LSPFNQTLKD MKDVIKGTTL EEIFSLDYFN KTLTQSGIDI  240
YNSVIGGRTP EEGKTKIKGL NEYINTDFNQ KQTDKKKRQP KFKQLYKQIL SDRQSLSFIA  300
EAFKNDTEIL EAIEKFYVNE LLHFSNEGKS TNVLDAIKNA VSNLESFNLT KMYFRSGASL  360
TDVSRKVFGE WSIINRALDN YYATTYPIKP REKSEKYEER KEKWLKQDFN VSLIQTAIDE  420
YDNETVKGKN SGKVIADYFA KFCDDKETDL IQKVNEGYIA VKDLLNTPCP ENEKLGSNKD  480
QVKQIKAFMD SIMDIMHFVR PLSLKDTDKE KDETFYSLFT PLYDHLTQTI ALYNKVRNYL  540
TQKPYSTEKI KLNFENSTLL GGWDLNKETD NTAIILRKDN LYYLGIMDKR HNRIFRNVPK  600
ADKKDFCYEK MVYKLLPGAN KMLPKVFFSQ SRIQEFTPSA KLLENYANET HKKGDNFNLN  660
HCHKLIDFFK DSINKHEDWK NFDFRFSATS TYADLSGFYH EVEHQGYKIS FQSVADSFID  720
DLVNEGKLYL FQIYNKDFSP FSKGKPNLHT LYWKMLFDEN NLKDVVYKLN GEAEVFYRKK  780
SIAEKNTTIH KANESIINKN PDNPKATSTF NYDIVKDKRY TIDKFQFHIP ITMNFKAEGI  840
```

-continued

```
FNMNQRVNQF LKANPDINII GIDRGERHLL YYALINQKGK ILKQDTLNVI ANEKQKVDYH  900
NLLDKKEGDR ATARQEWGVI ETIKELKEGY LSQVIHKLTD LMIENNAIIV MEDLNFGFKR  960
GRQKVEKQVY QKFEKMLIDK LNYLVDKNKK ANELGGLLNA FQLANKFESF QKMGKQNGFI  1020
FYVPAWNTSK TDPATGFIDF LKPRYENLNQ AKDFFEKFDS IRLNSKADYF EFAFDFKNFT  1080
EKADGGRTKW TVCTTNEDRY QWNRALNNNR GSQEKYDITA ELKSLFDGKV DYKSGKDLKQ  1140
QIASQESADF FKALMKNLSI TLSLRHNNGE KGDNEQDYIL SPVADSKGRF FDSRKADDDM  1200
PKNADANGAY HIALKGLWCL EQISKTDDLK KVKLAISNKE WLEFVQTLKG             1250

SEQ ID NO: 18          moltype = DNA  length = 3987
FEATURE                Location/Qualifiers
source                 1..3987
                       mol_type = other DNA
                       organism = synthetic construct
SEQUENCE: 18
atggccggga gcaagaagcg ccggataaag caggacacgc agttcgaggg cttcaccaac  60
ctgtaccaag tctccaagac gctccggttc gagcttatcc cgcaagggaa gaccctgaaa  120
cacatccagg aacaaggttt catcgaggag gacaaggccc gcaacgacca ctacaaggag  180
ctcaagccca taatcgatcg gatctacaag acgtacgccg accagtgcct ccaactggtg  240
cagctcgact gggagaacct gagcgccgcc attgacagct accgcaagga aaagacggag  300
gagacgcgca acgcccttat tgaggagcaa gccacctacc gcaacgccat ccacgactac  360
ttcatcgggc gcaccgacaa cctgacggac gcgatcaaca agcgccacgc ggaaatctac  420
aagggccttt tcaaggccga gctcttcaac gggaaggtcc taaaacagct cgggactgtc  480
acgacaaccg agcatgagaa cgccctcctt cgcagcttcg acaagttcac cacatacttc  540
tcgggcttct accggaaccg caagaacgtt ttcagcgccg aggacatctc caccgccatc  600
ccgcacagga tcgtccagga caacttcccc aagttcaagg agaactgcca catcttcacg  660
cgcctgatta cagccgtacc ttcacttcgt gagcacttcg agaacgtcaa aaaggccatc  720
gggatcttcg tctccacgtc catcgaggag gtattctctt tcccgttcta taaccagctc  780
ctgacccaga cgcagatcga cctctacaac cagctactgg gcggcatcag ccgggaggcc  840
gggaccgaga aaataaaggg cctcaacgaa gttctcaacc tggccatcca gaagaacgac  900
gagaccgcgc atatcatcgc atccctgccg catcgcttca ttcctttgtt caagcagata  960
ttgagcgacc ggaacaccct ctcgttcatc ctcgaagaat tcaagagcga cgaggaggtc  1020
attcagtctt tctgcaagta caagacgctc ctacggaatg agaatgtgct ggagaccgcg  1080
gaggcactct tcaatgagct gaactccatt gacctgaccc acatcttcat tagccacaag  1140
aaactggaga cgatctccag cgccctgtgc gaccactggg acactctccg caacgccctc  1200
tacgaacgcc ggatctccga acttaccggc aagataacta agtcggctaa ggagaaggtg  1260
caacggagcc tcaagcacga ggacatcaac cttcaggaaa tcatctcagc cgcgggcaag  1320
gagctgagcg aggcgtttaa gcagaaaaca tcggagatac tgagccacgc gcacgcggcc  1380
ctggatcaac cgctgccgac gactctcaag aagcaagagg agaaggaaat ccttaagtcc  1440
cagctcgact cgctgctcgg cctctatcac ttgctcgact ggttcgcggt tgatgagtcc  1500
aacgaggtgg acccggagtt ctccgcgcgc ctcacgggta ttaagctgga gatggagcca  1560
agcttaagct tctacaacaa ggcccgcaac tacgcgacca aaaaaccgta ctcagtcgag  1620
aaattcaagc tgaatttcca gatgcctaca ttggcgaggg ggtgggacgt gaaccgcgag  1680
aagaacaatg gagccatcct gttcgtcaaa aatgggttgt actacctggg catcatgccc  1740
aagcagaagg gccgttacaa ggccctgtca ttcgagccta ccgagaagac ctcggagggc  1800
ttcgacaaga tgtactacga ctatttcccg gacgccgcca agatgatccc gaagtgctcc  1860
acgcagctca aagccgtcac ggcccacttc cagacgcata ccacgccgat acttctgagc  1920
aacaacttca ttgagccgct agagatcacg aaggagatat acgacctaaa caaccccgaa  1980
aaggagccca agaagttcca gacagcctac gctaagaaga caggtgatca gaagggatat  2040
agggaggcac tctgcaagtg gatcgacttc acgcgcgact tcctgtcgaa atatacaaag  2100
acgaccagca ttgacctaag ttctctccgc ccatcctccc agtacaagga tctgggcgag  2160
tattatgcgg agctgaaccc attgctgtac cacatcagct tccagaggat cgccgagaag  2220
gagattatgg acgcggtgga gacggggaaa ctatacctgt tccaaatata taacaaggac  2280
ttcgctaaag ggcaccacgg gaagcccaac ctgcacacac tctactggac gggcttgttt  2340
tcgccagaaa atttggccaa gacttcgatc aagctcaacg gccaggcgga gttgttttac  2400
cgtcccaagt ctcgcatgaa gcgcatggcg catcgcctcg gagagaaaat gcttaacaag  2460
aagctcaagg atcagaagac gcccatacct gatacgttgt accaggaatt gtacgactac  2520
gtgaaccacc gcctatcgca cgacctctca gacgaggccc gcgccctcct cccaaacgtg  2580
attactaagg aggtttccca tgaaataatc aaggaccgac ggttcaccag cgacaaattt  2640
tttttccacg tgcctatcac gctcaattac caggcggcca actccccatc gaagttcaac  2700
cagcgcgtga acgcctacct taaggagcac ccggagaccc caatcatcgg gatcgaccgt  2760
ggcgagcgga acctgatcta tattacggtg atcgatagca ccgggaagat cctggagcag  2820
cgctccctga acacaatcca gcagtttgac taccagaaga aactcgacaa ccgggagaag  2880
gagcgcgtcg cagcccggca agcatggagt gtggtcggca ccataaagga cctgaaacag  2940
ggttacctaa gtcaagttat ccacgagatc gttgacctga tgatacacta tcaagccgta  3000
gtcgtgctgg agaacctcaa cttcgggttt aagtccaagc gcaccggcat cgcggagaag  3060
gcggtgtacc agcagttcga gaagatgctg atcgacaagc tgaactgcct ggtgctcaag  3120
gactaccctg cggagaaggt cggcggggtc ttgaacccgt accagctaac cgaccagttc  3180
acgagcttcg ccaaaatggg cacgcagtcc ggattcttgt tttatgtccc ggctccatat  3240
acaagtaaga tcgacccgct gacagggttt gttgacccat tcgtgtggaa gaccatcaag  3300
aaccacgaga gcaggaaaca cttcttagag ggcttcgact tcctgcatta cgacgttaag  3360
acaggcgact tcatcctgca cttcaagatg aaccgcaacc tgtcgttcca gaggggcctg  3420
cccggcttca tgcccgcctg ggatatcgtc tttgagaaga atgagacgca gttcgacgcg  3480
aaggggacgc cgttcatcgc tggaaagcgg atcgtgccgg tcatcgagaa ccaccgcttc  3540
acgggtcgct accgagattt ataccccgcc aacgaactaa ttgcgctgct ggaggagaag  3600
gggatcgtgt tccgagatgg cagcaacatt ctcccgaagc tgctggagaa cgacgactcg  3660
cacgctattg acacgatggt cgccctcata cggagcgtgc ttcagatgcg gaacagtaac  3720
gctgccacgg gcgaggacta cattaactcc cccgtccgcg acctcaacgg ggtctgcttc  3780
gatagccgct tccagaaccc ggagtggcct atggatgcgg acgcgaacgg ggcctaccac  3840
atcgccctca agggccaact cctgctcaac cacttgaagg aaagcaaaga cctcaaattg  3900
```

```
cagaatggca tcagtaacca ggactggctc gcgtacatcc aggaactgag aaacgggtcc  3960
aagaagcggc gtatcaagca agattga                                      3987

SEQ ID NO: 19          moltype = DNA  length = 3987
FEATURE                Location/Qualifiers
source                 1..3987
                       mol_type = other DNA
                       organism = synthetic construct
SEQUENCE: 19
atggcgggaa gcaaaaagcg ccggattaag caagacacgc agttcgaggg cttcacgaac  60
ctctaccaag tcagcaagac cctccggttc gagctgatac cacagggaaa gacgctcaag  120
cacatccagg aacagggctt catcgaggag gacaaggcgc gcaacgacca ctacaaggag  180
ttgaaaccga tcatcgaccg catctacaag acgtacgccg accagtgcct ccagctcgtg  240
cagctcgact gggagaacct ctccgccgcc attgactcgt accggaagga gaagactgag  300
gagacccgca acgccctgat cgaggagcaa gcaacctacc ggaacgccat ccacgactac  360
ttcatcggcc gcaccgacaa cctcaccgac gcgatcaaca agcggcacgc ggagatatac  420
aaagggctgt tcaaggcgga gctgttcaac ggcaaggtgc tcaagcagct agggacggtg  480
accacgaccg agcacgagaa cgcgctcctc cgcagcttcg acaagttcac cacctacttc  540
agcggcttct accggaaccg caagaatgtg ttcagcgcgg aggacatcag cacggccatc  600
ccgcaccgca tcgtccagga caacttcccg aagttcaagg agaactgcca catcttcacc  660
cgcctgataa ccgccgtccc ctccctgcgg gagcacttcg agaacgtcaa aaaggcaatt  720
gggatcttcg tctcgaccag cattgaggag gtgttcagct tccccttcta caaccagctc  780
ctcacccaga cgcagatcga cctgtacaat cagttgctcg gcgggataag ccgcgaggcg  840
ggaaccgaaa aaatcaaggg gctgaacgaa gtgttgaacc tcgccatcca gaagaacgac  900
gagaccgcgc acatcatcgc ctccctgccc caccggttca tcccgctgtt caagcagatc  960
ctctctgacc ggaacaccct gtccttcatt cttgaggagt tcaagtcgga cgaggaggtc  1020
atccagagct tctgcaagta caagacgctg ctacggaacg agaacgtgct ggagacggcg  1080
gaggcactgt tcaacgagct aaacagcatc gacctcacgc acatcttcat cagtcacaag  1140
aaactggaga ccatctcctc cgcgctgtgc gaccactggg acacgctcag gaacgcgctc  1200
tacgagcgcc gaatcagtga gctgacgggc aagatcacga agtccgcgaa ggagaaggtg  1260
cagcggtccc tcaagcacga ggacatcaac ctccaggaga tcatctcagc ggctgggaaa  1320
gagctgtccg aggcgttcaa gcagaaaacg agcgaaatcc tgtcccacgc gcacgcggcc  1380
ctggatcagc ctctgccgac gaccctcaag aaacaagaag aaaaggaaat cctcaagtcg  1440
cagctcgact cgctgctggg cctgtaccat ctcctcgact ggttcgccgt ggacgagagc  1500
aacgaggtgg accccgagtt ctccgcgcgg cttacgggga tcaagctgga gatggagccc  1560
agcctgtcct tctacaacaa ggcgcgcaac tacgccacca agaagcccta cagcgtggag  1620
aagttcaagc tcaacttcca gatgcccact ctcgcacgtg ggtgggacgt caaccgcgaa  1680
aaaaataatg gggcgatcct gttcgtcaag aacggcctgt actacttggg catcatgccg  1740
aaacagaagg gccgctacaa ggccctgagc ttcgaaccga ccgagaaaac gagcgagggg  1800
ttcgacaaga tgtactacga ctacttcccc gacgccgcga agatgattcc aaagtgctcc  1860
acgcagctta aggccgtgac ggcccacttc cagacgcaca cgaccccgat cctcctcagc  1920
aacaacttca tcgagcccct ggagatcacg aaggagatat acgacctgaa caacccggag  1980
aaggagccca agaaattcca gaccgcctac gccaagaaga caggcgacca aaagggttac  2040
agggaggccc tctgcaagtg gatcgacttc actagggact tcctgtccaa gtacaccaag  2100
actacctcta tcgacctgtc cagcctccgc ccgtcgtccc agtacaaaga tttgggcgag  2160
tattacgcgg agctgaaccc actgctctac cacatcagct tccagcgcat cgcggagaag  2220
gagatcatgg acgcagtgga gacgggcaag ctatacctat ttcagatata caacaaagac  2280
ttcgctaagg gacaccacgg caagcctaac ctgcacaccc tctactggac ggggctcttc  2340
agcccggaga acctcgccaa gacctcgatc aagctcaacg gccaggccga gctgttctac  2400
cggcccaagt cccgcatgaa gcggatggcc caccggctcg gggagaaaat gctcaacaag  2460
aaattgaagg accaaaaaac gccgataccc gacaccctat accaggagct gtacgactat  2520
gtgaaccacc gcctgagcca cgacctcagc gacgaggcgc gggccctcct gccgaacgtc  2580
atcacaaagg aggtcagcca cgagatcatc aaggaccggc gcttcacctc cgacaagttt  2640
ttctttcacg tgcccatcac gctcaactac caggccgcca actcgccgtc caagttcaac  2700
cagcgcgtga acgcctacct caaggagcac cccgagaccc cgatcatcgg gattgaccga  2760
ggggagcgga acctcatcta catcaccgtc atcgacagca ccgggaagat ccttgaacag  2820
cggtcgctca acaccatcca gcagttcgac taccagaaga aactcgacaa ccgggagaag  2880
gagagagtgg cggcccgcca ggcttggtcc gtcgtcggga cgattaagga cttgaaacaa  2940
ggttacctgt cgcaagtgat ccacgagatc gttgacctga tgatccacta ccaagccgtc  3000
gtggtcctgg agaacctcaa cttcggcttc aagagcaaac gaaccggcat cgcggagaag  3060
gccgtgtacc agcagttcga aaaaatgctg atcgacaagc tgaactgcct cgtgctcaag  3120
gactaccccg ctgagaaggt cggcggggtg ctgaacccgt accagctcac tgaccagttc  3180
accagcttcg caaagatggg cacccagtcc ggcttcctgt tctacgtgcc tgcgccatac  3240
acctcgaaga tcgacccgct caccgggttc gtggacccct tcgtctggaa gaccatcaag  3300
aaccacgaga gccgcaagca cttcctggag ggcttcgact tcctccacta cgacgtcaag  3360
accggggact tcatcctgca cttcaagatg aaccgcaacc tcagtttcca gcgcggcctg  3420
ccggggttca tgcccgcttg ggatatagtc ttcgagaaga atgagacgca gttcgacgcg  3480
aagggcaccc cgttcatcgc cgggaagcgc atcgtgccgg tcatcgagaa ccaccggttc  3540
accgggcgct accgcgacct atacccggcg aacgagttga tcgccctcct ggaggagaag  3600
ggcatcgtgt tccgcgacgg ctccaacatc ctcccgaagc tgctcgaaaa cgacgactcc  3660
cacgccatcg acacgatggt cgcgctgatc cggtcggtgc tccagatgcg gaactccaac  3720
gccgcgacgg gcgaggacta catcaacagt ccggtccgcg atctgaacgg cgtctgcttc  3780
gactcccggt tccagaaccc cgagtggccg atggacgcgg acgcgaacgg cgcataccac  3840
atcgccctaa aagggcaatt gctgctcaac cacctcaagg aatccaaaga cctaaagctc  3900
cagaacggca tctccaacca ggactggctg gcgtacatcc aggaactgcg gaacgggagc  3960
aaaaaacgtc ggatcaagca agattga                                      3987

SEQ ID NO: 20          moltype = DNA  length = 3987
FEATURE                Location/Qualifiers
```

-continued

```
source                1..3987
                      mol_type = other DNA
                      organism = synthetic construct
SEQUENCE: 20
atggcgggct ccaagaaacg ccggattaag caagataccc agttcgaggg gttcacgaac  60
ctctaccaag tgagcaagac cctccgattc gaactgattc ctcaggggaa gaccctcaag  120
cacatccagg agcaagggtt catcgaggag gacaaggcgc ggaacgacca ctacaaggaa  180
ctcaaaccca tcatcgaccg catctacaag acctacgccg atcagtgcct ccagctcgtg  240
cagttggact gggagaacct cagcgcggcc attgactcct accggaagga gaaaacggag  300
gagacgcgca acgcgctcat cgaggaacag gcaacctatc gcaacgccat ccacgactac  360
ttcatcggga ggactgacaa cctcactgac gcgattaaca agcgccacgc ggagatatac  420
aagggactct tcaaagcgga gctgtttaac ggcaaggttc tcaagcaact cggcactgtg  480
accacgaccg agcatgagaa cgccctgctc cgctccttcg acaagttcac cacctacttc  540
tccgggttct accgcaaccg caagaatgtc ttcagcgcgg aggacatcag cacggccatt  600
ccacatcgaa tcgtccaaga taacttcccg aagttcaagg agaactgcca catcttcacc  660
cgactcatta ctgctgtacc gtcgttacgc gaacacttcg agaacgtcaa gaaggcaatt  720
ggaatcttcg tctctacgtc aatagaggag gtgttcagct tccctttcta caaccagctc  780
cttacgcaga cccagataga cctgtacaat cagctcctcg gtgggatcag ccgggaggcg  840
gggactgaga agattaaagg gctcaacgag gtcttgaacc tggccatcca aaaaaacgat  900
gagacggcgc acatcatcgc ctcgctgccc caccggttca tcccgctgtt caagcagatc  960
ctcagtgaca ggaacacctt gagctttatc ctagaggagt tcaagagcga cgaggaggtg  1020
atccagagct tctgcaagta caaaaccctg ctgaggaacg agaacgtcct ggagacggcg  1080
gaggcgctgt tcaacgagct gaactctatc gacttaactc acatattcat ctcgcacaag  1140
aagctggaga ctattagctc tgcactctgc gaccactggg acaccctccg caacgcgctc  1200
tacgagcgcc gcatctcgga gctgaccggg aagatcacca aatccgcgaa ggaaaaggtc  1260
cagcgttccc tcaaacacga ggatattaac ttacaggaga ttatctcagc ggctgggaag  1320
gagttgtcag aggcgttcaa gcagaaaact tccgagatcc tgagccacgc gcacgcagcg  1380
ctcgaccagc ctctgcccac caccctcaaa aagcaggaag aaaaagagat cctcaagagc  1440
cagttggact ccctgctggg gctctatcac cttctcgact ggttcgccgt cgatgagtcg  1500
aacgaggtgg accccgagtt ctccgcccgg ctgaccggca tcaagctaga gatggagccg  1560
tccctcagct tctacaataa ggcccgcaac tacgcgacca aaaaacccta cagcgtggag  1620
aagttcaagc tgaacttcca gatgccgacc ttagcacgcg gttgggacgt aaacagggag  1680
aagaacaatg gagccatcct gttcgtcaag aacgggcttt actacctcgg gataatgccc  1740
aagcagaagg gccgctacaa ggccctttcc ttcgagccga cggagaaaac ctccgagggg  1800
ttcgacaaga tgtactacga ctacttcccc gacgccgcca agatgatccc gaagtgctca  1860
acgcagctaa aagccgtgac cgcccacttc cagacccaca cgacgccgat cctgctgagc  1920
aacaacttca tcgagcccct tgagatcact aaggagatat acgacctgaa caaccccgag  1980
aaggagccca agaagtttca aaccgcctac gccaaaaaaa ctggcgacca aaagggctac  2040
agggaggcgc tgtgtaagtg gatcgacttc acacgcgact tcctttcgaa gtatacgaag  2100
acaacctcta ttgacctgag cagcctgcgt cctagctccc agtacaaaga tttgggcgag  2160
tactacgcgg agcttaatcc actactctac cacatctcat tccagcgcat cgctgagaag  2220
gaaatcatgg acgcggtgga gacaggcaaa ctgtacctct tccagatata caacaaagac  2280
ttcgctaagg ggcaccacgg gaagcccaac cttcatacgc tctactggac gggcctattc  2340
agccccgaaa atctggccaa gacctccatc aagctgaacg gccaagcgga gctgttctac  2400
agacccaaga gccggatgaa gcggatggcc cacaggctcg gcgagaaaat gcttaacaaa  2460
aagttgaagg accagaaaac ccctatcccc gacaccctct accaggaact gtacgactac  2520
gtgaaccaca ggctctcgca cgacctttcc gacgaggccc gtgccctact cccgaacgtc  2580
attaccaaag aggtttcgca cgagatcatc aaggaccggc ggttcacgag cgacaagttt  2640
ttctttcacg tccccatcac ccttaactac caggcggcca actccccatc caagttcaac  2700
cagcgtgtga atgcctacct caaggagcac ccagagaccc cgatcattgg gatcgaccgg  2760
ggcgagcgga acctgatcta catcaccgtc atcgactcga cgggcaagat tcttgagcag  2820
agatcgttga ataccataca gcagttcgac taccagaaga aactcgacaa ccgcgagaag  2880
gagcgcgtgg cggcccgcca ggcgtggtcc gtcgttggga cgattaagga cttgaaacaa  2940
ggttatctgt cccaagtcat ccacgagatc gttgatctga tgatccacta tcaggcagtg  3000
gtggtgctgg agaatctcaa cttcggcttc aagagtaagc ggacgggaat cgccgagaag  3060
gccgtgtacc agcagttcga gaagatgctg atcgacaagc tcaactgcct tgtgctgaaa  3120
gactacccgg ccgagaaggt cggcggcgtc ctcaacccgt accaacttac cgaccagttc  3180
acctccttcg ccaagatggg cactcagtcc gggttcttgt tctacgtccc cgcaccttac  3240
acctctaaga tcgaccctct gactggcttc gtagatccat tcgtgtggaa gaccattaag  3300
aaccacgaga gccgcaagca cttcctggag ggcttcgact tcctgcacta cgacgtgaag  3360
accggggact tcatccttca cttcaagatg aaccggaacc tcagcttcca gcggggcctg  3420
ccggggttca tgcccgcctg ggacatcgtg ttcgagaaga acgagaccca gttcgacgcg  3480
aagggcacgc ccttcatcgc cgggaagcgt atcgtgccgg tgatcgagaa ccatcgtttc  3540
acgggtcgct accgtgacct ctacccggcg aacgagctta tcgcactcct ggaggagaag  3600
ggcatcgtct tccgggacgg ctccaacatc ctcccgaaac tgctggaaaa cgacgactct  3660
cacgccatcg acacgatggt ggccctcatc cggtccgtgc tccaaatgcg gaacagcaac  3720
gccgccaccg gtgaggacta catcaacagc ccggtccggg atctgaacgg ggtgtgcttc  3780
gattcgcggt tccagaatcc tgagtggccg atggacgcgg atgcaaacgg ggcgtaccac  3840
atcgcgctca agggccagtt acttctgaac caccttaagg agtctaaaga tttgaaactc  3900
cagaacggga tctcgaacca ggactggctg gcctacatcc aagagttgcg gaacggcagc  3960
aagaagcggc ggattaagca agattag                                    3987

SEQ ID NO: 21         moltype = DNA  length = 1592
FEATURE               Location/Qualifiers
source                1..1592
                      mol_type = other DNA
                      organism = Medicago truncatula
```

```
SEQUENCE: 21
actgttaata atttttaaac gtcagcgcac taaaaaaacg aaaagacgga cacgtgaaaa  60
taaaaaacac acactagttt atgacgcaat actattttac ttatgatttg ggtacattag  120
acaaaaccgt gaaagagatg tatcagctat gaaacctgta tacttcaata cagagactta  180
ctcatatcgg atacgtacgc acgaagtatc atattaatta ttttaatttt taataaatat  240
tttatcggat acttatgtga tactctacat atacacaagg atatttctaa gatactttat  300
agatacgtat cctagaaaaa catgaagagt aaaaaagtga gacaatgttg taaaaattca  360
ttataaatgt atatgattca attttagata tgcatcagta taattgattc tcgatgaaac  420
acttaaaatt atatttcttg tggaagaacg tagcgagaga ggtgattcag ttagacaaca  480
ttaaataaaa ttaatgttaa gttcttttaa tgatgtttct ctcaatatca catcatatga  540
aaatgtaata tgatttataa gaaaattttt aaaaaaattta ttttaataat cacatgtact  600
attttttaaa aattgtatct tttataataa tacaataata aagagtaatc agtgttaatt  660
tttcttcaaa tataagtttt attataaatc attgttaacg tatcataagt cattaccgta  720
tcgtatctta attttttttt aaaaaccgct aattcacgta cccgtattgt attgtacccg  780
cacctgtatc acaatcgatc ttagttagaa gaattgtctc gaggcggtgc aagacagcat  840
ataatagacg tggactctct tataccaaac gttgtcgtat cacaaagggt taggtaacaa  900
gtcacagttt gtccacgtgt cacgttttaa ttggaagagg tgccgttggc gtaatataac  960
agccaatcga tttttgctat aaaagcaaat caggtaaact aaacttcttc attcttttct  1020
tccccatcgc tacaaaaccg gttcctttgg aaaagagatt cattcaaacc tagcacccaa  1080
ttccgtttca aggtataatc tactttctat tcttcgatta ttttattatt attagctact  1140
atcgtttaat cgatcttttc ttttgatccg tcaaatttaa attcaattag ggttttgttc  1200
ttttctttca tctgattgaa atccttctga attgaaccgt ttacttgatt ttactgttta  1260
ttgtatgatt taatcctttg tttttcaaag acagtcttta gattgtgatt aggggttcat  1320
ataaattttt agatttggat ttttgtattg tatgattcaa aaaatacgtc ctttaattag  1380
attagtacat ggatattttt tacccgattt attgattgtc agggagaatt tgatgagcaa  1440
gttttttga tgtctgttgt aaattgaatt gattataatt gctgatctgc tgcttccagt  1500
tttcataacc catattcttt taaccttgtt gtacacacaa tgaaaaattg gtgattgatt  1560
catttgtttt tctttgtttt ggattataca gg                                1592

SEQ ID NO: 22          moltype = DNA  length = 2000
FEATURE                Location/Qualifiers
source                 1..2000
                       mol_type = other DNA
                       organism = Zea mays
SEQUENCE: 22
gtcgtgcccc tctctagaga taaagagcat tgcatgtcta aagtataaaa aattaccaca  60
tattttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
ctaattttta gtacatccat tttattcttt ttagtctcta aatttttaa aactaaaact  420
ctattttagt tttttattta ataatttaga tataaaatga aataaaataa attgactaca  480
aataaaacaa ataccttta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacaccccct ccacaccctc tttccccaac ctcgtgttcg ttcggagcgc  900
acacacacgc aaccagatct cccccaaatc cagccgtcgg cacctccgct tcaaggtacg  960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc                                              2000

SEQ ID NO: 23          moltype = AA  length = 228
FEATURE                Location/Qualifiers
source                 1..228
                       mol_type = protein
                       organism = Rattus norvegicus
SEQUENCE: 23
SSETGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPHVT LFIYIARLYH  120
```

-continued

```
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLK              228

SEQ ID NO: 24          moltype = AA  length = 199
FEATURE                Location/Qualifiers
source                 1..199
                       mol_type = protein
                       organism = Homo sapiens
SEQUENCE: 24
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                               199

SEQ ID NO: 25          moltype = DNA  length = 621
FEATURE                Location/Qualifiers
source                 1..621
                       mol_type = other DNA
                       organism = Petromyzon marinus
SEQUENCE: 25
acagatgcag agtatgtgag aattcacgaa aagctggaca tctatacctt caagaagcag  60
ttctttaaca ataagaagtc tgtgagccat aggtgctacg tgctgttcga gctgaagaga  120
aggggtgaaa gaagggcatg tttttggggg tatgctgtga acaagcccca gtctggaact  180
gagagaggca ttcacgccga aattttcagc atcagaaagg tggaggaata cctgagggat  240
aaccctggac agtttacaat taattggtat tctagctggt ctccatgcgc tgactgtgcc  300
gagaagatcc tggaatggta caaccaggag ctgagaggaa atggccatac cctgaagatt  360
tgggcctgca agctgtacta tgaaaagaac gcaagaaatc agatcggact gtggaacctg  420
agggataatg gtgtggggct gaacgtgatg gtgtccgagc actatcagtg ctgtagaaag  480
attttcattc agtcctcaca taatcagctg aacgagaata gatggctgga aaagactctg  540
aagagggctg agaagagaag gtccgaactg tcaattatga tccaggtgaa gatcctgcac  600
accactaagt cacctgccgt g                                            621

SEQ ID NO: 26          moltype = AA  length = 160
FEATURE                Location/Qualifiers
source                 1..160
                       mol_type = protein
                       organism = synthetic construct
SEQUENCE: 26
FERNYDPREL RKETYLLYEI KWGKSGKLWR HWCQNNRTQH AEVYFLENIF NARRFNPSTH  60
CSITWYLSWS PCAECSQKIV DFLKEHPNVL EIYVARLYYH EDERNRQGLR DLVNSGVTIR  120
IMDLPDYNYC WKTFVSDQGG DEDYWPGHFA PWIKQYSLKL                        160

SEQ ID NO: 27          moltype = AA  length = 207
FEATURE                Location/Qualifiers
source                 1..207
                       mol_type = protein
                       organism = synthetic construct
SEQUENCE: 27
TDAEYVRIHE KLDIYTFKKQ FSNNKKSVSH RCYVLFELKR RGERRACFWG YAVNKPQSGT  60
ERGIHAEIFS IRKVEEYLRD NPGQFTINWY SSWSPCADCA EKILEWYNQE LRGNGHTLKI  120
WVCKLYYEKN ARNQIGLWNL RDNGVGLNVM VSEHYQCCRK IFIQSSHNQL NENRWLEKTL  180
KRAEKRRSEL SIMFQVKILH TTKSPAV                                      207

SEQ ID NO: 28          moltype = AA  length = 228
FEATURE                Location/Qualifiers
source                 1..228
                       mol_type = protein
                       organism = synthetic construct
SEQUENCE: 28
SSKTGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPNVT LFIYIARLYH  120
LANPRNRQGL RDLISSGVTI QIMTEQESGY CWHNFVNYSP SNESHWPRYP HLWVRLYVLE  180
LYCIILGLPP CLNILRRKQS QLTSFTIALQ SCHYQRLPPH ILWATGLK              228

SEQ ID NO: 29          moltype = AA  length = 162
FEATURE                Location/Qualifiers
source                 1..162
                       mol_type = protein
                       organism = synthetic construct
SEQUENCE: 29
SFERNYDPRE LRKETYLLYE IKWGKSGKLW RHWCQNNRTQ HAEVYFLENI FNARRFNPST  60
HCSITWYLSW SPCAECSQKI VDFLKEHPNV NLEIYVARLY YPENERNRQG LRDLVNSGVT  120
IRIMDLPDYN YCWKTFVSDQ GGDEDYWPGH FAPWIKQYSL KL                     162

SEQ ID NO: 30          moltype = AA  length = 166
FEATURE                Location/Qualifiers
source                 1..166
                       mol_type = protein
                       organism = Escherichia coli
```

SEQUENCE: 30
SEVEFSHEYW MRHALTLAKR AWDEREVPVG AVLVHNNRVI GEGWNRPIGR HDPTAHAEIM 60
ALRQGGLVMQ NYRLIDATLY VTLEPCVMCA GAMIHSRIGR VVFGARDAKT GAAGSLMDVL 120
HHPGMNHRVE ITEGILADEC AALLSDFFRM RRQEIKAQKK AQSSTD 166

SEQ ID NO: 31 moltype = AA length = 166
FEATURE Location/Qualifiers
source 1..166
mol_type = protein
organism = synthetic construct
SEQUENCE: 31
SEVEFSHEYW MRHALTLAKR ARDEREVPVG AVLVLNNRVI GEGWNRAIGL HDPTAHAEIM 60
ALRQGGLVMQ NYRLIDATLY VTFEPCVMCA GAMIHSRIGR VVFGVRNAKT GAAGSLMDVL 120
HYPGMNHRVE ITEGILADEC AALLCYFFRM PRQVFNAQKK AQSSTD 166

SEQ ID NO: 32 moltype = AA length = 166
FEATURE Location/Qualifiers
source 1..166
mol_type = protein
organism = synthetic construct
SEQUENCE: 32
SEVEFSHEYW MRHALTLAKR AWDEREVPVG AVLVLNNRVI GEGWNRSIGL HDPTAHAEIM 60
ALRQGGLVMQ NYRLIDATLY VTFEPCVMCA GAMIHSRIGR VVFGVRNAKT GAAGSLMDVL 120
HYPGMNHRVE ITEGILADEC AALLCYFFRM RRQVFNAQKK AQSSTD 166

SEQ ID NO: 33 moltype = AA length = 166
FEATURE Location/Qualifiers
source 1..166
mol_type = protein
organism = synthetic construct
SEQUENCE: 33
SEVEFSHEYW MRHALTLAKR ALDEREVPVG AVLVLNNRVI GEGWNRAIGL HDPTAHAEIM 60
ALRQGGLVMQ NYRLIDATLY VTFEPCVMCA GAMIHSRIGR VVFGVRNAKT GAAGSLMDVL 120
HYPGMNHRVE ITEGILADEC NALLCYFFRM RRQVFNAQKK AQSSTD 166

SEQ ID NO: 34 moltype = AA length = 166
FEATURE Location/Qualifiers
source 1..166
mol_type = protein
organism = synthetic construct
SEQUENCE: 34
SEVEFSHEYW MRHALTLAKR ALDEREVPVG AVLVLNNRVI GEGWNRAIGL HDPTAHAEIM 60
ALRQGGLVMQ NYRLIDATLY VTFEPCVMCA GAMIHSRIGR VVFGVRNAKT GAAGSLMDVL 120
HYPGMNHRVE ITEGILADEC NALLCYFFRM PRQVFNAQKK AQSSTD 166

SEQ ID NO: 35 moltype = AA length = 1763
FEATURE Location/Qualifiers
source 1..1763
mol_type = protein
organism = synthetic construct
SEQUENCE: 35
SEVEFSHEYW MRHALTLAKR AWDEREVPVG AVLVHNNRVI GEGWNRPIGR HDPTAHAEIM 60
ALRQGGLVMQ NYRLIDATLY VTLEPCVMCA GAMIHSRIGR VVFGARDAKT GAAGSLMDVL 120
HHPGMNHRVE ITEGILADEC AALLSDFFRM RRQEIKAQKK AQSSTDSGGS SGGSSGSETP 180
GTSESATPES SGGSSGGSSE VEFSHEYWMR HALTLAKRAR DEREVPVGAV LVLNNRVIGE 240
GWNRAIGLHD PTAHAEIMAL RQGGLVMQNY RLIDATLYVT FEPCVMCAGA MIHSRIGRVV 300
FGVRNAKTGA AGSLMDVLHY PGMNHRVEIT EGILADECAA LLCYFFRMPR QVFNAQKKAQ 360
SSTDSGGSSG GSSGSETPGT SESATPESSG GSSGGSDKKY SIGLAIGTNS VGWAVITDEY 420
KVPSKKFKVL GNTDRHSIKK NLIGALLFDS GETAEATRLK RTARRRYTRR KNRICYLQEI 480
FSNEMAKVDD SFFHRLEESF LVEEDKKHER HPIFGNIVDE VAYHEKYPTI YHLRKKLVDS 540
TDKADLRLIY LALAHMIKFR GHFLIEGDLN PDNSDVDKLF IQLVQTYNQL FEENPINASG 600
VDAKAILSAR LSKSRRLENL IAQLPGEKKN GLFGNLIALS LGLTPNFKSN FDLAEDAKLQ 660
LSKDTYDDDL DNLLAQIGDQ YADLFLAAKN LSDAILLSDI LRVNTEITKA PLSASMIKRY 720
DEHHQDLTLL KALVRQQLPE KYKEIFFDQS KNGYAGYIDG GASQEEFYKF IKPILEKMDG 780
TEELLVKLNR EDLLRKQRTF DNGSIPHQIH LGELHAILRR QEDFYPFLKD NREKIEKILT 840
FRIPYYVGPL ARGNSRFAWM TRKSEETITP WNFEEVVDKG ASAQSFIERM TNFDKNLPNE 900
KVLPKHSLLY EYFTVYNELT KVKYVTEGMR KPAFLSGEQK KAIVDLLFKT NRKVTVKQLK 960
EDYFKKIECF DSVEISGVED RFNASLGTYH DLLKIIKDKD FLDNEENEDI LEDIVLTLTL 1020
FEDREMIEER LKTYAHLFDD KVMKQLKRRR YTGWGRLSRK LINGIRDKQS GKTILDFLKS 1080
DGFANRNFMQ LIHDDSLTFK EDIQKAQVSG QGDSLHEHIA NLAGSPAIKK GILQTVKVVD 1140
ELVKVMGRHK PENIVIEMAR ENQTTQKGQK NSRERMKRIE EGIKELGSQI LKEHPVENTQ 1200
LQNEKLYLYY LQNGRDMYVD QELDINRLSD YDVDHIVPQS FLKDDSIDNK VLTRSDKNRG 1260
KSDNVPSEEV VKKMKNYWRQ LLNAKLITQR KFDNLTKAER GGLSELDKAG FIKRQLVETR 1320
QITKHVAQIL DSRMNTKYDE NDKLIREVKV ITLKSKLVSD FRKDFQFYKV REINNYHHAH 1380
DAYLNAVVGT ALIKKYPKLE SEFVYGDYKV YDVRKMIAKS EQEIGKATAK YFFYSNIMNF 1440
FKTEITLANG EIRKRPLIET NGETGEIVWD KGRDFATVRK VLSMPQVNIV KKTEVQTGGF 1500
SKESILPKRN SDKLIARKKD WDPKKYGGFD SPTVAYSVLV VAKVEKGKSK KLKSVKELLG 1560
ITIMERSSFE KNPIDFLEAK GYKEVKKDLI IKLPKYSLFE LENGRKRMLA SAGELQKGNE 1620
LALPSKYVNF LYLASHYEKL KGSPEDNEQK QLFVEQHKHY LDEIIEQISE FSKRVILADA 1680

-continued

```
NLDKVLSAYN KHRDKPIREQ AENIIHLFTL TNLGAPAAFK YFDTTIDRKR YTSTKEVLDA  1740
TLIHQSITGL YETRIDLSQL GGD                                         1763

SEQ ID NO: 36          moltype = AA  length = 1565
FEATURE                Location/Qualifiers
source                 1..1565
                       mol_type = protein
                       organism = synthetic construct
SEQUENCE: 36
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNSKR GAAGSLMNVL  120
NYPGMNHRVE ITEGILADEC AALLCDFYRM PRQVFNAQKK AQSSINSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565

SEQ ID NO: 37          moltype = AA  length = 1565
FEATURE                Location/Qualifiers
source                 1..1565
                       mol_type = protein
                       organism = synthetic construct
SEQUENCE: 37
SEVEFSHEYW MRHALTLAKR ARDEREVPVG AVLVLNNRVI GEGWNRAIGL HDPTAHAEIM  60
ALRQGGLVMQ NYRLYDATLY STFEPCVMCA GAMIHSRIGR VVFGVRNAKT GAAGSLMDVL  120
HHPGMNHRVE ITEGILADEC AALLCRFFRM PRRVFNAQKK AQSSTDSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565

SEQ ID NO: 38          moltype = AA  length = 364
FEATURE                Location/Qualifiers
source                 1..364
                       mol_type = protein
                       organism = synthetic construct
SEQUENCE: 38
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
```

```
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTD                                                              364

SEQ ID NO: 39          moltype = AA  length = 167
FEATURE                Location/Qualifiers
source                 1..167
                       mol_type = protein
                       organism = synthetic construct
SEQUENCE: 39
MSEVEFSHEY WMRHALTLAK RARDEREVPV GAVLVLNNRV IGEGWNRAIG LHDPTAHAEI  60
MALRQGGLVM QNYRLYDATL YSTFEPCVMC AGAMIHSRIG RVVFGVRNAK TGAAGSLMDV  120
LHHPGMNHRV EITEGILADE CAALLCRFFR MPRRVFNAQK KAQSSTD                167

SEQ ID NO: 40          moltype = AA  length = 167
FEATURE                Location/Qualifiers
source                 1..167
                       mol_type = protein
                       organism = synthetic construct
SEQUENCE: 40
MSEVEFSHEY WMRHALTLAK RARDEREVPV GAVLVLNNRV IGEGWNRAIG LHDPTAHAEI  60
MALRQGGLVM QNYRLIDATL YVTFEPCVMC AGAMIHSRIG RVVFGVRNSK RGAAGSLMNV  120
LNYPGMNHRV EITEGILADE CAALLCDFYR MPRQVFNAQK KAQSSIN                167

SEQ ID NO: 41          moltype = AA  length = 83
FEATURE                Location/Qualifiers
source                 1..83
                       mol_type = protein
                       organism = Bacillus phage AR9
SEQUENCE: 41
TNLSDIIEKE TGKQLVIQES ILMLPEEVEE VIGNKPESDI LVHTAYDEST DENVMLLTSD  60
APEYKPWALV IQDSNGENKI KML                                          83

SEQ ID NO: 42          moltype = AA  length = 24
FEATURE                Location/Qualifiers
source                 1..24
                       mol_type = protein
                       organism = synthetic construct
SEQUENCE: 42
EELLSKNYHL ENEVARLKKG SGSG                                         24

SEQ ID NO: 43          moltype = AA  length = 241
FEATURE                Location/Qualifiers
source                 1..241
                       mol_type = protein
                       organism = synthetic construct
SEQUENCE: 43
EEELLSKNYH LENEVARLKK GSGSGEELLS KNYHLENEVA RLKKGSGSGE ELLSKNYHLE  60
NEVARLKKGS GSGEELLSKN YHLENEVARL KKGSGSGEEL LSKNYHLENE VARLKKGSGS  120
GEELLSKNYH LENEVARLKK GSGSGEELLS KNYHLENEVA RLKKGSGSGE ELLSKNYHLE  180
NEVARLKKGS GSGEELLSKN YHLENEVARL KKGSGSGEEL LSKNYHLENE VARLKKGSGS  240
G                                                                  241

SEQ ID NO: 44          moltype = AA  length = 277
FEATURE                Location/Qualifiers
source                 1..277
                       mol_type = protein
                       organism = synthetic construct
SEQUENCE: 44
MGPDIVMTQS PSSLSASVGD RVTITCRSST GAVTTSNYAS WVQEKPGKLF KGLIGGTNNR  60
APGVPSRFSG SLIGDKATLT ISSLQPEDFA TYFCALWYSN HWVFGQGTKV ELKRGGGGSG  120
GGGSGGGGSS GGGSEVKLLE SGGGLVQPGG SLKLSCAVSG FSLTDYGVNW VRQAPGRGLE  180
WIGVIWGDGI TDYNSALKDR FIISKDNGKN TVYLQMSKVR SDDTALYYCV TGLFDYWGQG  240
TLVTVSSYPY DVPDYAGGGG GSGGGGSGGG GSGGGGS                           277

SEQ ID NO: 45          moltype = DNA  length = 66
FEATURE                Location/Qualifiers
source                 1..66
                       mol_type = other DNA
                       organism = Saccharomyces bayanus
SEQUENCE: 45
ttcttgtcgt acttatagat cgctacgtta tttcaatttt gaaaatctga gtcctgggag  60
tgcgga                                                             66

SEQ ID NO: 46          moltype = AA  length = 605
FEATURE                Location/Qualifiers
```

```
source                1..605
                      mol_type = protein
                      organism = Homo sapiens
SEQUENCE: 46
MSGWESYYKT EGDEEAEEEQ EENLEASGDY KYSGRDSLIF LVDASKAMFE SQSEDELTPF  60
DMSIQCIQSV YISKIISSDR DLLAWFYGTE KDKNSVNFKI YVLQELDNPG AKRILELDQF  120
KGQQGQKRFQ DMMGHGSDYS LSEVLWVCAN LFSDVQFKMS HKRIMLFTNE DNPHGNDSAK  180
ASRARTKAGD LRDTGIFLDL HLKKPGGFDI SLFYRDIISI AEDEDLRVHF EESSKLEDLL  240
RKVRAKETRK RALSRLKLKL NKDIVISVGI YNLVQKALKP PPIKLYRETN EPVKTKTRTF  300
NTSTGGLLLP SDTKRSQIYG SRQIILEKEE TEELKRFDDP GLMLMGFKPL VLLKKHHYLR  360
PSLFVYPEES LVIGSSTLFS ALLIKCLEKE VAALCRYTPR RNIPPYFVAL VPQEEELDDQ  420
KIQVTPPGFQ LVFLPFADDK RKMPFTEKIM ATPEQVGKMK AIVEKLRFTY RSDSFENPVL  480
QQHFRNLEAL ALDLMEPEQA VDLTLPKVEA MNKRLGSLVD EFKELVYPPD YNPEGKVTKR  540
KHDNEGSGSK RPKVEYSEEE LKTHISKGTL GKFTVPLKEA CRAYGLKSGL KKQELLEALT  600
KHFQD                                                              605

SEQ ID NO: 47         moltype = AA  length = 482
FEATURE               Location/Qualifiers
source                1..482
                      mol_type = protein
                      organism = synthetic construct
SEQUENCE: 47
MVRSGNKAAW LCMDVGFTMS NSIPGIESPF EQAKKVITMF VQRQVFAENK DEIALVLFGT  60
DGTDNPLSGG DQYQNITVHR HLMLPDFDLL EDIESKIQPG SQQADFLDAL IVSMDVIQHE  120
TIGKKFEKRH IEIFTDLSSR FSKSQLDIII HSLKKCDISE RHSIHWPCRL TIGSNLSIRI  180
AAYKSILQER VKKTTWDAKT LKKEDIQKET VYCLNDDDET EVLKEDIIQG FRYGSDIVPF  240
SKVDEEQMKY KSEGKCFSVL GFCKSSQVQR RFFMGNQVLK VFAARDDEAA AVALSSLIHA  300
LDDLDIWAIV RYAYDKRANP QVGVAFPHIK HNYECLVYVQ LPFMEDLRQY MFSSLKNSKK  360
YAPTEAQLNA VDALIDSMSL AKKDEKTDTL EDLFPTTKIP NPRFQRLFQC LLHRALHPRE  420
PLPPIQQHIW NMLNPPAEVT TKSQIPLSKI KTLFPLIEAK KKDQVTAQEI FQDNHEDGPT  480
AK                                                                 482

SEQ ID NO: 48         moltype = DNA  length = 10
FEATURE               Location/Qualifiers
source                1..10
                      mol_type = other DNA
                      organism = Methanobacterium thermoautotrophicum
SEQUENCE: 48
aatttttgga                                                         10

SEQ ID NO: 49         moltype = AA  length = 83
FEATURE               Location/Qualifiers
source                1..83
                      mol_type = protein
                      organism = Methanobacterium thermoautotrophicum
SEQUENCE: 49
GSVIDVSSQR VNVQRPLDAL GNSLNSPVII KLKGDREFRG VLKSFDLHMN LVLNDAEELE  60
DGEVTRRLGT VLIRGDNIVY ISP                                          83

SEQ ID NO: 50         moltype = DNA  length = 25
FEATURE               Location/Qualifiers
source                1..25
                      mol_type = other DNA
                      organism = Bacteriophage MS2
SEQUENCE: 50
gcgcacatga ggatcaccca tgtgc                                        25

SEQ ID NO: 51         moltype = AA  length = 116
FEATURE               Location/Qualifiers
source                1..116
                      mol_type = protein
                      organism = Bacteriophage MS2
SEQUENCE: 51
MASNFTQFVL VDNGGTGDVT VAPSNFANGI AEISSNSRSQ AYKVTCSVRQ SSAQNRKYTI  60
KVEVPKGAWR SYLNMELTIP IFATNSDCEL IVKAMQGLLK DGNPIPSAIA ANSGIY      116

SEQ ID NO: 52         moltype = DNA  length = 26
FEATURE               Location/Qualifiers
source                1..26
                      mol_type = other DNA
                      organism = Bacteriophage PP7
SEQUENCE: 52
ataaggagtt tatatggaaa ccctta                                       26

SEQ ID NO: 53         moltype = AA  length = 127
FEATURE               Location/Qualifiers
source                1..127
                      mol_type = protein
                      organism = Bacteriophage PP7
```

-continued

```
SEQUENCE: 53
MSKTIVLSVG EATRTLTEIQ STADRQIFEE KVGPLVGRLR LTASLRQNGA KTAYRVNLKL  60
DQADWDCSTS VCGELPKVRY TQVWSHDVTI VANSTEASRK SLYDLTKSLV ATSQVEDLVV  120
NLVPLGR                                                           127

SEQ ID NO: 54          moltype = DNA  length = 19
FEATURE                Location/Qualifiers
source                 1..19
                       mol_type = other DNA
                       organism = Shigella phage
SEQUENCE: 54
ctgaatgcct gcgagcatc                                              19

SEQ ID NO: 55          moltype = AA  length = 62
FEATURE                Location/Qualifiers
source                 1..62
                       mol_type = protein
                       organism = Shigella phage
SEQUENCE: 55
MKSIRCKNCN KLLFKADSFD HIEIRCPRCK RHIIMLNACE HPTEKHCGKR EKITHSDETV  60
RY                                                                62

SEQ ID NO: 56          moltype = AA  length = 1367
FEATURE                Location/Qualifiers
source                 1..1367
                       mol_type = protein
                       organism = synthetic construct
SEQUENCE: 56
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 57          moltype = AA  length = 1367
FEATURE                Location/Qualifiers
source                 1..1367
                       mol_type = protein
                       organism = synthetic construct
SEQUENCE: 57
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLADDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PALESEFVYG DYKVYDVRKM  1020
IAKSEQEIGK ATAKYFFYSN IMNFFKTEIT LANGEIRKAP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
```

-continued

```
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 58          moltype = DNA  length = 4101
FEATURE                Location/Qualifiers
source                 1..4101
                       mol_type = other DNA
                       organism = synthetic construct
SEQUENCE: 58
gacaagaagt acagcatcgg gctggcgatc gggaccaact ccgtcggctg ggctgtgatt  60
accgacgagt acaaggtgcc atccaagaag ttcaaggtcc tcggcaacac tgaccggcac  120
agcattaaga agaacctgat tggggcgctg ctgttcgatt cgggggagac tgcggaggcg  180
accaggctga agcggactgc gcgccggagg tacaccagga ggaagaatcg gatctgctac  240
ctccaggaga ttttctcgaa tgagatggcc aaggtggacg attccttctt ccatcgcctg  300
gaggagtcgt tcctcgttga ggaggacaag aagcatgaga ggcatcccat tttcgggaat  360
atcgttgacg aggtggctta ccatgagaag tacccgacca tctaccatct gcggaagaag  420
ctcgtcgatt cgaccgataa ggccgacctg cggctgatct acctggccct cgcgcacatg  480
attaagttcc ggggccattt cctcatcgag ggcgacctca acccggacaa ctcggacgtg  540
gataagctct tcattcagct cgtgcagaca tacaaccagc tcttcgagga gaatcccatt  600
aacgcctcgg gggtcgacgc taaggctatt ctctcggctc ggctgtcgaa gtcgcgccgg  660
ctggagaatc tcattgccca gctcccaggc gagaagaaga acggcctctt cggcaacctg  720
attgccctgt cgctggggct cacaccgaat ttcaagtcga acttcgacct cgccgaggac  780
gctaagctcc agctcagcaa ggatacttac gatgatgacc tcgataacct gctcgcccag  840
attggggatc agtacgcgga tctgttcctc gcggccaaga atctcagcga tgctattctc  900
ctgtcggaca ttctccgcgt caacacagag attactaagg ccccactgtc ggcgagcatg  960
attaagaggt acgatgagca tcatcaggac ctgacactgc tcaaggcgct ggtccggcag  1020
cagctccccg agaagtacaa ggagattttc ttcgatcagt caaagaatgg gtacgcgggc  1080
tacattgatg gcggcgcgtc ccaggaggag ttctacaagt tcattaagcc catcctggag  1140
aagatggacg ggaccgagga gctgctggtg aagctcaatc gggaggacct gctccggaag  1200
cagcgcacat tcgacaatgg ctcgattcct caccagattc acctgggcga gctgcacgcc  1260
attctccgca ggcaggagga cttctacccg ttcctcaagg acaaccgcga gaagatcgag  1320
aagatcctga ccttccggat tccatactac gtggggccgc tcgcgcgggg gaactcccgg  1380
ttcgcgtgga tgactcgcaa gtccgaagaa acgattacac cgtggaattt cgaggaggtc  1440
gtcgacaagg gcgctagtgc gcagtcattc attgagagga tgaccaattt cgataagaac  1500
ctgcctaacg agaaggtgct gccgaagcat tcgctgctct acgagtactt caccgtttac  1560
aatgagctga ccaaggtgaa gtatgtgact gagggcatga ggaagccagc gttcctgagc  1620
ggcgagcaga agaaggctat cgtggacctg ctcttcaaga ctaaccggaa ggtgactgtg  1680
aagcagctca aggaggacta cttcaagaag attgagtgct tcgattccgt tgagattagc  1740
ggggtggagg atcggttcaa tgcttcgctc gggacatacc acgatctcct gaagatcatt  1800
aaggataagg acttcctcga caacgaggag aacgaggaca ttctcgaaga tattgtcctg  1860
accctcaccc tcttcgagga tcgggagatg atcgaggaga ggctcaagac atacgctcat  1920
ctgttcgatg ataaggtcat gaagcagctg aagcgcaggc ggtacacagg gtgggggcgg  1980
ctgagccgga agctgatcaa cgggattcgg gataagcagt ccgggaagac aattctcgac  2040
ttcctcaagt ccgacgggtt cgctaaccgg aacttcatgc agctcattca tgatgactcg  2100
ctgacattca aggaggatat tcagaaggcg caggtttcgg ggcagggcga ctcgctccac  2160
gagcatattg cgaatctggc gggctccccc gcgattaaga agggcattct gcaaaccgtc  2220
aaggtggttg atgagctggt caaggtcatg gggcggcata agccagagaa tattgtcatc  2280
gagatggcgc gggagaatca gaccacacag aagggggcaga agaactcacg ggagcggatg  2340
aagcgcatcg aggagggcat caaggagctg gggtcgcaga tcctgaagga gcatcccgtg  2400
gagaacactc agctgcaaaa tgagaagctg tacctctact acctccagaa cgggagggac  2460
atgtatgtgg atcaggagct ggatattaat aggctgagcg attacgatgt cgaccacatt  2520
gtcccacagt cgttcctgaa ggacgacagc attgacaaca aggtgctgac ccgctcggat  2580
aagaacaggg gcaagagcga taatgttcca agcgaggagg ttgtgaagaa gatgaagaac  2640
tactggcggc agctcctgaa cgcgaagctc atcacacagc ggaagttcga caacctcacc  2700
aaggctgagc gcgggggcct gagcgagctg gacaaggcgg ggttcattaa gaggcagctg  2760
gtcgagacac ggcagattac aaagcatgtt gcgcagattc tcgattcccg gatgaacacc  2820
aagtacgatg agaacgataa gctgattcgg gaggtcaagg taattaccct gaagtccaag  2880
ctggtgtccg acttcaggaa ggacttccag ttctacaagg ttcgggagat caacaactac  2940
caccacgcgc atgatgccta cctcaacgcg gtcgtgggga ccgctctcat caagaagtac  3000
ccaaagctgg agtcagagtt cgtctacggg gattacaagg tttacgacgt gcggaagatg  3060
atcgctaaga gcgagcagga gattggcaag gctaccgcta agtacttctt ctactccaac  3120
atcatgaact tcttcaagac agagattacc ctcgcgaatg gcgagatccg gaagaggccc  3180
ctcatcgaga caaatgggga gacaggggag attgtctggg ataaggggcg ggatttcgcg  3240
accgtccgga aggtcctgtc gatgccccag gttaatattg tcaagaagac tgaggtccag  3300
actggcggct tctcaaagga gtcgattctc ccaaagagga actccgataa gctcattgct  3360
cggaagaagg attgggaccc caagaagtac ggggggattcg actcccccac tgttgcttac  3420
tctgttctgg ttgttgctaa ggtggagaag gggaagtcga agaagctgaa gagcgtgaag  3480
gagctgctcg ggattacaat tatggagagg tcatccttcg agaagaatcc catcgacttc  3540
ctggaggcca agggctacaa ggaggtgaag aaggacctga ttattaagct gcccaagtac  3600
tcgctcttcg agctggagaa tgggcggaag cggatgctgg cgtccgcggg ggagctgcaa  3660
aaggggaacg agctggcgct cccctccaag tatgtgaact tcctctacct ggcgtcgcac  3720
tacgagaagc tgaaggggtc cccagaggat aatgagcaga agcagctctt cgtcgagcag  3780
cataagcact acctggacga gattatcgag cagattagcg agttctcgaa gcgggtcatc  3840
ctcgcggatg cgaacctgga taaggtgctc agcgcctaca ataagcaccg ggacaagccg  3900
attcgggagc aggcggagaa tattattcac ctcttcacac tcaccaacct cggggcacca  3960
gctgcgttca agtacttcga cactactatc gaccggaagc ggtacacctc gacgaaggag  4020
gtgctcgacg ccaccctcat tcaccagtcg atcacaggcc tgtacgagac acggattgac  4080
ctgtcccagc tcgggggcga c                                            4101
```

```
SEQ ID NO: 59          moltype = DNA  length = 4101
FEATURE                Location/Qualifiers
source                 1..4101
                       mol_type = other DNA
                       organism = synthetic construct
SEQUENCE: 59
gacaagaagt actccattgg cctggcgatt gggacaaact cggtggggtg ggccgtgatt  60
acggatgagt acaaggttcc aagcaagaag ttcaaggtcc tcgggaacac agatcggcat  120
tcgattaaga agaatctcat tggggcgctc ctcttcgact cgggggagac agcggaggct  180
accaggctca agcggacagc caggcggcgg tacacaaggc ggaagaatcg catctgctac  240
ctccaggaga ttttctcgaa tgagatggcg aaggtggacg acagcttctt ccatcggctg  300
gaggagtcct tcctggtgga ggaggataag aagcacgaga ggcatccaat tttcgggaac  360
atcgtggacg aggttgcgta ccatgagaag taccctacaa tctaccatct gcggaagaag  420
ctggttgact ccacagacaa ggcggacctg aggctgatct acctcgctct ggcccacatg  480
attaagttcc gcgggcattt cctgatcgag gggcacctga atcccgacaa ttcggatgtg  540
gacaagctct tcatccagct ggtgcagacc tacaaccagc tgttcgagga gaatcccatc  600
aatgcgtcgg gcgttgacgc taaggccatt ctgtccgcta ggctgtcgaa gagcaggagg  660
ctggagaacc tgatcgccca gctgccaggc gagaagaaga atgggctctt cgggaatctg  720
attgcgctct ccctggggct gacaccgaac ttcaagagca atttcgatct ggctgaggac  780
gcgaagctcc agctctcgaa ggacacttac gacgatgacc tcgataacct cctcgcgcag  840
atcggggacc agtacgctga tctcttcctc gccgctaaga acctctcgga tgctatcctg  900
ctctccgaca ttctccgggt taataccgag attacaaagg ccccactgtc ggcgtccatg  960
atcaagcggt acgatgagca tcatcaggat ctcaccctgc tcaaggccct cgtgcggcag  1020
cagctgcccg agaagtacaa ggagattttc ttcgaccaga gcaagaatgg gtacgctggc  1080
tacattgacg gcggggcctc acaggaggag ttctacaagt tcatcaagcc aatcctggag  1140
aagatggatg ggacagagga gctgctggtg aagctcaacc gggaggatct gctcaggaag  1200
cagcggacgt tcgacaacgg gtcgattccc catcagatcc acctgggggga gctgcacgcg  1260
atcctgcgcc ggcaggagga tttctaccct ttcctgaagg ataatcggga gaagatcgag  1320
aagattctca ccttccggat tccctactac gtcgggccac tcgcgcgggg caatagcagg  1380
ttcgcctgga tgacacggaa gagcgaggag acaatcaccc cctggaactt cgaggaggtt  1440
gtcgacaagg gggcgtccgc ccagtcattc attgagcgga tgaccaattt cgacaagaat  1500
ctgccaaatg agaaggttct cccaaagcat agcctcctct acgagtactt cactgtttac  1560
aacgagctga ccaaggtgaa gtatgtgacc gagggcatgc ggaagcccgc gttcctgtcc  1620
ggcgagcaga agaaggccat tgtggacctc ctgttcaaga ccaatcgcaa ggtcacagtc  1680
aagcagctca aggaggatta cttcaagaag atcgagtgct tcgactcggt tgagattagc  1740
ggggtggagg atcggttcaa cgcgagcctc ggcacttacc acgacctcct gaagatcatc  1800
aaggataagg acttcctcga caacgaggag aacgaggata ttctggagga catcgtgctc  1860
accctgacgc tgttcgagga tcgggagatg atcgaggagc gcctgaagac ctacgctcat  1920
ctcttcgatg ataaggtcat gaagcagctg aagaggaggc ggtacaccgg gtggggccgc  1980
ctgagcagga agctcattaa cgggatcagg gacaagcaga gcggcaagac catcctggac  2040
ttcctcaaga gcgatggctt cgccaaccgg aatttcatgc agctcatcca cgacgactcc  2100
ctcaccttca aggaggacat tcagaaggct caggtcagcg gccagggcga ctcgctgcat  2160
gagcacatcg ctaacctggc gggcagccca gccatcaaga agggcatcct ccagacagtg  2220
aaggtcgtgg atgagctggt gaaggtcatg ggccggcata agcccgagaa tattgtgatt  2280
gagatggcgc gggagaatca gaccactcag aagggccaga agaactcgcg ggagcgcatg  2340
aagaggatcg aggaggggat taaggagctg ggcagccaga ttctcaagga gcaccccgtg  2400
gagaataccc agctccagaa cgagaagctg tacctctact acctccagaa tgggcgggac  2460
atgtatgttg atcaggagct ggacatcaat cgcctctcgg attacgacgt ggaccacatc  2520
gtgccccaga gcttcctgaa ggatgatagc atcgacaata aggtcctgac ccgctccgac  2580
aagaatcgcg gcaagagcga caacgtgccg agcgaggagg tcgtgaagaa gatgaagaac  2640
tactggcggc agctgctgaa cgcgaagctc attacacagc ggaagttcga taacctgacg  2700
aaggcggaga ggggcggcct ctccgagctg gacaaggcgg gcttcattaa gaggcagctc  2760
gtggagactc gccagatcac caagcacgtg gctcagatcc tcgatagccg gatgaatacg  2820
aagtacgatg agaatgacaa gctcatccgg gaggtgaagg taatcaccct gaagtcaaag  2880
ctcgttagcg atttccggaa ggacttccag ttctacaagg tgcgggagat taacaactac  2940
catcatgcgc acgatgcgta cctcaatgcg gtggtgggca cagccctgat taagaagtac  3000
cccaagctgg agagcgagtt cgtctacggg gactacaagg tgtacgatgt tcggaagatg  3060
atcgccaaga gcgagcagga gattgggaag gccaccgcta agtacttctt ctactcgaat  3120
attatgaatt tcttcaagac cgagatcaca ctcgctaatg gggagattcg gaagcggccc  3180
ctcatcgaga ctaacgggga gactggcgag attgtgtggg acaaggggcg cgacttcgct  3240
accgtgcgca aggtcctctc gatgccccag gttaatattg ttaagaagac agaggtgcag  3300
acgggcgggt tctccaagga gtctatcctg ccgaagcgga actcggacaa gctgatcgcc  3360
cgcaagaagg attgggaccc caagaagtac gggggattcg atagcccaac cgtggcttac  3420
agcgtcctgg tggtcgccaa ggttgagaag gggaagtcga agaagctcaa gagcgttaag  3480
gagctgctgg gcatcaccat catggagcgg tccagcttcg agaagaatcc tatcgacttc  3540
ctggaggcta aggggtacaa ggaggtcaag aaggacctga tcattaagct gcccaagtac  3600
tctctgttcg agctggagaa cgggaggaag cggatgctgg cgtctgctgg cgagctacag  3660
aagggcaatg agctggcgct cccctcgaag tatgtcaact tcctctacct ggcttcccat  3720
tacgagaagc tgaagggctc gcccgaggat aatgagcaga agcagctctt cgtggagcag  3780
cacaagcact acctcgacga gatcattgag cagatttcgg agttctcgaa gcgggtcatt  3840
ctcgcggacg cgaacctcga caaggtcctc tcggcgtaca acaagcaccg ggacaagccc  3900
atccgggagc aggccgagaa cattatccac ctcttcacac tgaccaacct cggcgctccc  3960
gccgcgttca agtacttcga caccaccatt gaccgcaaga gatacacatc caccaaggag  4020
gtgctggacg cgaccctcat ccaccagagc atcacaggcc tctacgagac acggatcgac  4080
ctctcgcagc tcgggggcga t                                            4101

SEQ ID NO: 60          moltype = DNA  length = 4092
FEATURE                Location/Qualifiers
```

```
source                 1..4092
                       mol_type = other DNA
                       organism = synthetic construct
SEQUENCE: 60
gacaagaagt actcgatcgg cctggcgatt ggcacaaaca gcgtggggtg ggctgtgatc  60
actgatgagt acaaggtgcc atcgaagaag ttcaaggtgc tggggaatac agaccggcat  120
tcgatcaaga agaatctcat tggcgctctc ctcttcgatt ccggcgagac tgctgaggcg  180
acccgcctga agcgcaccgc ccggcggcgc tacactcggc ggaagaatag gatttgctac  240
ctccaggaga ttttctcgaa tgagatggcc aaggtggatg acagcttctt ccaccgcctg  300
gaggagtcgt tcctggtcga ggaggacaag aagcatgagc ggcaccctat cttcgggaat  360
atcgttgatg aggtcgccta ccacgagaag taccccacta tctaccatct ccgcaagaag  420
ctcgtggaca gcacagataa ggccgacctc cgcctgatct acctcgccct cgcgcacatg  480
attaagttcc gggggcactt cctcattgag ggggatctga atcccgataa ctccgacgtg  540
gacaagctgt tcatccagct ggtgcagaca tacaaccagc tgttcgagga gaatcccatc  600
aacgcgagcg gcgtggacgc taaggccatt ctgtcggcta ggctctcgaa gtcgaggcgg  660
ctggagaacc tgattgcgca gctccccggc gagaagaaga acgggctgtt cgggaatctc  720
atcgccctct ccctcggcct cacaccaaac ttcaagagca atttcgacct ggctgaggac  780
gctaagctgc aactctcaaa ggatacatac gatgacgacc tggacaatct cctggctcag  840
atcggcgacc agtacgctga cctgttcctc gcggccaaga atctgtcgga cgcgattctc  900
ctcagcgaca tcctgcgcgt caataccgag attacgaagg ctccactgtc tgcgtcaatg  960
attaagcggt acgatgagca tcaccaggat ctgaccctcc tgaaggcgct cgtgcggcag  1020
cagctgcccg agaagtacaa ggagattttc ttcgatcaga gcaagaatgg ctacgccggc  1080
tacatcgacg gggcgcgag ccaggaggag ttctacaagt tcatcaagcc catcctggag  1140
aagatggacg gcaccgagga gctactcgtg aagctcaatc gggaggatct cctccggaag  1200
cagcggacat tcgataacgg gtctatccca caccagatcc acctcggcga gctgcatgcg  1260
attctgcggc ggcaggagga tttctaccct ttcctgaagg acaaccggga gaagatcgag  1320
aagatcctca cattccggat tccatactac gtcggccccc tggcgagggg caatagccgg  1380
ttcgcgtgga tgacaaggaa gtccgaggag actattaccc cgtggaattt cgaggaggtg  1440
gttgacaagg gcgcttccgc gcagagcttc attgagcgga tgacaaactt cgacaagaat  1500
ctccccaacg agaaggtcct gccgaagcat agcctcctgt acgagtactt caccgtctac  1560
aatgagctaa ctaaggtcaa gtatgtgaca gagggcatga ggaagccagc cttcctctca  1620
ggcgagcaga agaaggccat tgtggacctc ctgttcaaga caaaccgcaa ggtgacagtg  1680
aagcagctga aggaggatta cttcaagaag attgagtgct tcgactcagt ggagatttca  1740
ggcgtggagg atcggttcaa cgcgagcctg ggacttacc acgacctgct gaagattatt  1800
aaggacaagg acttcctgga taacgaggag aatgaggaca tcctggagga tattgtgctc  1860
accctcaccc tgttcgagga cagggagatg attgaggaga ggctcaagac ctacgcgcac  1920
ctgttcgatg acaaggtcat gaagcagctg aagaggcggc gctacactgg gtggggccgc  1980
ctgtcgcgga agctgatcaa cggcattcgg gataagcagt ccgggaagac cattctggat  2040
ttcctgaagt cggacggctt cgccaacagg aatttcatgc agctgatcca cgacgactcc  2100
ctcaccttca aggaggacat tcagaaggcc caggttagcg gccagggga ctcactccac  2160
gagcatattg ccaatctggc cggctctcca gctatcaaga agggcatcct gcaaacagtt  2220
aaggttgttg acgagctggt taaggtcatg gggcggcata agcccgagaa cattgtcatc  2280
gagatggctc gggagaacca gacaactcag aagggccaga agaactccag ggagcgcatg  2340
aagcggattg aggagggcat taaggagctg gggtcccaga tcctcaagga gcaccctgtc  2400
gagaacactc agctgcaaaa cgagaagctc tacctgtact acctccagaa cgggcgggat  2460
atgtatgtgg atcaggagct ggacatcaac aggctctccg actacgacgt ggatcacatt  2520
gtcccacagt ctttcctcaa ggatgattcc atcgacaaca aggtgctgac gcgcagcgac  2580
aagaataggg ggaagtcgga caacgttccg agcgaggagg tcgtgaagaa gatgaagaat  2640
tactggaggc agctcctgaa tgcgaagctg atcactcaga ggaagttcga caatctgaca  2700
aaggcggaga ggggcgggct ctcggagctg gataaggcgg gcttcatcaa gcggcagctc  2760
gttgaaaccc ggcagatcac caagcatgtc gcccagatcc tcgatagccg catgaacacc  2820
aagtacgatg agaacgacaa gctcattcgg gaggttaagg tcattacgct gaagtccaag  2880
ctcgtcagcg acttcaggaa ggatttccag ttctacaagg ttcgggagat taacaactac  2940
caccacgcgc atgatgcgta cctgaacgct gttgtcggca ctgctctcat caagaagtac  3000
ccaaagctgg agtccgagtt cgtctacggg gactacaagg tctacgatgt ccggaagatg  3060
atcgccaagt cggagcagga gatcgggaag gctactgcga agtacttctt ctacagcaac  3120
attatgaatt tcttcaagac ggagattacg ctggcgaacg gggagattag gaagaggccc  3180
ctcattgaga ctaatgggga gacaggcgag attgtttggg acaagggccg cgacttcgcg  3240
actgtgcgga aggtcctgtc catgccacag gtgaatattg ttaagaagac agaggtgcag  3300
actgggggct tctcgaagga gagcattctc ccaaagcgga acagcgataa gctcatcgcg  3360
cgcaagaagg attgggaccc taagaagtac ggcggcttcg attctcccac tgtggcctac  3420
tccgttctcg tggttgccaa ggttgagaag gggaagtcga agaagctgaa gtcggtcaag  3480
gagctgctcg ggattacaat catggagcgg agcagcttcg agaagaaccc tattgatttc  3540
ctggaggcca agggctacaa ggaggttaag aaggatctca ttatcaagct ccctaagtac  3600
tctctgttcg agctggagaa tggccggaag aggatgctgg cctcggctgg cgagctacag  3660
aaggggaatg agctggccct cccgtcgaag tatgtgaatt tcctgtacct cgcgtcgcac  3720
tacgagaagc tcaagggcag cccggaggat aatgagcaga agcagctctt cgtggagcag  3780
cataagcact acctggacga gatcattgag cagatcagcg agttctcgaa gcgggttatt  3840
ctggctgatg ctaacctgga caaggttctg agcgcctaca ataagcatcg cgacaagccg  3900
attcgcgagc aggcggagaa tattatccac ctgttcaccc tcactaacct cggggctccc  3960
gcggccttca agtacttcga taccacaata gataggaagc ggtacacctc gacgaaggag  4020
gtcctcgacg ccacactcat ccatcagtcg attacaggcc tgtacgagac acggattgac  4080
ctctcgcagc tg                                                      4092

SEQ ID NO: 61          moltype = DNA  length = 4101
FEATURE                Location/Qualifiers
source                 1..4101
                       mol_type = other DNA
                       organism = synthetic construct
```

```
SEQUENCE: 61
gacaagaagt attccatagg cctggctatc ggcaccaaca gcgtgggctg ggccgtcatc  60
accgacgagt acaaagtgcc gagtaaaaag ttcaaagtgc tcggcaacac cgaccgccac  120
tccataaaga aaaacctgat cggggcgctc ctgttcgaca gcggcgagac ggcggaggcc  180
acccgcttga aacgcacggc ccgacggcgc tacacgcggc gcaagaaccg gatctgttac  240
ctacaggaga ttttctctaa cgagatggcg aaggtggacg actcgttctt tcaccgcctc  300
gaagagtcct tcctcgtgga ggaggacaag aaacacgagc gccacccgat cttcggcaac  360
atcgtggacg aggtggccta ccacgagaag tacccgacca tctaccacct ccggaagaaa  420
ctcgtggaca gcacggacaa ggccgacctg aggctcatct acctcgccct ggcgcacatg  480
attaagttcc ggggccactt cctgatcgag ggcgacctga acccggacaa cagcgacgtg  540
gacaagctgt tcatccagct agtccagacc tacaaccagc ttttcgagga aaaccccatc  600
aacgccagcg gggtggacgc gaaggcgatc ctgtccgccc ggctgagcaa gtcccggcgg  660
ctggagaacc tcatcgcgca gttgcccggc gagaagaaga acgggctgtt cgggaacctg  720
atcgccctct ccctggggct caccccgaac ttcaagtcca acttcgacct cgccgaggac  780
gccaaactac agctgagcaa ggacacctac gacgacgacc tcgacaacct gctggcccag  840
atcggggacc agtacgcaga cctgttcctc gccgccaaga acctctccga cgccatcctg  900
ctgtcggaca tcctgcgggt gaacacggag atcacgaagg ccccgctctc ggcctcgatg  960
attaaacgct acgacgagca ccaccaggac ttgaccctcc tcaaggcgct ggtccgccag  1020
cagcttcccg agaagtacaa ggaaatcttt ttcgatcaga gcaagaacgg gtacgccggg  1080
tacatcgacg gcggggcgtc ccaggaggag ttctacaagt tcatcaagcc catcctggag  1140
aaaatggacg ggaccgagga gctgctcgtg aagctcaacc gcgaagattt gctccgcaag  1200
cagcgcacgt tcgacaacgg gtcgatcccg caccagatcc acctgggcga gctgcacgcg  1260
atcctcaggc gtcaggaaga cttctacccc ttcctcaagg acaaccgcga gaagatagag  1320
aagattctga ccttcagaat tccttattac gtgggcccgc tggctcgggg caactcgcgc  1380
ttcgcctgga tgacgcgcaa gtccgaggag accatcaccc cgtggaactt cgaggaggtg  1440
gtggataagg gtgcctcggc ccagtccttc atcgagcgga tgaccaactt cgacaagaac  1500
ctgccgaacg agaaggtgct ccccaagcac agcctgctct acgaatattt cacggtgtac  1560
aacgagctga cgaaggtcaa gtacgtgacc gagggaatga ggaaacctgc attcctctcc  1620
ggggagcaga agaaagccat agtcgacctc ctgttcaaga ccaaccggaa ggtcaccgtc  1680
aagcagctca aggaggacta cttcaagaag atcgagtgct tcgattcagt ggagatcagc  1740
ggcgtcgagg accggttcaa cgccagcctg ggcacctacc acgacctgct caagatcatc  1800
aaggacaagg acttcctcga caacgaggag aacgaggaca tcctggagga catcgtgctg  1860
accctgacgc tcttcgagga ccgcgagatg atcgaggagc gcctcaagac ctacgcccac  1920
ctgttcgacg acaaggtgat gaagcagctc aagcggcgga gatatactgg gtggggccgc  1980
ctctcccgga agctcattaa cggtatcagg gataagcagt ccgggaagac gatcctcgac  2040
ttcctcaagt cggacgggtt cgccaaccgc aacttcatgc agctcatcca cgacgactcc  2100
ctgacgttca aggaggacat ccagaaggcc caagtgtctg gtcaaggtga ctcgctccac  2160
gagcacatcg ccaacctcgc gggcagcccg gccatcaaga agggaatact ccagaccgtc  2220
aaggtggtgg acgagctggt gaaggtcatg ggccgccaca agccggagaa catcgtcatc  2280
gagatggcgc gggagaacca gaccacgcag aaggggcaga aaaatagccg tgagcgcatg  2340
aagcgcatcg aggaggggat taaggagttg ggcagccaga tcctcaagga gcaccctgtg  2400
gagaacacgc agttgcaaaa cgagaagctc tacctgtact acctccagaa cgggagggat  2460
atgtacgtgg accaagaact ggacatcaac cgcctgtccg actacgacgt ggaccacatc  2520
gtgccgcaga gcttcctcaa ggacgacagc atcgacaaca aggtgctcac ccggtccgac  2580
aagaatcggg gcaagtccga caacgtgccc agcgaggagg tcgtcaaaaa gatgaaaaac  2640
tactggcgac aactactgaa cgccaagctc atcacccagc gcaagttcga caacctcaca  2700
aaagccgagc gcggcgggtt gagcgagctg gacaaggccg ggttcatcaa gcgccagctc  2760
gtcgagacgc gccagatcac gaagcacgtc gcgcagatac tcgacagccg gatgaacacc  2820
aagtacgacg agaacgacaa gctcatccgg gaggtgaagg tcatcaccct caagtcgaag  2880
ctcgtgagcg acttccgcaa ggacttccag ttctacaagg tccgggagat caacaactac  2940
caccacgccc acgatgctta tcttaacgcc gtggtgggga cggccctcat taagaaatac  3000
ccgaagctgg agtcggagtt cgtgtacggc gactacaagg tgtacgacgt caggaagatg  3060
atcgccaagt ccgaacagga gatcgggaag gccacggcga aatacttctt ctacagcaac  3120
atcatgaact tcttcaagac cgagatcacc ctcgccaacg gcgagatccg caagcgcccg  3180
ctcatcgaga cgaacgggga gaccggcgag atcgtctggg acaaggggcg cgacttcgcc  3240
actgtgcgga aggtgctgtc gatgccccag gtcaacatcg tcaagaagac ggaggtccag  3300
acgggcgggt tcagcaagga gagcatcctg ccgaagcgca acagcgacaa gctgatcgcc  3360
cgcaaaaagg actgggatcc aaaaaagtac ggcggcttcg acagccccac cgtcgcctac  3420
agcgtcctcg tcgtcgctaa agtcgagaag ggcaagtcca aaaagctcaa gagcgtcaag  3480
gagctgctcg ggatcaccat catggagcgg tccagcttcg agaagaaccc aattgatttc  3540
ctggaggcga agggctacaa ggaggtcaag aaagacctca tcataaagct gccgaagtac  3600
tcactcttcg agctggagaa cggcgcgaag cggatgctgg cgtcggccgg agagctccaa  3660
aagggcaacg agctggcgct gccgagcaag tacgtgaact tcctctacct ggcgtcccac  3720
tacgagaagc tcaagggcag tccagaggat aacgagcaga agcagctatt cgtggagcag  3780
cacaagcact acctggacga gatcatcgag cagatcagcg agttctccaa gcgcgtcatc  3840
ctggcggacg ccaacctgga caaggtgctg tccgcgtaca acaagcaccg cgacaagccg  3900
atccgcgagc aagccgagaa catcatccac ctgttcaccc tcacgaacct cggggcaccc  3960
gccgccttca aatatttcga cacgaccatc gaccgcaagc gctacaccag cacgaaggag  4020
gtgctcgacg ccaccctgat ccaccagagc atcaccgggc tgtacgagac ccgcatcgac  4080
ctctcgcagc tcggcgggga c                                            4101

SEQ ID NO: 62          moltype = DNA  length = 4101
FEATURE                Location/Qualifiers
source                 1..4101
                       mol_type = other DNA
                       organism = synthetic construct
SEQUENCE: 62
gacaagaagt acagtattgg attggccatc gggacgaaca gcgtgggctg ggccgtcatc  60
accgacgagt acaaggtgcc atccaagaag tttaaggttc tggggaatac cgaccgccac  120
```

```
tcgatcaaga aaaatctcat cggggcgctg cttttcgaca gcggcgagac ggcggaagcg  180
acgcggctca agcggacggc tcgtcgccgt tacacccggc gtaagaaccg catctgttac  240
ctccaggaga tattcagcaa cgagatggcg aaggtggacg actccttttt ccaccgtctt  300
gaggagtcct tcctggtcga ggaggacaag aagcacgagc gccacccgat cttcgggaac  360
atcgtggacg aggtggccta ccacgagaag taccccacga tctaccacct ccgcaaaaaa  420
ctcgtggact caactgacaa ggccgatttg aggcttatct acctcgccct cgcccacatg  480
attaagttcc gtgggcactt cctaatcgag ggtgacctca accccgacaa ctctgacgtg  540
gacaagctgt tcatccagct tgtgcagacc tacaatcagc tctttgagga gaatccgatc  600
aacgcatctg gtgtggacgc aaaggccatc ctcagcgcgc ggctgagcaa gtctaggcgg  660
ttggagaacc tgatcgccca actgcccggc gagaagaaaa atggcctctt cggcaacctg  720
atcgccctgt cgctggggct cacgccgaac ttcaagagta actttgacct ggcggaggac  780
gctaagctcc agctatctaa ggacacatac gacgacgacc tggacaacct gctggcccag  840
atcggcgacc agtacgccga cctcttccta gccgccaaga acctgtccga cgccatcctc  900
ctcagcgaca tcctgcgcgt gaacacggag atcacgaagg ctccgctcag cgcctccatg  960
attaagcggt acgacgagca ccaccaagac ctaactttac tcaaagccct cgtgcggcag  1020
cagcttcccg agaagtacaa agagatattt tttgatcagt ccaagaacgg ttatgcgggc  1080
tacatcgacg gcggcgcgag ccaggaggag ttctacaagt tcatcaagcc catcctggag  1140
aagatggacg gcacggagga gctgctcgtg aagctcaacc gtgaagacct cctgcgaaag  1200
cagcgaacct tcgacaacgg ttcgatcccg caccagatcc acctcgggga gctgcacgcc  1260
atcctgaggc gacaggagga cttctaccct ttcctaaagg acaaccgcga gaagattgaa  1320
aaaatcctga cgtttcgcat accctactac gtcggcccgc tggcgcgcgg caactcccgg  1380
ttcgcctgga tgacccgtaa gagcgaggag acgatcaccc cgtggaactt cgaggaggtc  1440
gtggacaagg gcgcgagcgc gcagagcttc atcgagcgca tgaccaactt cgacaagaac  1500
ctcccgaacg agaaggtgct cccaaagcac tccctcctgt acgagtattt caccgtgtac  1560
aacgagttga caaaggtgaa gtacgtgacg gagggaatgc ggaagcctgc gttcctctcg  1620
ggcgagcaga agaaggcaat cgtggacctg ctcttcaaga ccaaccggaa ggtgacggtg  1680
aagcagctca aggaggacta cttcaaaaaa atcgagtgct tcgactccgt ggagataagc  1740
ggcgtggagg accgattcaa cgcctccctc ggcacctacc acgacctcct taagatcatc  1800
aaggacaagg acttcctgga caacgaggag aacgaggaca tcctggagga catcgtgctc  1860
accctgaccc tcttcgagga ccgggagatg atcgaggagc gcctcaagac gtacgcccac  1920
ttgttcgacg acaaggtgat gaagcagctc aagcggcggc gatacaccgg gtggggccgc  1980
ctatcccgca aacttatcaa cggcatccgc gacaagcagt ccggcaagac gatcctggat  2040
ttcctcaagt cggacgggtt cgccaaccgg aacttcatgc agctcatcca cgacgacagc  2100
ctcacgttca aggaggacat ccagaaggcc caagtgagcg gtcaagggga cagcctccac  2160
gagcacattg cgaaccttgc tgggagccct gcgatcaaga aggggatatt gcaaaccgtg  2220
aaggtcgtgg acgagttggt gaaggtcatg gggcgacaca agcccgagaa catcgtgatc  2280
gagatggcca gggaaaatca gaccacgcag aagggccaaa aaaacagccg cgagcggatg  2340
aagcggatcg aggagggcat caaggagctg gggtcgcaga tcctcaagga gcacccggtg  2400
gagaacacgc agctccagaa cgagaagctg tacctctatt acctacagaa cgggcgggat  2460
atgtacgtgg accaggagct agacatcaac cgcctgtccg actacgacgt ggaccatatc  2520
gtcccgcagt cgttcttgaa ggacgacagc atcgacaaca aggtgctcac aagatcggat  2580
aagaatcgag gcaagtccga caacgtgccc tcggaggagg tggtcaagaa aatgaaaaac  2640
tactggcggc agttgctgaa cgccaagctc attacgcagc ggaagttcga caacctgacg  2700
aaggctgaac gtggtgggct cagcgagcta gacaaggcgg ggttcatcaa gcggcagctc  2760
gtcgagaccc ggcagatcac caagcacgtg gcgcagatcc tggactcgcg catgaacacc  2820
aagtacgacg agaacgacaa gctcatccgt gaggtgaagg tcatcaccct taagtctaag  2880
ctggtcagtg acttccgcaa ggacttccag ttctacaagg tccgggagat caacaactac  2940
caccacgcgc acgacgccta cctcaacgcg gtggtgggga cggcgcttat taagaaatat  3000
cccaagctgg aaagcgagtt cgtttacggc gactacaagg tgtacgacgt ccgcaagatg  3060
atcgcaaagt cggaacagga aatcggaaag gcgacggcca aatatttctt ttactccaac  3120
atcatgaatt tttttaagac ggagatcacc ctggcgaacg gggagatccg caagcggccc  3180
ctcatcgaga ccaacgggga gacgggcgag atcgtctggg acaagggccg ggacttcgcc  3240
accgtgcgga aggtgctttc tatgcctcaa gtcaatatcg tcaaaaagac agaggtgcag  3300
accggcgggt tcagcaagga gtctatcctg ccgaagcgca actcggacaa gctcatcgcg  3360
cgcaagaaag actgggaccc caaaaaatat ggcgggttcg actcgccgac cgtcgcctac  3420
agcgtcctcg tggtggctaa ggtcgagaag ggcaagagca aaaagctaaa gtcggtgaag  3480
gagctgctgg gcatcaccat catggagcgc tcgtctttcg agaagaatcc aatcgacttc  3540
ctagaggcga aggggtacaa ggaggtcaaa aaggatctta tcatcaaact gccgaagtac  3600
agtctgttcg agctggagaa cgggcggaag cggatgctgg ctagtgcggg cgagttgcag  3660
aagggcaacg agttggcact gccctccaag tacgtgaact tcctgtacct ggcctcccac  3720
tacgagaagc tcaaggggag ccccgaggac aacgagcaga agcagctatt cgtcgagcag  3780
cacaagcact acctggacga gatcatcgag cagatcagtg agttctccaa gcgggtcatc  3840
ctcgcggacg ccaacctgga caaggtgctg agcgcgtaca acaagcacag ggacaagcca  3900
atcagggaac aggccgagaa catcatccac ctgttcaccc tgaccaacct gggtgcaccg  3960
gctgccttca agtactttga cacgaccatc gaccggaagc gctacacctc cacgaaggag  4020
gtgctggacg ccacgctgat ccaccagagc atcaccgggc tctacgagac acggatcgac  4080
ctgagccagc ttggcgggga c                                            4101

SEQ ID NO: 63          moltype = DNA  length = 4092
FEATURE                Location/Qualifiers
source                 1..4092
                       mol_type = other DNA
                       organism = synthetic construct
SEQUENCE: 63
gacaaaaagt attccattgg actcgctatc ggcacgaaca gcgtcgggtg ggcggtcatc  60
actgacgagt acaaggtgcc gagcaagaag tttaaggtgc tgggaaacac cgacaggcac  120
tcgatcaaga aaaatcttat cggggcccta ctcttcgact ccggagaaac cgccgaggcc  180
acccggttga agcgcacggc ccgccgtcgc tacaccaggc gcaagaaccg gatctgctac  240
ctccaggaga tattcagcaa tgagatggcg aaggtggacg actcgttttt tcacaggcta  300
```

-continued

```
gaggagtctt tcctcgtgga ggaggacaag aaacacgagc gccaccccat cttcggcaac  360
atcgtggatg aggtggcata tcacgagaag tacccaacca tctaccacct ccgcaaaaag  420
ctcgtggact ctaccgacaa ggccgacctc cgtctgatct acctcgcgct ggcccacatg  480
attaagttcc gaggacactt tctgatcgag ggcgacctga acccagacaa cagcgacgtg  540
gacaagctgt tcatccaact tgtccagacc tacaatcagc tcttcgagga gaaccctatc  600
aacgcctcgg gcgtggacgc gaaggccatc ctgtccgccc gcctgagcaa gtcgcggcgg  660
ctggagaacc tgatcgccca gctccccggc gaaaaaaaga acggcctctt cggcaacctc  720
atcgcgttgt cgctggggct caccccgaac ttcaagtcca acttcgacct ggccgaggac  780
gctaaactcc agctctcgaa ggatacctac gacgacgacc tcgacaacct gctggcccag  840
atcggcgacc agtacgcgga ccttttcctg gcggccaaga acctgagcga cgcgatcctc  900
cttagcgaca tactccgtgt gaacaccgag atcacgaagg ccccgctctc cgcgtccatg  960
attaagcgct acgacgagca ccaccaagac cttaccctgc ttaaggcgct ggtcaggcag  1020
cagttaccgg agaagtacaa ggagatcttt tttgatcaat ctaagaacgg ttacgccggg  1080
tacatcgacg gcggcgcgtc ccaggaggag ttctacaagt tcatcaagcc gatcttggag  1140
aaaatggacg ggaccgagga gctgctcgtg aagctcaacc gcgaagacct cctccgcaag  1200
cagcgcacct tcgacaacgg gagcatcccg caccagatcc acctgggaga gctgcacgcg  1260
atcctgcgga gacaagagga cttctacccc ttcctcaagg acaaccggga gaagattgaa  1320
aaaatactta cttttcgtat cccgtactac gtcgggcccc ttgcgagggg caactccaga  1380
ttcgcgtgga tgacccgcaa gtccgaggag accatcaccc cgtggaactt cgaggaggtg  1440
gtggacaagg gcgcgtcggc ccagtcgttc atcgagcgca tgaccaactt cgacaagaac  1500
cttccgaacg agaaggtgct cccgaagcac agcctgctct acgaatattt tactgtgtac  1560
aacgagctga cgaaggtcaa gtacgttacg gaggggatga ggaagcccgc cttcctctcc  1620
ggcgagcaga agaaagccat tgtggatctc ctgttcaaga ccaaccgcaa ggtgacggtg  1680
aaacagctca aagaggacta cttcaagaag atcgagtgct tcgactccgt agagatcagc  1740
ggggtcgagg accgcttcaa cgcctcgctg ggcacgtacc acgacctgct aaagattatc  1800
aaggacaaag acttcctaga caatgaggag aacgaggaca ttctggagga catcgtgctg  1860
actctgacgc tgttcgaaga ccgcgagatg atcgaggagc ggcttaagac gtacgcccac  1920
ctgttcgacg acaaggtgat gaagcagttg aaacggcggc gctacaccgg gtggggccgc  1980
ctctcccgca agctcatcaa cggcatccgc gacaagcagt cggggaagac gatcctggac  2040
ttcctcaaga gcgacggctt cgccaaccga aacttcatgc agctaatcca cgacgacagc  2100
ctgacgttca aggaggacat ccagaaggcc caagtgagcg gccagggaga ctcgctacac  2160
gagcatatcg ccaacctggc tggcagcccg gcgattaaga aggaatcct ccaaaccgtc  2220
aaagtggtgg acgagctggt gaaggtgatg ggccgccaca agcccgagaa cattgtgatc  2280
gagatggcgc gggagaacca gacgacgcag aagggccaaa aaaatagcag ggaaaggatg  2340
aagcgaatag aggaggggat caaggagctg ggagccaga ttctcaaaga gcacccggtc  2400
gagaacacac agctccagaa cgagaagctg tacctctact acctccaaaa cggccgcgat  2460
atgtacgtgg accaggaact agacatcaac cggctgagcg actatgacgt ggaccacatc  2520
gtgccgcagt ccttcctcaa ggacgactcg attgacaaca aagtgctcac tagatccgac  2580
aagaacagag gcaagagcga taacgtcccg tcggaggagg tcgtcaagaa aatgaaaaac  2640
tactggcggc agctcctaaa cgccaagctc atcacgcagc gtaagttcga caacctgacg  2700
aaggcggagc ggggcgggct gagcgagctg gacaaagcgg ggttcatcaa gcggcagctc  2760
gttgagacgc ggcagatcac aaagcacgtc gcgcaaatcc tcgactcccg catgaacacc  2820
aagtacgacg agaacgacaa gctcatccgg gaggtgaagg tcattaccct taaatcgaag  2880
ctcgtcagcg actttcgtaa ggacttccag ttctacaagg tcagagagat caacaactac  2940
caccacgccc acgacgccta tctgaacgcc gtggtgggca ccgcgcttat taagaagtac  3000
cccaagctgg agtccgagtt cgtgtacggc gactacaagg tttatgacgt caggaagatg  3060
atcgccaagt cggaacagga gatcggaaaa gctaccgcca aatatttctt ctatagcaac  3120
atcatgaact tcttcaaaac cgagatcacc ctcgccaacg gcgagatccg gaagcgcccg  3180
ctcatcgaga ccaacgggga gaccggggag atcgtctggg acaaggggcg ggacttcgct  3240
actgtccgaa aggtgctctc catgccacaa gtgaatatcg tcaagaaaac agaggtgcag  3300
accggagggt tcagtaagga gtccatcctg cccaagcgga actccgacaa gctaattgct  3360
cgcaaaaagg attgggatcc taaaaaatat ggcggcttcg actcgcccac ggtcgcctac  3420
tctgtgctgg tcgtggcgaa ggtggagaag ggcaagtcca agaagctcaa gagcgtcaag  3480
gagctgctgg ggatcacgat catggagcgt agttcgtttg agaagaatcc catcgacttc  3540
ctggaggcta agggctacaa ggaggtcaaa aaggacctca tcattaagct gccgaagtac  3600
agcctcttcg agctggagaa cggcggaag cgtatgctcg cctccgctgg ggagttacaa  3660
aaggggaacg agctggcgct gccgtctaag tacgtcaact tcctgtacct ggcctcccac  3720
tacgagaagc tcaaggggtc gccggaggac aacgagcaga agcagctctt cgtagagcag  3780
cacaagcact acctggacga gatcatcgag cagatttcag agttctcaaa gcgggtcatc  3840
ctcgccgacg ccaacctgga caaggtgctc tcggcctaca acaagcaccg ggacaagccg  3900
atccgcgaac aggccgaaaa catcatccac ctgttcacgc tcaccaacct cggtgccccg  3960
gcggccttca agtactttga cacgaccatc gaccggaagc gctatacctc gacgaaggag  4020
gtgctggacg ccaccctgat ccaccagtcc atcaccgggc tttacgagac ccggatcgac  4080
ctctcgcagc ta                                                      4092

SEQ ID NO: 64          moltype = DNA  length = 4101
FEATURE                Location/Qualifiers
source                 1..4101
                       mol_type = other DNA
                       organism = synthetic construct
SEQUENCE: 64
gacaagaagt atagtattgg actcgccatc ggaaccaact ctgtggggtg ggctgttatt  60
acagatgaat ataaggtgcc atccaaaaag tttaaagttc tgggcaatac tgatagacac  120
tcaatcaaga agaatctgat aggtgcactt ctgtttgata gtggagagac tgccgaggca  180
accagactta aaaggactgc aagaagaaga tataccagaa gaaagaatag gatttgctat  240
ttgcaggaaa tcttcagcaa cgaaatggcc aaggttgatg actcattttt ccataggttg  300
gaggagagtt ttcttgtgga ggaagataag aagcacgaaa gacacccaat tttcgggaat  360
atagtggacg aggtggctta tcatgagaag tatcccacta tctaccacct gagaaagaaa  420
cttgtggact caaccgataa ggctgatctt aggcttatat acttggccct tgcacatatg  480
```

```
atcaaattca ggggccattt tcttatcgaa ggcgatctta atcccgataa ctcagatgtg  540
gacaagctgt ttatacaact tgtgcaaacc tacaatcaac tcttcgagga gaatcccatt  600
aacgcctccg gcgtggatgc aaaagccata ctgtcagcca gactgagcaa aagtaggaga  660
ctggagaatc ttatagccca actgcccggt gaaaagaaga atgggctctt cggaaatctg  720
atcgctcttt cattggggtt gacacccaac tttaagagta actttgactt ggcagaagat  780
gcaaagttgc agctcagtaa agacacatat gacgatgacc ttgacaatct cttggcacaa  840
atagggggatc aatacgctga ccttttcctc gctgccaaga acctcagcga cgctatactg  900
ttgtccgaca ttcttagggt taataccgaa attacaaagg cccctcttag tgcaagtatg  960
atcaaaaggt atgatgagca tcaccaagac cttacactgc tgaaggctct ggttagacag  1020
caactccctg aaaagtataa ggaaatattc ttcgaccaaa gtaagaacgg gtacgccggt  1080
tatattgatg gggcgcaag tcaagaagaa ttttacaaat tcatcaagcc aattcttgaa  1140
aagatggacg ggactgagga attgctggtg aaactgaata gagaggacct tcttagaaaa  1200
cagaggacat ttgacaatgg gtccatccca caccagattc atctggggga actccacgca  1260
atattgagga gacaagaaga cttttaccca ttccttaagg ataatagaga gaaaatcgaa  1320
aaaatcctga ctttcaggat tccttactat gttgggccac tggccagggg gaactcaaga  1380
ttcgcttgga tgacaaggaa gtcagaagaa accataaccc cttggaattt tgaagaggtg  1440
gttgataagg gggcatcagc ccagtctttc atagagagga tgaccaactt tgataaaaat  1500
cttccaaatg agaaggtttt gccaaaacat agtcttttgt acgagtactt tactgtttat  1560
aacgaattga ccaaggtgaa gtatgtgacc gagggaatga ggaagccagc atttttgtcc  1620
ggggagcaaa agaaagcaat cgttgatctt ctcttcaaga ccaacagaaa agtgaccgtg  1680
aaacaactga aggaagacta cttcaaaaag atagaatgtt tcgattcagt ggaaattagc  1740
ggtgttgaag acaggttcaa tgcttcattg ggtacttacc acgacctgtt gaagataatc  1800
aaagacaagg actttctcga taatgaggag aacgaagaca tcttggaaga cattgtgctt  1860
acactcactt tgtttgagga cagggaaatg attgaggaaa gactcaaaac ttacgctcat  1920
ttgtttgatg ataaggttat gaaacaacta aaaagaagaa ggtacaccgg ctggggaaga  1980
ttgagtagga aactgatcaa cggtattaga gataaacaat ccggaaagac tatcctcgat  2040
ttccttaaga gtgatggctt tgcaaatagg aattttatgc agctgattca tgacgactca  2100
cttaccttca aagaagacat ccaaaaagct caggtgtctg ggcaaggcga cagtctgcat  2160
gaacatatag ctaacttggc tgggagtccc gccatcaaga aggggatact tcaaacagtt  2220
aaagttgtgg acgaattggt gaaggtaatg ggaaggcaca agcctgaaaa tatagtgata  2280
gaaatggcaa gggaaaatca aacaacccag aagggacaga agaacagtag ggaaaggatg  2340
aaaaggatag aagaggggat caaagagctt ggtagccaga tcctcaagga acatccagtg  2400
gagaataccc aacttcaaaa cgagaaactc tatttgtact acttgcagaa cggaagagat  2460
atgtatgtgg accaagagct tgatattaac aggctgagcg attatgacgt tgaccacata  2520
gtgccccaat cattcctcaa ggatgactct attgataata aggtgctgac aaggagtgac  2580
aagaatagag ggaaatccga caacgttcca tccgaggaag ttgtgaagaa gatgaagaac  2640
tactggaggc agttgctgaa cgctaagctc attacccaga ggaaattcga taacctgacc  2700
aaagcagaga gaggcgggct gagcgaactc gataaagcag gtttcatcaa gagacaactc  2760
gtggagacta ggcaaattac taagcacgtg gctcaaatac tcgacagcag gatgaacaca  2820
aagtacgacg agaacgacaa gctcattaga gaggttaagg ttattactct gaaaagtaaa  2880
ttggttagcg atttcagaaa ggatttccaa ttctataagg ttagagagat caacaattat  2940
catcatgcac atgatgccta tctgaatgct gtggttggta cagcccttat caagaagtac  3000
cctaagctag agagcgagtt tgtgtacgga gattataagg tgtatgatgt gaggaaaatg  3060
atcgctaaaa gtgagcaaga gattggaaag gctaccgcca aatacttctt ttattccaat  3120
attatgaatt tcttcaagac agaaatcacc ctggctaacg gcgagataag gaagaggccg  3180
cttatcgaaa ctaatgggga gacaggcgaa atagtgtggg acaaagggag ggatttcgca  3240
actgtgagga aggttttgag catgcctcag gtgaatatcg ttaagaaaac cgaagttcaa  3300
actggagggt tctctaagga aagcattctc cccaagagga actccgacaa gctgattgct  3360
agaaagaaag actgggaccc caagaagtat ggcggattcg actcacccac tgtggcatat  3420
agcgttctcg tggtggcaaa ggttgaaaag ggtaaatcca aaaaactcaa atccgtgaag  3480
gaactccttg gcataactat tatggaaagg agtagctttg aaaagaatcc catcgacttt  3540
ctcgaagcta agggctataa ggaagttaag aaggacctta taatcaaact tccaaaatac  3600
tccctttttg agttggaaaa cggcagaaag agaatgttgg ccagtgccgg ggagcttcaa  3660
aagggcaacg aactggctct gcctagcaaa tatgtgaact tttgtatct ggcatcacac  3720
tacgagaaac ttaaaggctc tcctgaggac aacgagcaaa aacagctctt tgttgaacag  3780
cataagcact acctcgacga gattattgag cagatcagcg agttctcaaa gagagttatt  3840
ctggctgacg ctaatcttga caaggttttg tccgcttaca acaaacacag ggataagcca  3900
atcagggagc aggcagaaaa cataatccat ctctttaccc tgacaaacct cggtgccccc  3960
gctgctttca agtattttga tactaccatt gacaggaaga gatatacttc cactaaggaa  4020
gtgctcgacg caaccctcat acaccaaagt atcacaggcc tctatgaaac taggatagat  4080
ttgtctcaac ttgggggcga t                                            4101
```

```
SEQ ID NO: 65          moltype = DNA  length = 4101
FEATURE                Location/Qualifiers
source                 1..4101
                       mol_type = other DNA
                       organism = synthetic construct
SEQUENCE: 65
gacaaaaagt attccatcgg gcttgctatc ggaaccaact ctgtggggtg ggcagttatt  60
accgacgaat acaaggtgcc cagcaagaag tttaaggttc tggggaacac agatagacat  120
agcataaaga aaaacctgat aggcgcactg ttgttcgact ccggggaaac agccgaagct  180
accaggctga agagaactgc aagaagaagg tacaccagaa gaaaaaacag aatatgttat  240
ctccaagaga ttttctctaa cgagatggcc aaggtggacg actcattctt tcacagactg  300
gaagaatctt tccttgtgga agaagataag aaacacgaga ggcaccctat ttttggcaat  360
atcgtggatg aggtggctta ccacgaaaaa taccctacaa tataccacct caggaaaaaa  420
ttggttgata gtacagacaa ggccgacctc aggctcatct atttggccct ggcccatatg  480
attaaattca gggggcactt tctcatcgag ggagatttga accccgacaa cagtgatgtt  540
gataagctct ttattcagct cgtgcagact tacaatcagt tgtttgagga aaaccccatt  600
aatgcttccg gggtggacgc caaggcaatc ctttctgcaa gactctcaaa gtcaaggaga  660
```

-continued

```
ctcgaaaatc tgatagcaca gcttccagga gagaagaaga acgggctctt tggaaacctg  720
atcgctctgt cactcggact cacacccaat ttcaaaagca attttgattt ggcagaggac  780
gctaagctgc aactcagtaa ggatacctac gacgatgact tggataatct gctcgcacaa  840
attggggacc agtatgcaga cctgtttctc gcagctaaga acttgagtga cgccatattg  900
ctcagtgaca tcctcagggt taataccgag attacaaaag ctccactctc tgcaagcatg  960
atcaagaggt atgacgagca ccatcaagac ctgacactcc ttaaggcgtt ggttaggcag  1020
caacttcctg aaaagtataa ggaaatcttc ttcgatcaaa gcaaaaacgg ctacgccggc  1080
tatatagacg gggagcatc ccaagaagaa ttttataagt tcataaaacc tatattggag  1140
aagatggacg ggacagagga attgctcgtg aaactgaaca gggaggatct cctcaggaag  1200
caaaggacct tcgacaatgg ctccatccca catcagattc acctcggcga actgcacgca  1260
atactgagaa gacaagagga cttttatcct ttcctgaagg acaacaggga gaaaatcgag  1320
aaaatcttga cattcagaat cccatactac gttgggcctc tggccagagg taacagtagg  1380
ttcgcctgga tgactaggaa atcagaggag actattacac cctggaactt tgaagaagtt  1440
gttgataagg gagcttcagc acaatcattc atcgaaagaa tgacaaactt tgacaaaaat  1500
ctgcctaatg agaaagtgct cccaaaacat tccctgctgt atgagtattt taccgtttat  1560
aacgagctta ccaaggtgaa atacgttact gaaggtatga gaaagccagc ttttctttca  1620
ggggagcaaa agaaggctat cgtggatctt ctctttaaga ccaacagaaa ggttaccgtg  1680
aagcagctta aggaagacta ctttaaaaag atcgagtgtt ttgactcagt ggaaataagc  1740
ggtgttgaag atagattcaa cgcatccttg ggaacttatc atgatcttct taagataatc  1800
aaggataaag actttctcga caacgaggaa aacgaagata tactggagga catagttctg  1860
acacttactt tgttcgagga tagggagatg atcgaggaaa gactgaaaac atatgctcac  1920
cttttcgacg acaaagttat gaaacaactc aagagaagga gatatacagg gtgggggaga  1980
ttgagcagga aactgattaa tggtatcaga gacaaacagt caggaaaaac aatactcgac  2040
tttttgaaat cagacgggtt cgcaaatagg aatttcatgc agcttataca cgacgattca  2100
cttactttta aagaggacat tcaaaaggct caagttagtg gacaaggtga ctccctccac  2160
gaacacatcg caaatctcgc tggcagccct gcaattaaga agggtatact ccagacagtt  2220
aaggttgttg acgagctggt taaagtgatg ggaagacaca aacccgagaa catagtgata  2280
gagatggcca gggaaaacca aaccactcaa aaagggcaga aaaattccag agagaggatg  2340
aaaaggattg aagaaggtat caaggagctg ggtagccaaa ttctgaaaga acatcctgtg  2400
gaaaacactc aactccagaa tgagaaactc tatctgtact atctgcaaaa tgggagagat  2460
atgtatgtgg accaggaact ggacataaac aggctctcag attacgatgt ggatcatatc  2520
gtgccacagt cctttcttaa ggatgatagc atcgacaata aggtgcttac caggtccgac  2580
aagaacaggg gaaagtcaga taacgtgcct tctgaagaag ttgttaaaaa gatgaagaac  2640
tactggagac agctgcttaa cgctaagctc ataacacaga ggaagtttga caacttgacc  2700
aaggccgaga gaggcggact ctcagaattg gataaggcag ggttcataaa aaggcagctg  2760
gtggaaacaa ggcagataac taaacatgtg gctcagatcc tcgatagtag gatgaataca  2820
aaatacgatg agaacgacaa gctcataagg gaggttaaag tgataactct gaaatccaaa  2880
ctggttagcg attttaggaa ggatttccag ttttacaaag ttagggagat caacaattat  2940
catcacgccc acgatgccta cttgaacgca gttgtgggta ctgcacttat caaaaagtac  3000
cctaagctgg aatccgagtt tgtttatgga gactataagg tgtacgacgt tagaaaaatg  3060
attgcaaagt cagagcagga gatagggaaa gccactgcaa aatatttctt ttatagcaat  3120
atcatgaatt tctttaagac agaaatcaca ctggccaatg gggaaataag gaagaggccc  3180
ctgatcgaaa ctaatggcga gacaggggag attgtgtggg ataaaggtag ggactttgca  3240
acagtgagga aagtgctgag catgccccaa gttaatatcg ttaaaaagac cgaggttcaa  3300
acagggggct ttagtaagga aagcattttg cccaagagga atagtgacaa attgattgct  3360
aggaaaaaag attgggaccc caaaaagtat ggcggatttg atagccccac tgttgcttac  3420
tccgtgctcg tggttgcaaa ggtggagaag ggaaagagca agaaactgaa gtcagttaag  3480
gaactccttg gtatcactat catggaaaga agctcctttg agaagaaccc tattgacttc  3540
ctggaggcta aagggtacaa agaggttaag aaagacctta tcattaaatt gcccaaatat  3600
agtcttttcg agcttgaaaa cggaagaaag aggatgcttg catccgctgg cgaattgcaa  3660
aagggcaatg agcttgctct cccttccaag tatgtgaact tcctttatct tgcctcacac  3720
tatgaaaaac tcaaaggttc acccgaagac aacgaacaaa agcaactatt tgtggaacaa  3780
cacaagcact acctggacga aatcattgag caaatttctg agttttcaaa aagggtaatc  3840
ttggctgacg caaatctcga caaagttttg tcagcttaca acaaacatag agataagcca  3900
attagagagc aagctgagaa tatcatccat ctgtttaccc tgactaacct tggagcgcct  3960
gctgctttta aatatttcga caccacaatc gacaggaaga ggtacactag cactaaggaa  4020
gttctcgacg ccaccctcat ccaccagagt attacaggcc tgtacgagac aagaattgat  4080
ctttctcaac ttggtggtga c                                            4101
```

```
SEQ ID NO: 66           moltype = DNA  length = 4101
FEATURE                 Location/Qualifiers
source                  1..4101
                        mol_type = other DNA
                        organism = synthetic construct
SEQUENCE: 66
gataagaagt actcaatcgg tctggcaatc ggaaccaact ctgtgggttg ggcagtgatt  60
acagatgagt ataaggtgcc aagcaaaaaa ttcaaggtgc tgggtaatac cgacagacac  120
agcattaaga agaatttgat tggagcactc ctctttgact caggggaaac agcagaggca  180
acaaggctga agaggacagc aaggcggagg tacacaaggc ggaaaaacag gatatgctac  240
ctccaggaaa tctttagcaa cgagatggct aaagtggatg atagcttttt ccatagactc  300
gaagaatcct ttcttgttga agaggacaaa aagcatgaaa ggcatcccat cttcggcaat  360
atagttgatg aggttgcata ccatgagaag taccccacaa tctaccacct cagaaagaaa  420
cttgtggact ccacagataa agcagacctg aggctcatat acctcgcact cgcacacatg  480
atcaagttca gagggcactt tctcatcgaa ggtgacctga atccagataa ttcagatgtg  540
gataaactgt ttatacagct ggtgcaaaca tacaaccaac ttttcgagga aaacccaatc  600
aatgcctccg gtgttgatgc aaaggccatc ctgtcagcaa gactcagcaa aagcaggcgg  660
ctcgaaaacc tcatcgccca gcttcccggt gaaaagaaga acgggctctt tggtaatctc  720
atcgcattga gccttggtct tactccaaac ttcaagagca attttgatct ggcagaggat  780
gctaaactgc aactctcaaa ggacacatat gacgatgacc ttgacaatct gttggcccag  840
```

-continued

```
atcggggacc aatatgcaga cctcttcctg gccgcaaaga atctgtcaga tgcaatcctc  900
ttgtccgaca tactgagagt taacactgag atcacaaagg cacctctgtc cgcctccatg  960
attaagagat acgatgagca tcaccaggat ctgactttgc tcaaagccct cgttagacag  1020
cagttgccag aaaagtacaa agaaatattc tttgatcaat caaaaaacgg atatgcaggg  1080
tacatcgacg gtggggcaag ccaggaagag ttctacaaat tcatcaaacc tatcctggaa  1140
aagatggatg ggacagaaga gctgctggtt aagctgaata gggaagacct cctcagaaag  1200
cagaggacat ttgataacgg gagcatccct catcaaatcc acctcggtga actccatgct  1260
atcctgagaa ggcaggaaga cttttatcca tttttgaagg acaataggga gaaaatcgaa  1320
aaaatcctga cattcagaat cccatactac gttggtcctc tggcaagagg taacagtagg  1380
ttcgcatgga tgacaaggaa aagcgaggag acaatcacac cctggaattt tgaggaagtt  1440
gttgacaagg gtgccagcgc acaatccttt atcgaaagaa tgacaaattt cgacaagaat  1500
ctgcctaacg aaaaggttct cccaaagcat tcactcctgt acgaatattt tacagtttat  1560
aacgaactga ctaaagttaa atacgttacc gagggtatga ggaagccagc attcctttcc  1620
ggggaacaga agaaagctat tgtggacctc ctgttcaaga caaatagaaa agtgacagtt  1680
aagcaactca aagaggatta cttcaaaaag atcgaatgtt ttgactctgt ggagatcagc  1740
ggggtggagg atagattcaa cgccagcctg ggtacatatc atgatctcct gaaaatcatt  1800
aaagacaagg acttccttga caacgaggag aacgaggaca ttctggaaga cattgttctg  1860
accctcacac tctttgagga tagggagatg attgaggaaa gactgaagac ctacgcccac  1920
ctctttgacg ataaagtgat gaaacagctc aagagaagaa ggtatacagg ttgggggaga  1980
ctgagcagga agttgatcaa tgggattagg gacaaacagt ccgggaaaac aatcctcgat  2040
tttctgaagt cagacggttt cgcaaacaga aattttatgc agctcattca cgatgacagc  2100
ttgacattca aggaagacat ccaaaaggct caagtgagcg gccaagggga tagcctccac  2160
gagcatattg caaatctggc aggttcacca gccatcaaaa agggcatact tcagacagtt  2220
aaggttgtgg acgaattggt taaagttatg ggcaggcata agccagagaa tatcgttatc  2280
gaaatggcaa gggagaacca aacaactcaa aaagggcaga aaaatagcag agagaggatg  2340
aaaagaatcg aggaagggat caaggaactt gggtcccaaa tcctcaagga gcacccagtt  2400
gaaaatactc aactgcaaaa cgagaagctc tatctctact atctccaaaa cgggagggat  2460
atgtatgttg accaggagct ggatattaac agactgtcag attatgatgt tgatcatatc  2520
gtgccccagt cattcctgaa ggacgattcc atcgacaaca aagttctcac aaggtccgat  2580
aaaaacaggg gcaagtccga taacgttcca agcgaagaag tggtgaaaaa gatgaaaaac  2640
tattggagac aacttctgaa tgcaaagttg attactcaga gaaagtttga caacctcaca  2700
aaagcagaaa gaggcgggct tagcgaactc gataaggcag ggtttatcaa aagacagctg  2760
gttgagacaa ggcagatcac aaaacatgtg gcacagatcc ttgactcaag gatgaatacc  2820
aagtatgatg agaatgataa gttgatcagg gaggttaaag ttatcacact caaatccaaa  2880
ctggtgtcag acttcaggaa agactttcaa ttttataagg tgagggagat caataactac  2940
caccatgcac atgacgccta cctgaacgca gtggtgggta cagcattgat taaaaaatac  3000
cctaagctgg agtctgagtt tgtgtacggg gactacaagg tgtacgacgt gaggaaaatg  3060
atagccaagt ccgagcagga gatcgggaaa gcaacagcta agtatttctt ttacagtaat  3120
atcatgaatt tctttaaaac tgagattact ctggcaaacg gggagatcag gaaaagaccc  3180
ctcatcgaga ctaatggtga aacaggtgag atcgtttggg acaaggggag ggattttgct  3240
actgttagaa aagttctgag tatgccacaa gtgaatattg tgaaaaagac agaagttcag  3300
acaggtgggt tctccaaaga atccatcctg cccaagagaa attcagacaa gctcatcgca  3360
agaaagaagg actgggaccc taagaagtac ggaggatttg acagccccac cgtggcctat  3420
tccgtgcttg ttgtggcaaa ggtggagaaa gggaagagca aaaaactgaa atccgtgaaa  3480
gaactgctgg gaattaccat catggaaaga agctcctttg agaagaaccc aatcgacttc  3540
ctggaagcaa aaggatataa ggaagtgaaa aaggacctca ttatcaagct cccaaaatac  3600
tcacttttcg agttggagaa cggtagaaag aggatgctgg caagcgcagg ggaacttcag  3660
aaaggcaatg agctggcatt gccatcaaag tatgtgaact tcctctactt ggccagccat  3720
tacgagaaac ttaaaggtag cccagaagat aacgagcaaa aacagctctt tgtggaacag  3780
cataagcatt atctggatga gatcatagaa caaatctcag agttttccaa gagagttatc  3840
ctcgcagatg caaacctgga taaggttctc tcagcctata ataagcatag agacaagcca  3900
attagagagc aagcagagaa cattatccac ttgttcactc ttacaaacct gggggcacca  3960
gccgccttca aatatttcga tacaacaata gacagaaaga ggtataccag caccaaagaa  4020
gttctcgacg ccacactgat ccatcaatca atcacaggcc tttacgaaac taggatcgac  4080
ttgtcacaac tgggtgggga t                                             4101
```

```
SEQ ID NO: 67          moltype = DNA  length = 3307
FEATURE                Location/Qualifiers
source                 1..3307
                       mol_type = other DNA
                       organism = synthetic construct
SEQUENCE: 67
gagcaaggac acctacgacg acgacttgga caacctattg gcccagatag gtgaccagta  60
tgcagacctc ttccttgcgg ccaagaactt gagtgacgct atactgctca gtgacatcct  120
gagggtgaac actgagatca ctaaggcccc tctctctgcc tcaatgatta agcgttacga  180
cgagcatcac caggatctca ccctgcttaa ggcccttgtt cggcagcagc tccctgagaa  240
gtacaaggag atatttttg accagtctaa gaacggctac gccggttaca ttgacggtgg  300
ggcaagccag gaggagttct acaagttcat caagccgatc cttgagaaga tggacggcac  360
cgaggagcta cttgtcaagt tgaaccggga agacctgctc cggaaacagc gtacattcga  420
caacggcagc atccctcacc agatccacct gggcgaacta cacgccatcc tccgacgtca  480
ggaggacttc tatccattct tgaaagataa cagggaaaaa atcgaaaaaa tacttacgtt  540
tcgaatacct tactacgtgg ggccccttgc tcggggaaac tccagattcg catggatgac  600
caggaagtca gaggagacca tcacaccctg gaactttgag gaggtggttg acaaaggtgc  660
ttctgcccag tccttcattg agcggatgac taacttcgac aagaacctgc ccaacgagaa  720
ggtgctgcca aagcacagcc tgctctacga atactttact gtgtacaatg agctgacgaa  780
ggtgaagtac gtgacagagg ggatgcggaa gcccgctttc ctgagcggcg agcaaaaaaa  840
agcaatcgtg gacctactgt tcaagaccaa ccgaaaggtg acagtgaagc agctcaagga  900
ggactacttc aaaaaaatcg agtgcttcga ctctgttgag ataagcggcg tggaggaccg  960
attcaacgcc tcattgggaa cctatcacga cctgctcaag atcattaagg acaaggactt  1020
```

-continued

```
cctggataat gaggagaatg aggacatcct ggaggatatt gtgctgaccc ttactctatt  1080
cgaggacagg gagatgatcg aggagcgact caagacctac gctcacctgt tcgacgacaa  1140
ggttatgaag caattgaagc gtaggcgata cacggggtgg ggaagactct cccgaaaact  1200
gataaacggc atcagggaca agcagtcagg gaagacgatc ttggacttcc tgaaatccga  1260
cgggttcgcc aaccgcaact tcatgcagct cattcacgac gactcactaa cgttcaaaga  1320
ggacattcag aaggctcaag tcagtggaca aggcgactcc ctgcacgagc acattgcaaa  1380
ccttgcgggc tccccggcga ttaaaaaggg cattctccaa acggttaagg tggtggacga  1440
gctggtgaag gtgatgggcc gacacaagcc tgagaacatc gtgatcgaga tggccaggga  1500
gaaccagact acccagaagg gtcagaagaa ctctcgggaa cgtatgaagc gtattgagga  1560
ggggattaag gagttgggct ctcaaatcct caaggagcac cctgtggaga acactcagct  1620
ccaaaacgag aagctgtacc tgtactacct gcaaaacggg cgcgatatgt acgtggatca  1680
ggagttggac atcaacaggc ttagcgatta cgacgtggac cacatcgtgc cacagtcatt  1740
cttaaaggac gacagcatcg acaacaaggt tctgacgagg agcgacaaga atcgagggaa  1800
aagtgacaat gttccatccg aggaggtggt caagaaaatg aagaactatt ggcgtcagct  1860
tctgaacgcc aagctcatca cccagcggaa attcgacaac ctgactaagg ctgagcgagg  1920
cggactctcc gagcttgaca aggctggctt catcaagcgg cagttggtcg aaacccgaca  1980
gataacgaag cacgttgccc agatacttga ctcccgtatg aacaccaagt acgacgagaa  2040
cgacaagctc atcagggagg tgaaggtcat tacccttaag tccaaactcg tcagcgactt  2100
tcgtaaggac ttccagttct acaaggtgcg cgagatcaat aactaccacc acgcacacga  2160
cgcctacctg aacgcagtgg ttggaaccgc gttgattaaa aagtacccca agttggagtc  2220
ggagttcgtt tacggggact acaaggtgta cgacgttcgg aagatgatcg ccaagtctga  2280
acaggagatc gggaaagcaa ccgccaagta tttcttctat agcaacatca tgaacttctt  2340
taaaaccgag atcacacttg ccaatggcga gatccgtaag aggccgctga tcgagacaaa  2400
tggggagact ggcgagatcg tgtgggacaa gggccgcgac ttcgcaaccg ttcggaaagt  2460
cttgtccatg cctcaagtca acatcgtcaa gaagactgag gtgcaaacag gcgggttctc  2520
gaaggagtcc atactgccca agaggaactc agacaagctc atagcacgca aaaaagactg  2580
ggatccaaag aaatacggcg ggttcgactc gccgacagtc gcatactccg tgttagtggt  2640
ggctaaagtg gaaaagggga agtccaagaa gctcaagtcc gtcaaggagt tgctcgggat  2700
caccattatg gaacggtcct cattcgagaa gaatcccatt gacttcctag aggcgaaggg  2760
ctacaaagag gtcaaaaagg acctaattat taagctcccc aagtattcac tcttcgaact  2820
tgaaaatggt cgtaagcgga tgttggcaag cgctggagag cttcagaagg ggaacgagct  2880
tgcactgcct tccaagtacg tgaacttcct gtacctcgcc tctcattacg agaagttgaa  2940
gggctcaccg gaggacaacg agcagaagca gttgttcgtg gagcagcaca agcactacct  3000
cgacgagatc attgagcaga taagtgagtt cagcaaacgg gtgatccttg ccgacgctaa  3060
cctggacaag gtgctgagcg cctacaacaa gcacagagac aagccgatcc gagagcaagc  3120
ggagaacatc atacacctgt tcaccctcac gaacctcggg gctcccgcag ccttcaaata  3180
ttttgacacg accatcgacc gtaaacgcta cactagcacg aaggaggtgc tggacgctac  3240
ccttatccac cagtccatca ccggcctgta cgagacgaga atcgacttgt cgcagctcgg  3300
tggtgac                                                            3307
```

```
SEQ ID NO: 68           moltype = DNA  length = 4101
FEATURE                 Location/Qualifiers
source                  1..4101
                        mol_type = other DNA
                        organism = synthetic construct
SEQUENCE: 68
gacaaaaaat actcaattgg tctggcaatt gggaccaaca gtgtcggatg ggccgtgatt  60
accgacgagt acaaggtgcc gtccaaaaaa ttcaaggtgc ttgggaacac cgaccgccac  120
tcgatcaaga aaaacctaat cggtgcgttg cttttcgaca gtggggagac cgccgaggca  180
acacgcttaa aacgcacagc taggaggaga tatacacggc gcaagaaccg aatatgctac  240
ttacaggaga tattctccaa tgagatggcg aaggtggacg actctttctt ccatcggctt  300
gaggaatcct tcctggtcga ggaggacaag aagcacgagc gacacccgat attcgggaac  360
atcgttgatg aggtggcgta ccacgagaag tacccaacga tataccactt acgcaagaag  420
ctcgtggact ctacggacaa ggccgacttg cgccttatct acttggcact ggcccacatg  480
attaagttcc gaggccactt ccttatcgag ggtgacctga accccgataa ctccgacgtg  540
gacaagctct tcatccaact cgtccagaca tacaaccagc tattcgagga gaatcctatc  600
aacgcctctg ggtggacgc taaagctatc ctctcagccc gcctgtcaaa gtcgaggagg  660
ttggagaacc taatcgccca gcttccaggc gagaagaaaa atgggctgtt cggaaacctt  720
atcgcactct cactgggcct aaccccgaac ttcaagtcca acttcgacct ggcagaggac  780
gcgaaattgc agttgtcgaa agacacctat gacgatgacc tggacaacct gttggcccag  840
atagggggacc agtacgccga cctgttccta gcggccaaga acctgtccga cgccatcttg  900
ctgtcggata tactgcgggt gaacaccgag atcactaaag cacctctctc cgccagcatg  960
attaagcgtt acgacgagca ccaccaagat ttgaccctgc taaaggcact tgtacggcag  1020
cagcttcccg agaagtacaa ggagatcttt ttcgaccaaa gcaagaacgg ctacgccggg  1080
tacatcgacg gaggtgccag ccaggaggag ttctacaagt tcattaagcc catcctggag  1140
aagatggacg ggactgagga actacttgtg aagctgaacc gggaagactt actacggaag  1200
cagcgtacct tcgacaacgg ttctatccca catcagatcc atcttgggga gttgcacgcg  1260
atcctgcgac gccaggagga cttttacccc ttcctgaaag acaaccgcga gaaaatcgag  1320
aagatactga ccttcagaat accttactac gtcggacccc ttgcgcgagg caactcaaga  1380
ttcgcgtgga tgaccaggaa atcagaggag accatcacac cctggaattt cgaggaggtg  1440
gttgacaagg gtgcctccgc ccagtccttt atcgaacgaa tgaccaactt cgacaagaac  1500
ttgcccaacg agaaggtgct ccccaaacac agcctcctct acgaatattt cacagtgtac  1560
aacgagctta ctaaagttaa gtatgttact gagggcatga ggaaacccgc cttcctgtca  1620
ggcgagcaga agaaagctat tgtggacctc cttttcaaga ccaaccggaa ggtgacagtg  1680
aagcagctca aggaggacta cttcaagaag atagagtgct tcgacagcgt ggagatcagc  1740
ggggtggagg acagattcaa tgcctctctc ggaacatacc acgacttgct taagatcatc  1800
aaggacaagg acttcctcga caacgaggaa aacgaggata ttctggagga tattgttctg  1860
actcttaccc tgttcgagga ccgggagatg atcgaggagc gtctcaagac ctacgcccac  1920
ctgttcgacg acaaagttat gaagcagctc aagcgtcgga gatataccgg atggggccgt  1980
```

```
ctgtctcgga agctcatcaa cgggatcagg gacaagcagt cagggaagac gatcttagac  2040
ttccttaagt ctgacggctt cgccaacagg aacttcatgc agttgatcca cgacgacagc  2100
cttaccttca aggaggacat ccagaaggcc caagtgagtg gccagggtga cagcctccac  2160
gagcatattg ctaatcttgc gggttcccca gcgattaaaa agggcatact tcaaaccgtt  2220
aaggtggtgg acgagcttgt caaggtgatg gggcgacaca agcccgagaa catcgtgatc  2280
gagatggcca gggagaacca gaccacccag aaggggcaga agaatagccg agaacgcatg  2340
aagcgcatcg aggaggggat taaggagcta gggagccaga tcctcaagga acatcccgtc  2400
gagaacaccc agctccagaa cgagaagcta tacctctact acttgcaaaa cgggagggat  2460
atgtacgtgg atcaggagtt ggacattaac cgcctaagcg actacgacgt agatcacatc  2520
gtgcctcagt cattcctcaa agacgacagc attgacaaca aagtcttgac ccgatccgac  2580
aagaaccgag gaaaatccga caatgtgccc tcagaggagg tcgtcaagaa aatgaagaac  2640
tattggaggc agctacttaa cgccaaactc ataacccagc ggaagttcga caacctgaca  2700
aaggctgagc ggggtgggct cagcgagctt gacaaggctg gcttcatcaa gcggcagttg  2760
gtggagacaa gacagataac gaagcacgtg gctcagatcc tggactctcg catgaacacg  2820
aagtacgacg agaacgacaa attgatccgc gaggtcaagg ttattacgct caagagcaaa  2880
cttgtcagcg atttccgcaa ggacttccag ttctacaagg tgagggagat taacaactac  2940
caccatgcac atgatgccta cttgaacgca gtggtgggga ccgcgcttat taaaaagtac  3000
cctaagttgg agtcagagtt cgtttatggg gactacaagg tgtacgacgt ccggaagatg  3060
attgcaaagt ctgaacagga aatcgggaag gccaccgcca aatatttctt ctacagtaac  3120
attatgaatt tttttaagac tgaaattact ctcgcaaacg gcgagatcag gaagcgtccc  3180
ctcatcgaga caaacgggga gaccggggag atagtctggg acaaggggcg ggacttcgct  3240
acggtgagga aggtgctctc gatgccacaa gtgaacatcg tcaaaaagac agaggtgcag  3300
accggtggct tctcaaagga gtcaatcctg ccaaaacgta acagcgacaa gctcatcgcc  3360
cgcaagaaag actgggaccc taagaagtat ggtgggttcg actcaccgac ggtcgcatac  3420
tccgttctgg tcgtggcaaa ggtggaaaag ggcaagtcca aaaaactgaa atccgtgaag  3480
gagttgcttg gcattaccat catggaacgc agcagcttcg agaagaaccc cattgacttc  3540
ctggaggcta aagggtacaa ggaggtcaag aaagatttaa ttattaagct acctaagtac  3600
agcttgttcg agctggagaa cggccgaaaa cgaatgctcg catccgccgg ggaacttcaa  3660
aagggcaacg agcttgcgct gccctccaag tacgtgaact tcctgtactt ggcatcccac  3720
tacgagaaac tcaagggtag cccagaggac aacgagcaga agcagctatt cgtggagcag  3780
cacaagcact acctcgacga gataatcgag cagatcagtg agttcagtaa gcgggtgata  3840
ctcgcggacg ccaacttgga caaggtgctt agtgcctaca acaagcaccg tgacaagccc  3900
atccgagaac aggctgagaa catcatccac cttttcactc tgacaaacct cggtgctccc  3960
gccgccttca aatacttcga cactaccatc gacaggaagc gctacacatc tacgaaggaa  4020
gttcttgacg ctacgcttat tcatcagtct atcacagggc tgtacgagac aaggatcgac  4080
cttagccaac tcggcgggga t                                           4101

SEQ ID NO: 69           moltype = DNA  length = 10248
FEATURE                 Location/Qualifiers
source                  1..10248
                        mol_type = genomic DNA
                        organism = Brassica napus
SEQUENCE: 69
ttaatcatca agcttaccta ccctcgctct ctctagatca atcatctccc tcctcttttt  60
gttgttttta ttcatttctt gatattacag aatcaatgga ggaaggtggg agtagtcacg  120
acgcagagag taacaagaag ctagtgagag ggaagataga gataaagagg atagagaaca  180
cgacaagtcg tcaggtaact ttctgcaaac gacgcaatgg tcttctcaag aaagcttatg  240
agctctctgt cttgtgtgat gcggaagttg cacttgttgt cttttccact cgtggccgtc  300
tctatgagta cgctaacaac aggtacgctt ctcctacacc attgattgat ctgctactgc  360
aaataatatt agttatttta ttagtgatga tggacacgag aggtttagag ccaagattag  420
ggtttttatt agttacaatc ctggattttt ttaaattaaa ttttaccatt atctctctag  480
atttctttat atattttttt ttgaacaaga tttctttata tttatgtgta tgtgtgtgta  540
tgcaaaatat gagaaggaaa tatttgtctt gtcttctcaa ctcgttagcc gtttttagtt  600
tcactcgttt tatgaaacat tggaacctga tgcatgtctg gttacgttct atacaacact  660
taattagttt tgacgatcca taatttttct ctattcaaat tattgctagg attttatcag  720
gaaaagagtt gggacaaagc ctaatgatga gttatcaata gagatccttt taataattta  780
aactaacccc caacaccaaa tgaaaactga gaattagtta tactctggag tgggtcttga  840
gaaaatatgt aactgaaagc tagtatttta cgtttttttct ctccattttt catatttatt  900
ttgaaggata gttgaagaag tcctttaaaa caatatacgc acatatatgt gacttagtct  960
agcattcact cactgaattt aaaaaaaact agattttgac ccgcgcttag aaagcgcggg  1020
tttgtttgtt tttcatttat taatcgaaaa ctgatttgca aattaccatt atttttgttt  1080
cgaaccataa caattgagtt tttagggttt tatcattttt tttctcttca aaatatggta  1140
ttttttttgaa atatggtagt tgttctatga taatatttga gttttaagat ttgttttcat  1200
atctgaccta gattcatggt tggacctata gatccaatac attgtatata atccggttcg  1260
gatttaatga aaaattcgtt aattaaaaat ctgatataac caggtaaaaa tccaaaaact  1320
cactattaac ctgcaatctg ataccattga tctgattaca aaatatttaa tagtaatttt  1380
ttttaaaaat tgattaaatt actcatatat ttattaatat tacataaatt agtgattcct  1440
tagaatttga taaaatttttg ttatgttatc caaataaaaa atgataatac aaaaaactta  1500
ttgatatgac aatattagtt tatttcgtct ttaataacct attataagtt ggtgttttta  1560
ttttagattt aaaaattaat tttaatatag tttttaaaat tttcttgaac actcgtaatt  1620
ggcatatcaa tattatgtat aaaatgacat tataaatgga aaaatgatat tcaaatatgt  1680
atatgatata tggtgtagga tatatgattt tggtttatat tgaaaaaatg tataatattc  1740
aaatgatctg ttttgaatat tgatatgtat atttaagaaa gtgatatttt catgtttgct  1800
aatttattta tagttcgtaa tatatttata catatttttt tttttgtcat caacaataca  1860
gactcataca gactctgtaa accaaaccgg gtgatctgaa tccatgtgaa caacaaaaga  1920
cggttgcttt ctagcactgc gcgctaaacg atccgccttt gaattttgcg tccgtggtac  1980
atagataatc tctgatcggg tgaagctctc tttcagggtc ttgatatctt ccaaataatt  2040
tgcaaaaact ggccattctt ctggttcgga aaccatcttt accaattgag aacaatccgt  2100
tgcaaacgta acctgaaatt gacgtaaatt cctcatacat tccattgccc agagcaacgc  2160
```

-continued

```
ttcaatctct gcatgaagag gcgatagact agccctaaca ttcctcgccc ccaacaatcc  2220
atcaaaacct tccaaagtac taagccaacc ttgtcctgaa aaaccatccc cctctttcca  2280
cgagccatct gtaaaacacc atcgtcctga gatcgacggc aatatcgcat ctattatttg  2340
tggtgtcgtc ctctggtcat tcactacttg tgcctcagcc cacagtgttg actctgtatc  2400
agccaattta agcgtatcca taggatctat atccaaatta ctgaaaactt tattattcct  2460
agctttccaa atataccata gtatccatgc aaactgatga tcctccatct gcgggagaac  2520
tctccagaat agatgatcca tatttgtgaa gagggatcta gttggaaaaa tatcttgatt  2580
tgatggtatc ttcgaaagag cccagacctg aagagctgga ggacattcaa aaaatacatg  2640
atttgtcgat tcctcaggag ctccacatct ggcacaacaa atatccccat ggatccccct  2700
cgcttgtaaa ttcttccgca ctgctataca tcctgacacc agttgccata agaaatgttt  2760
caactttggt gggcaccgta ttttccagca gtaagccttc aaaacatcaa ctgtgggacc  2820
aatcagtagc ggtggtcttt ctctatctgg ataaatccgc tcgacctgat atcctgattt  2880
gaccgtatat tttccatttt ttgtaaagtg ccatccatct ttatccaccc tctgagtcct  2940
gctcaatggt atgctttcta taagtttcgc atcctgagga tccaccaatg tccgaattgc  3000
ctctaaattc caagtacgcg aagtagagtc aatgagggac tctacagtaa ggtccggata  3060
taaattgtgt tgatttttat tagctggtct cgggcgagtg gttgggagcc aaggatcatt  3120
ccatacagat atagaagacc ctgatcccac ccgtttaatt agtcctttgc taaccagaga  3180
tctagcagaa acaatactcc gccagccata tgacggagaa tatgaacgaa tcggttccaa  3240
gggggaagca ttcctataat accgaccttt gaaaactcga gaaaataaag tgtttggctt  3300
ttctatcaga cgccatagct gtttacccag catcgccgta ttgaaatcag tgatgtcttt  3360
aaaccccaaa cctccttcat ccttatttgc acataccttg tcccatgatt tccaatgcat  3420
accccttgtg cttctccctg gactccacca gaattgtgat accgcactcg ttagtttctt  3480
tactgttgct tttggtaatc ggtagcagga catcgtatga tttggtaatg ctgtaatcac  3540
tgatttaatg atcacttcct ttcctccttt tgtaaagaac ttaaaagtcc acccattgac  3600
tcgattattt aaacgatctt gtacaaaact aaacacttgg atctttgagc cccccatatt  3660
ttccggtaaa cccaggtagg atcccattcc tccaagattc tggattccca aaatatctct  3720
taattcttgc ctaacagatt cttcaatctt atatccaaat tgtattgaag acttatcaaa  3780
atttattaat tgtcctgaaa ctgcctcata ctcctttaaa attctgagaa tggtttgaca  3840
ctcttctttt tgagctttac aaaagaaaag gctatcatcc gcaaaaagca aatgagaaat  3900
cgacgggcag gctcttgcta ccttcatccc tgttaattga tgccctctct ctgccttctt  3960
tatatttgca attaaagcct cagtacacag aataaataga taaggtgata aaggatctcc  4020
ttgacgtaag cccctacggg gaataatgca gccacgtggt tgtccattta tgagaaccct  4080
atattccacc gatgatatac attccatcat tcatttaatc caatgaaggt caaatcccag  4140
tttctgtaat aaggccttta taaagtccca ctccactcta tcatacgctt tgctcatatc  4200
cgttttgatt gccatatact ttcctttaca tgctttatta gtccgcagtc catgaaacat  4260
ctcctgagcg ataagaatat tatcagagat caaccttcct accacaaaag ccgactgagt  4320
ttcggaaatg agcaaaggaa gataaatttt cagccgctgg cataaaacct tcgaaataat  4380
tttgtaccct acattacaaa gactaatagg cctcaattcc gtcatccttg tgggtctctc  4440
tgtttttgga atcatacata tattagtaat atttaatctt gtatccattt ctcccgaaac  4500
caaaaaatta ttcaccatct ctactaaatc attcttaata atatgccatg agtgttggaa  4560
gaacagagct gtcattccat ccggtcctgg cgccttttct gggtgcatca taaacaaaac  4620
ctctttaacc tcctcctccg tcgctagcct caacaaatgt tgattcatct gaggagtaat  4680
tcccggtgta acctctgtaa gaaaactatc gaattccgat ggggaggtgg tactaaatag  4740
atcctcaaaa taatcaattg ccaccttttc cacgccagta tcctctgtaa tccaattccc  4800
atcaatatca tgtaatccaa caattctatt acggaccctt cgttgcttag ttagagcatg  4860
ataaaatttt gtattaagat ctccagatga ataccacatg ttccgacttt tctggtgcca  4920
gtaatcttcc tcgtccttat atgcatcttg taatttccta gaaacctcca aaatatcctc  4980
ttgagaccta gaattatctg tttggaccgc ttcaagagct tgttgtaatt cacttatttt  5040
ttcctttcca taagggggat tatctttccg ccacttagca atttcgtgac gacaattact  5100
aattttttcc acgatgttct gtgatcttcc ttcatctcgt ctttcgttat agtctatcca  5160
acccattgta attgattcca tgagacccgc ctgtccaatc cacctcttat caaaccgaaa  5220
ttgtcctttc cttctagtga ctttatcctc aagataagcc accattggcc gatgatcaga  5280
agacaccaat cctaaatact ctgtaaaaga acatggaaat aaggtgtgcc actcttcatt  5340
cgccaaagca cgatctagac gacatctaac tgtcactgcc cctttgcctt ttcctcttct  5400
cccttgccat gacattttgt tcccccgtgc cgggaactcg agtaagccac tattccgtat  5460
catattatta aaaggaataa aagaatccgc actcctcaaa gatcctccat ctttttcatg  5520
atttcctctg atctcattaa gatcaccaat aataaaccag ggctcagaac gcactagtcc  5580
atacctagtt aaacgttccc acacttgctc tcgcatcttt tgaaccggat ccccataaac  5640
aaaggtaata taaacctttt taccaagagc ctccgcttcc acatcaatca ttcgattgct  5700
agaatataat accctcacct gatactcgtt attataaaaa agtgctagtc ccccacttct  5760
ccccaatgga tctactgtaa ccaaattatc atatccaaag tgatcttgaa atttttggac  5820
aaatcctggt tcttgctttg tttctgctaa aaacagaaaa tccggtttat gtttatgtct  5880
tatctcgctc aaatagctta tagtccactt gctgcccatt cctcgacaat tccaacttaa  5940
aactctcatt taaaaaaaaa aataataatc ttttaaatgc tccaaagagt caaaattacg  6000
ggtgtaatga taccctcttt ctccaatcca aatatattcc attcgttgta accattccat  6060
aaaactccat aaaaactcag agagagccac cagtcacctc tataccactt tgtaatgttc  6120
ctttccgtac atcccaaact aaactgtatt tggtttaaag agaccaaatg cagccattgc  6180
atcagctgca ccaaagaaaa ccccattctc ccattttgac caaaagaata ggacgtacat  6240
gtatttgtaa tattatacaa tgaccaagag taccactgga tatatatttt tgaaaaaaac  6300
atattacaaa cacagtaaaa ctcagctgaa tccagtttag tcccacacat aaacacacca  6360
atattacaca cacttaccaa tagactacta tgattacaaa aattcgcacc aagatagtat  6420
aaaaggacat tcttagtacc caccgtaaat ccaaacgtaa cagccccgct gtcaaccaaa  6480
atcaccaata ataacagatc caaaccactg aagcttacac acccccgatc ttcatagaga  6540
atgtaatcca ttagcttcat taagtcatca atcattgtca cgtccttctg tctgtagacc  6600
agaatgccat acctttgtag ccttattctc cattccataa tcactacctt gcttgtccac  6660
tcctgcctga gcacttggtc agccttgtaa tcaaaataac tatatactag tttagtctgt  6720
gcctggtaaa aacaaaaaca acataaccat cttccccata cagaaagcaa cgtccacatg  6780
aaattaaagc tatcaaccca catagccaca aatacctttc cacacatccc atataaaata  6840
aaaaagccac aatatataac agaaacaatt atgaaagcca tctctaaagt cccgaagtgc  6900
```

-continued

```
cagcaaacca aacgcccatt attattccac cggttataca aaatatcaag cttcgcaaag  6960
actcttaagg accaaagaat aactaaaacc ataataccca taaccccaaa gaacaaacaa  7020
caaagagaaa accagcacag ccttttatat tgatcccaaa tttccctttc tccacaccag  7080
agaatttttt gataatacta tatctttccg aatcgatact ttcaaactca atctcgaaat  7140
tgtatcgcga atccgttatc gtccataata tttcattacc aattccacaa tagatcccaa  7200
ttctccatac cccattgatt ctccctattc tttccaaaca aaagaaagtc gtagtagtgg  7260
agtaatcaga ggttatacct ttattatcct gcaatttcgt cttgatgatg accgaaatcg  7320
agatcagctt cgctattatc ctgattttcc ttagtgtccc caattcccat tttcctctta  7380
tcacttcaaa tcgcctgaga tctgaaagaa atctcttttc cgtatctcca tgaatcttat  7440
cttgatgatt tcctattcca atccaaacct cctcaccgat tccgggatcc catcgccgag  7500
agaacatcaa aaccctagat cgcttcttga gttgccatca cacatattat gcttttcatt  7560
tattgaatgg aaactgaaat ttattttaat taatcttaaa aaatatattt atacatatat  7620
tatatttaaa gttagtatat cttttaaata tacataggcc cattatttat agatctattt  7680
agatgtacat gtaggcccaa aaccaaaaga cttaaatgcc attaatgaat tttattcatc  7740
ctttgtaaaa ataagggtat ttttgagaaa ctgtaatttt cattaagtga atgattctct  7800
tttaatggta ttgatattga tattaatata taggtccttt tggaatgtat atatgcttta  7860
tatatttagt ccgttgatat ataataatga gagggagata actcagagaa gtgtcggaaa  7920
tcaatgtggt acgaaccagt gggaatttct ggcattctga gctccattta cttattctta  7980
aatttgaaaa gaaatctgat ctataaataa tactcctatt ttggtgacat tgaatcatat  8040
aaatggtgac caaagaataa agagaaacaa tgcattcctt aatatttcta aaaataattt  8100
accattcata aggaataaat tttcctttc attcatttcc attcttttg ttgtagaaaa  8160
atatagaaca aatttattct tcactaaata tataaaaaat cattattctt catcattctt  8220
ataattttat tcattttcgt tcctttcata tctgttctca atgtttatgt gatggttatc  8280
agttagacct tgggtgaacc ttgttgtgta ttcctcctca aatcgtaatt aattaccaat  8340
ttgaaaccat aataaatacc actagtagta atagtatagt tacttatata tccttacaca  8400
ctttaattaa ttgcattaac agccattttt atctatgtaa attacctcga gaatatattg  8460
tagtcatgca aaatgtgttt gattaaaaac tttatcctcg taactggtcc aaaacttcaa  8520
agccatgcat tcctttctcg tcgattttta ggtttttctg ccggaaaata aattttccaa  8580
aatcttaacc aagaattata aatattaaat atattaaatt ctctaattaa cagtttacat  8640
ttattaaatc taatctaatg gttttatctt aaacttttta gtgtgaaggg tacaattgaa  8700
aggtacaaga aagcttgttc cgatgccgtc aaccctccta ctgtgaccga agctaatact  8760
caggtacatt attttctgtt ttattcttta caaaaaaaaa aacattactg aaaaaaagag  8820
tggtgtttgt atgcatggaa ctccgaagta ttatcagcaa gaagcctcta agcttcggag  8880
gcagattcgg gacattcaaa attctaacag gtaaagtatc aacacttcat gaggtttcag  8940
atatggtttc ttgttctgaa cactacatta taaagctgag catttcgatt tgttcaagtg  9000
aaatgagtta aggtgcacat gttagcttgt agttttctaa agaagttgtt ttgtttatta  9060
atgttcatgt ttataaaatg aaggcatatt gttggagaat cacttggttc cttgaacttc  9120
aaggaactca aaaacctaga aggaaggctt gaaaaaggaa taaaccgcgt ccgatccaag  9180
aaggtatact taatacatgc acctacgtct atctgtttct ttatagttta catagttttt  9240
ctcacactta catggaaatt cgcagaatga gttgttagtg gcagagcttg agtatatgca  9300
gaagagggta agcaacattt cttcctctgc aagtaacatt ttttccatct atgtcgtgtc  9360
ttcttcttgg aggttgagtt ttgtcaaaaa tcatgtagga gatagagttg caacatgata  9420
acatgtacct gagagctaag gttactcacg ttttctttac aatctttatt taaatctcta  9480
ctctctactt cattctctca caagtcacaa ccaaacttct tattcggttt ttgcagataa  9540
cacactgcgc taggctggat ccggaacaac aggaatcgag tgtgatacaa ggaactgcgg  9600
tttatgaatc tggtctgtct tctcatgatc agtcgcagaa ttataaccgg agctatattc  9660
cggtgaacct tcttgaaccg aatcaacaat tctccggtca agaccaacct cctcttcaac  9720
ttgtttaagc tttaacatga tgaaaacttg tttcttccac tcgaaacgat ctagagagca  9780
ggagtacata tatttatgcg acttcttatg catagtttag gttccgatga taataaaaca  9840
taactcttgt tcctattgcc ttttttagtt ttgtcaaaat aaaaatgatt tgacaaaact  9900
taacttcatt atggaattat tccattttat actacatcga agatgctctt agccggcagg  9960
ataatgtgac tttcagttct ctttacagtg tctctacatc ttgctccttt gtattttcag  10020
ttatttgaaa ccaaaacttt gaattagttt gatatgaaga tttgaagggt acaagaatac  10080
aaatgaatag caaaaatgac attctcataa tattaatgcg tttgaccacc ccaaaagtta  10140
aaaattacaa aaaaaaaagg aacaaagttg ttgactgaac aaactgagaa tccttcttac  10200
aaatctgaag tatccttaac aaattgtgat acatctgata ccaaacca              10248
```

```
SEQ ID NO: 70          moltype = DNA  length = 749
FEATURE                Location/Qualifiers
source                 1..749
                       mol_type = other DNA
                       organism = Brassica napus
SEQUENCE: 70
atggaggaag gtgggagtag tcacgacgca gagagtaaca agaagctagt gagagggaag  60
atagagataa agaggataga gaacacgaca agtcgtcagg taactttctg caaacgacgc  120
aatggtcttc tcaagaaagc ttatgagctc tctgtcttgt gtgatgcgga agttgcactt  180
gttgtctttt ccactcgtgg ccgtctctat gagtacgcta acaacagtgt gaagggtaca  240
attgaaaggt acaagaaagc ttgttccgat gccgtcaacc ctcctactgt gaccgaagct  300
aatactcagt attatcagca agaagcctct aagcttcgga ggcagattcg ggacattcaa  360
aattctaaca ggcatattgt tggagaatca cttggttcct tgaacttcaa ggaactcaaa  420
aacctagaag gaaggcttga aaaaggaata aaccgcgtcc gatccaagaa gaatgagttg  480
ttagtggcag agcttgagta tatgcagaag agggagatag agttgcaaca tgataacatg  540
tacctgagag ctaagataac acactgcgct aggctggatc cggaacaaca ggaatcgagt  600
gtgatacaag gaactgcggt ttatgaatct ggtctgtctt ctcatgatca gtcgcagaat  660
tataaccgga gctatattcc ggtgaacctt cttgaaccga atcaacaatt ctccggtcaa  720
gaccaacctc ctcttcaact tgtttaagc                                   749
```

```
SEQ ID NO: 71          moltype = AA  length = 248
FEATURE                Location/Qualifiers
```

-continued

```
source                  1..248
                        mol_type = protein
                        organism = Brassica napus
SEQUENCE: 71
MEEGGSSHDA ESNKKLVRGK IEIKRIENTT SRQVTFCKRR NGLLKKAYEL SVLCDAEVAL  60
VVFSTRGRLY EYANNSVKGT IERYKKACSD AVNPPTVTEA NTQYYQQEAS KLRRQIRDIQ  120
NSNRHIVGES LGSLNFKELK NLEGRLEKGI NRVRSKKNEL LVAELEYMQK REIELQHDNM  180
YLRAKITHCA RLDPEQQESS VIQGTAVYES GLSSHDQSQN YNRSYIPVNL LEPNQQFSGQ  240
DQPPLQLV                                                          248

SEQ ID NO: 72           moltype = DNA  length = 531
FEATURE                 Location/Qualifiers
source                  1..531
                        mol_type = other DNA
                        organism = Brassica napus
SEQUENCE: 72
agaagagggt aagcaacatt tcttcctctg caagtaacat tttttccatc tatgtcgtgt  60
cttcttcttg gaggttgagt tttgtcaaaa atcatgtagg agatagagtt gcaacatgat  120
aacatgtacc tgagagctaa ggttactcac gttttcttta caatctttat ttaaatctct  180
actctctact tcattctctc acaagtcaca accaaacttc ttattcggtt tttgcagata  240
acacactgcg ctaggctgga tccggaacaa caggaatcga gtgtgataca aggaactgcg  300
gtttatgaat ctggtctgtc ttctcatgat cagtcgcaga attataaccg gagctatatt  360
ccggtgaacc ttcttgaacc gaatcaacaa ttctccggtc aagaccaacc tcctcttcaa  420
cttgtttaag ctttaacatg atgaaaactt gtttcttcca ctcgaaacga tctagagagc  480
aggagtacat atatttatgc gacttcttat gcatagttta ggttccgatg a          531

SEQ ID NO: 73           moltype = DNA  length = 452
FEATURE                 Location/Qualifiers
source                  1..452
                        mol_type = other DNA
                        organism = Brassica napus
SEQUENCE: 73
tttttccatc tatgtcgtgt cttcttcttg gaggttgagt tttgtcaaaa atcatgtagg  60
agatagagtt gcaacatgat aacatgtacc tgagagctaa ggttactcac gttttcttta  120
caatctttat ttaaatctct actctctact tcattctctc acaagtcaca accaaacttc  180
ttattcggtt tttgcagata acacactgcg ctaggctgga tccggaacaa caggaatcga  240
gtgtgataca aggaactgcg gtttatgaat ctggtctgtc ttctcatgat cagtcgcaga  300
attataaccg gagctatatt ccggtgaacc ttcttgaacc gaatcaacaa ttctccggtc  360
aagaccaacc tcctcttcaa cttgtttaag ctttaacatg atgaaaactt gtttcttcca  420
ctcgaaacga tctagagagc aggagtacat at                                452

SEQ ID NO: 74           moltype = DNA  length = 371
FEATURE                 Location/Qualifiers
source                  1..371
                        mol_type = other DNA
                        organism = Brassica napus
SEQUENCE: 74
tttgtcaaaa atcatgtagg agatagagtt gcaacatgat aacatgtacc tgagagctaa  60
ggttactcac gttttcttta caatctttat ttaaatctct actctctact tcattctctc  120
acaagtcaca accaaacttc ttattcggtt tttgcagata acacactgcg ctaggctgga  180
tccggaacaa caggaatcga gtgtgataca aggaactgcg gtttatgaat ctggtctgtc  240
ttctcatgat cagtcgcaga attataaccg gagctatatt ccggtgaacc ttcttgaacc  300
gaatcaacaa ttctccggtc aagaccaacc tcctcttcaa cttgtttaag ctttaacatg  360
atgaaaactt g                                                       371

SEQ ID NO: 75           moltype = DNA  length = 331
FEATURE                 Location/Qualifiers
source                  1..331
                        mol_type = other DNA
                        organism = Brassica napus
SEQUENCE: 75
agatagagtt gcaacatgat aacatgtacc tgagagctaa ggttactcac gttttcttta  60
caatctttat ttaaatctct actctctact tcattctctc acaagtcaca accaaacttc  120
ttattcggtt tttgcagata acacactgcg ctaggctgga tccggaacaa caggaatcga  180
gtgtgataca aggaactgcg gtttatgaat ctggtctgtc ttctcatgat cagtcgcaga  240
attataaccg gagctatatt ccggtgaacc ttcttgaacc gaatcaacaa ttctccggtc  300
aagaccaacc tcctcttcaa cttgtttaag c                                 331

SEQ ID NO: 76           moltype = DNA  length = 241
FEATURE                 Location/Qualifiers
source                  1..241
                        mol_type = other DNA
                        organism = Brassica napus
SEQUENCE: 76
agaagagggt aagcaacatt tcttcctctg caagtaacat tttttccatc tatgtcgtgt  60
cttcttcttg gaggttgagt tttgtcaaaa atcatgtagg agatagagtt gcaacatgat  120
aacatgtacc tgagagctaa ggttactcac gttttcttta caatctttat ttaaatctct  180
actctctact tcattctctc acaagtcaca accaaacttc ttattcggtt tttgcagata  240
a                                                                  241
```

```
SEQ ID NO: 77          moltype = DNA  length = 201
FEATURE                Location/Qualifiers
source                 1..201
                       mol_type = other DNA
                       organism = Brassica napus
SEQUENCE: 77
tttttccatc tatgtcgtgt cttcttcttg gaggttgagt tttgtcaaaa atcatgtagg  60
agatagagtt gcaacatgat aacatgtacc tgagagctaa ggttactcac gttttcttta  120
caatctttat ttaaatctct actctctact tcattctctc acaagtcaca accaaacttc  180
ttattcggtt tttgcagata a                                            201

SEQ ID NO: 78          moltype = DNA  length = 161
FEATURE                Location/Qualifiers
source                 1..161
                       mol_type = other DNA
                       organism = Brassica napus
SEQUENCE: 78
tttttccatc tatgtcgtgt cttcttcttg gaggttgagt tttgtcaaaa atcatgtagg  60
agatagagtt gcaacatgat aacatgtacc tgagagctaa ggttactcac gttttcttta  120
caatctttat ttaaatctct actctctact tcattctctc a                      161

SEQ ID NO: 79          moltype = DNA  length = 121
FEATURE                Location/Qualifiers
source                 1..121
                       mol_type = other DNA
                       organism = Brassica napus
SEQUENCE: 79
cttcttcttg gaggttgagt tttgtcaaaa atcatgtagg agatagagtt gcaacatgat  60
aacatgtacc tgagagctaa ggttactcac gttttcttta caatctttat ttaaatctct  120
a                                                                  121

SEQ ID NO: 80          moltype = DNA  length = 80
FEATURE                Location/Qualifiers
source                 1..80
                       mol_type = other DNA
                       organism = Brassica napus
SEQUENCE: 80
ttgtcaaaaa tcatgtagga gatagagttg caacatgata acatgtacct gagagctaag  60
gttactcacg ttttctttac                                              80

SEQ ID NO: 81          moltype = DNA  length = 41
FEATURE                Location/Qualifiers
source                 1..41
                       mol_type = other DNA
                       organism = Brassica napus
SEQUENCE: 81
agatagagtt gcaacatgat aacatgtacc tgagagctaa g                      41

SEQ ID NO: 82          moltype = DNA  length = 394
FEATURE                Location/Qualifiers
source                 1..394
                       mol_type = other DNA
                       organism = Brassica napus
SEQUENCE: 82
taaggttact cacgttttct ttacaatctt tatttaaatc tctactctct acttcattct  60
ctcacaagtc acaaccaaac ttcttattcg gtttttgcag ataacacact gcgctaggct  120
ggatccggaa caacaggaat cgagtgtgat acaaggaact gcggtttatg aatctggtct  180
gtcttctcat gatcagtcgc agaattataa ccggagctat attccggtga accttcttga  240
accgaatcaa caattctccg gtcaagacca acctcctctt caacttgttt aagctttaac  300
atgatgaaaa cttgtttctt ccactcgaaa cgatctagag agcaggagta catatattta  360
tgcgacttct tatgcatagt ttaggttccg atga                              394

SEQ ID NO: 83          moltype = DNA  length = 312
FEATURE                Location/Qualifiers
source                 1..312
                       mol_type = other DNA
                       organism = Brassica napus
SEQUENCE: 83
actctctact tcattctctc acaagtcaca accaaacttc ttattcggtt tttgcagata  60
acacactgcg ctaggctgga tccggaacaa caggaatcga gtgtgataca aggaactgcg  120
gtttatgaat ctggtctgtc ttctcatgat cagtcgcaga attataaccg gagctatatt  180
ccggtgaacc ttcttgaacc gaatcaacaa ttctccggtc aagaccaacc tcctcttcaa  240
cttgtttaag ctttaacatg atgaaaactt gtttcttcca ctcgaaacga tctagagagc  300
aggagtacat at                                                      312

SEQ ID NO: 84          moltype = DNA  length = 272
FEATURE                Location/Qualifiers
```

-continued

```
source                  1..272
                        mol_type = other DNA
                        organism = Brassica napus
SEQUENCE: 84
acaagtcaca accaaacttc ttattcggtt tttgcagata acacactgcg ctaggctgga  60
tccggaacaa caggaatcga gtgtgataca aggaactgcg gtttatgaat ctggtctgtc  120
ttctcatgat cagtcgcaga attataaccg gagctatatt ccggtgaacc ttcttgaacc  180
gaatcaacaa ttctccggtc aagaccaacc tcctcttcaa cttgtttaag ctttaacatg  240
atgaaaactt gtttcttcca ctcgaaacga tc                                272

SEQ ID NO: 85           moltype = DNA  length = 234
FEATURE                 Location/Qualifiers
source                  1..234
                        mol_type = other DNA
                        organism = Brassica napus
SEQUENCE: 85
ttcttattcg gtttttgcag ataacacact gcgctaggct ggatccggaa caacaggaat  60
cgagtgtgat acaaggaact gcggtttatg aatctggtct gtcttctcat gatcagtcgc  120
agaattataa ccggagctat attccggtga accttcttga accgaatcaa caattctccg  180
gtcaagacca acctcctctt caacttgttt aagctttaac atgatgaaaa cttg        234

SEQ ID NO: 86           moltype = DNA  length = 194
FEATURE                 Location/Qualifiers
source                  1..194
                        mol_type = other DNA
                        organism = Brassica napus
SEQUENCE: 86
ataacacact gcgctaggct ggatccggaa caacaggaat cgagtgtgat acaaggaact  60
gcggtttatg aatctggtct gtcttctcat gatcagtcgc agaattataa ccggagctat  120
attccggtga accttcttga accgaatcaa caattctccg gtcaagacca acctcctctt  180
caacttgttt aagc                                                    194

SEQ ID NO: 87           moltype = DNA  length = 155
FEATURE                 Location/Qualifiers
source                  1..155
                        mol_type = other DNA
                        organism = Brassica napus
SEQUENCE: 87
ggatccggaa caacaggaat cgagtgtgat acaaggaact gcggtttatg aatctggtct  60
gtcttctcat gatcagtcgc agaattataa ccggagctat attccggtga accttcttga  120
accgaatcaa caattctccg gtcaagacca acctc                             155

SEQ ID NO: 88           moltype = DNA  length = 115
FEATURE                 Location/Qualifiers
source                  1..115
                        mol_type = other DNA
                        organism = Brassica napus
SEQUENCE: 88
cgagtgtgat acaaggaact gcggtttatg aatctggtct gtcttctcat gatcagtcgc  60
agaattataa ccggagctat attccggtga accttcttga accgaatcaa caatt       115

SEQ ID NO: 89           moltype = DNA  length = 223
FEATURE                 Location/Qualifiers
source                  1..223
                        mol_type = other DNA
                        organism = Brassica napus
SEQUENCE: 89
aactgcggtt tatgaatctg gtctgtcttc tcatgatcag tcgcagaatt ataaccggag  60
ctatattccg gtgaaccttc ttgaaccgaa tcaacaattc tccggtcaag accaacctcc  120
tcttcaactt gtttaagctt taacatgatg aaaacttgtt tcttccactc gaaacgatct  180
agagagcagg agtacatata tttatgcgac ttcttatgca tag                    223

SEQ ID NO: 90           moltype = DNA  length = 144
FEATURE                 Location/Qualifiers
source                  1..144
                        mol_type = other DNA
                        organism = Brassica napus
SEQUENCE: 90
tcgcagaatt ataaccggag ctatattccg gtgaaccttc ttgaaccgaa tcaacaattc  60
tccggtcaag accaacctcc tcttcaactt gtttaagctt taacatgatg aaaacttgtt  120
tcttccactc gaaacgatct agag                                         144

SEQ ID NO: 91           moltype = DNA  length = 104
FEATURE                 Location/Qualifiers
source                  1..104
                        mol_type = other DNA
                        organism = Brassica napus
```

```
SEQUENCE: 91
ctatattccg gtgaaccttc ttgaaccgaa tcaacaattc tccggtcaag accaacctcc  60
tcttcaactt gtttaagctt taacatgatg aaaacttgtt tctt                   104

SEQ ID NO: 92          moltype = DNA  length = 63
FEATURE                Location/Qualifiers
source                 1..63
                       mol_type = other DNA
                       organism = Brassica napus
SEQUENCE: 92
ttgaaccgaa tcaacaattc tccggtcaag accaacctcc tcttcaactt gtttaagctt  60
taa                                                                63

SEQ ID NO: 93          moltype = DNA  length = 235
FEATURE                Location/Qualifiers
source                 1..235
                       mol_type = other DNA
                       organism = Brassica napus
SEQUENCE: 93
agatagagtt gcaacatgat aacatgtacc tgagagctaa gataacacac tgcgctaggc  60
tggatccgga acaacaggaa tcgagtgtga tacaaggaac tgcggtttat gaatctggtc  120
tgtcttctca tgatcagtcg cagaattata accggagcta tattccggtg aaccttcttg  180
aaccgaatca acaattctcc ggtcaagacc aacctcctct tcaacttgtt taagc       235

SEQ ID NO: 94          moltype = DNA  length = 157
FEATURE                Location/Qualifiers
source                 1..157
                       mol_type = other DNA
                       organism = Brassica napus
SEQUENCE: 94
agataacaca ctgcgctagg ctggatccgg aacaacagga atcgagtgtg atacaaggaa  60
ctgcggttta tgaatctggt ctgtcttctc atgatcagtc gcagaattat aaccggagct  120
atattccggt gaaccttctt gaaccgaatc aacaatt                           157

SEQ ID NO: 95          moltype = DNA  length = 117
FEATURE                Location/Qualifiers
source                 1..117
                       mol_type = other DNA
                       organism = Brassica napus
SEQUENCE: 95
ctggatccgg aacaacagga atcgagtgtg atacaaggaa ctgcggttta tgaatctggt  60
ctgtcttctc atgatcagtc gcagaattat aaccggagct atattccggt gaacctt     117

SEQ ID NO: 96          moltype = DNA  length = 77
FEATURE                Location/Qualifiers
source                 1..77
                       mol_type = other DNA
                       organism = Brassica napus
SEQUENCE: 96
atcgagtgtg atacaaggaa ctgcggttta tgaatctggt ctgtcttctc atgatcagtc  60
gcagaattat aaccgga                                                 77

SEQ ID NO: 97          moltype = AA  length = 76
FEATURE                Location/Qualifiers
source                 1..76
                       mol_type = protein
                       organism = Brassica napus
SEQUENCE: 97
IELQHDNMYL RAKITHCARL DPEQQESSVI QGTAVYESGL SSHDQSQNYN RSYIPVNLLE  60
PNQQFSGQDQ PPLQLV                                                  76

SEQ ID NO: 98          moltype = AA  length = 13
FEATURE                Location/Qualifiers
source                 1..13
                       mol_type = protein
                       organism = Brassica napus
SEQUENCE: 98
IELQHDNMYL RAK                                                     13

SEQ ID NO: 99          moltype = AA  length = 63
FEATURE                Location/Qualifiers
source                 1..63
                       mol_type = protein
                       organism = Brassica napus
SEQUENCE: 99
ITHCARLDPE QQESSVIQGT AVYESGLSSH DQSQNYNRSY IPVNLLEPNQ QFSGQDQPPL  60
QLV                                                                63

SEQ ID NO: 100         moltype = DNA  length = 6608
```

-continued

```
FEATURE                 Location/Qualifiers
source                  1..6608
                        mol_type = genomic DNA
                        organism = Brassica napus
SEQUENCE: 100
aaatgcttac ctaatgtata tatgtgatgt attagagtaa atgcaattag taattacaag  60
gaaaagtgatg gaggcatgag caaaaagagt ttctataatt tgtacacaaa tagttaatgt  120
gaactatgag aaaggtttgt gaatgattat gactatacgt atgattggtc accacttaat  180
ggattcctta atttcttgtt ccctcattaa gttgtcgtct catcatttct tttcatttct  240
agacccatgg tctcagattg gacttttaaa ggtagatttc aatatcaatg gtcgcacttt  300
tttagtccaa ttcattttca agttctcaaa caagtgtggt gattattttg cagttcttat  360
tcacacgtct aacttctatt atgtatgtca ttttctacgg ataagaagcg taagcgttgc  420
aaataatatt atctcgaatt aaatgggatt aattaggcca taatctagat tctatgtatc  480
ttttatatat ataaaaacaa aacatacgct caaatttagt tgcgtatttg agtagatatt  540
gtcttcatta cttgtaagaa aaaactcgtt ggactgcaca atagttttgt taacgtgtaa  600
ttaaatagcg tatttgtaag atttgagatt caaaatcgtc tttgacagct atgctcaaca  660
tgctttgaat cataagcact gtctagattc tcagcatgta acttatattt cagatcagat  720
tgactgcaaa acgaggtccc acgcaagaag gaaaagacaa gtatgatgtt cttggtctgg  780
agttctcagt cgagcatgtt attaaggggt gcaagagtgg atttccaaca aaaaacaagc  840
tttatgggac aaaaatcgaa gaaagaataa agatagaggg tgaaaacaca atatatgatt  900
tgttatcgcc tatttcccat aaaggattca gatactagga gaagttgatg ccaatttcac  960
atgcaagtct ctttcattac atctccatat tttaccgcac ctacgtctct atgtttacat  1020
tcttgtcatc gactttttca tgaataattt ttttttgcaa tttttatttc acttacaatt  1080
atgaatttct tatatatatt cttccaagtt gtaacgatca aataaaatatg catgcattat  1140
gtcatatatg gctatacatc attttagatt attgattttt gcagtatctt atttgaaacc  1200
tttagttcta tctacggata tcaatgtcta aacttttgat tctttattta gattgtgttc  1260
ttcaatcaaa gattcccctc ataaattgtg tattctttgc aaaaaaagga gttcacttat  1320
ttcacttgtg attgtgaaca tattataaat tgtacttata aaaacattct gcagttaaaa  1380
gaaaattaaa catcaaagtt agaaaaatta actttatgaa aaaaatacct actagctagt  1440
tagtagtaag agcatcttca ttcatggttc ttaaaacaaa aaatacaagt agtttaatat  1500
aatttaaata aaaaaacgaa atttttattt tgaaataaga tttgaacaag ttgagaattg  1560
acaagtgttt attagggttt gaaaagttga tcaaatgtta tgattcatcg tcttctctct  1620
ctctctttac cttttctttg tttaatggtg agaactttct atgaaagtgt gtatttggtt  1680
acttgaacta atatttttat gactgacttt atgaaaacaa cacaatctac tagctacatg  1740
gactgtagaa tacaatttat attttagatt gctaagaagt tatcagttta tctacagttt  1800
ggttgaatta attcaactag gttatggacc ttatggttag acttggttag gttcaatatg  1860
aacacgtata gatacagaga ggagcatcta attaattgaa acgcagacgt gtttaaaaag  1920
aaagagagaa agattaccat aaaaagggag tttccaaaag atggttctga tgtgaaacag  1980
agccccatcc ctctcccttt ccctttctc gtgaaagata ttggatggtc ctccttcaat  2040
gtccaccacc tactactcat cttctctttt ttctttaatt agttttcaat ttcaatttca  2100
gtttaagttc ctataattta taaatatttc atatctattt atatgaaatg tgtagagaat  2160
aaaaagtgtg agtttatata tttgtcgagt atgtttgttt tgacaattgg tatataattt  2220
atctgcttat tatagatgta cgtataaata tatttcagct aagaaaaact tgtaaacttc  2280
tgtgtgttct gcaagtgggg tcttaatacc ttcaaaaaat agtccttcaa atgaaactga  2340
tcataaacca aatttgaaaa gagagagatg tatttttcaa aaacgacata attattagaa  2400
aagcagaaaa aaacagttaa gtgatactga gatcaataat aatatatagt atctcttcaa  2460
gaacaatatc tcattaccca cttctccttt gtgctgatct atcataaact ttaaaccccca  2520
ggtaaggttc tgaatgttat acagtttata tagaataact ctaatatcaa atatttatat  2580
tcggagttct tttcatttct ttttcaattc aatatctgat cctttgttac ctagatttga  2640
tatgtttatt tattattgtt tatctgcaaa gagatttgat cattttaacc ctaaacctaa  2700
gtttcgtacc caaatcatac gatctatctt ttggttattc ttgatctgca aaatgattaa  2760
tttaatcatc aatcttaatt agcttctcta gagcaatatt tttttttctt aagctttgct  2820
ctagatcaat ctctctccct cttattatgt tattttattc atctggtgat atcacagaat  2880
caatggagga aggtgggagt agtcacgacg cagagagtag caagaagcta gtaagaggga  2940
agatagagat aaagaggata gagaacacaa caagtcgtca agtaactttc tgtaaacgac  3000
gcaatggtct tcttaagaaa gcttatgagc tttctgtctt gtgtgatgct gaagttgccc  3060
tcgtcatctt ctccactcgt ggccgtctct atgagtacgc caacaacagg tacgcttctc  3120
ctgcaccttt gatctttgct ttcttggttt actactacta ctacaagaaa atcttagtta  3180
aatgtatgga gaagtgactt gtagagtcaa gattagggtt tttgttaaat tacaatcctg  3240
ggtttttttcc catgccaaaa aaaaaaaatc ctgggttttt ttgttttttc taaattaaat  3300
atcgatctct ctagagctac cataactatg tgtgtgtgtg tgtttgtgta agcaagtaat  3360
gaagaaggaa gaaagctgtc ttgtcttctc aacttctagt tagccttctc gttagccttt  3420
tttggtgtca ctctttttct gcaaatcatt agaacctgat gcatgtcagc ttctccatga  3480
aatttcttta ttcaaattca aattagggtt tgatcagtaa acaagttggg tactttcttg  3540
gcacgaaata gcatgtatat tatataaata tgcaagactt atgttaccct ctgcctagtg  3600
taacttggga caaagcctaa tgaccatttg tcacttgtca ctagctaggg atccctataa  3660
ttatttaatc tagccaccaa aggcaaatga aaaccgaaaa tttcatattc ttgagttggt  3720
cttgagaaat ataatatgtg gctgaaataa aattgtcctg gtatgcaagt tcagaatttc  3780
aactctcttt ctaaaaaact gtaaatatat atacttctca tgtaaccgat tgtttacatt  3840
taatgtttaa ctttaccaaa gatgtagtta gagagcaaga tgtataacaa tataaatgca  3900
gtttttatgt ttctaatcta aaatgagttt tttcgatgta ataatctaaa atgagttgct  3960
accattatac tccctctgtt tccgaaagaa atattttcta gagtattcat gcatattaaa  4020
gaaacaatta atttttttata attgaattta ttatttattt tactatacat tttccaataa  4080
atattaacca atagtattca accaattcaa atattttcaa ttaatgtttt ttaaaagtct  4140
acaacttttc aacattaact actaaaagta ctttaaaatt ttagaaaatc tatcattttg  4200
gaacaaaaaa taaatctaga aaatcctact ttcaggaaca gaaggtgtat atatatatag  4260
cttttgttac aatagttgac gaagaacttc aaattaaaca ataaacacac atgagtttaa  4320
tttgtctaat attgaaatca ctcatcgact gttaaaaaaa acaatattca tattaatata  4380
taagccattg ctgaatttat acatatgtag tccttggata tattaatgag agggagataa  4440
```

-continued

```
ctcagagaag tgtcagaact cgaaatggta cgggccaatg agaagctctg gcattctgag  4500
ctctatttat ctgttattat tatctgtaaa aaattactga tcctttaagc atattgtgat  4560
gaaattgaat catataatat gcatggacgt tgttgtgttt accaatttga aatcatacta  4620
ctagtgtaat acttaattac ttatatcctt actttagtta actgcattga cagacattta  4680
ttatttgatg taaattacct tggaaaaata tggtttgatt gaaattatct cttcatactg  4740
gcaatcagaa actggtccaa acttcaaaac cacacattcc tttctggttg attttaaggt  4800
ttttggccgg gaaaataaac tttccaaaac cctaatcaaa atacagtacg tactatgttt  4860
aagagtttat atttattaaa ttaaatctaa taggttctcg aactgaactt tttagcgtga  4920
agggtacaat tgaaagatac aagaaagctt gttccgatgc cgttaaccct ccttctgtca  4980
ccgaagctaa tactcaggta ccattcttta gttttttttt tttagttctt ttggccggga  5040
aagctttttt gcgatttcga cagtgtttaa gctttgccta acgatagctg atctctttac  5100
cttttattta gccttaaatt gttcaccatg aattagttta agcctaatta accttgtgtt  5160
taaaaatctt tttatctttt tggggttatt agatagctca ttgctaagtc ttagcagttt  5220
taggccatga ttatcgctaa aactgttttc tgggtttttt aatttttttt ttgtttttttc  5280
tgattaaaaa aggaaaaaat taaaaaaaag tcaatcgcgg gtcgtcacgt gtcagtgtag  5340
cccgtaaaaa gtacaagaaa caaactaaag ttgatccttc ttttgcgact ttagtaaccg  5400
ataatcgtgc tcttagattc aagtctttct tctatctcaa tgtcattttt acgaaatgaa  5460
ttcacatttt gtcaaaaaaa aaattagttc ttttattctt cccctctttt tttgtctttt  5520
tttttgtgat gaccaattaa cattacaaaa aaaataaaaa aaatttggat gggttcttga  5580
aacgttttgg tgtttatatg catggaactc tgaagtacta tcagcaagaa gcatctaagc  5640
ttcggaggca gattcgtgac attcagaatt ctaacaggta aataaggcag tcttaatgtt  5700
caaaaaaaaat aaaaaaataag acagtctttt ggtagtgttt caaaaaaaaa aaacgacagt  5760
cttttggttt gatcactact tctctattat agatgttgtt ttgattattt aatgttgtga  5820
cttgaaaggc atatagttgg ggaatcactt ggttccttga acttcaagga actcaaaaac  5880
ctcgaaggac gtcttgaaaa aggaatcagc cgtgtccgat ccaagaaggt acttacccta  5940
acgtctcttt gtctctctat aacttatatt gtttcttac tcttatatga aaatctcgca  6000
gaatgagctg ttaatggcag agatagagta tatgcagaag agggtaagta acgtttcttc  6060
catatctttc accgtctttt taggtttttg agttcctata aatcgtgtag gaaatggagt  6120
tgcaacacga taacatgtac ctgcgagcta aggttagtct aaatctctct tctttacatc  6180
atcgcctacc cgagaagata acgtgtgtaa caaaccaaac tttgatgttc ggtctttgca  6240
gatatcacaa ggtgcgagat tgaatccgga gcagcaggat tcgagtgtaa tacaaggaac  6300
agcggtttac gaatccggtt tatcttccca tgatcagtca cagcattata accggaacta  6360
tattccggtt aaccttcttg aaccgaatca acaattctcc ggtcaagacc aacctcctct  6420
ccaacttgtc taagttttaa acatgaaaaa aaaaacttgt ttcttcccct caaaacgatt  6480
gttcagagaa agacactaag ggtatgactg gttttcccgc taccacccgc aaacgcagct  6540
tttgcggttg gtagcggttg ctggcgtttt gcaacaatcg ctcaaaccgc tctaaaccgc  6600
tccaaatc                                                          6608
```

```
SEQ ID NO: 101          moltype = DNA  length = 1047
FEATURE                 Location/Qualifiers
source                  1..1047
                        mol_type = other DNA
                        organism = Brassica napus
SEQUENCE: 101
atgattatga ctatacgtat gattggtcac cacttaatgg attccttaat ttcttgttcc  60
ctcattaagt tgtcgtctca tcatttcttt tcatttctag acccatggtc tcagattgga  120
cttttaaaga tcagattgac tgcaaaacga ggtcccacgc aagaaggaaa agacaagtat  180
gatgttcttg gtctggagtt ctcagtcgag catgttatta aggggtgcaa gagtggattt  240
ccaacaaaaa acaagcttta tgggacaaaa atcgaagaaa gaataaagat agaggaatca  300
atggaggaag gtgggagtag tcacgacgca gagagtagca agaagctagt aagagggaag  360
atagagataa agaggataga gaacacaaca agtcgtcaag taactttctg taaacgacgc  420
aatggtcttc ttaagaaagc ttatgagctt tctgtcttgt gtgatgctga agttgccctc  480
gtcatcttct ccactcgtgg ccgtctctat gagtacgcca acaacagcgt gaagggtaca  540
attgaaagat acaagaaagc ttgttccgat gccgttaacc ctccttctgt caccgaagct  600
aatactcagt actatcagca agaagcatct aagcttcgga ggcagattcg tgacattcag  660
aattctaaca ggcatatagt tggggaatca cttggttcct tgaacttcaa ggaactcaaa  720
aacctcgaag gacgtcttga aaaaggaatc agccgtgtcc gatccaagaa gaatgagctg  780
ttaatggcag agatagagta tatgcagaag agggaaatgg agttgcaaca cgataacatg  840
tacctgcgag ctaagatatc acaaggtgcg agattgaatc cggagcagca ggattcgagt  900
gtaatacaag gaacagcggt ttacgaatcc ggtttatctt cccatgatca gtcacagcat  960
tataaccgga actatattcc ggttaacctt cttgaaccga atcaacaatt ctccggtcaa  1020
gaccaacctc ctctccaact tgtctaa                                     1047
```

```
SEQ ID NO: 102          moltype = AA  length = 348
FEATURE                 Location/Qualifiers
source                  1..348
                        mol_type = protein
                        organism = Brassica napus
SEQUENCE: 102
MIMTIRMIGH HLMDSLISCS LIKLSSHHFF SFLDPWSQIG LLKIRLTAKR GPTQEGKDKY  60
DVLGLEFSVE HVIKGCKSGF PTKNKLYGTK IEERIKIEES MEEGGSSHDA ESSKKLVRGK  120
IEIKRIENTT SRQVTFCKRR NGLLKKAYEL SVLCDAEVAL VIFSTRGRLY EYANNSVKGT  180
IERYKKACSD AVNPPSVTEA NTQYYQQEAS KLRRQIRDIQ NSNRHIVGES LGSLNFKELK  240
NLEGRLEKGI SRVRSKKNEL LMAEIEYMQK REMELQHDNM YLRAKISQGA RLNPEQQDSS  300
VIQGTAVYES GLSSHDQSQH YNRNYIPVNL LEPNQQFSGQ DQPPLQLV              348
```

```
SEQ ID NO: 103          moltype = DNA  length = 533
FEATURE                 Location/Qualifiers
```

```
source                  1..533
                        mol_type = other DNA
                        organism = Brassica napus
SEQUENCE: 103
taatggcaga gatagagtat atgcagaaga gggtaagtaa cgtttcttcc atatctttca  60
ccgtcttttt aggtttttga gttcctataa atcgtgtagg aaatggagtt gcaacacgat  120
aacatgtacc tgcgagctaa ggttagtcta aatctctctt ctttacatca tcgcctaccc  180
gagaagataa cgtgtgtaac aaaccaaact ttgatgttcg gtctttgcag atatcacaag  240
gtgcgagatt gaatccggag cagcaggatt cgagtgtaat acaaggaaca gcggtttacg  300
aatccggttt atcttcccat gatcagtcac agcattataa ccggaactat attccggtta  360
accttcttga accgaatcaa caattctccg gtcaagacca acctcctctc caacttgtct  420
aagttttaaa catgaaaaaa aaaacttgtt tcttcccctc aaaacgattg ttcagagaaa  480
gacactaagg gtatgactgg ttttcccgct accacccgca aacgcagctt ttg         533

SEQ ID NO: 104          moltype = DNA  length = 453
FEATURE                 Location/Qualifiers
source                  1..453
                        mol_type = other DNA
                        organism = Brassica napus
SEQUENCE: 104
cgtttcttcc atatctttca ccgtcttttt aggtttttga gttcctataa atcgtgtagg  60
aaatggagtt gcaacacgat aacatgtacc tgcgagctaa ggttagtcta aatctctctt  120
ctttacatca tcgcctaccc gagaagataa cgtgtgtaac aaaccaaact ttgatgttcg  180
gtctttgcag atatcacaag gtgcgagatt gaatccggag cagcaggatt cgagtgtaat  240
acaaggaaca gcggtttacg aatccggttt atcttcccat gatcagtcac agcattataa  300
ccggaactat attccggtta accttcttga accgaatcaa caattctccg gtcaagacca  360
acctcctctc caacttgtct aagttttaaa catgaaaaaa aaaacttgtt tcttcccctc  420
aaaacgattg ttcagagaaa gacactaagg gta                               453

SEQ ID NO: 105          moltype = DNA  length = 413
FEATURE                 Location/Qualifiers
source                  1..413
                        mol_type = other DNA
                        organism = Brassica napus
SEQUENCE: 105
ccgtcttttt aggtttttga gttcctataa atcgtgtagg aaatggagtt gcaacacgat  60
aacatgtacc tgcgagctaa ggttagtcta aatctctctt ctttacatca tcgcctaccc  120
gagaagataa cgtgtgtaac aaaccaaact ttgatgttcg gtctttgcag atatcacaag  180
gtgcgagatt gaatccggag cagcaggatt cgagtgtaat acaaggaaca gcggtttacg  240
aatccggttt atcttcccat gatcagtcac agcattataa ccggaactat attccggtta  300
accttcttga accgaatcaa caattctccg gtcaagacca acctcctctc caacttgtct  360
aagttttaaa catgaaaaaa aaaacttgtt tcttcccctc aaaacgattg ttc         413

SEQ ID NO: 106          moltype = DNA  length = 372
FEATURE                 Location/Qualifiers
source                  1..372
                        mol_type = other DNA
                        organism = Brassica napus
SEQUENCE: 106
gttcctataa atcgtgtagg aaatggagtt gcaacacgat aacatgtacc tgcgagctaa  60
ggttagtcta aatctctctt ctttacatca tcgcctaccc gagaagataa cgtgtgtaac  120
aaaccaaact ttgatgttcg gtctttgcag atatcacaag gtgcgagatt gaatccggag  180
cagcaggatt cgagtgtaat acaaggaaca gcggtttacg aatccggttt atcttcccat  240
gatcagtcac agcattataa ccggaactat attccggtta accttcttga accgaatcaa  300
caattctccg gtcaagacca acctcctctc caacttgtct aagttttaaa catgaaaaaa  360
aaaacttgtt tc                                                      372

SEQ ID NO: 107          moltype = DNA  length = 333
FEATURE                 Location/Qualifiers
source                  1..333
                        mol_type = other DNA
                        organism = Brassica napus
SEQUENCE: 107
aaatggagtt gcaacacgat aacatgtacc tgcgagctaa ggttagtcta aatctctctt  60
ctttacatca tcgcctaccc gagaagataa cgtgtgtaac aaaccaaact ttgatgttcg  120
gtctttgcag atatcacaag gtgcgagatt gaatccggag cagcaggatt cgagtgtaat  180
acaaggaaca gcggtttacg aatccggttt atcttcccat gatcagtcac agcattataa  240
ccggaactat attccggtta accttcttga accgaatcaa caattctccg gtcaagacca  300
acctcctctc caacttgtct aagttttaaa cat                               333

SEQ ID NO: 108          moltype = DNA  length = 241
FEATURE                 Location/Qualifiers
source                  1..241
                        mol_type = other DNA
                        organism = Brassica napus
SEQUENCE: 108
taatggcaga gatagagtat atgcagaaga gggtaagtaa cgtttcttcc atatctttca  60
ccgtcttttt aggtttttga gttcctataa atcgtgtagg aaatggagtt gcaacacgat  120
aacatgtacc tgcgagctaa ggttagtcta aatctctctt ctttacatca tcgcctaccc  180
```

-continued

```
gagaagataa cgtgtgtaac aaaccaaact ttgatgttcg gtctttgcag atatcacaag  240
g                                                                  241

SEQ ID NO: 109         moltype = DNA  length = 161
FEATURE                Location/Qualifiers
source                 1..161
                       mol_type = other DNA
                       organism = Brassica napus
SEQUENCE: 109
cgtttcttcc atatctttca ccgtcttttt aggtttttga gttcctataa atcgtgtagg  60
aaatggagtt gcaacacgat aacatgtacc tgcgagctaa ggttagtcta aatctctctt  120
ctttacatca tcgcctaccc gagaagataa cgtgtgtaac a                      161

SEQ ID NO: 110         moltype = DNA  length = 121
FEATURE                Location/Qualifiers
source                 1..121
                       mol_type = other DNA
                       organism = Brassica napus
SEQUENCE: 110
ccgtcttttt aggtttttga gttcctataa atcgtgtagg aaatggagtt gcaacacgat  60
aacatgtacc tgcgagctaa ggttagtcta aatctctctt ctttacatca tcgcctaccc  120
g                                                                  121

SEQ ID NO: 111         moltype = DNA  length = 81
FEATURE                Location/Qualifiers
source                 1..81
                       mol_type = other DNA
                       organism = Brassica napus
SEQUENCE: 111
gttcctataa atcgtgtagg aaatggagtt gcaacacgat aacatgtacc tgcgagctaa  60
ggttagtcta aatctctctt c                                            81

SEQ ID NO: 112         moltype = DNA  length = 223
FEATURE                Location/Qualifiers
source                 1..223
                       mol_type = other DNA
                       organism = Brassica napus
SEQUENCE: 112
tcgcagaatg agctgttaat ggcagagata gagtatatgc agaagagggt aagtaacgtt  60
tcttccatat ctttcaccgt ctttttaggt ttttgagttc ctataaatcg tgtaggaaat  120
ggagttgcaa cacgataaca tgtacctgcg agctaaggtt agtctaaatc tctcttcttt  180
acatcatcgc ctacccgaga agataacgtg tgtaacaaac caa                    223

SEQ ID NO: 113         moltype = DNA  length = 143
FEATURE                Location/Qualifiers
source                 1..143
                       mol_type = other DNA
                       organism = Brassica napus
SEQUENCE: 113
agaagagggt aagtaacgtt tcttccatat ctttcaccgt ctttttaggt ttttgagttc  60
ctataaatcg tgtaggaaat ggagttgcaa cacgataaca tgtacctgcg agctaaggtt  120
agtctaaatc tctcttcttt aca                                          143

SEQ ID NO: 114         moltype = DNA  length = 103
FEATURE                Location/Qualifiers
source                 1..103
                       mol_type = other DNA
                       organism = Brassica napus
SEQUENCE: 114
tcttccatat ctttcaccgt ctttttaggt ttttgagttc ctataaatcg tgtaggaaat  60
ggagttgcaa cacgataaca tgtacctgcg agctaaggtt agt                    103

SEQ ID NO: 115         moltype = DNA  length = 63
FEATURE                Location/Qualifiers
source                 1..63
                       mol_type = other DNA
                       organism = Brassica napus
SEQUENCE: 115
ctttttaggt ttttgagttc ctataaatcg tgtaggaaat ggagttgcaa cacgataaca  60
tgt                                                                63

SEQ ID NO: 116         moltype = DNA  length = 223
FEATURE                Location/Qualifiers
source                 1..223
                       mol_type = other DNA
                       organism = Brassica napus
SEQUENCE: 116
gaagagggta agtaacgttt cttccatatc tttcaccgtc tttttaggtt tttgagttcc  60
tataaatcgt gtaggaaatg gagttgcaac acgataacat gtacctgcga gctaaggtta  120
```

-continued

```
gtctaaatct ctcttcttta catcatcgcc tacccgagaa gataacgtgt gtaacaaacc  180
aaactttgat gttcggtctt tgcagatatc acaaggtgcg aga                    223

SEQ ID NO: 117          moltype = DNA  length = 143
FEATURE                 Location/Qualifiers
source                  1..143
                        mol_type = other DNA
                        organism = Brassica napus
SEQUENCE: 117
tttttaggtt tttgagttcc tataaatcgt gtaggaaatg gagttgcaac acgataacat  60
gtacctgcga gctaaggtta gtctaaatct ctcttcttta catcatcgcc tacccgagaa  120
gataacgtgt gtaacaaacc aaa                                          143

SEQ ID NO: 118          moltype = DNA  length = 103
FEATURE                 Location/Qualifiers
source                  1..103
                        mol_type = other DNA
                        organism = Brassica napus
SEQUENCE: 118
tataaatcgt gtaggaaatg gagttgcaac acgataacat gtacctgcga gctaaggtta  60
gtctaaatct ctcttcttta catcatcgcc tacccgagaa gat                    103

SEQ ID NO: 119          moltype = DNA  length = 63
FEATURE                 Location/Qualifiers
source                  1..63
                        mol_type = other DNA
                        organism = Brassica napus
SEQUENCE: 119
gagttgcaac acgataacat gtacctgcga gctaaggtta gtctaaatct ctcttcttta  60
cat                                                                63

SEQ ID NO: 120          moltype = DNA  length = 41
FEATURE                 Location/Qualifiers
source                  1..41
                        mol_type = other DNA
                        organism = Brassica napus
SEQUENCE: 120
aaatggagtt gcaacacgat aacatgtacc tgcgagctaa g                      41

SEQ ID NO: 121          moltype = DNA  length = 403
FEATURE                 Location/Qualifiers
source                  1..403
                        mol_type = other DNA
                        organism = Brassica napus
SEQUENCE: 121
tgcgagctaa ggttagtcta aatctctctt ctttacatca tcgcctaccc gagaagataa  60
cgtgtgtaac aaaccaaact ttgatgttcg gtctttgcag atatcacaag gtgcgagatt  120
gaatccggag cagcaggatt cgagtgtaat acaaggaaca gcggtttacg aatccggttt  180
atcttcccat gatcagtcac agcattataa ccggaactat attccggtta accttcttga  240
accgaatcaa caattctccg gtcaagacca acctcctctc caacttgtct aagttttaaa  300
catgaaaaaa aaaacttgtt tcttcccctc aaaacgattg ttcagagaaa gacactaagg  360
gtatgactgg ttttcccgct accacccgca aacgcagctt ttg                    403

SEQ ID NO: 122          moltype = DNA  length = 323
FEATURE                 Location/Qualifiers
source                  1..323
                        mol_type = other DNA
                        organism = Brassica napus
SEQUENCE: 122
tcgcctaccc gagaagataa cgtgtgtaac aaaccaaact ttgatgttcg gtctttgcag  60
atatcacaag gtgcgagatt gaatccggag cagcaggatt cgagtgtaat acaaggaaca  120
gcggtttacg aatccggttt atcttcccat gatcagtcac agcattataa ccggaactat  180
attccggtta accttcttga accgaatcaa caattctccg gtcaagacca acctcctctc  240
caacttgtct aagttttaaa catgaaaaaa aaaacttgtt tcttcccctc aaaacgattg  300
ttcagagaaa gacactaagg gta                                          323

SEQ ID NO: 123          moltype = DNA  length = 283
FEATURE                 Location/Qualifiers
source                  1..283
                        mol_type = other DNA
                        organism = Brassica napus
SEQUENCE: 123
cgtgtgtaac aaaccaaact ttgatgttcg gtctttgcag atatcacaag gtgcgagatt  60
gaatccggag cagcaggatt cgagtgtaat acaaggaaca gcggtttacg aatccggttt  120
atcttcccat gatcagtcac agcattataa ccggaactat attccggtta accttcttga  180
accgaatcaa caattctccg gtcaagacca acctcctctc caacttgtct aagttttaaa  240
catgaaaaaa aaaacttgtt tcttcccctc aaaacgattg ttc                    283

SEQ ID NO: 124          moltype = DNA  length = 243
```

-continued

```
FEATURE                Location/Qualifiers
source                 1..243
                       mol_type = other DNA
                       organism = Brassica napus
SEQUENCE: 124
ttgatgttcg gtctttgcag atatcacaag gtgcgagatt gaatccggag cagcaggatt  60
cgagtgtaat acaaggaaca gcggtttacg aatccggttt atcttcccat gatcagtcac  120
agcattataa ccggaactat attccggtta accttcttga accgaatcaa caattctccg  180
gtcaagacca acctcctctc caacttgtct aagttttaaa catgaaaaaa aaaacttgtt  240
tct                                                                243

SEQ ID NO: 125         moltype = DNA  length = 203
FEATURE                Location/Qualifiers
source                 1..203
                       mol_type = other DNA
                       organism = Brassica napus
SEQUENCE: 125
atatcacaag gtgcgagatt gaatccggag cagcaggatt cgagtgtaat acaaggaaca  60
gcggtttacg aatccggttt atcttcccat gatcagtcac agcattataa ccggaactat  120
attccggtta accttcttga accgaatcaa caattctccg gtcaagacca acctcctctc  180
caacttgtct aagttttaaa cat                                          203

SEQ ID NO: 126         moltype = DNA  length = 165
FEATURE                Location/Qualifiers
source                 1..165
                       mol_type = other DNA
                       organism = Brassica napus
SEQUENCE: 126
tgaatccgga gcagcaggat tcgagtgtaa tacaaggaac agcggtttac gaatccggtt  60
tatcttccca tgatcagtca cagcattata accggaacta tattccggtt aaccttcttg  120
aaccgaatca acaattctcc ggtcaagacc aacctcctct ccaac                  165

SEQ ID NO: 127         moltype = DNA  length = 125
FEATURE                Location/Qualifiers
source                 1..125
                       mol_type = other DNA
                       organism = Brassica napus
SEQUENCE: 127
tcgagtgtaa tacaaggaac agcggtttac gaatccggtt tatcttccca tgatcagtca  60
cagcattata accggaacta tattccggtt aaccttcttg aaccgaatca acaattctcc  120
ggtca                                                              125

SEQ ID NO: 128         moltype = DNA  length = 85
FEATURE                Location/Qualifiers
source                 1..85
                       mol_type = other DNA
                       organism = Brassica napus
SEQUENCE: 128
agcggtttac gaatccggtt tatcttccca tgatcagtca cagcattata accggaacta  60
tattccggtt aaccttcttg aaccg                                        85

SEQ ID NO: 129         moltype = DNA  length = 223
FEATURE                Location/Qualifiers
source                 1..223
                       mol_type = other DNA
                       organism = Brassica napus
SEQUENCE: 129
acacgataac atgtacctgc gagctaaggt tagtctaaat ctctcttctt tacatcatcg  60
cctacccgag aagataacgt gtgtaacaaa ccaaactttg atgttcggtc tttgcagata  120
tcacaaggtg cgagattgaa tccggagcag caggattcga gtgtaataca aggaacagcg  180
gtttacgaat ccggtttatc ttcccatgat cagtcacagc att                    223

SEQ ID NO: 130         moltype = DNA  length = 143
FEATURE                Location/Qualifiers
source                 1..143
                       mol_type = other DNA
                       organism = Brassica napus
SEQUENCE: 130
ctctcttctt tacatcatcg cctacccgag aagataacgt gtgtaacaaa ccaaactttg  60
atgttcggtc tttgcagata tcacaaggtg cgagattgaa tccggagcag caggattcga  120
gtgtaataca aggaacagcg gtt                                          143

SEQ ID NO: 131         moltype = DNA  length = 103
FEATURE                Location/Qualifiers
source                 1..103
                       mol_type = other DNA
                       organism = Brassica napus
```

```
SEQUENCE: 131
cctacccgag aagataacgt gtgtaacaaa ccaaactttg atgttcggtc tttgcagata  60
tcacaaggtg cgagattgaa tccggagcag caggattcga gtg                    103

SEQ ID NO: 132         moltype = DNA  length = 63
FEATURE                Location/Qualifiers
source                 1..63
                       mol_type = other DNA
                       organism = Brassica napus
SEQUENCE: 132
gtgtaacaaa ccaaactttg atgttcggtc tttgcagata tcacaaggtg cgagattgaa  60
tcc                                                                63

SEQ ID NO: 133         moltype = DNA  length = 223
FEATURE                Location/Qualifiers
source                 1..223
                       mol_type = other DNA
                       organism = Brassica napus
SEQUENCE: 133
aacagcggtt tacgaatccg gtttatcttc ccatgatcag tcacagcatt ataaccggaa  60
ctatattccg gttaaccttc ttgaaccgaa tcaacaattc tccggtcaag accaacctcc  120
tctccaactt gtctaagttt taaacatgaa aaaaaaaact tgtttcttcc cctcaaaacg  180
attgttcaga gaaagacact aagggtatga ctggttttcc cgc                    223

SEQ ID NO: 134         moltype = DNA  length = 143
FEATURE                Location/Qualifiers
source                 1..143
                       mol_type = other DNA
                       organism = Brassica napus
SEQUENCE: 134
tcacagcatt ataaccggaa ctatattccg gttaaccttc ttgaaccgaa tcaacaattc  60
tccggtcaag accaacctcc tctccaactt gtctaagttt taaacatgaa aaaaaaaact  120
tgtttcttcc cctcaaaacg att                                          143

SEQ ID NO: 135         moltype = DNA  length = 103
FEATURE                Location/Qualifiers
source                 1..103
                       mol_type = other DNA
                       organism = Brassica napus
SEQUENCE: 135
ctatattccg gttaaccttc ttgaaccgaa tcaacaattc tccggtcaag accaacctcc  60
tctccaactt gtctaagttt taaacatgaa aaaaaaaact tgt                    103

SEQ ID NO: 136         moltype = DNA  length = 63
FEATURE                Location/Qualifiers
source                 1..63
                       mol_type = other DNA
                       organism = Brassica napus
SEQUENCE: 136
ttgaaccgaa tcaacaattc tccggtcaag accaacctcc tctccaactt gtctaagttt  60
taa                                                                63

SEQ ID NO: 137         moltype = DNA  length = 224
FEATURE                Location/Qualifiers
source                 1..224
                       mol_type = other DNA
                       organism = Brassica napus
SEQUENCE: 137
tatcttccca tgatcagtca cagcattata accggaacta tattccggtt aaccttcttg  60
aaccgaatca acaattctcc ggtcaagacc aacctcctct ccaacttgtc taagttttaa  120
acatgaaaaa aaaaacttgt ttcttcccct caaaacgatt gttcagagaa agacactaag  180
ggtatgactg gttttcccgc taccacccgc aaacgcagct tttg                   224

SEQ ID NO: 138         moltype = DNA  length = 143
FEATURE                Location/Qualifiers
source                 1..143
                       mol_type = other DNA
                       organism = Brassica napus
SEQUENCE: 138
attccggtta accttcttga accgaatcaa caattctccg gtcaagacca acctcctctc  60
caacttgtct aagttttaaa catgaaaaaa aaaacttgtt tcttcccctc aaaacgattg  120
ttcagagaaa gacactaagg gta                                          143

SEQ ID NO: 139         moltype = DNA  length = 103
FEATURE                Location/Qualifiers
source                 1..103
                       mol_type = other DNA
                       organism = Brassica napus
```

-continued

```
SEQUENCE: 139
accgaatcaa caattctccg gtcaagacca acctcctctc caacttgtct aagttttaaa  60
catgaaaaaa aaaacttgtt tcttcccctc aaaacgattg ttc                   103

SEQ ID NO: 140         moltype = DNA  length = 63
FEATURE                Location/Qualifiers
source                 1..63
                       mol_type = other DNA
                       organism = Brassica napus
SEQUENCE: 140
gtcaagacca acctcctctc caacttgtct aagttttaaa catgaaaaaa aaaacttgtt  60
tct                                                                 63

SEQ ID NO: 141         moltype = DNA  length = 233
FEATURE                Location/Qualifiers
source                 1..233
                       mol_type = other DNA
                       organism = Brassica napus
SEQUENCE: 141
aaatggagtt gcaacacgat aacatgtacc tgcgagctaa gatatcacaa ggtgcgagat  60
tgaatccgga gcagcaggat tcgagtgtaa tacaaggaac agcggtttac gaatccggtt  120
tatcttccca tgatcagtca cagcattata accggaacta tattccggtt aaccttcttg  180
aaccgaatca acaattctcc ggtcaagacc aacctcctct ccaacttgtc taa         233

SEQ ID NO: 142         moltype = DNA  length = 155
FEATURE                Location/Qualifiers
source                 1..155
                       mol_type = other DNA
                       organism = Brassica napus
SEQUENCE: 142
agatatcaca aggtgcgaga ttgaatccgg agcagcagga ttcgagtgta atacaaggaa  60
cagcggttta cgaatccggt ttatcttccc atgatcagtc acagcattat aaccggaact  120
atattccggt taaccttctt gaaccgaatc aacaa                             155

SEQ ID NO: 143         moltype = DNA  length = 115
FEATURE                Location/Qualifiers
source                 1..115
                       mol_type = other DNA
                       organism = Brassica napus
SEQUENCE: 143
ttgaatccgg agcagcagga ttcgagtgta atacaaggaa cagcggttta cgaatccggt  60
ttatcttccc atgatcagtc acagcattat aaccggaact atattccggt taacc       115

SEQ ID NO: 144         moltype = DNA  length = 75
FEATURE                Location/Qualifiers
source                 1..75
                       mol_type = other DNA
                       organism = Brassica napus
SEQUENCE: 144
ttcgagtgta atacaaggaa cagcggttta cgaatccggt ttatcttccc atgatcagtc  60
acagcattat aaccg                                                    75

SEQ ID NO: 145         moltype = AA  length = 76
FEATURE                Location/Qualifiers
source                 1..76
                       mol_type = protein
                       organism = Brassica napus
SEQUENCE: 145
MELQHDNMYL RAKISQGARL NPEQQDSSVI QGTAVYESGL SSHDQSQHYN RNYIPVNLLE  60
PNQQFSGQDQ PPLQLV                                                   76

SEQ ID NO: 146         moltype = AA  length = 13
FEATURE                Location/Qualifiers
source                 1..13
                       mol_type = protein
                       organism = Brassica napus
SEQUENCE: 146
MELQHDNMYL RAK                                                      13

SEQ ID NO: 147         moltype = AA  length = 63
FEATURE                Location/Qualifiers
source                 1..63
                       mol_type = protein
                       organism = Brassica napus
SEQUENCE: 147
ISQGARLNPE QQDSSVIQGT AVYESGLSSH DQSQHYNRNY IPVNLLEPNQ QFSGQDQPPL  60
QLV                                                                 63

SEQ ID NO: 148         moltype = DNA  length = 4088
```

```
FEATURE                Location/Qualifiers
source                 1..4088
                       mol_type = genomic DNA
                       organism = Brassica napus
SEQUENCE: 148
tagaacctag atagtagcta gctatagtag atggagtcca aaaagatttt atttgatctc  60
tctcagcttg tgtgtagtgt ttgaccgtgt ttggtttatc tttaagctat agggttgata  120
taaatggagg gtggtgcgag tgatgaagta gcagagagca gcaagaagat agggagaggg  180
aagatagaga taaagaggat agagaacacc acgaatcgcc aagtcacttt ctgcaaaaga  240
cgcaatggtc tgctcaagaa agcttatgag ctctctgtct tgtgtgacgc tgaggttgct  300
cttgtcatct tctccactcg cggtcgtctc tacgagtacg ccaacaacag gtaagataag  360
catctattaa cttcttttag atcttgattg tttgttttct ctgggttttg aatctttatg  420
ggttttctct ttgtggtttc ttttctcttc ttttaaagtt tctctgagtc tcaactcttt  480
gctgaaaact ttgatttata tgtgtgtacc aaaattaggg tttgtaccca agaaccctag  540
ttttgctttg gggaaaactc taatctattt gcttctctct cttgaaaaag ctgtgaggtc  600
ttctatgata ataattaatt agcatctcca taccttgtac cagtcacttt ttttttcttt  660
tactagatct ttatagtaca gcctatctgt atctatctat gtatgtcagt tctacatgac  720
atttcgataa atttgatgac ccatcaggtt tatttctgca gattgatcat aattaggatt  780
ccatcatagt agtgaaaaaa gtagggttct tgacaaaata taatattata tatcatataa  840
tggctatata aagctaagta gattccttaa aaaaatgata cactagctag ggggagacgg  900
gtgttttgtc ttctgacact tctctataaa accagtgatt tgatctgtta aatcaagaaa  960
tgtttagggg acaaagcttg tggttgtgtc actaattaat taatcatcaa tcaatcaaaa  1020
aataaaaata aacagaaaat ttgacttttg ttattagttt ccccactcca agttggggac  1080
tagtcatttc catttctatc aaagtttcca gctattaaca gctcatgttc ctttctacat  1140
tttgattgtt ttagaaaaga ttaatctgtt gatttttggt tggttgatac cacagataag  1200
ttgaggatct ataatctaat tttcttaaag tcaagtctca tatcatggat ttaagactta  1260
actagaaaat ttgtagttac aatgtagact tcacacgact aaagaatatt ttcattattt  1320
accaacgtgt aaagattcta catatagtaa atgtgtatgt gacatcacga ttttataaaa  1380
gtaggtttag ttgaataccc aactaatctg attaacaaaa gaggaatgca ttaggtctag  1440
ctagtaggta ggtatgtaga aatttgcaat ttctaggttt ctattttcaa atgcgtagct  1500
aaaatttaca ctatctttct tatttcaaac gtcctcatgc tttaatgcct tttgacattt  1560
ctcaacctca acttgtcatc atacatcaca aattaaatag tgaaaatgat aacgttatat  1620
gtgtttcaaa aaaaaaaaaa aaagataacg ttatatacaa atatgtctag cttttttctc  1680
aaatttaagg atctaggaat ttcacttcct tggttaaaac agtaatcgct cccaattaat  1740
tctattcatt tacacatgtt gtagtactaa ctaaaactct aattcaggta tgatatgtat  1800
tatatatatc tttttttatt ttattttatt ttgaaacact tttattatag ccaaaaatac  1860
atgttataag ggaaatctca agtctagtag tgttttcgaa cctataagga aatttggatt  1920
ttgtattata tgaaaatttg gacacgttag aaaatttcca ttcctaagaa gcttataata  1980
aggtttcata ttgatgtatt tttattttta cctaccacaa aaataaatca acaaaatgaa  2040
attagacatc tatacattag tacccatata gtaatgtcac tcttataatg aacttggtta  2100
taacatatca aacgattcat aatgaaatat ttttggtcaa atcgatcact gaatagatta  2160
accatgcgta gaagtcgata aagatgtaat ttatatatag gatatgtaca atatgtcttt  2220
gcttatagcc ttctaattta ctaactcttg tattttattt ttgtggatgt tggcgaaatc  2280
gtacaactaa tcaaaagtgt aagaggaacg atcgaaaggt acaagaaagc ttgctccgac  2340
gctgttaatc ctccttccgt caccgaagct aatactcaag taagcttccg taattagtta  2400
ctttaccact acgtttcttc ttgtttcagt ttctgacttt actgaatcct ttgtggggtc  2460
gaacacttga tgaagtacta tcagcaagag tcatctaagc tacggagaca gatccgggac  2520
attcagaatc tgaacagaca cattcttggt gaatctctcg gttccttgaa cctcaaggaa  2580
ctcaagaacc tcgaaggtag gcttgaaaaa ggcatcggtc gtgtccgctc caagaaggtt  2640
aataactttc aattccttca atccctttat atgcttcgac ttgatctgat tcttgaccct  2700
tacgttttat tcttcgccca gcatgagatg ctagttgcag agatagagta catgcaaaaa  2760
agggtaaaaa acatatcttc ctcaacaagt aaccctactt tctataacaa tcttctcttt  2820
cataatatag ctcccgtttc tgttcatgta ggagatcgag cttcaaaacg ataacatgta  2880
tctccgatcc aaggtcttat caatactctc tctttttcag aaatataaat atttttataa  2940
tacatttatt tattaaaata tactattggt ataaaattat tggaagttga taagtacgaa  3000
aatacaatac atttatttat taaaatttaa tatattttta atacgtatca aagcatagac  3060
atatatcttt tacaaacata gctagggagt atatgctttt tgtttgcatt ttgatttttt  3120
tttcaatata tatacaattt atctcttcga tgagcaagtt aattttatat aattctacag  3180
attaatgaaa gagcgggaat gcagcagcag gaagcgagtg tgatacatca acaagggacg  3240
gtttacgagt catcttctca tcagtcggag cagtacaacc ggaactatat tccggttaac  3300
cttcttgaac caaatcagaa ctcctccgac caaaaccaac cacctctcca acttgtttaa  3360
gtaaagtcta atcaacaaaa taagctcctt atgcatttgt ctattcatgt tacaattatg  3420
gttaaacaac ttaaaataaa gacgggtaac gatttgagag ggacctaagt tacatatgta  3480
ccttgattat ttatatgtaa tgtattgtgt acgttccagc tagtaacttt aagacaagag  3540
acttaactaa atttctagtt tctaataaag ctaatacata atttacacca gagagaacgt  3600
agatagtacc tcatgattac taattgtaga caagaccact gaaacacaaa agggtttgtg  3660
gatttctcga gtcttgcacg ccaagtaact tcagtgaaac aggatcttaa atcgagcgac  3720
atgtcatcaa ggaacaaaag gatgcgttaa ggtctttgac agcgagttac taaagctggt  3780
ggtagaagct agcaatcctc agattaacac tgtgcagtat atgagaatct gttagttcaa  3840
tgagacttag aaaggtctct tgaattagtg aggagtatat atagcagggg aatgagattg  3900
atactcacgg tgcttgaaga aatgtatacc tgaaaattaa agcgcagcga tgaggaaaga  3960
agcttgaaat gagaaactga tgatattaca aatgatgcat ctctcacacc atggttttat  4020
atagtaaacc aagattccac tgttacaaag caaggacaca tgaaagacct aacttttact  4080
gcagcaga                                                          4088

SEQ ID NO: 149         moltype = DNA  length = 737
FEATURE                Location/Qualifiers
```

-continued

```
source                 1..737
                       mol_type = other DNA
                       organism = Brassica napus
SEQUENCE: 149
atggagggtg gtgcgagtga tgaagtagca gagagcagca agaagatagg gagagggaag  60
atagagataa agaggataga gaacaccacg aatcgccaag tcactttctg caaaagacgc  120
aatggtctgc tcaagaaagc ttatgagctc tctgtcttgt gtgacgctga ggttgctctt  180
gtcatcttct ccactcgcgg tcgtctctac gagtacgcca acaacagtgt aagaggaacg  240
atcgaaaggt acaagaaagc ttgctccgac gctgttaatc ctccttccgt caccgaagct  300
aatactcaat actatcagca agagtcatct aagctacgga gacagatccg ggacattcag  360
aatctgaaca gacacattct tggtgaatct ctcggttcct tgaacctcaa ggaactcaag  420
aacctcgaag gtaggcttga aaaaggcatc ggtcgtgtcc gctccaagaa gcatgagatg  480
ctagttgcag agatagagta catgcaaaaa agggagatcg agcttcaaaa cgataacatg  540
tatctccgat ccaagattaa tgaaagagcg ggaatgcagc agcaggaagc gagtgtgata  600
catcaacaag ggacggttta cgagtcatct tctcatcagt cggagcagta caaccggaac  660
tatattccgg ttaaccttct tgaaccaaat cagaactcct ccgaccaaaa ccaaccacct  720
ctccaacttg tttaagt                                                 737

SEQ ID NO: 150         moltype = AA  length = 244
FEATURE                Location/Qualifiers
source                 1..244
                       mol_type = protein
                       organism = Brassica napus
SEQUENCE: 150
MEGGASDEVA ESSKKIGRGK IEIKRIENTT NRQVTFCKRR NGLLKKAYEL SVLCDAEVAL  60
VIFSTRGRLY EYANNSVRGT IERYKKACSD AVNPPSVTEA NTQYYQQESS KLRRQIRDIQ  120
NLNRHILGES LGSLNLKELK NLEGRLEKGI GRVRSKKHEM LVAEIEYMQK REIELQNDNM  180
YLRSKINERA GMQQQEASVI HQQGTVYESS SHQSEQYNRN YIPVNLLEPN QNSSDQNQPP  240
LQLV                                                               244

SEQ ID NO: 151         moltype = DNA  length = 709
FEATURE                Location/Qualifiers
source                 1..709
                       mol_type = other DNA
                       organism = Brassica napus
SEQUENCE: 151
gcaaaaaagg gtaaaaaaca tatcttcctc aacaagtaac cctactttct ataacaatct  60
tctctttcat aatatagctc ccgtttctgt tcatgtagga gatcgagctt caaaacgata  120
acatgtatct ccgatccaag gtcttatcaa tactctctct ttttcagaaa tataaatatt  180
tttataatac atttatttat taaaatatac tattggtata aaattattgg aagttgataa  240
gtacgaaaat acaatacatt tatttattaa aatttaatat atttttaata cgtatcaaag  300
catagacata tatcttttac aaacatagct agggagtata tgctttttgt ttgcattttg  360
attttttttt caatatatat acaatttatc tcttcgatga gcaagttaat tttatataat  420
tctacagatt aatgaaagag cgggaatgca gcagcaggaa gcgagtgtga tacatcaaca  480
agggacggtt tacgagtcat cttctcatca gtcggagcag tacaaccgga actatattcc  540
ggttaacctt cttgaaccaa atcagaactc ctccgaccaa aaccaaccac ctctccaact  600
tgtttaagta aagtctaatc aacaaaataa gctccttatg catttgtcta ttcatgttac  660
aattatggtt aaacaactta aaataaagac gggtaacgat ttgagaggg              709

SEQ ID NO: 152         moltype = DNA  length = 629
FEATURE                Location/Qualifiers
source                 1..629
                       mol_type = other DNA
                       organism = Brassica napus
SEQUENCE: 152
cctactttct ataacaatct tctctttcat aatatagctc ccgtttctgt tcatgtagga  60
gatcgagctt caaaacgata acatgtatct ccgatccaag gtcttatcaa tactctctct  120
ttttcagaaa tataaatatt tttataatac atttatttat taaaatatac tattggtata  180
aaattattgg aagttgataa gtacgaaaat acaatacatt tatttattaa aatttaatat  240
atttttaata cgtatcaaag catagacata tatcttttac aaacatagct agggagtata  300
tgctttttgt ttgcattttg attttttttt caatatatat acaatttatc tcttcgatga  360
gcaagttaat tttatataat tctacagatt aatgaaagag cgggaatgca gcagcaggaa  420
gcgagtgtga tacatcaaca agggacggtt tacgagtcat cttctcatca gtcggagcag  480
tacaaccgga actatattcc ggttaacctt cttgaaccaa atcagaactc ctccgaccaa  540
aaccaaccac ctctccaact tgtttaagta aagtctaatc aacaaaataa gctccttatg  600
catttgtcta ttcatgttac aattatggt                                    629

SEQ ID NO: 153         moltype = DNA  length = 589
FEATURE                Location/Qualifiers
source                 1..589
                       mol_type = other DNA
                       organism = Brassica napus
SEQUENCE: 153
tctctttcat aatatagctc ccgtttctgt tcatgtagga gatcgagctt caaaacgata  60
acatgtatct ccgatccaag gtcttatcaa tactctctct ttttcagaaa tataaatatt  120
tttataatac atttatttat taaaatatac tattggtata aaattattgg aagttgataa  180
gtacgaaaat acaatacatt tatttattaa aatttaatat atttttaata cgtatcaaag  240
catagacata tatcttttac aaacatagct agggagtata tgctttttgt ttgcattttg  300
attttttttt caatatatat acaatttatc tcttcgatga gcaagttaat tttatataat  360
```

-continued

```
tctacagatt aatgaaagag cgggaatgca gcagcaggaa gcgagtgtga tacatcaaca  420
agggacggtt tacgagtcat cttctcatca gtcggagcag tacaaccgga actatattcc  480
ggttaacctt cttgaaccaa atcagaactc ctccgaccaa aaccaaccac ctctccaact  540
tgtttaagta aagtctaatc aacaaaataa gctccttatg catttgtct             589

SEQ ID NO: 154         moltype = DNA  length = 548
FEATURE                Location/Qualifiers
source                 1..548
                       mol_type = other DNA
                       organism = Brassica napus
SEQUENCE: 154
cgtttctgtt catgtaggag atcgagcttc aaaacgataa catgtatctc cgatccaagg  60
tcttatcaat actctctctt tttcagaaat ataaatattt ttataataca tttatttatt  120
aaaatatact attggtataa aattattgga agttgataag tacgaaaata caatacattt  180
atttattaaa atttaatata tttttaatac gtatcaaagc atagacatat atcttttaca  240
aacatagcta gggagtatat gctttttgtt tgcattttga tttttttttc aatatatata  300
caatttatct cttcgatgag caagttaatt ttatataatt ctacagatta atgaaagagc  360
gggaatgcag cagcaggaag cgagtgtgat acatcaacaa gggacggttt acgagtcatc  420
ttctcatcag tcggagcagt acaaccggaa ctatattccg gttaaccttc ttgaaccaaa  480
tcagaactcc tccgaccaaa accaaccacc tctccaactt gtttaagtaa agtctaatca  540
acaaaata                                                          548

SEQ ID NO: 155         moltype = DNA  length = 470
FEATURE                Location/Qualifiers
source                 1..470
                       mol_type = other DNA
                       organism = Brassica napus
SEQUENCE: 155
tttttcagaa atataaatat ttttataata catttattta ttaaaatata ctattggtat  60
aaaattattg gaagttgata agtacgaaaa tacaatacat ttatttatta aaatttaata  120
tatttttaat acgtatcaaa gcatagacat atatctttta caaacatagc tagggagtat  180
atgctttttg tttgcatttt gatttttttt tcaatatata tacaatttat ctcttcgatg  240
agcaagttaa ttttatataa ttctacagat taatgaaaga gcgggaatgc agcagcagga  300
agcgagtgtg atacatcaac aagggacggt ttacgagtca tcttctcatc agtcggagca  360
gtacaaccgg aactatattc cggttaacct tcttgaacca aatcagaact cctccgacca  420
aaaccaacca cctctccaac ttgtttaagt aaagtctaat caacaaaata             470

SEQ ID NO: 156         moltype = DNA  length = 509
FEATURE                Location/Qualifiers
source                 1..509
                       mol_type = other DNA
                       organism = Brassica napus
SEQUENCE: 156
gatcgagctt caaaacgata acatgtatct ccgatccaag gtcttatcaa tactctctct  60
ttttcagaaa tataaatatt tttataatac atttatttat taaaatatac tattggtata  120
aaattattgg aagttgataa gtacgaaaat acaatacatt tatttattaa aatttaatat  180
atttttaata cgtatcaaag catagacata tatcttttac aaacatagct agggagtata  240
tgctttttgt ttgcattttg attttttttt caatatatat acaatttatc tcttcgatga  300
gcaagttaat tttatataat tctacagatt aatgaaagag cgggaatgca gcagcaggaa  360
gcgagtgtga tacatcaaca agggacggtt tacgagtcat cttctcatca gtcggagcag  420
tacaaccgga actatattcc ggttaacctt cttgaaccaa atcagaactc ctccgaccaa  480
aaccaaccac ctctccaact tgtttaagt                                   509

SEQ ID NO: 157         moltype = DNA  length = 240
FEATURE                Location/Qualifiers
source                 1..240
                       mol_type = other DNA
                       organism = Brassica napus
SEQUENCE: 157
gcaaaaaagg gtaaaaaaca tatcttcctc aacaagtaac cctactttct ataacaatct  60
tctctttcat aatatagctc ccgtttctgt tcatgtagga gatcgagctt caaaacgata  120
acatgtatct ccgatccaag gtcttatcaa tactctctct ttttcagaaa tataaatatt  180
tttataatac atttatttat taaaatatac tattggtata aaattattgg aagttgataa  240

SEQ ID NO: 158         moltype = DNA  length = 160
FEATURE                Location/Qualifiers
source                 1..160
                       mol_type = other DNA
                       organism = Brassica napus
SEQUENCE: 158
cctactttct ataacaatct tctctttcat aatatagctc ccgtttctgt tcatgtagga  60
gatcgagctt caaaacgata acatgtatct ccgatccaag gtcttatcaa tactctctct  120
ttttcagaaa tataaatatt tttataatac atttatttat                        160

SEQ ID NO: 159         moltype = DNA  length = 120
FEATURE                Location/Qualifiers
source                 1..120
                       mol_type = other DNA
                       organism = Brassica napus
```

```
SEQUENCE: 159
tctctttcat aatatagctc ccgtttctgt tcatgtagga gatcgagctt caaaacgata  60
acatgtatct ccgatccaag gtcttatcaa tactctctct ttttcagaaa tataaatatt  120

SEQ ID NO: 160         moltype = DNA  length = 79
FEATURE                Location/Qualifiers
source                 1..79
                       mol_type = other DNA
                       organism = Brassica napus
SEQUENCE: 160
ccgtttctgt tcatgtagga gatcgagctt caaaacgata acatgtatct ccgatccaag  60
gtcttatcaa tactctctc                                                79

SEQ ID NO: 161         moltype = DNA  length = 40
FEATURE                Location/Qualifiers
source                 1..40
                       mol_type = other DNA
                       organism = Brassica napus
SEQUENCE: 161
gatcgagctt caaaacgata acatgtatct ccgatccaag                        40

SEQ ID NO: 162         moltype = DNA  length = 382
FEATURE                Location/Qualifiers
source                 1..382
                       mol_type = other DNA
                       organism = Brassica napus
SEQUENCE: 162
gctagggagt atatgctttt tgtttgcatt ttgatttttt tttcaatata tatacaattt  60
atctcttcga tgagcaagtt aattttatat aattctacag attaatgaaa gagcgggaat  120
gcagcagcag gaagcgagtg tgatacatca acaagggacg gtttacgagt catcttctca  180
tcagtcggag cagtacaacc ggaactatat tccggttaac cttcttgaac caaatcagaa  240
ctcctccgac caaaaccaac cacctctcca acttgtttaa gtaaagtcta atcaacaaaa  300
taagctcctt atgcatttgt ctattcatgt tacaattatg gttaaacaac ttaaaataaa  360
gacgggtaac gatttgagag gg                                            382

SEQ ID NO: 163         moltype = DNA  length = 302
FEATURE                Location/Qualifiers
source                 1..302
                       mol_type = other DNA
                       organism = Brassica napus
SEQUENCE: 163
tttcaatata tatacaattt atctcttcga tgagcaagtt aattttatat aattctacag  60
attaatgaaa gagcgggaat gcagcagcag gaagcgagtg tgatacatca acaagggacg  120
gtttacgagt catcttctca tcagtcggag cagtacaacc ggaactatat tccggttaac  180
cttcttgaac caaatcagaa ctcctccgac caaaaccaac cacctctcca acttgtttaa  240
gtaaagtcta atcaacaaaa taagctcctt atgcatttgt ctattcatgt tacaattatg  300
gt                                                                  302

SEQ ID NO: 164         moltype = DNA  length = 262
FEATURE                Location/Qualifiers
source                 1..262
                       mol_type = other DNA
                       organism = Brassica napus
SEQUENCE: 164
atctcttcga tgagcaagtt aattttatat aattctacag attaatgaaa gagcgggaat  60
gcagcagcag gaagcgagtg tgatacatca acaagggacg gtttacgagt catcttctca  120
tcagtcggag cagtacaacc ggaactatat tccggttaac cttcttgaac caaatcagaa  180
ctcctccgac caaaaccaac cacctctcca acttgtttaa gtaaagtcta atcaacaaaa  240
taagctcctt atgcatttgt ct                                            262

SEQ ID NO: 165         moltype = DNA  length = 222
FEATURE                Location/Qualifiers
source                 1..222
                       mol_type = other DNA
                       organism = Brassica napus
SEQUENCE: 165
aattttatat aattctacag attaatgaaa gagcgggaat gcagcagcag gaagcgagtg  60
tgatacatca acaagggacg gtttacgagt catcttctca tcagtcggag cagtacaacc  120
ggaactatat tccggttaac cttcttgaac caaatcagaa ctcctccgac caaaaccaac  180
cacctctcca acttgtttaa gtaaagtcta atcaacaaaa ta                      222

SEQ ID NO: 166         moltype = DNA  length = 182
FEATURE                Location/Qualifiers
source                 1..182
                       mol_type = other DNA
                       organism = Brassica napus
SEQUENCE: 166
attaatgaaa gagcgggaat gcagcagcag gaagcgagtg tgatacatca acaagggacg  60
gtttacgagt catcttctca tcagtcggag cagtacaacc ggaactatat tccggttaac  120
```

-continued

```
cttcttgaac caaatcagaa ctcctccgac caaaaccaac cacctctcca acttgtttaa  180
gt                                                                 182

SEQ ID NO: 167         moltype = DNA  length = 144
FEATURE                Location/Qualifiers
source                 1..144
                       mol_type = other DNA
                       organism = Brassica napus
SEQUENCE: 167
tgcagcagca ggaagcgagt gtgatacatc aacaagggac ggtttacgag tcatcttctc  60
atcagtcgga gcagtacaac cggaactata ttccggttaa ccttcttgaa ccaaatcaga  120
actcctccga ccaaaaccaa ccac                                         144

SEQ ID NO: 168         moltype = DNA  length = 104
FEATURE                Location/Qualifiers
source                 1..104
                       mol_type = other DNA
                       organism = Brassica napus
SEQUENCE: 168
gtgatacatc aacaagggac ggtttacgag tcatcttctc atcagtcgga gcagtacaac  60
cggaactata ttccggttaa ccttcttgaa ccaaatcaga actc                   104

SEQ ID NO: 169         moltype = DNA  length = 64
FEATURE                Location/Qualifiers
source                 1..64
                       mol_type = other DNA
                       organism = Brassica napus
SEQUENCE: 169
ggtttacgag tcatcttctc atcagtcgga gcagtacaac cggaactata ttccggttaa  60
cctt                                                               64

SEQ ID NO: 170         moltype = DNA  length = 222
FEATURE                Location/Qualifiers
source                 1..222
                       mol_type = other DNA
                       organism = Brassica napus
SEQUENCE: 170
gatcgagctt caaaacgata acatgtatct ccgatccaag attaatgaaa gagcgggaat  60
gcagcagcag gaagcgagtg tgatacatca acaagggacg gtttacgagt catcttctca  120
tcagtcggag cagtacaacc ggaactatat tccggttaac cttcttgaac caaatcagaa  180
ctcctccgac caaaaccaac cacctctcca acttgtttaa gt                     222

SEQ ID NO: 171         moltype = DNA  length = 144
FEATURE                Location/Qualifiers
source                 1..144
                       mol_type = other DNA
                       organism = Brassica napus
SEQUENCE: 171
gattaatgaa agagcgggaa tgcagcagca ggaagcgagt gtgatacatc aacaagggac  60
ggtttacgag tcatcttctc atcagtcgga gcagtacaac cggaactata ttccggttaa  120
ccttcttgaa ccaaatcaga actc                                         144

SEQ ID NO: 172         moltype = DNA  length = 105
FEATURE                Location/Qualifiers
source                 1..105
                       mol_type = other DNA
                       organism = Brassica napus
SEQUENCE: 172
tgcagcagca ggaagcgagt gtgatacatc aacaagggac ggtttacgag tcatcttctc  60
atcagtcgga gcagtacaac cggaactata ttccggttaa ccttc                  105

SEQ ID NO: 173         moltype = DNA  length = 65
FEATURE                Location/Qualifiers
source                 1..65
                       mol_type = other DNA
                       organism = Brassica napus
SEQUENCE: 173
gtgatacatc aacaagggac ggtttacgag tcatcttctc atcagtcgga gcagtacaac  60
cggaa                                                              65

SEQ ID NO: 174         moltype = AA  length = 72
FEATURE                Location/Qualifiers
source                 1..72
                       mol_type = protein
                       organism = Brassica napus
SEQUENCE: 174
IELQNDNMYL RSKINERAGM QQQEASVIHQ QGTVYESSSH QSEQYNRNYI PVNLLEPNQN  60
SSDQNQPPLQ LV                                                      72
```

```
SEQ ID NO: 175          moltype = AA  length = 59
FEATURE                 Location/Qualifiers
source                  1..59
                        mol_type = protein
                        organism = Brassica napus
SEQUENCE: 175
INERAGMQQQ EASVIHQQGT VYESSSHQSE QYNRNYIPVN LLEPNQNSSD QNQPPLQLV   59

SEQ ID NO: 176          moltype = AA  length = 13
FEATURE                 Location/Qualifiers
source                  1..13
                        mol_type = protein
                        organism = Brassica napus
SEQUENCE: 176
IELQNDNMYL RSK                                                     13

SEQ ID NO: 177          moltype = DNA  length = 5152
FEATURE                 Location/Qualifiers
source                  1..5152
                        mol_type = genomic DNA
                        organism = Brassica napus
SEQUENCE: 177
ttgtagatct atataaatat acgtatcttt atatgcatgt ctagaggata aaaagtgtga  60
gctttgttgt gtatatgtgc tttttgacag ttgctagata attggtacgc ttgtttttct  120
ttttcttcta tgtacaaata catttcagct aagaaagaac ttgtaacctt ctgttttctg  180
caagtggggt caaaatatct tcagagaaat attctttcaa atgaaactca taaaccaaaa  240
caaaattaca aaaagaaaga gagatatttt tcaagaacat tattattacg aaagcagaag  300
caagacttaa gttacactga gatcaataat aattataata tatattatcg cttcagaacc  360
agtttctcat tagtaacttc tccgtgtgta ctctccaggt aaggttgtga atgatacagt  420
atatatatta accctaaaaa acaaggttta tgataaaata tctgatcctt gatttaacaa  480
ctcgtgggtc tgatatcgtt cttggtttgt ttatttatta ttacagttga aatcaaccct  540
aaaatcccaa atttggagtt caaagttttt ttctttgttt gaattacaat ctcagctgat  600
tgattttttg agtgaccaaa tcatttgata tatttatttt gcctctcttg atctgcaaaa  660
atatttgatc ataaacttaa atagcatcgc tctctagttc aatatctctc cccttctttt  720
tcggtggttt attcatttgg tgacatatca cagaagcaat ggatgaaggt gggagtagtc  780
actatgcaga gagtagcaag aagataggta gagggaagat agagataaag aggatagaga  840
acacaacaaa tcgtcaagta accttctgca aacgacgcaa tggtcttctc aagaaagctt  900
atgagctctc tgtcttgtgt gatgcggaag ttgccctcgt tatcttttcc actcgtggcc  960
gtctttatga gtacgccagc aacaggtatg cttctcctac ctacaccttg atctagcttt  1020
cttgattaat ttactactac aatcctagtt aaaatgagcc aagattaggg ttttgtttag  1080
attacaatcc ttgattttct atttttatat aaaaattaga tctcaataga gctaccattg  1140
tctctctaga tctgtgtata tccaaataat gaagacggga gaaagctgtc ttgtcttctc  1200
aacttctcgt tagtctgatc ttagttagtt tcactctttt tctgcagatc attagaacct  1260
gtttcatgtc atgtcagctt ctataaaata cttttatctc gacgacccat actatgtctt  1320
tctttaaata ttattagggt ttcgtcagta aaaaaaaact gggtacttct tgacacgcaa  1380
tagcatgcat atatgtaaat atgcaagaca tatgtaaccc tcctgtcttg tgaaacttgg  1440
gacataacct aatgatggtt gtcactatgg atccctttaa tttttcccta acccaagaaa  1500
acaaatgccc accgataaaa ctttagttat atattatatc tatctatctg gagttcgtat  1560
gttgagaata tatatatgtg actatttaaa aatctaggcc cttaaaatat gtgtatccat  1620
taatatatta atgagaggga gataactcag agagaagtgt ctgaaatcaa agtggtacga  1680
gccaatggga atctatggca ctctgagctc catttatatg tgctattgtc tttggaaaaa  1740
aaaaacagtt actcatcctt aaagcatact ttgataccat ataatatgca tggaccttgt  1800
tctgtattcc tcctcaaacc gtaagtaatt accagtttga aaccatcctt atattaatta  1860
attgctgcat cagccatttt taaatatgta cattgaaaaa gtagtttact cgagcacaat  1920
gtgtgtcatt gaagtttctc ctcgtactgg taaaaaaact ggtccaaacc tcaaagccat  1980
cacattcctt tcttgtcgat tttaaggttt tgccccccaaa ataaacattc caaaacctta  2040
atcaagaaat gtcgtcccaa ttatctctgt tttaagagta tattaattaa attaaatata  2100
atggtttctt gaactttcta gtgtgaaggg tacaattgaa aggtacaaga aagcttgttc  2160
cgatgccgtt aaccctccta ctgtcactga agctaatact aaggtaccat tcttgtataa  2220
tttttttctt actagccctc tcttttttct tatttttatg atcaattatt aacgttgaga  2280
aagtgaaatc tttttaaaat gtgtatatat atgtggtttc ttgtttctat gatgatcaat  2340
tatgtatacg tgtcaaaaga acgttactaa caaaattctt aacatttaca cccaaaagta  2400
aaaacattat taactaaaag agtggattcc tgaaatgcat tgagacggtt gtatttgtat  2460
gcatggaacc cttcagtact atcagcaaga agcctctaag cttcggaggc agattcggga  2520
cattcagaat tcgaacaggt aagtaactaa agctcttcat gaggtttctt gttttgatca  2580
ctactttcct attatatagc tgatcatttc gattagttta actgaaaaaa aattacagaa  2640
cctgagtcac gtaagttata attcattcaa aatcgttcat tctaaataat tttttttctt  2700
tttttgttag gattgttagc tcggtttact tacttggaat tgcttgaatt tctgcttggt  2760
tttgtgatat atggtatatg gaaccttaaa taaaaacttg ggtttaattt tcgtgttttt  2820
ttttgccaaa tagtttactt ttagttacgt ttgaacgagt gcaaatgttt attaatgttc  2880
atgtttatga attgaaggca tattgttgga gaatcacttg gttcattgaa cttcaaggaa  2940
ctcaaaaacc tagaaggacg gcttgaaaaa ggaatcagcc gcgtccgatc caagaaggta  3000
cgtactgata aacctatacg tctatgtctc tctatagttt atatatagtt tcctcgctct  3060
tatatgaata tttttcagag tgaactttta gtggcagaga tagagtatat gcagaagagg  3120
gtaagtaacg tttcttccca atctttcatc gttcttttac atgggttttg agttttgaca  3180
taaaccatgt aggaaatgga gttgcagcac gataacatgt acctaagagc taaggttagt  3240
cacgtcttca tccgggaaaa gtgccaattt cgacccccaac tatttcagtc gtgccaaata  3300
cgacccaaac aattgatcag tgccaaatac gacctcaact caattataat tcgaaaaaac  3360
tacccaaact tcttaaaatg tgcttagatc tacattgact ataacagaag ttagccaatc  3420
```

-continued

```
gttaacaaga taaaacgacg tcgttttgat atacgaggaa aagtgccaat ttcgacccca  3480
acactctcag tcgtgccaaa taagacccga acaaatggtc agtgccaaaa acgacctcaa  3540
ctcaattata ttttaagaaa aattatccaa tttttttaaa acgtgtctaa atctacatta  3600
actctaacag aagttaatca acctttaaca aagataagac gacgttgttt tgatatatgt  3660
attttcttaa aaaaatatgt tcattttggg attcaaatcc gtgctgggat atccttttaa  3720
aggggcacac taacaactag actaaaataa ttttttgaaa tattattaca aattgaaatt  3780
ctccattata taaactacta ttcttcttca tcttatccaa tttaaaactt tggtgattgc  3840
tttatacatt ttagttattg tttaatttgt ctaatatttt gtacaacata tcttagtgaa  3900
agaaaggtaa aaggtctctt aacatttttg aacaaaatat caaaatatat aatatcaact  3960
ttgaaaacta aaaaaattcc cacttaattt taaaaattaa aaataattta tataagaaaa  4020
ttgtataaat aaattcaaaa gttttaagca tatttaagat cgtataataa taaatatttt  4080
attatttata ttttagtaag atataatttt attaaagata tgataaataa gaaaaacgtg  4140
ttaatgtatt tatataaatc agaaacaatt gtcaccaaaa tttttaattg gataagatga  4200
agaataatag tagtttatat aatttcaaat ttgtaatagt attttaaaaa gttactttta  4260
tctagttgtt agtgtgccca tttaaaaggg tatcacaaca tggtttgagt ttcggaatga  4320
acatattttt tttaaaaaaa tagatatata tatatatatg tatatatgaa cgacgtcttc  4380
ttatcttgtt aacggttgac taacttctgt tagagtcaat gtagatttat gcacatttta  4440
agaagttcag gtagttttc ttaaattata cttaagttga ggccggtttt ggcactgccc  4500
atttgttcgg gtcctatttg gcacgactga gagtgttggg gtcgaaattg gcacttttcc  4560
tcgtatatca aaacgacgtc gttttatcga ttggctaact tctgttaaag tcaatgtaga  4620
tctaagcaca ttttaagaag tttggatagt tttttcgaat tataattgag ttgaggtcgt  4680
atttggcact gatcaattgt ttgggtcgta tttggcacga ctgaaatagt tggggtcgaa  4740
attggcactt ttcccgtctt catcctctaa ccgagataag gaacgtgtat cacaaccaaa  4800
ctttgatgtt cggtttgtgc agatagaaca aggcgcgaga ttgaatccgg aacagcatgg  4860
atccggtgta atacaaggga cggcggttta tgagtccggt ctgtcttctt ctcatgatca  4920
gtcgcagcat tataatcgga attatattcc ggttaacctt cttgaaccga atcaacaatt  4980
ctccggtcaa gaccaacctc ctcttcaact tgtttaagct taatcatgac taaaacttct  5040
ttctcccct cccctccaa acgtttttca gagagagaga gacaaagagt aaattatatt  5100
tatgcgacat tcttattcat agttaaggtt ccaataataa caaaaacaaa ac          5152

SEQ ID NO: 178         moltype = DNA  length = 749
FEATURE                Location/Qualifiers
source                 1..749
                       mol_type = other DNA
                       organism = Brassica napus
SEQUENCE: 178
atggatgaag gtgggagtag tcactatgca gagagtagca agaagatagg tagagggaag  60
atagagataa agaggataga gaacacaaca aatcgtcaag taaccttctg caaacgacgc  120
aatggtcttc tcaagaaagc ttatgagctc tctgtcttgt gtgatgcgga agttgccctc  180
gttatctttt ccactcgtgg ccgtctttat gagtacgcca gcaacagtgt gaagggtaca  240
attgaaaggt acaagaaagc ttgttccgat gccgttaacc ctcctactgt cactgaagct  300
aatactaagt actatcagca agaagcctct aagcttcgga ggcagattcg ggacattcag  360
aattcgaaca ggcatattgt tggagaatca cttggttcat tgaacttcaa ggaactcaaa  420
aacctagaag gacggcttga aaaaggaatc agccgcgtcc gatccaagaa gagtgaactt  480
ttagtggcag agatagagta tatgcagaag agggaaatgg agttgcagca cgataacatg  540
tacctaagag ctaagataga acaaggcgcg agattgaatc cggaacagca tggatccggt  600
gtaatacaag ggacggcggt ttatgagtcc ggtctgtctt cttctcatga tcagtcgcag  660
cattataatc ggaattatat tccggttaac cttcttgaac cgaatcaaca attctccggt  720
caagaccaac ctcctcttca acttgttta                                    749

SEQ ID NO: 179         moltype = AA  length = 249
FEATURE                Location/Qualifiers
source                 1..249
                       mol_type = protein
                       organism = Brassica napus
SEQUENCE: 179
MDEGGSSHYA ESSKKIGRGK IEIKRIENTT NRQVTFCKRR NGLLKKAYEL SVLCDAEVAL  60
VIFSTRGRLY EYASNSVKGT IERYKKACSD AVNPPTVTEA NTKYYQQEAS KLRRQIRDIQ  120
NSNRHIVGES LGSLNFKELK NLEGRLEKGI SRVRSKKSEL LVAEIEYMQK REMELQHDNM  180
YLRAKIEQGA RLNPEQHGSG VIQGTAVYES GLSSSHDQSQ HYNRNYIPVN LLEPNQQFSG  240
QDQPPLQLV                                                          249

SEQ ID NO: 180         moltype = DNA  length = 243
FEATURE                Location/Qualifiers
source                 1..243
                       mol_type = other DNA
                       organism = Brassica napus
SEQUENCE: 180
gcagagatag agtatatgca gaagagggta agtaacgttt cttcccaatc tttcatcgtt  60
cttttacatg ggttttgagt tttgacataa accatgtagg aaatggagtt gcagcacgat  120
aacatgtacc taagagctaa ggttagtcac gtcttcatcc gggaaaagtg ccaatttcga  180
ccccaactat ttcagtcgtg ccaaatacga cccaaacaat tgatcagtgc caaatacgac  240
ctc                                                                243

SEQ ID NO: 181         moltype = DNA  length = 161
FEATURE                Location/Qualifiers
source                 1..161
                       mol_type = other DNA
                       organism = Brassica napus
```

```
SEQUENCE: 181
cttcccaatc tttcatcgtt cttttacatg ggttttgagt tttgacataa accatgtagg  60
aaatggagtt gcagcacgat aacatgtacc taagagctaa ggttagtcac gtcttcatcc  120
gggaaaagtg ccaatttcga ccccaactat ttcagtcgtg c                      161

SEQ ID NO: 182         moltype = DNA  length = 121
FEATURE                Location/Qualifiers
source                 1..121
                       mol_type = other DNA
                       organism = Brassica napus
SEQUENCE: 182
cttttacatg ggttttgagt tttgacataa accatgtagg aaatggagtt gcagcacgat  60
aacatgtacc taagagctaa ggttagtcac gtcttcatcc gggaaaagtg ccaatttcga  120
c                                                                  121

SEQ ID NO: 183         moltype = DNA  length = 81
FEATURE                Location/Qualifiers
source                 1..81
                       mol_type = other DNA
                       organism = Brassica napus
SEQUENCE: 183
tttgacataa accatgtagg aaatggagtt gcagcacgat aacatgtacc taagagctaa  60
ggttagtcac gtcttcatcc g                                            81

SEQ ID NO: 184         moltype = DNA  length = 41
FEATURE                Location/Qualifiers
source                 1..41
                       mol_type = other DNA
                       organism = Brassica napus
SEQUENCE: 184
aaatggagtt gcagcacgat aacatgtacc taagagctaa g                      41

SEQ ID NO: 185         moltype = DNA  length = 394
FEATURE                Location/Qualifiers
source                 1..394
                       mol_type = other DNA
                       organism = Brassica napus
SEQUENCE: 185
gaaatagttg ggtcgaaat tggcactttt cccgtcttca tcctctaacc gagataagga  60
acgtgtatca caaccaaact ttgatgttcg gtttgtgcag atagaacaag gcgcgagatt  120
gaatccggaa cagcatggat ccggtgtaat acaagggacg gcggtttatg agtccggtct  180
gtcttcttct catgatcagt cgcagcatta taatcggaat tatattccgg ttaaccttct  240
tgaaccgaat caacaattct ccggtcaaga ccaacctcct cttcaacttg tttaagctta  300
atcatgacta aaacttcttt ctccccctcc ccctccaaac gtttttcaga gagagagaga  360
caaagagtaa attatattta tgcgacattc ttat                              394

SEQ ID NO: 186         moltype = DNA  length = 314
FEATURE                Location/Qualifiers
source                 1..314
                       mol_type = other DNA
                       organism = Brassica napus
SEQUENCE: 186
tcctctaacc gagataagga acgtgtatca caaccaaact ttgatgttcg gtttgtgcag  60
atagaacaag gcgcgagatt gaatccggaa cagcatggat ccggtgtaat acaagggacg  120
gcggtttatg agtccggtct gtcttcttct catgatcagt cgcagcatta taatcggaat  180
tatattccgg ttaaccttct tgaaccgaat caacaattct ccggtcaaga ccaacctcct  240
cttcaacttg tttaagctta atcatgacta aaacttcttt ctccccctcc ccctccaaac  300
gtttttcaga gaga                                                    314

SEQ ID NO: 187         moltype = DNA  length = 274
FEATURE                Location/Qualifiers
source                 1..274
                       mol_type = other DNA
                       organism = Brassica napus
SEQUENCE: 187
acgtgtatca caaccaaact ttgatgttcg gtttgtgcag atagaacaag gcgcgagatt  60
gaatccggaa cagcatggat ccggtgtaat acaagggacg gcggtttatg agtccggtct  120
gtcttcttct catgatcagt cgcagcatta taatcggaat tatattccgg ttaaccttct  180
tgaaccgaat caacaattct ccggtcaaga ccaacctcct cttcaacttg tttaagctta  240
atcatgacta aaacttcttt ctccccctcc ccct                              274

SEQ ID NO: 188         moltype = DNA  length = 234
FEATURE                Location/Qualifiers
source                 1..234
                       mol_type = other DNA
                       organism = Brassica napus
SEQUENCE: 188
ttgatgttcg gtttgtgcag atagaacaag gcgcgagatt gaatccggaa cagcatggat  60
ccggtgtaat acaagggacg gcggtttatg agtccggtct gtcttcttct catgatcagt  120
```

```
cgcagcatta taatcggaat tatattccgg ttaaccttct tgaaccgaat caacaattct  180
ccggtcaaga ccaacctcct cttcaacttg tttaagctta atcatgacta aaac        234

SEQ ID NO: 189         moltype = DNA  length = 194
FEATURE                Location/Qualifiers
source                 1..194
                       mol_type = other DNA
                       organism = Brassica napus
SEQUENCE: 189
atagaacaag gcgcgagatt gaatccggaa cagcatggat ccggtgtaat acaagggacg  60
gcggtttatg agtccggtct gtcttcttct catgatcagt cgcagcatta taatcggaat  120
tatattccgg ttaaccttct tgaaccgaat caacaattct ccggtcaaga ccaacctcct  180
cttcaacttg ttta                                                    194

SEQ ID NO: 190         moltype = DNA  length = 156
FEATURE                Location/Qualifiers
source                 1..156
                       mol_type = other DNA
                       organism = Brassica napus
SEQUENCE: 190
tgaatccgga acagcatgga tccggtgtaa tacaagggac ggcggtttat gagtccggtc  60
tgtcttcttc tcatgatcag tcgcagcatt ataatcggaa ttatattccg gttaaccttc  120
ttgaaccgaa tcaacaattc tccggtcaag accaac                            156

SEQ ID NO: 191         moltype = DNA  length = 115
FEATURE                Location/Qualifiers
source                 1..115
                       mol_type = other DNA
                       organism = Brassica napus
SEQUENCE: 191
tccggtgtaa tacaagggac ggcggtttat gagtccggtc tgtcttcttc tcatgatcag  60
tcgcagcatt ataatcggaa ttatattccg gttaaccttc ttgaaccgaa tcaac       115

SEQ ID NO: 192         moltype = DNA  length = 75
FEATURE                Location/Qualifiers
source                 1..75
                       mol_type = other DNA
                       organism = Brassica napus
SEQUENCE: 192
ggcggtttat gagtccggtc tgtcttcttc tcatgatcag tcgcagcatt ataatcggaa  60
ttatattccg gttaa                                                   75

SEQ ID NO: 193         moltype = DNA  length = 223
FEATURE                Location/Qualifiers
source                 1..223
                       mol_type = other DNA
                       organism = Brassica napus
SEQUENCE: 193
ggcggtttat gagtccggtc tgtcttcttc tcatgatcag tcgcagcatt ataatcggaa  60
ttatattccg gttaaccttc ttgaaccgaa tcaacaattc tccggtcaag accaacctcc  120
tcttcaactt gtttaagctt aatcatgact aaaacttctt tctccccctc cccctccaaa  180
cgtttttcag agagagagag acaaagagta aattatattt atg                    223

SEQ ID NO: 194         moltype = DNA  length = 145
FEATURE                Location/Qualifiers
source                 1..145
                       mol_type = other DNA
                       organism = Brassica napus
SEQUENCE: 194
gtcgcagcat tataatcgga attatattcc ggttaacctt cttgaaccga atcaacaatt  60
ctccggtcaa gaccaacctc ctcttcaact tgtttaagct taatcatgac taaaacttct  120
ttctccccct cccccctccaa acgtt                                       145

SEQ ID NO: 195         moltype = DNA  length = 104
FEATURE                Location/Qualifiers
source                 1..104
                       mol_type = other DNA
                       organism = Brassica napus
SEQUENCE: 195
attatattcc ggttaacctt cttgaaccga atcaacaatt ctccggtcaa gaccaacctc  60
ctcttcaact tgtttaagct taatcatgac taaaacttct ttct                   104

SEQ ID NO: 196         moltype = DNA  length = 64
FEATURE                Location/Qualifiers
source                 1..64
                       mol_type = other DNA
                       organism = Brassica napus
```

```
SEQUENCE: 196
cttgaaccga atcaacaatt ctccggtcaa gaccaacctc ctcttcaact tgtttaagct  60
taat                                                               64

SEQ ID NO: 197         moltype = DNA  length = 235
FEATURE                Location/Qualifiers
source                 1..235
                       mol_type = other DNA
                       organism = Brassica napus
SEQUENCE: 197
aaatggagtt gcagcacgat aacatgtacc taagagctaa gatagaacaa ggcgcgagat  60
tgaatccgga acagcatgga tccggtgtaa tacaagggac ggcggtttat gagtccggtc  120
tgtcttcttc tcatgatcag tcgcagcatt ataatcggaa ttatattccg gttaaccttc  180
ttgaaccgaa tcaacaattc tccggtcaag accaacctcc tcttcaactt gttta       235

SEQ ID NO: 198         moltype = DNA  length = 157
FEATURE                Location/Qualifiers
source                 1..157
                       mol_type = other DNA
                       organism = Brassica napus
SEQUENCE: 198
agatagaaca aggcgcgaga ttgaatccgg aacagcatgg atccggtgta atacaaggga  60
cggcggttta tgagtccggt ctgtcttctt ctcatgatca gtcgcagcat tataatcgga  120
attatattcc ggttaacctt cttgaaccga atcaaca                           157

SEQ ID NO: 199         moltype = DNA  length = 117
FEATURE                Location/Qualifiers
source                 1..117
                       mol_type = other DNA
                       organism = Brassica napus
SEQUENCE: 199
ttgaatccgg aacagcatgg atccggtgta atacaaggga cggcggttta tgagtccggt  60
ctgtcttctt ctcatgatca gtcgcagcat tataatcgga attatattcc ggttaac     117

SEQ ID NO: 200         moltype = DNA  length = 77
FEATURE                Location/Qualifiers
source                 1..77
                       mol_type = other DNA
                       organism = Brassica napus
SEQUENCE: 200
atccggtgta atacaaggga cggcggttta tgagtccggt ctgtcttctt ctcatgatca  60
gtcgcagcat tataatc                                                 77

SEQ ID NO: 201         moltype = DNA  length = 75
FEATURE                Location/Qualifiers
source                 1..75
                       mol_type = other DNA
                       organism = Brassica napus
SEQUENCE: 201
ttatattccg gttaaccttc ttgaaccgaa tcaacaattc tccggtcaag accaacctcc  60
tcttcaactt gttta                                                   75

SEQ ID NO: 202         moltype = DNA  length = 55
FEATURE                Location/Qualifiers
source                 1..55
                       mol_type = other DNA
                       organism = Brassica napus
SEQUENCE: 202
ttgaaccgaa tcaacaattc tccggtcaag accaacctcc tcttcaactt gttta       55

SEQ ID NO: 203         moltype = AA  length = 77
FEATURE                Location/Qualifiers
source                 1..77
                       mol_type = protein
                       organism = Brassica napus
SEQUENCE: 203
MELQHDNMYL RAKIEQGARL NPEQHGSGVI QGTAVYESGL SSSHDQSQHY NRNYIPVNLL  60
EPNQQFSGQD QPPLQLV                                                 77

SEQ ID NO: 204         moltype = AA  length = 64
FEATURE                Location/Qualifiers
source                 1..64
                       mol_type = protein
                       organism = Brassica napus
SEQUENCE: 204
IEQGARLNPE QHGSGVIQGT AVYESGLSSS HDQSQHYNRN YIPVNLLEPN QQFSGQDQPP  60
LQLV                                                               64

SEQ ID NO: 205         moltype = AA  length = 13
```

```
FEATURE                Location/Qualifiers
source                 1..13
                       mol_type = protein
                       organism = Brassica napus
SEQUENCE: 205
MELQHDNMYL RAK                                                      13

SEQ ID NO: 206         moltype = DNA  length = 5768
FEATURE                Location/Qualifiers
source                 1..5768
                       mol_type = genomic DNA
                       organism = Brassica napus
SEQUENCE: 206
ttaatttcta ggctattctt gatctgcaaa aatatttaat catcaagctt acttagcctc  60
gctctctcta gatcaatcat ctccctcctc tttttgttgt ttttattcat ttcttgatat  120
tacagaatca atggaggaag gtgggagtag tcacgacgca gagagtaaca agaagctagt  180
gagagggaag atagagataa agaggataga gaacacgaca agtcgtcaag taactttctg  240
caaacgacgc aatggtcttc tcaagaaagc ttatgagctc tctgtcttgt gtgatgcgga  300
agttgcactt gttgtcttct ccactcgtgg ccgtctctat gagtacgcta acaacaggta  360
cgaaaaaaaa aaaaaaaaaa aaaaaaaaac aacaggtacg cttctcctac accattgatt  420
gatctgctac tacaaataat attggttatt ttattagtga tgatggacac gagaggttta  480
gagccaagat tagggttttt attagttaca atcctggatt ttttttaaaa ttaaatttta  540
ccattatctc tctagatttc tttatattta tgtgtatgtg tgtgtatgca aaatatgaga  600
aggaaaaaat tgtcttgtct tctcaatttc tcgttagccg tttttagttt cactcggttt  660
atgaaacatt ggaacctgat gcatgtctgg ttctatacaa catttaatta gttttgacga  720
tccataattt ttatctattc aaattattgc taggatttta tcaggaaaat agttgggaca  780
aagcctaatg atgagttacc aatagggatc cttttaataa tttaaactaa cccccaacac  840
caaatgaaaa ctgagaatta gttatactct ggagttggtc ttgagaaaat atgtaactga  900
aagctagtat tttacgtttt ttctctccat ttttcatatt tattttgaag gatagttgaa  960
gaggtccttt aacaatatac gcacatatat gtgacttagt ctagcattca ctcactgaat  1020
tttaaaaaat attgatatta atatataggc ccttttggaa tgtatatatg ctttatatat  1080
ttagtccatt gatatataat aatgagaggg agataactca gggaagtgta ggaaatcaat  1140
gtgctacgaa ccagtgggaa tttctggcat tctgagctcc atttacttat tcttaaattt  1200
gaaaaaaaat ctgatctata aataatactc ctattttgtt gacattgaat catataatgt  1260
gcgtgaacct tgttctttat tcctcctcaa atctcttata tattaattga gaagcattac  1320
aacatttttt tttgtaccca cgtgtcatcg gaatgattct tagaatcctt agaaaaatag  1380
gttgatccac ctaaatatat aataaatttt ttattaaact aaccataaat acattattaa  1440
tgtgattcat tattttctta aataaaatta cggaatttct taatgtggct aaagtatata  1500
tgacaattaa tgattttgaa taataaagat ttgataaaaa tagttgtatc ttatattata  1560
tttgtttaac tattataaga cctgcgcctt gcgcaagata aatttatata aaaattattt  1620
taaaaatatt atacggaaaa ataaatttat attcttgatt gaattaatat tttggtcttt  1680
aaacaatttt tttaaatttt tggttaatta cataatttgt ttactgatga gctgatctca  1740
tttttttaaa aaaaaaggta ggtcaaaaaa tcacttacca tataaaaacc taacgtttag  1800
gtaaaaaaat ctcgggtcta tttgattaca atgaaactat gtcagctcgg tattatatca  1860
tgatttagta atctaaaaac taattatggt tatgagaagt ttacgttcac gtgtcaatcc  1920
tatctatctt caatattttt ctttttttcat tttggttatt gttggatata aatattgatt  1980
ttgaagttta ttcttatttc gtttgtttgt tttgacctga gatttagaaa attcctatga  2040
tttaaaataa ttaaagagat acatactcaa gttaagatct gcactttttg cagaataaat  2100
atttttacat ttattattta ttttatgttt ttctgcatat tatgaaataa taaaataata  2160
aatatatatt aaataactaa gaaatcagtt actattatgt aataaattgt cgtgtgcata  2220
taaatcaaac tatcactctt ggttattcac aatcatttta gggtaaataa atcaaaacaa  2280
tcaatcttat ctattgtata tgatatataa ttaaatataa atgatattaa catatatata  2340
tatatatagt acactttgaa tatgaatatt tattaaatga agtttatact catatgattt  2400
tatgattatt tgcgtattgt gtaacaaaat tttacaccaa cgattttttt taatgtggga  2460
taatttcaat aatttataat catttaaaaa acaatgaaga tttcaaaatt aaaatattaa  2520
cttttcgata tatgttcaat gcaaatatca aaatataagt atacattttc atacgatgta  2580
tagtttaatt caaacgatat gaaatatata tatatatgta tatatattaa cataaaaacc  2640
tattaaaata aaattatttc ttcatatggt cttataatca ttgtatctta atatagaaaa  2700
aaatttaaac cttgatcata aaagtttatg tgagactttt aatagtttta gtaatttata  2760
ctcattttga aaaattcaaa atacaacata tacaaaaaat ctagattttt atgatatgat  2820
taatgtaatt atgtaattta ttttaataat aaagaaataa actaaaatga taaaaagtat  2880
acaaattgtt atcaaatatt tattgtttaa aatcattaat tgctatatat atatatattt  2940
tagtcacatt agataattcc gtaggtttta tttaaggaaa gcctgcgaaa caataaatat  3000
ttgatatttg cgaccaacta agcctgcgaa atattatttt gctagaaagt ataattttta  3060
gactatagtt tatataaggt gctctaaatt tctttgaaat tggatttata aggcatacac  3120
aagtgccaca taggatgaat ttttttttta tttttacaaa atccaggtta taacttttta  3180
aaagatcctc aattaatata taggggattt taaactatta aaataaatta aacaaccata  3240
ttagccatat aataaaaatt tagattttttc tgtatatggt atattttgtt attttaaaaa  3300
cgagtataaa ttagtaaaac tgttgaaatt ctgacattca aattttgtga tccatggttt  3360
aaattttttg ttatgacatg atacaaatga ttacaaaatc atataatttg aaattataat  3420
ttaatcagta ttaagattaa aaaatatata aatatatatc attttaaatt taattatatg  3480
ccatataaaa atacataaat attttaattt tgaaatttac tttgaatttt tttttgataa  3540
aaactttgaa aaaatattga caacttaact tttaaaaata ttataaatta cctaaactat  3600
taatcacaca aggaaaattt tgttatgagt aatttaaagt ttttgctata acaaatacaa  3660
atgaacaaaa aaaaacaaat gagtagataa catcatttaa taaataataa tattaaaata  3720
tactatatat atatgttaat ataattcaaa tttaaatatt taccatatta agtagaaaaa  3780
aatctttttt ttggattaat aaaatatatt tatatgttcg caccaattta attatataag  3840
taacatttac tgacttttta attattcaat atatatttat tatttcataa tttgttaaaa  3900
aacatttaat acataaaata atttatatat atataatgtt catcgcggat cttaacctag  3960
```

-continued

```
tcgtaattaa ttaccaattt gaaaccataa taaataccac tagtagtata gttacttata  4020
tccttgcata ctttaattaa ttgcattaac agccattttc atctttgtaa attacctcga  4080
gaaaatatta tagtcatgca aaatgtgttt gattaaaaac tttatcctcg taccgtgatg  4140
atcagaaact ggtccaaaac ttcaaagcca tacattcctt tctcgtcgat ttttaggttt  4200
ttcgaccgga aaataaattt tccaaaacct taccaagaat tataatatat taaattctct  4260
aattgacagt ttacatttat tgaatctaat ctaatggttt tatcttaaac cttttagtgt  4320
gaagggtaca attgaaaggt acaagaaagc ttgttccgat gccgtcaacc ctcctactat  4380
caccgaagct aatactcagg tacattattt tctattttat tctttacaaa aaaaaacatt  4440
actgaaaaaa agagtgggtt cttgaaatgt tatggtgttt gtatgcatgg aactccgaag  4500
tattatcagc aagaagcctc taagcttcgg aggcagattc gggacattca aaattctaac  4560
aggtaaagta tcaacacttc atgaagtttc agatatggtt tctagttctg aacactacat  4620
tataaagctg agcatttcga tttgttcaag tggaatgagt taaggtgcac atgttagctt  4680
gtaattttct aaagaagttg ttttgtttat taatgttcat gtttataaaa tgaaggcata  4740
ttgttggaga atcacttggt tccttgaact tcaaggaact caaaaaccta gaaggaaggc  4800
ttgaaaaagg aataaaccgc gtccgatcca agaaggtact taatacatgc acctacgtct  4860
atctgtttct ttatagttta catagttttt ctcacactta catggaatat cgcagaatga  4920
gttgttagtg gcagagcttg agtatatgca gaagagggta agcaacattt gttcctctgc  4980
aagtaacgtt ttttccatct atgtcgtgtc ttcttcttgg aggttgagtt ttgtcaaaaa  5040
tcatgtagga gatggagttg caacatgata acatgtacct gagagctcag gttagtcacg  5100
ttttctttac aatctttatt taaatctcta ctctctactt cattctctca caagtcacaa  5160
ccaaactttt ttcggttttt gcagatagga aactgcgcta ggctggatcc ggaacaacag  5220
gaatcgagtg tgatacaagg aactgcggtt tatgaatctg gtctgtcttc tcatgatcag  5280
tcacagaatt ataaccggag ctatattccg gtgaaccttc ttgaaccgaa tcaacaattc  5340
tccggtcaag accaacctcc tcttcagctt gtttaagctt aacatgatga aaacttgatg  5400
aaaacttgtt tcttccactc gaaacgatct agagagcagg agtacatata tttatgcgac  5460
ttcttatgca tagtttaggt tccggtgata ataaaacata actcttgttc ctattgcctt  5520
ttgatctatc ttattaattt agaattaata caaagtcaat atgagtcttt aaggttgttg  5580
acagaaaaaa agggaattaa taccaaggac tgtccattac aaaacattag aacgtgcagc  5640
ttagagcatc acaaaaccta ttatatttct tacttctaaa tgggatttgg agtgaatctt  5700
ctctaacaca actccagaat agaataaaaa ggaagttatt ccaaaaataa aataatgaat  5760
ttatttt                                                            5768
```

```
SEQ ID NO: 207         moltype = DNA  length = 748
FEATURE                Location/Qualifiers
source                 1..748
                       mol_type = other DNA
                       organism = Brassica napus
SEQUENCE: 207
atggaggaag gtgggagtag tcacgacgca gagagtaaca agaagctagt gagagggaag  60
atagagataa agaggataga gaacacgaca agtcgtcaag taactttctg caaacgacgc  120
aatggtcttc tcaagaaagc ttatgagctc tctgtcttgt gtgatgcgga agttgcactt  180
gttgtcttct ccactcgtgg ccgtctctat gagtacgcta acaacagtgt gaagggtaca  240
attgaaaggt acaagaaagc ttgttccgat gccgtcaacc ctcctactat caccgaagct  300
aatactcagt attatcagca agaagcctct aagcttcgga ggcagattcg ggacattcaa  360
aattctaaca ggcatattgt tggagaatca cttggttcct tgaacttcaa ggaactcaaa  420
aacctagaag gaaggcttga aaaaggaata aaccgcgtcc gatccaagaa gaatgagttg  480
ttagtggcag agcttgagta tatgcagaag agggagatgg agttgcaaca tgataacatg  540
tacctgagag ctcagatagg aaactgcgct aggctggatc cggaacaaca ggaatcgagt  600
gtgatacaag gaactgcggt ttatgaatct ggtctgtctt ctcatgatca gtcacagaat  660
tataaccgga gctatattcc ggtgaacctt cttgaaccga atcaacaatt ctccggtcaa  720
gaccaacctc ctcttcagct tgtttaag                                     748
```

```
SEQ ID NO: 208         moltype = AA  length = 248
FEATURE                Location/Qualifiers
source                 1..248
                       mol_type = protein
                       organism = Brassica napus
SEQUENCE: 208
MEEGGSSHDA ESNKKLVRGK IEIKRIENTT SRQVTFCKRR NGLLKKAYEL SVLCDAEVAL  60
VVFSTRGRLY EYANNSVKGT IERYKKACSD AVNPPTITEA NTQYYQQEAS KLRRQIRDIQ  120
NSNRHIVGES LGSLNFKELK NLEGRLEKGI NRVRSKKNEL LVAELEYMQK REMELQHDNM  180
YLRAQIGNCA RLDPEQQESS VIQGTAVYES GLSSHDQSQN YNRSYIPVNL LEPNQQFSGQ  240
DQPPLQLV                                                           248
```

```
SEQ ID NO: 209         moltype = DNA  length = 528
FEATURE                Location/Qualifiers
source                 1..528
                       mol_type = other DNA
                       organism = Brassica napus
SEQUENCE: 209
agaagagggt aagcaacatt tgttcctctg caagtaacgt tttttccatc tatgtcgtgt  60
cttcttcttg gaggttgagt tttgtcaaaa atcatgtagg agatggagtt gcaacatgat  120
aacatgtacc tgagagctca ggttagtcac gttttcttta caatctttat ttaaatctct  180
actctctact tcattctctc acaagtcaca accaaacttt tttcggtttt tgcagatagg  240
aaactgcgct aggctggatc cggaacaaca ggaatcgagt gtgatacaag gaactgcggt  300
ttatgaatct ggtctgtctt ctcatgatca gtcacagaat tataaccgga gctatattcc  360
ggtgaacctt cttgaaccga atcaacaatt ctccggtcaa gaccaacctc ctcttcagct  420
tgtttaagct taacatgatg aaaacttgat gaaaacttgt ttcttccact cgaaacgatc  480
tagagagcag gagtacatat atttatgcga cttcttatgc atagttta               528
```

```
SEQ ID NO: 210         moltype = DNA  length = 448
FEATURE                Location/Qualifiers
source                 1..448
                       mol_type = other DNA
                       organism = Brassica napus
SEQUENCE: 210
tttttccatc tatgtcgtgt cttcttcttg gaggttgagt tttgtcaaaa atcatgtagg  60
agatggagtt gcaacatgat aacatgtacc tgagagctca ggttagtcac gttttcttta  120
caatctttat ttaaatctct actctctact tcattctctc acaagtcaca accaaacttt  180
tttcggtttt tgcagatagg aaactgcgct aggctggatc cggaacaaca ggaatcgagt  240
gtgatacaag gaactgcggt ttatgaatct ggtctgtctt ctcatgatca gtcacagaat  300
tataaccgga gctatattcc ggtgaacctt cttgaaccga atcaacaatt ctccggtcaa  360
gaccaacctc ctcttcagct tgtttaagct taacatgatg aaaacttgat gaaaacttgt  420
ttcttccact cgaaacgatc tagagagc                                    448

SEQ ID NO: 211         moltype = DNA  length = 408
FEATURE                Location/Qualifiers
source                 1..408
                       mol_type = other DNA
                       organism = Brassica napus
SEQUENCE: 211
cttcttcttg gaggttgagt tttgtcaaaa atcatgtagg agatggagtt gcaacatgat  60
aacatgtacc tgagagctca ggttagtcac gttttcttta caatctttat ttaaatctct  120
actctctact tcattctctc acaagtcaca accaaacttt tttcggtttt tgcagatagg  180
aaactgcgct aggctggatc cggaacaaca ggaatcgagt gtgatacaag gaactgcggt  240
ttatgaatct ggtctgtctt ctcatgatca gtcacagaat tataaccgga gctatattcc  300
ggtgaacctt cttgaaccga atcaacaatt ctccggtcaa gaccaacctc ctcttcagct  360
tgtttaagct taacatgatg aaaacttgat gaaaacttgt ttcttcca              408

SEQ ID NO: 212         moltype = DNA  length = 368
FEATURE                Location/Qualifiers
source                 1..368
                       mol_type = other DNA
                       organism = Brassica napus
SEQUENCE: 212
tttgtcaaaa atcatgtagg agatggagtt gcaacatgat aacatgtacc tgagagctca  60
ggttagtcac gttttcttta caatctttat ttaaatctct actctctact tcattctctc  120
acaagtcaca accaaacttt tttcggtttt tgcagatagg aaactgcgct aggctggatc  180
cggaacaaca ggaatcgagt gtgatacaag gaactgcggt ttatgaatct ggtctgtctt  240
ctcatgatca gtcacagaat tataaccgga gctatattcc ggtgaacctt cttgaaccga  300
atcaacaatt ctccggtcaa gaccaacctc ctcttcagct tgtttaagct taacatgatg  360
aaaacttg                                                          368

SEQ ID NO: 213         moltype = DNA  length = 328
FEATURE                Location/Qualifiers
source                 1..328
                       mol_type = other DNA
                       organism = Brassica napus
SEQUENCE: 213
agatggagtt gcaacatgat aacatgtacc tgagagctca ggttagtcac gttttcttta  60
caatctttat ttaaatctct actctctact tcattctctc acaagtcaca accaaacttt  120
tttcggtttt tgcagatagg aaactgcgct aggctggatc cggaacaaca ggaatcgagt  180
gtgatacaag gaactgcggt ttatgaatct ggtctgtctt ctcatgatca gtcacagaat  240
tataaccgga gctatattcc ggtgaacctt cttgaaccga atcaacaatt ctccggtcaa  300
gaccaacctc ctcttcagct tgtttaag                                    328

SEQ ID NO: 214         moltype = DNA  length = 241
FEATURE                Location/Qualifiers
source                 1..241
                       mol_type = other DNA
                       organism = Brassica napus
SEQUENCE: 214
agaagagggt aagcaacatt tgttcctctg caagtaacgt tttttccatc tatgtcgtgt  60
cttcttcttg gaggttgagt tttgtcaaaa atcatgtagg agatggagtt gcaacatgat  120
aacatgtacc tgagagctca ggttagtcac gttttcttta caatctttat ttaaatctct  180
actctctact tcattctctc acaagtcaca accaaacttt tttcggtttt tgcagatagg  240
a                                                                 241

SEQ ID NO: 215         moltype = DNA  length = 161
FEATURE                Location/Qualifiers
source                 1..161
                       mol_type = other DNA
                       organism = Brassica napus
SEQUENCE: 215
tttttccatc tatgtcgtgt cttcttcttg gaggttgagt tttgtcaaaa atcatgtagg  60
agatggagtt gcaacatgat aacatgtacc tgagagctca ggttagtcac gttttcttta  120
caatctttat ttaaatctct actctctact tcattctctc a                     161
```

-continued

```
SEQ ID NO: 216          moltype = DNA  length = 121
FEATURE                 Location/Qualifiers
source                  1..121
                        mol_type = other DNA
                        organism = Brassica napus
SEQUENCE: 216
cttcttcttg gaggttgagt tttgtcaaaa atcatgtagg agatggagtt gcaacatgat  60
aacatgtacc tgagagctca ggttagtcac gttttcttta caatctttat ttaaatctct  120
a                                                                  121

SEQ ID NO: 217          moltype = DNA  length = 81
FEATURE                 Location/Qualifiers
source                  1..81
                        mol_type = other DNA
                        organism = Brassica napus
SEQUENCE: 217
tttgtcaaaa atcatgtagg agatggagtt gcaacatgat aacatgtacc tgagagctca  60
ggttagtcac gttttcttta c                                            81

SEQ ID NO: 218          moltype = DNA  length = 41
FEATURE                 Location/Qualifiers
source                  1..41
                        mol_type = other DNA
                        organism = Brassica napus
SEQUENCE: 218
agatggagtt gcaacatgat aacatgtacc tgagagctca g                      41

SEQ ID NO: 219          moltype = DNA  length = 393
FEATURE                 Location/Qualifiers
source                  1..393
                        mol_type = other DNA
                        organism = Brassica napus
SEQUENCE: 219
gctcaggtta gtcacgtttt ctttacaatc tttatttaaa tctctactct ctacttcatt  60
ctctcacaag tcacaaccaa actttttcg gtttttgcag ataggaaact gcgctaggct  120
ggatccggaa caacaggaat cgagtgtgat acaaggaact gcggtttatg aatctggtct  180
gtcttctcat gatcagtcac agaattataa ccggagctat attccggtga accttcttga  240
accgaatcaa caattctccg gtcaagacca acctcctctt cagcttgttt aagcttaaca  300
tgatgaaaac ttgatgaaaa cttgtttctt ccactcgaaa cgatctagag agcaggagta  360
catatattta tgcgacttct tatgcatagt tta                               393

SEQ ID NO: 220          moltype = DNA  length = 313
FEATURE                 Location/Qualifiers
source                  1..313
                        mol_type = other DNA
                        organism = Brassica napus
SEQUENCE: 220
tctctactct ctacttcatt ctctcacaag tcacaaccaa actttttcg gtttttgcag  60
ataggaaact gcgctaggct ggatccggaa caacaggaat cgagtgtgat acaaggaact  120
gcggtttatg aatctggtct gtcttctcat gatcagtcac agaattataa ccggagctat  180
attccggtga accttcttga accgaatcaa caattctccg gtcaagacca acctcctctt  240
cagcttgttt aagcttaaca tgatgaaaac ttgatgaaaa cttgtttctt ccactcgaaa  300
cgatctagag agc                                                     313

SEQ ID NO: 221          moltype = DNA  length = 273
FEATURE                 Location/Qualifiers
source                  1..273
                        mol_type = other DNA
                        organism = Brassica napus
SEQUENCE: 221
ctctcacaag tcacaaccaa actttttcg gtttttgcag ataggaaact gcgctaggct  60
ggatccggaa caacaggaat cgagtgtgat acaaggaact gcggtttatg aatctggtct  120
gtcttctcat gatcagtcac agaattataa ccggagctat attccggtga accttcttga  180
accgaatcaa caattctccg gtcaagacca acctcctctt cagcttgttt aagcttaaca  240
tgatgaaaac ttgatgaaaa cttgtttctt cca                               273

SEQ ID NO: 222          moltype = DNA  length = 233
FEATURE                 Location/Qualifiers
source                  1..233
                        mol_type = other DNA
                        organism = Brassica napus
SEQUENCE: 222
actttttcg gtttttgcag ataggaaact gcgctaggct ggatccggaa caacaggaat  60
cgagtgtgat acaaggaact gcggtttatg aatctggtct gtcttctcat gatcagtcac  120
agaattataa ccggagctat attccggtga accttcttga accgaatcaa caattctccg  180
gtcaagacca acctcctctt cagcttgttt aagcttaaca tgatgaaaac ttg         233

SEQ ID NO: 223          moltype = DNA  length = 193
FEATURE                 Location/Qualifiers
```

-continued

```
source                  1..193
                        mol_type = other DNA
                        organism = Brassica napus
SEQUENCE: 223
ataggaaact gcgctaggct ggatccggaa caacaggaat cgagtgtgat acaaggaact  60
gcggtttatg aatctggtct gtcttctcat gatcagtcac agaattataa ccggagctat  120
attccggtga accttcttga accgaatcaa caattctccg gtcaagacca acctcctctt  180
cagcttgttt aag                                                     193

SEQ ID NO: 224          moltype = DNA  length = 155
FEATURE                 Location/Qualifiers
source                  1..155
                        mol_type = other DNA
                        organism = Brassica napus
SEQUENCE: 224
tggatccgga acaacaggaa tcgagtgtga tacaaggaac tgcggtttat gaatctggtc  60
tgtcttctca tgatcagtca cagaattata accggagcta tattccggtg aaccttcttg  120
aaccgaatca acaattctcc ggtcaagacc aacct                             155

SEQ ID NO: 225          moltype = DNA  length = 115
FEATURE                 Location/Qualifiers
source                  1..115
                        mol_type = other DNA
                        organism = Brassica napus
SEQUENCE: 225
tcgagtgtga tacaaggaac tgcggtttat gaatctggtc tgtcttctca tgatcagtca  60
cagaattata accggagcta tattccggtg aaccttcttg aaccgaatca acaat       115

SEQ ID NO: 226          moltype = DNA  length = 74
FEATURE                 Location/Qualifiers
source                  1..74
                        mol_type = other DNA
                        organism = Brassica napus
SEQUENCE: 226
gcggtttatg aatctggtct gtcttctcat gatcagtcac agaattataa ccggagctat  60
attccggtga acct                                                    74

SEQ ID NO: 227          moltype = DNA  length = 223
FEATURE                 Location/Qualifiers
source                  1..223
                        mol_type = other DNA
                        organism = Brassica napus
SEQUENCE: 227
aactgcggtt tatgaatctg gtctgtcttc tcatgatcag tcacagaatt ataaccggag  60
ctatattccg gtgaaccttc ttgaaccgaa tcaacaattc tccggtcaag accaacctcc  120
tcttcagctt gtttaagctt aacatgatga aaacttgatg aaaacttgtt tcttccactc  180
gaaacgatct agagagcagg agtacatata tttatgcgac ttc                    223

SEQ ID NO: 228          moltype = DNA  length = 144
FEATURE                 Location/Qualifiers
source                  1..144
                        mol_type = other DNA
                        organism = Brassica napus
SEQUENCE: 228
gtcacagaat tataaccgga gctatattcc ggtgaacctt cttgaaccga atcaacaatt  60
ctccggtcaa gaccaacctc ctcttcagct tgtttaagct taacatgatg aaaacttgat  120
gaaaacttgt ttcttccact cgaa                                         144

SEQ ID NO: 229          moltype = DNA  length = 104
FEATURE                 Location/Qualifiers
source                  1..104
                        mol_type = other DNA
                        organism = Brassica napus
SEQUENCE: 229
gctatattcc ggtgaacctt cttgaaccga atcaacaatt ctccggtcaa gaccaacctc  60
ctcttcagct tgtttaagct taacatgatg aaaacttgat gaaa                   104

SEQ ID NO: 230          moltype = DNA  length = 64
FEATURE                 Location/Qualifiers
source                  1..64
                        mol_type = other DNA
                        organism = Brassica napus
SEQUENCE: 230
cttgaaccga atcaacaatt ctccggtcaa gaccaacctc ctcttcagct tgtttaagct  60
taac                                                               64

SEQ ID NO: 231          moltype = DNA  length = 234
FEATURE                 Location/Qualifiers
```

```
source                  1..234
                        mol_type = other DNA
                        organism = Brassica napus
SEQUENCE: 231
agatggagtt gcaacatgat aacatgtacc tgagagctca gataggaaac tgcgctaggc  60
tggatccgga acaacaggaa tcgagtgtga tacaaggaac tgcggtttat gaatctggtc  120
tgtcttctca tgatcagtca cagaattata accggagcta tattccggtg aaccttcttg  180
aaccgaatca acaattctcc ggtcaagacc aacctcctct tcagcttgtt taag        234

SEQ ID NO: 232          moltype = DNA  length = 156
FEATURE                 Location/Qualifiers
source                  1..156
                        mol_type = other DNA
                        organism = Brassica napus
SEQUENCE: 232
agataggaaa ctgcgctagg ctggatccgg aacaacagga atcgagtgtg atacaaggaa  60
ctgcggttta tgaatctggt ctgtcttctc atgatcagtc acagaattat aaccggagct  120
atattccggt gaaccttctt gaaccgaatc aacaat                            156

SEQ ID NO: 233          moltype = DNA  length = 116
FEATURE                 Location/Qualifiers
source                  1..116
                        mol_type = other DNA
                        organism = Brassica napus
SEQUENCE: 233
ctggatccgg aacaacagga atcgagtgtg atacaaggaa ctgcggttta tgaatctggt  60
ctgtcttctc atgatcagtc acagaattat aaccggagct atattccggt gaacct      116

SEQ ID NO: 234          moltype = DNA  length = 76
FEATURE                 Location/Qualifiers
source                  1..76
                        mol_type = other DNA
                        organism = Brassica napus
SEQUENCE: 234
atcgagtgtg atacaaggaa ctgcggttta tgaatctggt ctgtcttctc atgatcagtc  60
acagaattat aaccgg                                                  76

SEQ ID NO: 235          moltype = DNA  length = 77
FEATURE                 Location/Qualifiers
source                  1..77
                        mol_type = other DNA
                        organism = Brassica napus
SEQUENCE: 235
ctatattccg gtgaaccttc ttgaaccgaa tcaacaattc tccggtcaag accaacctcc  60
tcttcagctt gtttaag                                                 77

SEQ ID NO: 236          moltype = DNA  length = 57
FEATURE                 Location/Qualifiers
source                  1..57
                        mol_type = other DNA
                        organism = Brassica napus
SEQUENCE: 236
ttgaaccgaa tcaacaattc tccggtcaag accaacctcc tcttcagctt gtttaag     57

SEQ ID NO: 237          moltype = AA  length = 76
FEATURE                 Location/Qualifiers
source                  1..76
                        mol_type = protein
                        organism = Brassica napus
SEQUENCE: 237
MELQHDNMYL RAQIGNCARL DPEQQESSVI QGTAVYESGL SSHDQSQNYN RSYIPVNLLE  60
PNQQFSGQDQ PPLQLV                                                  76

SEQ ID NO: 238          moltype = AA  length = 63
FEATURE                 Location/Qualifiers
source                  1..63
                        mol_type = protein
                        organism = Brassica napus
SEQUENCE: 238
IGNCARLDPE QQESSVIQGT AVYESGLSSH DQSQNYNRSY IPVNLLEPNQ QFSGQDQPPL  60
QLV                                                                63

SEQ ID NO: 239          moltype = AA  length = 13
FEATURE                 Location/Qualifiers
source                  1..13
                        mol_type = protein
                        organism = Brassica napus
SEQUENCE: 239
MELQHDNMYL RAQ                                                     13
```

```
SEQ ID NO: 240          moltype = DNA  length = 3588
FEATURE                 Location/Qualifiers
source                  1..3588
                        mol_type = genomic DNA
                        organism = Brassica napus
SEQUENCE: 240
cccacttctc ctttgtgctg atctatcata agctttaaac cccaggtacg gttctgaata  60
ttatacaatt tatatagaat aactctaata tacaagattt atattcagag ttcttttcat  120
tttcattttc aattcaatat ctgatccttt gttacctaga tttgatatgt ttatttatta  180
ttgtttacaa agagatttga tcattttaac cctaaaccta agttttgtac ccaaatcata  240
tgatctatct tttggttatt cttgatctgc aaaatgatta atttgatcat caatcttaat  300
tatattctct ataacaatct tttttttat taagctttgc tctgatcaat ctctctccct  360
cttattatgt tattttattc atctggtgat atcacagaat caatggagga aggtgggagt  420
agtcacgacg cagagagtaa caagaagcta gtaagaggga agatagagat aaagaggata  480
gagaacacaa caagtcgtca agtaactttc tgtaaacgac gcaatggtct tcttaagaaa  540
gcttatgagc tttctgtctt gtgtgatgct gaagttgccc tcgtcatctt ctcgactcgt  600
ggccgtctct atgagtacgc caacaacagg tacgcttctc ctgcaccttc ttgatctttg  660
ctttcttggt ttattactac tacaagaaaa tcttagttaa atgtatggag aagtgacttg  720
tcgagtcaag attagggttt ttgttaattt acaatcctgg gtttttttcc catgccaaaa  780
aacaaaatcc tgggtttttct tgttttccta aattaaatat ctctctagag ctaccataac  840
tatgtgtgtg tgtgtgtttg tgtaagcaaa taatgaagaa ggaagaaagc tgtcttgtct  900
tctcaacttc tagttagcct tctcgttagc ctttttttggt gtcactcttt ttctgcaaat  960
cattgaaacc tgatgcatgc cagcttctcc atgaaatttc tttactcaaa ttaatactag  1020
ggtttaatca gtaaacaagt tgggtacttt cttgacacga aatagcatgt atattatata  1080
aatatgcaag acttatgtaa ccctctgtct agtgtaactt gggacagagc ctaatgatca  1140
gttgtcacta gctagggatc cctataatta tttaatctag ccccccaaag gcaaatgaaa  1200
actgaaaatt tcatattctt gagttggtct tgagaaatat aatatgtggc tgaaataaaa  1260
ttgtcctggt atgcaagttc agaatttcaa ctctctttct aaaaaactgt atatatataa  1320
tatgtaaccg attgtttaca tttattttta actttaccaa agatgtagtt agagaggatt  1380
atgtataaca atataaatgc agtttttagg tttctaatct aaaatgagtt gctacaatct  1440
atatatattt gatctagaaa tgggatttgt aataaggttt aacatataat aatgggattt  1500
cttaatttct cttcacaagt cgcatatatc tttttgtctc atatatacat cttttgttac  1560
agtagttgac gaagaacttc aaattaaaca ataaacacac atgactttaa tttgtctaac  1620
attgaaatca ctcatcgtct gttgaaaaaa taatattgat attaatacat aagccattgc  1680
tgaatgtata catatgtagt ccttggatat attaatgaga gggagataac tcggagaagt  1740
gtcagaactc gaaattgtac gggccaatga gaagctctgg cattctgagc tccatttatt  1800
tgttattatc tctaaaaaaa ttactgatcc tttaagcata ttgtgatgaa attgaatcat  1860
ataatatgca tggacgttgt tgtgtactcc tcctaattac caatttgaaa tcatactact  1920
agtgtaatac ttaattactt atatccttac tttttatttt gtctcaacgt caactatttc  1980
attaaccgat aaattagtac aaagtatttg accacaccaa tttgaccaca catgcaacaa  2040
tgcatcttag taacacactg gaacactcac taggtgattt cttactcgga accagcgcaa  2100
cctgagtaca ttgctgcatt tttcacactt atatccttac tttagttaac tgcattagca  2160
gccatttatt atttgatgta aattaccttg gaaaaatatg atacttcagc ctgacataat  2220
atgtttgatt gaaattctct tcatcatcct ggcaatcaga gactggtcca aacttcaaag  2280
ccacacattc ctttcttgtc gattttaagg tttttggccg ggaaaataaa ctttcaaaaa  2340
ccctaatcaa agtacagtac ttactatgtt taagagtatg tttattaaat taaatctaat  2400
aggttctcca actttttagc gtgaagggta caattgaaag atacaagaaa gcttgttccg  2460
atgccgttaa ccctccttct gtcaccgaag ctaatactca ggtaccgttc tttagttctt  2520
ttattccccc tctcttttc tttttctcat cttttttttta tgatgaccaa ttaacgttac  2580
aaaaaaaatt aaaaaaattt ggatgggttc atgaaacgtt ttggtgtttg tatgcatgga  2640
actctgaagt actatcagca agaagcctct aagcttcgga ggcagattcg tgacattcaa  2700
aattctaaca ggtaaataag acggtctttt ggtttgatca ctacttctct attattgatg  2760
ttgttttgat tatttaatgt tgtgaaatga aaggcatata gttggggaat cacttggttc  2820
cttgaacttc aaggaactca aaaacctcga aggacgtctt gaaaaaggaa tcaaccgtgt  2880
ccgatccaag aaggtactta ccctaacgtc tctttgtctc tctataactt atatagtttt  2940
cttactctta taatgaaaat ctcgcagaat gagctgttaa tggcagagat agagtatatg  3000
cagaagaggg taagtaacgt ttcttccata tcttgcaccg tctttttagg tttttgagtt  3060
tcctataaat cgtgtaggaa atggagttgc aacacgataa catgtacctg cgagctaagg  3120
ttagtctaaa tctctcttct ttacatcatc gcctacccga gaagataacg tgtgtaacaa  3180
accaaacttt gatgttcggt ctttgcagat atcacaaggt gcgagattga atccggagca  3240
gcaggattcg agtgtaatac aaggaacagc ggtttacgaa cccggtctat cttcccatga  3300
ccagtcacag cattataacc ggaactatat tccggttaac cttcttgaac cgaatctaca  3360
tttctccggt caagaccaac ctcctcttca acttgtctaa gttttaaaca tgaaaaaaaa  3420
cacttgtttc ttcccctcaa aacggttgtt cagagaaaga cactaagagt aacttcttct  3480
catgcatagt tttttaggtt ccaataataa taacataaat aaatcaagtg ttacaaagat  3540
acaaacttac aaacatctat cttctgatgt gtagctataa ctaaacaa             3588

SEQ ID NO: 241          moltype = DNA  length = 747
FEATURE                 Location/Qualifiers
source                  1..747
                        mol_type = other DNA
                        organism = Brassica napus
SEQUENCE: 241
atggaggaag gtgggagtag tcacgacgca gagagtaaca agaagctagt aagagggaag  60
atagagataa agaggataga gaacacaaca agtcgtcaag taactttctg taaacgacgc  120
aatggtcttc ttaagaaagc ttatgagctt tctgtcttgt gtgatgctga agttgccctc  180
gtcatcttct cgactcgtgg ccgtctctat gagtacgcca acaacagcgt gaagggtaca  240
attgaaagat acaagaaagc ttgttccgat gccgttaacc ctccttctgt caccgaagct  300
```

```
aatactcagt actatcagca agaagcctct aagcttcgga ggcagattcg tgacattcaa  360
aattctaaca ggcatatagt tggggaatca cttggttcct tgaacttcaa ggaactcaaa  420
aacctcgaag gacgtcttga aaaaggaatc aaccgtgtcc gatccaagaa gaatgagctg  480
ttaatggcag agatagagta tatgcagaag agggaaatgg agttgcaaca cgataacatg  540
tacctgcgag ctaagatatc acaaggtgcg agattgaatc cggagcagca ggattcgagt  600
gtaatacaag gaacagcggt ttacgaaccc ggtctatctt cccatgacca gtcacagcat  660
tataaccgga actatattcc ggttaacctt cttgaaccga atctacattt ctccggtcaa  720
gaccaacctc ctcttcaact tgtctaa                                      747

SEQ ID NO: 242         moltype = AA  length = 248
FEATURE                Location/Qualifiers
source                 1..248
                       mol_type = protein
                       organism = Brassica napus
SEQUENCE: 242
MEEGGSSHDA ESNKKLVRGK IEIKRIENTT SRQVTFCKRR NGLLKKAYEL SVLCDAEVAL  60
VIFSTRGRLY EYANNSVKGT IERYKKACSD AVNPPSVTEA NTQYYQQEAS KLRRQIRDIQ  120
NSNRHIVGES LGSLNFKELK NLEGRLEKGI NRVRSKKNEL LMAEIEYMQK REMELQHDNM  180
YLRAKISQGA RLNPEQQDSS VIQGTAVYEP GLSSHDQSQH YNRNYIPVNL LEPNLHFSGQ  240
DQPPLQLV                                                           248

SEQ ID NO: 243         moltype = DNA  length = 522
FEATURE                Location/Qualifiers
source                 1..522
                       mol_type = other DNA
                       organism = Brassica napus
SEQUENCE: 243
aatggcagag atagagtata tgcagaagag ggtaagtaac gtttcttcca tatcttgcac  60
cgtcttttta ggtttttgag tttcctataa atcgtgtagg aaatggagtt gcaacacgat  120
aacatgtacc tgcgagctaa ggttagtcta aatctctctt ctttacatca tcgcctaccc  180
gagaagataa cgtgtgtaac aaaccaaact ttgatgttcg gtctttgcag atatcacaag  240
gtgcgagatt gaatccggag cagcaggatt cgagtgtaat acaaggaaca gcggtttacg  300
aacccggtct atcttcccat gaccagtcac agcattataa ccggaactat attccggtta  360
accttcttga accgaatcta catttctccg gtcaagacca acctcctctt caacttgtct  420
aagttttaaa catgaaaaaa aacacttgtt tcttcccctc aaaacggttg ttcagagaaa  480
gacactaaga gtaacttctt ctcatgcata gtttttttagg tt                     522

SEQ ID NO: 244         moltype = DNA  length = 443
FEATURE                Location/Qualifiers
source                 1..443
                       mol_type = other DNA
                       organism = Brassica napus
SEQUENCE: 244
gtttcttcca tatcttgcac cgtcttttta ggtttttgag tttcctataa atcgtgtagg  60
aaatggagtt gcaacacgat aacatgtacc tgcgagctaa ggttagtcta aatctctctt  120
ctttacatca tcgcctaccc gagaagataa cgtgtgtaac aaaccaaact ttgatgttcg  180
gtctttgcag atatcacaag gtgcgagatt gaatccggag cagcaggatt cgagtgtaat  240
acaaggaaca gcggtttacg aacccggtct atcttcccat gaccagtcac agcattataa  300
ccggaactat attccggtta accttcttga accgaatcta catttctccg gtcaagacca  360
acctcctctt caacttgtct aagttttaaa catgaaaaaa aacacttgtt tcttcccctc  420
aaaacggttg ttcagagaaa gac                                          443

SEQ ID NO: 245         moltype = DNA  length = 403
FEATURE                Location/Qualifiers
source                 1..403
                       mol_type = other DNA
                       organism = Brassica napus
SEQUENCE: 245
cgtcttttta ggtttttgag tttcctataa atcgtgtagg aaatggagtt gcaacacgat  60
aacatgtacc tgcgagctaa ggttagtcta aatctctctt ctttacatca tcgcctaccc  120
gagaagataa cgtgtgtaac aaaccaaact ttgatgttcg gtctttgcag atatcacaag  180
gtgcgagatt gaatccggag cagcaggatt cgagtgtaat acaaggaaca gcggtttacg  240
aacccggtct atcttcccat gaccagtcac agcattataa ccggaactat attccggtta  300
accttcttga accgaatcta catttctccg gtcaagacca acctcctctt caacttgtct  360
aagttttaaa catgaaaaaa aacacttgtt tcttcccctc aaa                    403

SEQ ID NO: 246         moltype = DNA  length = 363
FEATURE                Location/Qualifiers
source                 1..363
                       mol_type = other DNA
                       organism = Brassica napus
SEQUENCE: 246
tttcctataa atcgtgtagg aaatggagtt gcaacacgat aacatgtacc tgcgagctaa  60
ggttagtcta aatctctctt ctttacatca tcgcctaccc gagaagataa cgtgtgtaac  120
aaaccaaact ttgatgttcg gtctttgcag atatcacaag gtgcgagatt gaatccggag  180
cagcaggatt cgagtgtaat acaaggaaca gcggtttacg aacccggtct atcttcccat  240
gaccagtcac agcattataa ccggaactat attccggtta accttcttga accgaatcta  300
catttctccg gtcaagacca acctcctctt caacttgtct aagttttaaa catgaaaaaa  360
aac                                                                363
```

```
SEQ ID NO: 247         moltype = DNA  length = 322
FEATURE                Location/Qualifiers
source                 1..322
                       mol_type = other DNA
                       organism = Brassica napus
SEQUENCE: 247
aaatggagtt gcaacacgat aacatgtacc tgcgagctaa ggttagtcta aatctctctt  60
ctttacatca tcgcctaccc gagaagataa cgtgtgtaac aaaccaaact ttgatgttcg  120
gtctttgcag atatcacaag gtgcgagatt gaatccggag cagcaggatt cgagtgtaat  180
acaaggaaca gcggtttacg aacccggtct atcttcccat gaccagtcac agcattataa  240
ccggaactat attccggtta accttcttga accgaatcta catttctccg gtcaagacca  300
acctcctctt caacttgtct aa                                           322

SEQ ID NO: 248         moltype = DNA  length = 241
FEATURE                Location/Qualifiers
source                 1..241
                       mol_type = other DNA
                       organism = Brassica napus
SEQUENCE: 248
aatggcagag atagagtata tgcagaagag ggtaagtaac gtttcttcca tatcttgcac  60
cgtcttttta ggtttttgag tttcctataa atcgtgtagg aaatggagtt gcaacacgat  120
aacatgtacc tgcgagctaa ggttagtcta aatctctctt ctttacatca tcgcctaccc  180
gagaagataa cgtgtgtaac aaaccaaact ttgatgttcg gtctttgcag atatcacaag  240
g                                                                  241

SEQ ID NO: 249         moltype = DNA  length = 161
FEATURE                Location/Qualifiers
source                 1..161
                       mol_type = other DNA
                       organism = Brassica napus
SEQUENCE: 249
gtttcttcca tatcttgcac cgtcttttta ggtttttgag tttcctataa atcgtgtagg  60
aaatggagtt gcaacacgat aacatgtacc tgcgagctaa ggttagtcta aatctctctt  120
ctttacatca tcgcctaccc gagaagataa cgtgtgtaac a                      161

SEQ ID NO: 250         moltype = DNA  length = 120
FEATURE                Location/Qualifiers
source                 1..120
                       mol_type = other DNA
                       organism = Brassica napus
SEQUENCE: 250
gtctttttag gtttttgagt ttcctataaa tcgtgtagga aatggagttg caacacgata  60
acatgtacct gcgagctaag gttagtctaa atctctcttc tttacatcat cgcctacccg  120

SEQ ID NO: 251         moltype = DNA  length = 81
FEATURE                Location/Qualifiers
source                 1..81
                       mol_type = other DNA
                       organism = Brassica napus
SEQUENCE: 251
tttcctataa atcgtgtagg aaatggagtt gcaacacgat aacatgtacc tgcgagctaa  60
ggttagtcta aatctctctt c                                            81

SEQ ID NO: 252         moltype = DNA  length = 41
FEATURE                Location/Qualifiers
source                 1..41
                       mol_type = other DNA
                       organism = Brassica napus
SEQUENCE: 252
aaatggagtt gcaacacgat aacatgtacc tgcgagctaa g                      41

SEQ ID NO: 253         moltype = DNA  length = 392
FEATURE                Location/Qualifiers
source                 1..392
                       mol_type = other DNA
                       organism = Brassica napus
SEQUENCE: 253
tgcgagctaa ggttagtcta aatctctctt ctttacatca tcgcctaccc gagaagataa  60
cgtgtgtaac aaaccaaact ttgatgttcg gtctttgcag atatcacaag gtgcgagatt  120
gaatccggag cagcaggatt cgagtgtaat acaaggaaca gcggtttacg aacccggtct  180
atcttcccat gaccagtcac agcattataa ccggaactat attccggtta accttcttga  240
accgaatcta catttctccg gtcaagacca acctcctctt caacttgtct aagttttaaa  300
catgaaaaaa aacacttgtt tcttcccctc aaaacggttg ttcagagaaa gacactaaga  360
gtaacttctt ctcatgcata gttttttagg tt                                392

SEQ ID NO: 254         moltype = DNA  length = 312
FEATURE                Location/Qualifiers
```

```
source                  1..312
                        mol_type = other DNA
                        organism = Brassica napus
SEQUENCE: 254
tcgcctaccc gagaagataa cgtgtgtaac aaaccaaact ttgatgttcg gtctttgcag  60
atatcacaag gtgcgagatt gaatccggag cagcaggatt cgagtgtaat acaaggaaca  120
gcggtttacg aacccggtct atcttcccat gaccagtcac agcattataa ccggaactat  180
attccggtta accttcttga accgaatcta catttctccg gtcaagacca acctcctctt  240
caacttgtct aagttttaaa catgaaaaaa aacacttgtt tcttcccctc aaaacggttg  300
ttcagagaaa ga                                                      312

SEQ ID NO: 255          moltype = DNA  length = 272
FEATURE                 Location/Qualifiers
source                  1..272
                        mol_type = other DNA
                        organism = Brassica napus
SEQUENCE: 255
cgtgtgtaac aaaccaaact ttgatgttcg gtctttgcag atatcacaag gtgcgagatt  60
gaatccggag cagcaggatt cgagtgtaat acaaggaaca gcggtttacg aacccggtct  120
atcttcccat gaccagtcac agcattataa ccggaactat attccggtta accttcttga  180
accgaatcta catttctccg gtcaagacca acctcctctt caacttgtct aagttttaaa  240
catgaaaaaa aacacttgtt tcttcccctc aa                                272

SEQ ID NO: 256          moltype = DNA  length = 232
FEATURE                 Location/Qualifiers
source                  1..232
                        mol_type = other DNA
                        organism = Brassica napus
SEQUENCE: 256
ttgatgttcg gtctttgcag atatcacaag gtgcgagatt gaatccggag cagcaggatt  60
cgagtgtaat acaaggaaca gcggtttacg aacccggtct atcttcccat gaccagtcac  120
agcattataa ccggaactat attccggtta accttcttga accgaatcta catttctccg  180
gtcaagacca acctcctctt caacttgtct aagttttaaa catgaaaaaa aa          232

SEQ ID NO: 257          moltype = DNA  length = 192
FEATURE                 Location/Qualifiers
source                  1..192
                        mol_type = other DNA
                        organism = Brassica napus
SEQUENCE: 257
atatcacaag gtgcgagatt gaatccggag cagcaggatt cgagtgtaat acaaggaaca  60
gcggtttacg aacccggtct atcttcccat gaccagtcac agcattataa ccggaactat  120
attccggtta accttcttga accgaatcta catttctccg gtcaagacca acctcctctt  180
caacttgtct aa                                                      192

SEQ ID NO: 258          moltype = DNA  length = 154
FEATURE                 Location/Qualifiers
source                  1..154
                        mol_type = other DNA
                        organism = Brassica napus
SEQUENCE: 258
tgaatccgga gcagcaggat tcgagtgtaa tacaaggaac agcggtttac gaacccggtc  60
tatcttccca tgaccagtca cagcattata accggaacta tattccggtt aaccttcttg  120
aaccgaatct acatttctcc ggtcaagacc aacc                              154

SEQ ID NO: 259          moltype = DNA  length = 114
FEATURE                 Location/Qualifiers
source                  1..114
                        mol_type = other DNA
                        organism = Brassica napus
SEQUENCE: 259
tcgagtgtaa tacaaggaac agcggtttac gaacccggtc tatcttccca tgaccagtca  60
cagcattata accggaacta tattccggtt aaccttcttg aaccgaatct acat        114

SEQ ID NO: 260          moltype = DNA  length = 74
FEATURE                 Location/Qualifiers
source                  1..74
                        mol_type = other DNA
                        organism = Brassica napus
SEQUENCE: 260
agcggtttac gaacccggtc tatcttccca tgaccagtca cagcattata accggaacta  60
tattccggtt aacc                                                    74

SEQ ID NO: 261          moltype = DNA  length = 223
FEATURE                 Location/Qualifiers
source                  1..223
                        mol_type = other DNA
                        organism = Brassica napus
```

```
SEQUENCE: 261
cgcagaatga gctgttaatg gcagagatag agtatatgca gaagagggta agtaacgttt  60
cttccatatc ttgcaccgtc tttttaggtt tttgagtttc ctataaatcg tgtaggaaat  120
ggagttgcaa cacgataaca tgtacctgcg agctaaggtt agtctaaatc tctcttcttt  180
acatcatcgc ctacccgaga agataacgtg tgtaacaaac caa                     223

SEQ ID NO: 262          moltype = DNA  length = 143
FEATURE                 Location/Qualifiers
source                  1..143
                        mol_type = other DNA
                        organism = Brassica napus
SEQUENCE: 262
gaagagggta agtaacgttt cttccatatc ttgcaccgtc tttttaggtt tttgagtttc  60
ctataaatcg tgtaggaaat ggagttgcaa cacgataaca tgtacctgcg agctaaggtt  120
agtctaaatc tctcttcttt aca                                            143

SEQ ID NO: 263          moltype = DNA  length = 103
FEATURE                 Location/Qualifiers
source                  1..103
                        mol_type = other DNA
                        organism = Brassica napus
SEQUENCE: 263
cttccatatc ttgcaccgtc tttttaggtt tttgagtttc ctataaatcg tgtaggaaat  60
ggagttgcaa cacgataaca tgtacctgcg agctaaggtt agt                      103

SEQ ID NO: 264          moltype = DNA  length = 63
FEATURE                 Location/Qualifiers
source                  1..63
                        mol_type = other DNA
                        organism = Brassica napus
SEQUENCE: 264
tttttaggtt tttgagtttc ctataaatcg tgtaggaaat ggagttgcaa cacgataaca  60
tgt                                                                  63

SEQ ID NO: 265          moltype = DNA  length = 223
FEATURE                 Location/Qualifiers
source                  1..223
                        mol_type = other DNA
                        organism = Brassica napus
SEQUENCE: 265
aagagggtaa gtaacgtttc ttccatatct tgcaccgtct ttttaggttt ttgagtttcc  60
tataaatcgt gtaggaaatg gagttgcaac acgataacat gtacctgcga gctaaggtta  120
gtctaaatct ctcttcttta catcatcgcc tacccgagaa gataacgtgt gtaacaaacc  180
aaactttgat gttcggtctt tgcagatatc acaaggtgcg aga                     223

SEQ ID NO: 266          moltype = DNA  length = 144
FEATURE                 Location/Qualifiers
source                  1..144
                        mol_type = other DNA
                        organism = Brassica napus
SEQUENCE: 266
ttttaggttt ttgagtttcc tataaatcgt gtaggaaatg gagttgcaac acgataacat  60
gtacctgcga gctaaggtta gtctaaatct ctcttcttta catcatcgcc tacccgagaa  120
gataacgtgt gtaacaaacc aaac                                           144

SEQ ID NO: 267          moltype = DNA  length = 104
FEATURE                 Location/Qualifiers
source                  1..104
                        mol_type = other DNA
                        organism = Brassica napus
SEQUENCE: 267
tataaatcgt gtaggaaatg gagttgcaac acgataacat gtacctgcga gctaaggtta  60
gtctaaatct ctcttcttta catcatcgcc tacccgagaa gata                     104

SEQ ID NO: 268          moltype = DNA  length = 63
FEATURE                 Location/Qualifiers
source                  1..63
                        mol_type = other DNA
                        organism = Brassica napus
SEQUENCE: 268
gagttgcaac acgataacat gtacctgcga gctaaggtta gtctaaatct ctcttcttta  60
cat                                                                  63

SEQ ID NO: 269          moltype = DNA  length = 223
FEATURE                 Location/Qualifiers
source                  1..223
                        mol_type = other DNA
                        organism = Brassica napus
```

```
SEQUENCE: 269
acacgataac atgtacctgc gagctaaggt tagtctaaat ctctcttctt tacatcatcg  60
cctacccgag aagataacgt gtgtaacaaa ccaaactttg atgttcggtc tttgcagata  120
tcacaaggtg cgagattgaa tccggagcag caggattcga gtgtaataca aggaacagcg  180
gtttacgaac ccggtctatc ttcccatgac cagtcacagc att                    223

SEQ ID NO: 270         moltype = DNA  length = 143
FEATURE                Location/Qualifiers
source                 1..143
                       mol_type = other DNA
                       organism = Brassica napus
SEQUENCE: 270
ctctcttctt tacatcatcg cctacccgag aagataacgt gtgtaacaaa ccaaactttg  60
atgttcggtc tttgcagata tcacaaggtg cgagattgaa tccggagcag caggattcga  120
gtgtaataca aggaacagcg gtt                                          143

SEQ ID NO: 271         moltype = DNA  length = 103
FEATURE                Location/Qualifiers
source                 1..103
                       mol_type = other DNA
                       organism = Brassica napus
SEQUENCE: 271
cctacccgag aagataacgt gtgtaacaaa ccaaactttg atgttcggtc tttgcagata  60
tcacaaggtg cgagattgaa tccggagcag caggattcga gtg                    103

SEQ ID NO: 272         moltype = DNA  length = 63
FEATURE                Location/Qualifiers
source                 1..63
                       mol_type = other DNA
                       organism = Brassica napus
SEQUENCE: 272
gtgtaacaaa ccaaactttg atgttcggtc tttgcagata tcacaaggtg cgagattgaa  60
tcc                                                                63

SEQ ID NO: 273         moltype = DNA  length = 223
FEATURE                Location/Qualifiers
source                 1..223
                       mol_type = other DNA
                       organism = Brassica napus
SEQUENCE: 273
aacagcggtt tacgaacccg gtctatcttc ccatgaccag tcacagcatt ataaccggaa  60
ctatattccg gttaaccttc ttgaaccgaa tctacatttc tccggtcaag accaacctcc  120
tcttcaactt gtctaagttt taaacatgaa aaaaaacact tgtttcttcc cctcaaaacg  180
gttgttcaga gaaagacact aagagtaact tcttctcatg cat                    223

SEQ ID NO: 274         moltype = DNA  length = 143
FEATURE                Location/Qualifiers
source                 1..143
                       mol_type = other DNA
                       organism = Brassica napus
SEQUENCE: 274
tcacagcatt ataaccggaa ctatattccg gttaaccttc ttgaaccgaa tctacatttc  60
tccggtcaag accaacctcc tcttcaactt gtctaagttt taaacatgaa aaaaaacact  120
tgtttcttcc cctcaaaacg gtt                                          143

SEQ ID NO: 275         moltype = DNA  length = 103
FEATURE                Location/Qualifiers
source                 1..103
                       mol_type = other DNA
                       organism = Brassica napus
SEQUENCE: 275
ctatattccg gttaaccttc ttgaaccgaa tctacatttc tccggtcaag accaacctcc  60
tcttcaactt gtctaagttt taaacatgaa aaaaaacact tgt                    103

SEQ ID NO: 276         moltype = DNA  length = 63
FEATURE                Location/Qualifiers
source                 1..63
                       mol_type = other DNA
                       organism = Brassica napus
SEQUENCE: 276
ttgaaccgaa tctacatttc tccggtcaag accaacctcc tcttcaactt gtctaagttt  60
taa                                                                63

SEQ ID NO: 277         moltype = DNA  length = 223
FEATURE                Location/Qualifiers
source                 1..223
                       mol_type = other DNA
                       organism = Brassica napus
```

SEQUENCE: 277
atcttcccat gaccagtcac agcattataa ccggaactat attccggtta accttcttga 60
accgaatcta catttctccg gtcaagacca acctcctctt caacttgtct aagttttaaa 120
catgaaaaaa aacacttgtt tcttcccctc aaaacggttg ttcagagaaa gacactaaga 180
gtaacttctt ctcatgcata gtttttttagg ttccaataat aat 223

SEQ ID NO: 278 moltype = DNA length = 143
FEATURE Location/Qualifiers
source 1..143
mol_type = other DNA
organism = Brassica napus
SEQUENCE: 278
attccggtta accttcttga accgaatcta catttctccg gtcaagacca acctcctctt 60
caacttgtct aagttttaaa catgaaaaaa aacacttgtt tcttcccctc aaaacggttg 120
ttcagagaaa gacactaaga gta 143

SEQ ID NO: 279 moltype = DNA length = 103
FEATURE Location/Qualifiers
source 1..103
mol_type = other DNA
organism = Brassica napus
SEQUENCE: 279
accgaatcta catttctccg gtcaagacca acctcctctt caacttgtct aagttttaaa 60
catgaaaaaa aacacttgtt tcttcccctc aaaacggttg ttc 103

SEQ ID NO: 280 moltype = DNA length = 63
FEATURE Location/Qualifiers
source 1..63
mol_type = other DNA
organism = Brassica napus
SEQUENCE: 280
gtcaagacca acctcctctt caacttgtct aagttttaaa catgaaaaaa aacacttgtt 60
tct 63

SEQ ID NO: 281 moltype = DNA length = 223
FEATURE Location/Qualifiers
source 1..223
mol_type = other DNA
organism = Brassica napus
SEQUENCE: 281
ccggttaacc ttcttgaacc gaatctacat ttctccggtc aagaccaacc tcctcttcaa 60
cttgtctaag ttttaaacat gaaaaaaaac acttgtttct tcccctcaaa acggttgttc 120
agagaaagac actaagagta acttcttctc atgcatagtt ttttaggttc caataataat 180
aacataaata aatcaagtgt tacaaagata caaacttaca aac 223

SEQ ID NO: 282 moltype = DNA length = 143
FEATURE Location/Qualifiers
source 1..143
mol_type = other DNA
organism = Brassica napus
SEQUENCE: 282
aagaccaacc tcctcttcaa cttgtctaag ttttaaacat gaaaaaaaac acttgtttct 60
tcccctcaaa acggttgttc agagaaagac actaagagta acttcttctc atgcatagtt 120
ttttaggttc caataataat aac 143

SEQ ID NO: 283 moltype = DNA length = 103
FEATURE Location/Qualifiers
source 1..103
mol_type = other DNA
organism = Brassica napus
SEQUENCE: 283
cttgtctaag ttttaaacat gaaaaaaaac acttgtttct tcccctcaaa acggttgttc 60
agagaaagac actaagagta acttcttctc atgcatagtt ttt 103

SEQ ID NO: 284 moltype = DNA length = 63
FEATURE Location/Qualifiers
source 1..63
mol_type = other DNA
organism = Brassica napus
SEQUENCE: 284
gaaaaaaaac acttgtttct tcccctcaaa acggttgttc agagaaagac actaagagta 60
act 63

SEQ ID NO: 285 moltype = DNA length = 233
FEATURE Location/Qualifiers
source 1..233
mol_type = other DNA
organism = Brassica napus -continued

```
SEQUENCE: 285
aaatggagtt gcaacacgat aacatgtacc tgcgagctaa gatatcacaa ggtgcgagat  60
tgaatccgga gcagcaggat tcgagtgtaa tacaaggaac agcggtttac gaacccggtc  120
tatcttccca tgaccagtca cagcattata accggaacta tattccggtt aaccttcttg  180
aaccgaatct acatttctcc ggtcaagacc aacctcctct tcaacttgtc taa         233

SEQ ID NO: 286         moltype = DNA  length = 153
FEATURE                Location/Qualifiers
source                 1..153
                       mol_type = other DNA
                       organism = Brassica napus
SEQUENCE: 286
gatatcacaa ggtgcgagat tgaatccgga gcagcaggat tcgagtgtaa tacaaggaac  60
agcggtttac gaacccggtc tatcttccca tgaccagtca cagcattata accggaacta  120
tattccggtt aaccttcttg aaccgaatct aca                               153

SEQ ID NO: 287         moltype = DNA  length = 114
FEATURE                Location/Qualifiers
source                 1..114
                       mol_type = other DNA
                       organism = Brassica napus
SEQUENCE: 287
tgaatccgga gcagcaggat tcgagtgtaa tacaaggaac agcggtttac gaacccggtc  60
tatcttccca tgaccagtca cagcattata accggaacta tattccggtt aacc        114

SEQ ID NO: 288         moltype = DNA  length = 74
FEATURE                Location/Qualifiers
source                 1..74
                       mol_type = other DNA
                       organism = Brassica napus
SEQUENCE: 288
tcgagtgtaa tacaaggaac agcggtttac gaacccggtc tatcttccca tgaccagtca  60
cagcattata accg                                                    74

SEQ ID NO: 289         moltype = AA  length = 76
FEATURE                Location/Qualifiers
source                 1..76
                       mol_type = protein
                       organism = Brassica napus
SEQUENCE: 289
MELQHDNMYL RAKISQGARL NPEQQDSSVI QGTAVYEPGL SSHDQSQHYN RNYIPVNLLE  60
PNLHFSGQDQ PPLQLV                                                  76

SEQ ID NO: 290         moltype = AA  length = 63
FEATURE                Location/Qualifiers
source                 1..63
                       mol_type = protein
                       organism = Brassica napus
SEQUENCE: 290
ISQGARLNPE QQDSSVIQGT AVYEPGLSSH DQSQHYNRNY IPVNLLEPNL HFSGQDQPPL  60
QLV                                                                63

SEQ ID NO: 291         moltype = AA  length = 13
FEATURE                Location/Qualifiers
source                 1..13
                       mol_type = protein
                       organism = Brassica napus
SEQUENCE: 291
MELQHDNMYL RAK                                                     13

SEQ ID NO: 292         moltype = DNA  length = 23
FEATURE                Location/Qualifiers
source                 1..23
                       mol_type = other DNA
                       organism = synthetic construct
SEQUENCE: 292
ctataaatcg tgtaggaaat gga                                          23

SEQ ID NO: 293         moltype = DNA  length = 23
FEATURE                Location/Qualifiers
source                 1..23
                       mol_type = other DNA
                       organism = synthetic construct
SEQUENCE: 293
gactaacctt agctcgcagg tac                                          23

SEQ ID NO: 294         moltype = DNA  length = 23
FEATURE                Location/Qualifiers
```

```
source                  1..23
                        mol_type = other DNA
                        organism = synthetic construct
SEQUENCE: 294
atgttcggtc tttgcagata tca                                          23

SEQ ID NO: 295          moltype = DNA  length = 23
FEATURE                 Location/Qualifiers
source                  1..23
                        mol_type = other DNA
                        organism = synthetic construct
SEQUENCE: 295
tctgaacaac cgttttgagg gga                                          23

SEQ ID NO: 296          moltype = DNA  length = 23
FEATURE                 Location/Qualifiers
source                  1..23
                        mol_type = other DNA
                        organism = synthetic construct
SEQUENCE: 296
atgtttaaaa cttagacaag ttg                                          23

SEQ ID NO: 297          moltype = DNA  length = 23
FEATURE                 Location/Qualifiers
source                  1..23
                        mol_type = other DNA
                        organism = synthetic construct
SEQUENCE: 297
tccggtcaag accaacctcc tct                                          23

SEQ ID NO: 298          moltype = DNA  length = 6581
FEATURE                 Location/Qualifiers
source                  1..6581
                        mol_type = other DNA
                        organism = synthetic construct
SEQUENCE: 298
aaatgcttac ctaatgtata tatgtgatgt attagagtaa atgcaattag taattacaag  60
gaaagtgatg gaggcatgag caaaaagagt ttctataatt tgtacacaaa tagttaatgt  120
gaactatgag aaaggtttgt gaatgattat gactatacgt atgattggtc accacttaat  180
ggattcctta atttcttgtt ccctcattaa gttgtcgtct catcatttct tttcatttct  240
agacccatgg tctcagattg gacttttaaa ggtagatttc aatatcaatg gtcgcacttt  300
tttagtccaa ttcattttca agttctcaaa caagtgtggt gattattttg cagttcttat  360
tcacacgtct aacttctatt atgtatgtca ttttctacgg ataagaagcg taagcgttgc  420
aaataatatt atctcgaatt aaatgggatt aattaggcca taatctagat tctatgtatc  480
ttttatatat ataaaaacaa aacatacgct caaatttagt tgcgtatttg agtagatatt  540
gtcttcatta cttgtaagaa aaaactcgtt ggactgcaca atagttttgt taacgtgtaa  600
ttaaatagcg tatttgtaag atttgagatt caaaatcgtc tttgacagct atgctcaaca  660
tgctttgaat cataagcact gtctagattc tcagcatgta acttatattt cagatcagat  720
tgactgcaaa acgaggtccc acgcaagaag gaaaagacaa gtatgatgtt cttggtctgg  780
agttctcagt cgagcatgtt attaaggggt gcaagagtgg atttccaaca aaaaacaagc  840
tttatgggac aaaaatcgaa gaaagaataa agatagaggg tgaaaacaca atatatgatt  900
tgttatcgcc tatttcccat aaaggattca gatactagga gaagttgatg ccaatttcac  960
atgcaagtct ctttcattac atctccatat tttaccgcac ctacgtctct atgtttacat  1020
tcttgtcatc gactttttca tgaataattt ttttttgcaa ttttatttc acttacaatt  1080
atgaatttct tatatatatt cttccaagtt gtaacgatca aataaaatatg catgcattat  1140
gtcatatatg gctatacatc attttagatt attgattttt gcagtatctt atttgaaacc  1200
tttagttcta tctacggata tcaatgtcta aacttttgat tctttattta gattgtgttc  1260
ttcaatcaaa gattcccctc ataaattgtg tattctttgc aaaaaaagga gttcacttat  1320
ttcacttgtg attgtgaaca tattataaat tgtacttata aaaacattct gcagttaaaa  1380
gaaaattaaa catcaaagtt agaaaaatta actttatgaa aaaaatacct actagctagt  1440
tagtagtaag agcatcttca ttcatggttc ttaaaacaaa aaatacaagt agtttaatat  1500
aatttaaata aaaaaacgaa atttttattt tgaaataaga tttgaacaag ttgagaattg  1560
acaagtgttt attagggttt gaaaagttga tcaaatgtta tgattcatcg tcttctctct  1620
ctctctttac cttttctttg tttaatggtg agaactttct atgaaagtgt gtatttggtt  1680
acttgaacta atatttttat gactgacttt atgaaaacaa cacaatctac tagctacatg  1740
gactgtagaa tacaatttat attttagatt gctaagaagt tatcagttta tctacagttt  1800
ggttgaatta attcaactag gttatggacc ttatggttag acttggttag gttcaatatg  1860
aacacgtata gatacagaga ggagcatcta attaattgaa acgcagacgt gtttaaaaag  1920
aaagagagaa agattaccat aaaaagggag tttccaaaag atggttctga tgtgaaacag  1980
agccccatcc ctctcccttt ccctttctc gtgaaagata ttggatggtc ctccttcaat  2040
gtccaccacc tactactcat cttctctttt ttctttaatt agttttcaat ttcaatttca  2100
gtttaagttc ctataattta taaatatttc atatctattt atatgaaatg tgtagagaat  2160
aaaaagtgtg agtttatata tttgtcgagt atgtttgttt tgacaattgg tatataattt  2220
atctgcttat tatagatgta cgtataaata tatttcagct aagaaaaact tgtaaacttc  2280
tgtgtgttct gcaagtgggg tcttaatacc ttcaaaaaat agtccttcaa atgaaactga  2340
tcataaacca aatttgaaaa gagagagatg tatttttcaa aaacgacata attattagaa  2400
aagcagaaaa aaacagttaa gtgatactga gatcaataat aatatatagt atctcttcaa  2460
gaacaatatc tcattaccca cttctccttt gtgctgatct atcataaact ttaaacccca  2520
ggtaaggttc tgaatgttat acagtttata tagaataact ctaatatcaa atatttatat  2580
```

-continued

```
tcggagttct tttcatttct ttttcaattc aatatctgat cctttgttac ctagatttga  2640
tatgtttatt tattattgtt tatctgcaaa gagatttgat cattttaacc ctaaacctaa  2700
gtttcgtacc caaatcatac gatctatctt ttggttattc ttgatctgca aaatgattaa  2760
tttaatcatc aatcttaatt agcttctcta gagcaatatt ttttttttctt aagctttgct  2820
ctagatcaat ctctctccct cttattatgt tattttattc atctggtgat atcacagaat  2880
caatggagga aggtgggagt agtcacgacg cagagagtag caagaagcta gtaagaggga  2940
agatagagat aaagaggata gagaacacaa caagtcgtca agtaactttc tgtaaacgac  3000
gcaatggtct tcttaagaaa gcttatgagc tttctgtctt gtgtgatgct gaagttgccc  3060
tcgtcatctt ctccactcgt ggccgtctct atgagtacgc caacaacagg tacgcttctc  3120
ctgcaccttt gatctttgct ttcttggttt actactacta ctacaagaaa atcttagtta  3180
aatgtatgga gaagtgactt gtagagtcaa gattagggtt tttgttaaat tacaatcctg  3240
ggttttttcc catgccaaaa aaaaaaaatc ctgggttttt ttgtttttttc taaattaaat  3300
atcgatctct ctagagctac cataactatg tgtgtgtgtg tgtttgtgta agcaagtaat  3360
gaagaaggaa gaaagctgtc ttgtcttctc aacttctagt tagccttctc gttagccttt  3420
tttggtgtca ctctttttct gcaaatcatt agaacctgat gcatgtcagc ttctccatga  3480
aatttcttta ttcaaattca aattagggtt tgatcagtaa acaagttggg tactttcttg  3540
gcacgaaata gcatgtatat tatataaata tgcaagactt atgttaccct ctgcctagtg  3600
taacttggga caaagcctaa tgaccatttg tcacttgtca ctagctaggg atccctataa  3660
ttatttaatc tagccaccaa aggcaaatga aaaccgaaaa tttcatattc ttgagttggt  3720
cttgagaaat ataatatgtg gctgaaataa aattgtcctg gtatgcaagt tcagaatttc  3780
aactctcttt ctaaaaaact gtaaatatat atacttctca tgtaaccgat tgtttacatt  3840
taatgtttaa ctttaccaaa gatgtagtta gagagcaaga tgtataacaa tataaatgca  3900
gtttttatgt ttctaatcta aaatgagttt tttcgatgta ataatctaaa atgagttgct  3960
accattatac tccctctgtt tccgaaagaa atattttcta gagtattcat gcatattaaa  4020
gaaacaatta atttttata attgaattta ttatttattt tactatacat tttccaataa  4080
atattaacca atagtattca accaattcaa atattttcaa ttaatgtttt ttaaaagtct  4140
acaacttttc aacattaact actaaaagta ctttaaaatt ttagaaaatc tatcattttg  4200
gaacaaaaaa taaatctaga aaatcctact ttcaggaaca gaaggtgtat atatatatag  4260
cttttgttac aatagttgac gaagaacttc aaattaaaca ataaacacac atgagtttaa  4320
tttgtctaat attgaaatca ctcatcgact gttaaaaaaa acaatattca tattaatata  4380
taagccattg ctgaatttat acatatgtag tccttggata tattaatgag agggagataa  4440
ctcagagaag tgtcagaact cgaaatggta cgggccaatg agaagctctg gcattctgag  4500
ctctatttat ctgttattat tatctgtaaa aaattactga tcctttaagc atattgtgat  4560
gaaattgaat catataatat gcatggacgt tgttgtgttt accaatttga aatcatacta  4620
ctagtgtaat acttaattac ttatatcctt actttagtta actgcattga cagacattta  4680
ttatttgatg taaattacct tggaaaaata tggtttgatt gaaattatct cttcatactg  4740
gcaatcagaa actggtccaa acttcaaaac cacacattcc tttctggttg attttaaggt  4800
ttttggccgg gaaaataaac tttccaaaac cctaatcaaa atacagtacg tactatgttt  4860
aagagtttat atttattaaa ttaaatctaa taggttctcg aactgaactt tttagcgtga  4920
agggtacaat tgaaagatac aagaaagctt gttccgatgc cgttaaccct ccttctgtca  4980
ccgaagctaa tactcaggta ccattcttta gtttttttttt tttagttctt ttggccggga  5040
aagctttttt gcgatttcga cagtgtttaa gctttgccta acgatagctg atctctttac  5100
cttttattta gccttaaatt gttcaccatg aattagttta agcctaatta accttgtgtt  5160
taaaaatctt tttatctttt tggggttatt agatagctca ttgctaagtc ttagcagttt  5220
taggccatga ttatcgctaa aactgtttc tgggtttttt aatttttttt ttgttttttc  5280
tgattaaaaa aggaaaaaat taaaaaaaag tcaatcgcgg gtcgtcacgt gtcagtgtag  5340
cccgtaaaaa gtacaagaaa caaactaaag ttgatccttc ttttgcgact ttagtaaccg  5400
ataatcgtgc tcttagattc aagtctttct tctatctcaa tgtcattttt acgaaatgaa  5460
ttcacatttt gtcaaaaaaa aaattagttc ttttattctt cccctctttt tttgtctttt  5520
tttttgtgat gaccaattaa cattacaaaa aaaataaaaa aaatttggat gggttcttga  5580
aacgttttgg tgtttatatg catggaactc tgaagtacta tcagcaagaa gcatctaagc  5640
ttcggaggca gattcgtgac attcagaatt ctaacaggta aataaggcag tcttaatgtt  5700
caaaaaaaat aaaaaataag acagtctttt ggtagtgttt caaaaaaaaa aaacgacagt  5760
cttttggttt gatcactact tctctattat agatgttgtt ttgattattt aatgttgtga  5820
cttgaaaggc atatagttgg ggaatcactt ggttccttga acttcaagga actcaaaaac  5880
ctcgaaggac gtcttgaaaa aggaatcagc cgtgtccgat ccaagaaggt acttacccta  5940
acgtctcttt gtctctctat aacttatatt gttttcttac tcttatatga aaatctcgca  6000
gaatgagctg ttaatggcag agatagagta tatgcagaag agggtaagta acgtttcttc  6060
catatctttc accgtctttt taggtttttg agttcctata aatcgtgtag gaaatggagt  6120
tgcaacacga taacatgagc taaggttagt ctaaatctct cttctttaca tcatcgccta  6180
cccgagaaga taacgtgtgt aacaaaccaa actttgatgt tcggtctttc aaggtgcgag  6240
attgaatccg gagcagcagg attcgagtgt aatacaagga acagcggttt acgaatccgg  6300
tttatcttcc catgatcagt cacagcatta taaccggaac tatattccgg ttaaccttct  6360
tgaaccgaat caacaattct ccggtcaaga ccaacctcct ctctaagttt taaacatgaa  6420
aaaaaaaact tgtttcttcc cctcaaaacg attgttcaga gaaagacact aagggtatga  6480
ctggttttcc cgctaccacc cgcaaacgca gcttttgcgg ttggtagcgg ttgctggcgt  6540
tttgcaacaa tcgctcaaac cgctctaaac cgctccaaat c                        6581
```

```
SEQ ID NO: 299          moltype = AA  length = 186
FEATURE                 Location/Qualifiers
source                  1..186
                        mol_type = protein
                        organism = synthetic construct
SEQUENCE: 299
MEEGGSSHDA ESSKKLVRGK IEIKRIENTT SRQVTFCKRR NGLLKKAYEL SVLCDAEVAL  60
VIFSTRGRLY EYANNSVKGT IERYKKACSD AVNPPSVTEA NTQYYQQEAS KLRRQIRDIQ  120
NSNRHIVGES LGSLNFKELK NLEGRLEKGI SRVRSKKNEL LMAEIEYMQK REMELQHDNM  180
SYKVRD                                                            186
```

-continued

```
SEQ ID NO: 300          moltype = DNA  length = 6584
FEATURE                 Location/Qualifiers
source                  1..6584
                        mol_type = other DNA
                        organism = synthetic construct
SEQUENCE: 300
aaatgcttac ctaatgtata tatgtgatgt attagagtaa atgcaattag taattacaag  60
gaaagtgatg gaggcatgag caaaaagagt ttctataatt tgtacacaaa tagttaatgt  120
gaactatgag aaaggtttgt gaatgattat gactatacgt atgattggtc accacttaat  180
ggattcctta atttcttgtt ccctcattaa gttgtcgtct catcatttct tttcatttct  240
agacccatgg tctcagattg gacttttaaa ggtagatttc aatatcaatg gtcgcacttt  300
tttagtccaa ttcattttca agttctcaaa caagtgtggt gattattttg cagttcttat  360
tcacacgtct aacttctatt atgtatgtca ttttctacgg ataagaagcg taagcgttgc  420
aaataatatt atctcgaatt aaatgggatt aattaggcca taatctagat tctatgtatc  480
ttttatatat ataaaaacaa aacatacgct caaatttagt tgcgtatttg agtagatatt  540
gtcttcatta cttgtaagaa aaaactcgtt ggactgcaca atagttttgt taacgtgtaa  600
ttaaatagcg tatttgtaag atttgagatt caaaatcgtc tttgacagct atgctcaaca  660
tgctttgaat cataagcact gtctagattc tcagcatgta acttatattt cagatcagat  720
tgactgcaaa acgaggtccc acgcaagaag gaaaagacaa gtatgatgtt cttggtctgg  780
agttctcagt cgagcatgtt attaaggggt gcaagagtgg atttccaaca aaaaacaagc  840
tttatgggac aaaaatcgaa gaaagaataa agatagaggg tgaaaacaca atatatgatt  900
tgttatcgcc tatttcccat aaaggattca gatactagga gaagttgatg ccaatttcac  960
atgcaagtct ctttcattac atctccatat tttaccgcac ctacgtctct atgtttacat  1020
tcttgtcatc gacttttcca tgaataattt ttttttgcaa tttttatttc acttacaatt  1080
atgaatttct tatatatatt cttccaagtt gtaacgatca aataaatatg catgcattat  1140
gtcatatatg gctatacatc attttagatt attgattttt gcagtatctt atttgaaacc  1200
tttagttcta tctacggata tcaatgtcta aacttttgat tctttattta gattgtgttc  1260
ttcaatcaaa gattcccctc ataaattgtg tattctttgc aaaaaaagga gttcacttat  1320
ttcacttgtg attgtgaaca tattataaat tgtacttata aaaacattct gcagttaaaa  1380
gaaaattaaa catcaaagtt agaaaaatta actttatgaa aaaaatacct actagctagt  1440
tagtagtaag agcatcttca ttcatggttc ttaaaacaaa aaatacaagt agtttaatat  1500
aatttaaata aaaaaacgaa atttttattt tgaaataaga tttgaacaag ttgagaattg  1560
acaagtgttt attagggttt gaaaagttga tcaaatgtta tgattcatcg tcttctctct  1620
ctctctttac cttttctttg tttaatggtg agaactttct atgaaagtgt gtatttggtt  1680
acttgaacta atatttttat gactgacttt atgaaaacaa cacaatctac tagctacatg  1740
gactgtagaa tacaatttat attttagatt gctaagaagt tatcagttta tctacagttt  1800
ggttgaatta attcaactag gttatggacc ttatggttag acttggttag gttcaatatg  1860
aacacgtata gatacagaga ggagcatcta attaattgaa acgcagacgt gtttaaaaag  1920
aaagagagaa agattaccat aaaaagggag tttccaaaag atggttctga tgtgaaacag  1980
agccccatcc ctctcccttt ccctttctc gtgaaagata ttggatggtc ctccttcaat  2040
gtccaccacc tactactcat cttctctttt ttctttaatt agttttcaat ttcaatttca  2100
gtttaagttc ctataattta taaatatttc atatctattt atatgaaatg tgtagagaat  2160
aaaaagtgtg agtttatata tttgtcgagt atgtttgttt tgacaattgg tatataattt  2220
atctgcttat tatagatgta cgtataaata tatttcagct aagaaaaact tgtaaacttc  2280
tgtgtgttct gcaagtgggg tcttaatacc ttcaaaaaat agtccttcaa atgaaactga  2340
tcataaacca aatttgaaaa gagagagatg tatttttcaa aaacgacata attattagaa  2400
aagcagaaaa aaacagttaa gtgatactga gatcaataat aatatatagt atctcttcaa  2460
gaacaatatc tcattaccca cttctccttt gtgctgatct atcataaact ttaaaccccca  2520
ggtaaggttc tgaatgttat acagtttata tagaataact ctaatatcaa atatttatat  2580
tcggagttct tttcatttct ttttcaattc aatatctgat cctttgttac ctagatttga  2640
tatgtttatt tattattgtt tatctgcaaa gagatttgat cattttaacc ctaaacctaa  2700
gtttcgtacc caaatcatac gatctatctt ttggttattc ttgatctgca aaatgattaa  2760
tttaatcatc aatcttaatt agcttctcta gagcaatatt tttttttctt aagctttgct  2820
ctagatcaat ctctctccct cttattatgt tattttattc atctggtgat atcacagaat  2880
caatggagga aggtgggagt agtcacgacg cagagagtag caagaagcta gtaagaggga  2940
agatagagat aaagaggata gagaacacaa caagtcgtca agtaactttc tgtaaacgac  3000
gcaatggtct tcttaagaaa gcttatgagc tttctgtctt gtgtgatgct gaagttgccc  3060
tcgtcatctt ctccactcgt ggccgtctct atgagtacgc caacaacagg tacgcttctc  3120
ctgcaccttt gatctttgct ttcttggttt actactacta ctacaagaaa atcttagtta  3180
aatgtatgga gaagtgactt gtagagtcaa gattagggtt tttgttaaat tacaatcctg  3240
ggttttttcc catgccaaaa aaaaaaaatc ctgggttttt ttgttttttc taaattaaat  3300
atcgatctct ctagagctac cataactatg tgtgtgtgtg tgtttgtgta agcaagtaat  3360
gaagaaggaa gaaagctgtc ttgtcttctc aacttctagt tagccttctc gttagccttt  3420
tttggtgtca ctctttttct gcaaatcatt agaacctgat gcatgtcagc ttctccatga  3480
aatttcttta ttcaaattca aattagggtt tgatcagtaa acaagttggg tactttcttg  3540
gcacgaaata gcatgtatat tatataaata tgcaagactt atgttaccct ctgcctagtg  3600
taacttggga caaagcctaa tgaccatttg tcacttgtca ctagctaggg atccctataa  3660
ttatttaatc tagccaccaa aggcaaatga aaaccgaaaa tttcatattc ttgagttggt  3720
cttgagaaat ataatatgtg gctgaaataa aattgtcctg gtatgcaagt tcagaatttc  3780
aactctcttt ctaaaaaact gtaaatatat atacttctca tgtaaccgat tgtttacatt  3840
taatgtttaa ctttaccaaa gatgtagtta gagagcaaga tgtataacaa tataaatgca  3900
gtttttatgt ttctaatcta aaatgagttt tttcgatgta ataatctaaa atgagttgct  3960
accattatac tccctctgtt tccgaaagaa atattttcta gagtattcat gcatattaaa  4020
gaaacaatta attttttata attgaattta ttatttattt tactatacat tttccaataa  4080
atattaacca atagtattca accaattcaa atattttcaa ttaatgtttt ttaaaagtct  4140
acaacttttc aacattaact actaaaagta ctttaaaatt ttagaaaatc tatcattttg  4200
gaacaaaaaa taaatctaga aaatcctact ttcaggaaca gaaggtgtat atatatatag  4260
cttttgttac aatagttgac gaagaacttc aaattaaaca ataaacacac atgagtttaa  4320
tttgtctaat attgaaatca ctcatcgact gttaaaaaaa acaatattca tattaatata  4380
```

-continued

```
taagccattg ctgaatttat acatatgtag tccttggata tattaatgag agggagataa  4440
ctcagagaag tgtcagaact cgaaatggta cgggccaatg agaagctctg gcattctgag  4500
ctctatttat ctgttattat tatctgtaaa aaattactga tcctttaagc atattgtgat  4560
gaaattgaat catataatat gcatggacgt tgttgtgttt accaatttga aatcatacta  4620
ctagtgtaat acttaattac ttatatcctt actttagtta actgcattga cagacattta  4680
ttatttgatg taaattacct tggaaaaata tggtttgatt gaaattatct cttcatactg  4740
gcaatcagaa actggtccaa acttcaaaac cacacattcc tttctggttg attttaaggt  4800
ttttggccgg gaaaataaac tttccaaaac cctaatcaaa atacagtacg tactatgttt  4860
aagagtttat atttattaaa ttaaatctaa taggttctcg aactgaactt tttagcgtga  4920
agggtacaat tgaaagatac aagaaagctt gttccgatgc cgttaaccct ccttctgtca  4980
ccgaagctaa tactcaggta ccattcttta gttttttttt tttagttctt ttggccggga  5040
aagctttttt gcgatttcga cagtgtttaa gctttgccta acgatagctg atctctttac  5100
cttttattta gccttaaatt gttcaccatg aattagttta agcctaatta accttgtgtt  5160
taaaaatctt tttatctttt tggggttatt agatagctca ttgctaagtc ttagcagttt  5220
taggccatga ttatcgctaa aactgttttc tgggtttttt aatttttttt ttgtttttc  5280
tgattaaaaa aggaaaaaat taaaaaaaag tcaatcgcgg gtcgtcacgt gtcagtgtag  5340
cccgtaaaaa gtacaagaaa caaactaaag ttgatccttc ttttgcgact ttagtaaccg  5400
ataatcgtgc tcttagattc aagtctttct tctatctcaa tgtcattttt acgaaatgaa  5460
ttcacatttt gtcaaaaaaa aaattagttc ttttattctt cccctctttt tttgtctttt  5520
tttttgtgat gaccaattaa cattacaaaa aaaataaaaa aaatttggat gggttcttga  5580
aacgttttgg tgtttatatg catggaactc tgaagtacta tcagcaagaa gcatctaagc  5640
ttcggaggca gattcgtgac attcagaatt ctaacaggta aataaggcag tcttaatgtt  5700
caaaaaaaat aaaaaaataag acagtctttt ggtagtgttt caaaaaaaaa aaacgacagt  5760
cttttggttt gatcactact tctctattat agatgttgtt ttgattattt aatgttgtga  5820
cttgaaaggc atatagttgg ggaatcactt ggttccttga acttcaagga actcaaaaac  5880
ctcgaaggac gtcttgaaaa aggaatcagc cgtgtccgat ccaagaaggt acttacccta  5940
acgtctcttt gtctctctat aacttatatt gttttcttac tcttatatga aaatctcgca  6000
gaatgagctg ttaatggcag agatagagta tatgcagaag agggtaagta acgtttcttc  6060
catatctttc accgtctttt taggtttttg agttcctata aatcgtgtag gaaatggagt  6120
tgcaacacga taacaagcta aggttagtct aaatctctct tctttacatc atcgcctacc  6180
cgagaagata acgtgtgtaa caaaccaaac tttgatgttc ggtctttgca gatatcacaa  6240
ggtgcgagat tgaatccgga gcagcaggat tcgagtgtaa tacaaggaac agcggtttac  6300
gaatccggtt tatcttccca tgatcagtca cagcattata accggaacta tattccggtt  6360
aaccttcttg aaccgaatca acaattctcc ggtcaagacc aacctccaag ttttaaacat  6420
gaaaaaaaaa acttgtttct tcccctcaaa acgattgttc agagaaagac actaagggta  6480
tgactggttt tcccgctacc acccgcaaac gcagcttttg cggttggtag cggttgctgg  6540
cgttttgcaa caatcgctca aaccgctcta aaccgctcca aatc                 6584

SEQ ID NO: 301         moltype = AA  length = 188
FEATURE                Location/Qualifiers
source                 1..188
                       mol_type = protein
                       organism = synthetic construct
SEQUENCE: 301
MEEGGSSHDA ESSKKLVRGK IEIKRIENTT SRQVTFCKRR NGLLKKAYEL SVLCDAEVAL  60
VIFSTRGRLY EYANNSVKGT IERYKKACSD AVNPPSVTEA NTQYYQQEAS KLRRQIRDIQ  120
NSNRHIVGES LGSLNFKELK NLEGRLEKGI SRVRSKKNEL LMAEIEYMQK REMELQHDNK  180
LRYHKVRD                                                          188

SEQ ID NO: 302         moltype = DNA  length = 6548
FEATURE                Location/Qualifiers
source                 1..6548
                       mol_type = other DNA
                       organism = synthetic construct
SEQUENCE: 302
aaatgcttac ctaatgtata tatgtgatgt attagagtaa atgcaattag taattacaag  60
gaaagtgatg gaggcatgag caaaaagagt ttctataatt tgtacacaaa tagttaatgt  120
gaactatgag aaaggtttgt gaatgattat gactatacgt atgattggtc accacttaat  180
ggattcctta atttcttgtt ccctcattaa gttgtcgtct catcatttct tttcatttct  240
agacccatgg tctcagattg gacttttaaa ggtagatttc aatatcaatg gtcgcacttt  300
tttagtccaa ttcattttca agttctcaaa caagtgtggt gattattttg cagttcttat  360
tcacacgtct aacttctatt atgtatgtca ttttctacgg ataagaagcg taagcgttgc  420
aaataatatt atctcgaatt aaatgggatt aattaggcca taatctagat tctatgtatc  480
ttttatatat ataaaaacaa aacatacgct caaatttagt tgcgtatttg agtagatatt  540
gtcttcatta cttgtaagaa aaaactcgtt ggactgcaca atagttttgt taacgtgtaa  600
ttaaatagcg tatttgtaag atttgagatt caaaatcgtc tttgacagct atgctcaaca  660
tgctttgaat cataagcact gtctagattc tcagcatgta acttatattt cagatcagat  720
tgactgcaaa acgaggtccc acgcaagaag gaaaagacaa gtatgatgtt cttggtctgg  780
agttctcagt cgagcatgtt attaaggggt gcaagagtgg atttccaaca aaaaacaagc  840
tttatgggac aaaaatcgaa gaaagaataa agatagaggg tgaaaacaca atatatgatt  900
tgttatcgcc tatttcccat aaaggattca gatactagga gaagttgatg ccaatttcac  960
atgcaagtct ctttcattac atctccatat tttaccgcac ctacgtctct atgtttacat  1020
tcttgtcatc gactttttca tgaataattt ttttttgcaa tttttatttc acttacaatt  1080
atgaatttct tatatatatt cttccaagtt gtaacgatca aataaatatg catgcattat  1140
gtcatatatg gctatacatc attttagatt attgattttt gcagtatctt atttgaaacc  1200
tttagttcta tctacggata tcaatgtcta aacttttgat tctttattta gattgtgttc  1260
ttcaatcaaa gattcccctc ataaattgtg tattctttgc aaaaaaagga gttcacttat  1320
ttcacttgtg attgtgaaca tattataaat tgtacttata aaaacattct gcagttaaaa  1380
gaaaattaaa catcaaagtt agaaaaatta actttatgaa aaaaatacct actagctagt  1440
```

-continued

```
tagtagtaag agcatcttca ttcatggttc ttaaaacaaa aaatacaagt agtttaatat  1500
aatttaaata aaaaaacgaa atttttattt tgaaataaga tttgaacaag ttgagaattg  1560
acaagtgttt attagggttt gaaaagttga tcaaatgtta tgattcatcg tcttctctct  1620
ctctctttac cttttctttg tttaatggtg agaactttct atgaaagtgt gtatttggtt  1680
acttgaacta atatttttat gactgacttt atgaaaacaa cacaatctac tagctacatg  1740
gactgtagaa tacaatttat attttagatt gctaagaagt tatcagttta tctacagttt  1800
ggttgaatta attcaactag gttatggacc ttatggttag acttggttag gttcaatatg  1860
aacacgtata gatacagaga ggagcatcta attaattgaa acgcagacgt gtttaaaaag  1920
aaagagagaa agattaccat aaaaagggag tttccaaaag atggttctga tgtgaaacag  1980
agccccatcc ctctcccttt ccctttctc gtgaaagata ttggatggtc ctccttcaat  2040
gtccaccacc tactactcat cttctctttt ttctttaatt agttttcaat ttcaatttca  2100
gtttaagttc ctataattta taaatatttc atatctattt atatgaaatg tgtagagaat  2160
aaaaagtgtg agtttatata tttgtcgagt atgtttgttt tgacaattgg tatataattt  2220
atctgcttat tatagatgta cgtataaata tatttcagct aagaaaaact tgtaaacttc  2280
tgtgtgttct gcaagtgggg tcttaatacc ttcaaaaaat agtccttcaa atgaaactga  2340
tcataaacca aatttgaaaa gagagagatg tatttttcaa aaacgacata attattagaa  2400
aagcagaaaa aaacagttaa gtgatactga gatcaataat aatatatagt atctcttcaa  2460
gaacaatatc tcattaccca cttctccttt gtgctgatct atcataaact ttaaacccca  2520
ggtaaggttc tgaatgttat acagtttata tagaataact ctaatatcaa atatttatat  2580
tcggagttct tttcatttct ttttcaattc aatatctgat cctttgttac ctagatttga  2640
tatgtttatt tattattgtt tatctgcaaa gagatttgat cattttaacc ctaaacctaa  2700
gtttcgtacc caaatcatac gatctatctt ttggttattc ttgatctgca aaatgattaa  2760
tttaatcatc aatcttaatt agcttctcta gagcaatatt tttttttctt aagctttgct  2820
ctagatcaat ctctctccct cttattatgt tattttattc atctggtgat atcacagaat  2880
caatggagga aggtgggagt agtcacgacg cagagagtag caagaagcta gtaagaggga  2940
agatagagat aaagaggata gagaacacaa caagtcgtca agtaactttc tgtaaacgac  3000
gcaatggtct tcttaagaaa gcttatgagc tttctgtctt gtgtgatgct gaagttgccc  3060
tcgtcatctt ctccactcgt ggccgtctct atgagtacgc caacaacagg tacgcttctc  3120
ctgcaccttt gatctttgct ttcttggttt actactacta ctacaagaaa atcttagtta  3180
aatgtatgga gaagtgactt gtagagtcaa gattagggtt tttgttaaat tacaatcctg  3240
ggttttttcc catgccaaaa aaaaaaaatc ctgggttttt ttgtttttc taaattaaat  3300
atcgatctct ctagagctac cataactatg tgtgtgtgtg tgtttgtgta agcaagtaat  3360
gaagaaggaa gaaagctgtc ttgtcttctc aacttctagt tagccttctc gttagccttt  3420
tttggtgtca ctctttttct gcaaatcatt agaacctgat gcatgtcagc ttctccatga  3480
aatttcttta ttcaaattca aattagggtt tgatcagtaa acaagttggg tactttcttg  3540
gcacgaaata gcatgtatat tatataaata tgcaagactt atgttaccct ctgcctagtg  3600
taacttggga caaagcctaa tgaccatttg tcacttgtca ctagctaggg atccctataa  3660
ttatttaatc tagccaccaa aggcaaatga aaaccgaaaa tttcatattc ttgagttggt  3720
cttgagaaat ataatatgtg gctgaaataa aattgtcctg gtatgcaagt tcagaatttc  3780
aactctcttt ctaaaaaact gtaaatatat atacttctca tgtaaccgat tgtttacatt  3840
taatgtttaa ctttaccaaa gatgtagtta gagagcaaga tgtataacaa tataaatgca  3900
gtttttatgt ttctaatcta aaatgagttt tttcgatgta ataatctaaa atgagttgct  3960
accattatac tccctctgtt tccgaaagaa atattttcta gagtattcat gcatattaaa  4020
gaaacaatta attttttata attgaattta ttatttattt tactatacat tttccaataa  4080
atattaacca atagtattca accaattcaa atattttcaa ttaatgtttt ttaaaagtct  4140
acaacttttc aacattaact actaaaagta ctttaaaatt ttagaaaatc tatcattttg  4200
gaacaaaaaa taaatctaga aaatcctact ttcaggaaca gaaggtgtat atatatatag  4260
cttttgttac aatagttgac gaagaacttc aaattaaaca ataaacacac atgagtttaa  4320
tttgtctaat attgaaatca ctcatcgact gttaaaaaaa acaatattca tattaatata  4380
taagccattg ctgaatttat acatatgtag tccttggata tattaatgag agggagataa  4440
ctcagagaag tgtcagaact cgaaatggta cgggccaatg agaagctctg gcattctgag  4500
ctctatttat ctgttattat tatctgtaaa aaattactga tcctttaagc atattgtgat  4560
gaaattgaat catataatat gcatggacgt tgttgtgttt accaatttga aatcatacta  4620
ctagtgtaat acttaattac ttatatcctt actttagtta actgcattga cagacattta  4680
ttatttgatg taaattacct tggaaaaata tggtttgatt gaaattatct cttcatactg  4740
gcaatcagaa actggtccaa acttcaaaac cacacattcc tttctggttg attttaaggt  4800
ttttggccgg gaaaataaac tttccaaaac cctaatcaaa atacagtacg tactatgttt  4860
aagagtttat atttattaaa ttaaatctaa taggttctcg aactgaactt tttagcgtga  4920
agggtacaat tgaaagatac aagaaagctt gttccgatgc cgttaaccct ccttctgtca  4980
ccgaagctaa tactcaggta ccattcttta gttttttttt tttagttctt ttggccggga  5040
aagctttttt gcgatttcga cagtgtttaa gctttgccta acgatagctg atctctttac  5100
cttttattta gccttaaatt gttcaccatg aattagttta agcctaatta accttgtgtt  5160
taaaaatctt tttatctttt tggggttatt agatagctca ttgctaagtc ttagcagttt  5220
taggccatga ttatcgctaa aactgttttc tgggtttttt aatttttttt ttgtttttttc  5280
tgattaaaaa aggaaaaaat taaaaaaaag tcaatcgcgg gtcgtcacgt gtcagtgtag  5340
cccgtaaaaa gtacaagaaa caaactaaag ttgatccttc ttttgcgact ttagtaaccg  5400
ataatcgtgc tcttagattc aagtctttct tctatctcaa tgtcattttt acgaaatgaa  5460
ttcacatttt gtcaaaaaaa aaattagttc ttttattctt cccctctttt tttgtctttt  5520
tttttgtgat gaccaattaa cattacaaaa aaaataaaaa aaatttggat gggttcttga  5580
aacgttttgg tgtttatatg catggaactc tgaagtacta tcagcaagaa gcatctaagc  5640
ttcggaggca gattcgtgac attcagaatt ctaacaggta aataaggcag tcttaatgtt  5700
caaaaaaaat aaaaaaataag acagtctttt ggtagtgttt caaaaaaaaa aaacgacagt  5760
cttttggttt gatcactact tctctattat agatgttgtt ttgattattt aatgttgtga  5820
cttgaaaggc atatagttgg ggaatcactt ggttccttga acttcaagga actcaaaaac  5880
ctcgaaggac gtcttgaaaa aggaatcagc cgtgtccgat ccaagaaggt acttacccta  5940
acgtctcttt gtctctctat aacttatatt gttttcttac tcttatatga aaatctcgca  6000
gaatgagctg ttaatggcag agatagagta tatgcagaag agggtaagta acgtttcttc  6060
catatctttc accgtctttt taggtttttg agttcctata aatcgtgtag gaaatggagt  6120
tgcaatcttt acatcatcgc ctacccgaga agataacgtg tgtaacaaac caaactttga  6180
```

```
tgttcggtct ttgcagatat cacaaggtgc gagattgaat ccggagcagc aggattcgag  6240
tgtaatacaa ggaacagcgg tttacgaatc cggtttatct tcccatgatc agtcacagca  6300
ttataaccgg aactatattc cggttaacct tcttgaaccg aatcaacaat tctccggtca  6360
agaccaacct taagttttaa acatgaaaaa aaaaacttgt ttcttcccct caaaacgatt  6420
gttcagagaa agacactaag ggtatgactg gttttcccgc taccacccgc aaacgcagct  6480
tttgcggttg gtagcggttg ctggcgtttt gcaacaatcg ctcaaaccgc tctaaaccgc  6540
tccaaatc                                                           6548

SEQ ID NO: 303         moltype = AA  length = 184
FEATURE                Location/Qualifiers
source                 1..184
                       mol_type = protein
                       organism = synthetic construct
SEQUENCE: 303
MEEGGSSHDA ESSKKLVRGK IEIKRIENTT SRQVTFCKRR NGLLKKAYEL SVLCDAEVAL  60
VIFSTRGRLY EYANNSVKGT IERYKKACSD AVNPPSVTEA NTQYYQQEAS KLRRQIRDIQ  120
NSNRHIVGES LGSLNFKELK NLEGRLEKGI SRVRSKKNEL LMAEIEYMQK REMELQNNNN  180
NNNN                                                               184

SEQ ID NO: 304         moltype = DNA  length = 3567
FEATURE                Location/Qualifiers
source                 1..3567
                       mol_type = other DNA
                       organism = synthetic construct
SEQUENCE: 304
cccacttctc ctttgtgctg atctatcata agctttaaac cccaggtacg gttctgaata  60
ttatacaatt tatatagaat aactctaata tacaagattt atattcagag ttcttttcat  120
tttcattttc aattcaatat ctgatccttt gttacctaga tttgatatgt ttatttatta  180
ttgtttacaa agagatttga tcattttaac cctaaaccta agttttgtac ccaaatcata  240
tgatctatct tttggttatt cttgatctgc aaaatgatta atttgatcat caatcttaat  300
tatattctct ataacaatct ttttttttat taagctttgc tctgatcaat ctctctccct  360
cttattatgt tattttattc atctggtgat atcacagaat caatggagga aggtgggagt  420
agtcacgacg cagagagtaa caagaagcta gtaagaggga agatagagat aaagaggata  480
gagaacacaa caagtcgtca agtaactttc tgtaaacgac gcaatggtct tcttaagaaa  540
gcttatgagc tttctgtctt gtgtgatgct gaagttgccc tcgtcatctt ctcgactcgt  600
ggccgtctct atgagtacgc caacaacagg tacgcttctc ctgcaccttc ttgatctttg  660
ctttcttggt ttattactac tacaagaaaa tcttagttaa atgtatggag aagtgacttg  720
tcgagtcaag attagggttt ttgttaattt acaatcctgg gttttttttcc catgccaaaa  780
aacaaaatcc tgggttttct tgttttccta aattaaatat ctctctagag ctaccataac  840
tatgtgtgtg tgtgtgtttg tgtaagcaaa taatgaagaa ggaagaaagc tgtcttgtct  900
tctcaacttc tagttagcct tctcgttagc cttttttggt gtcactcttt ttctgcaaat  960
cattgaaacc tgatgcatgc cagcttctcc atgaaatttc tttactcaaa ttaatactag  1020
ggtttaatca gtaaacaagt tgggtacttt cttgacacga aatagcatgt atattatata  1080
aatatgcaag acttatgtaa ccctctgtct agtgtaactt gggacagagc ctaatgatca  1140
gttgtcacta gctagggatc cctataatta tttaatctag ccccccaaag gcaaatgaaa  1200
actgaaaatt tcatattctt gagttggtct tgagaaatat aatatgtggc tgaaataaaa  1260
ttgtcctggt atgcaagttc agaatttcaa ctctctttct aaaaaactgt atatatataa  1320
tatgtaaccg attgtttaca tttattttta actttaccaa agatgtagtt agagaggatt  1380
atgtataaca atataaatgc agtttttagg tttctaatct aaaatgagtt gctacaatct  1440
atatatattt gatctagaaa tgggatttgt aataaggttt aacatataat aatgggattt  1500
cttaatttct cttcacaagt cgcatatatc tttttgtctc atatatacat cttttgttac  1560
agtagttgac gaagaacttc aaattaaaca ataaacacac atgactttaa tttgtctaac  1620
attgaaatca ctcatcgtct gttgaaaaaa taatattgat attaatacat aagccattgc  1680
tgaatgtata catatgtagt ccttggatat attaatgaga gggagataac tcggagaagt  1740
gtcagaactc gaaattgtac gggccaatga gaagctctgg cattctgagc tccatttatt  1800
tgttattatc tctaaaaaaa ttactgatcc tttaagcata ttgtgatgaa attgaatcat  1860
ataaatatgca tggacgttgt tgtgtactcc tcctaattac caatttgaaa tcatactact  1920
agtgtaatac ttaattactt atatccttac tttttatttt gtctcaacgt caactatttc  1980
attaaccgat aaattagtac aaagtatttg accacaccaa tttgaccaca catgcaacaa  2040
tgcatcttag taacacactg gaacactcac taggtgattt cttactcgga accagcgcaa  2100
cctgagtaca ttgctgcatt tttcacactt atatccttac tttagttaac tgcattagca  2160
gccatttatt atttgatgta aattaccttg gaaaaatatg atacttcagc ctgacataat  2220
atgtttgatt gaaattctct tcatcatcct ggcaatcaga gactggtcca aacttcaaag  2280
ccacacattc ctttcttgtc gattttaagg tttttggccg ggaaaataaa ctttcaaaaa  2340
ccctaatcaa agtacagtac ttactatgtt taagagtatg tttattaaat taaatctaat  2400
aggttctcca actttttagc gtgaagggta caattgaaag atacaagaaa gcttgttccg  2460
atgccgttaa ccctccttct gtcaccgaag ctaatactca ggtaccgttc tttagttctt  2520
ttattccccc tctcttttttc tttttctcat cttttttttta tgatgaccaa ttaacgttac  2580
aaaaaaaatt aaaaaaattt ggatgggttc atgaaacgtt ttggtgtttg tatgcatgga  2640
actctgaagt actatcagca agaagcctct aagcttcgga ggcagattcg tgacattcaa  2700
aattctaaca ggtaaataag acggtctttt ggtttgatca ctacttctct attattgatg  2760
ttgttttgat tatttaatgt tgtgaaatga aaggcatata gttggggaat cacttggttc  2820
cttgaacttc aaggaactca aaaacctcga aggacgtctt gaaaaaggaa tcaaccgtgt  2880
ccgatccaag aaggtactta ccctaacgtc tctttgtctc tctataactt atatagtttt  2940
cttactctta taatgaaaat ctcgcagaat gagctgttaa tggcagagat agagtatatg  3000
cagaagaggg taagtaacgt ttcttccata tcttgcaccg tctttttagg tttttgagtt  3060
tcctataaat cgtgtaggaa atggagttgc aacacgataa catcgagcta aggttagtct  3120
aaatctctct tctttacatc atcgcctacc cgagaagata acgtgtgtaa caaaccaaac  3180
tttgatgttc ggtctttgca gatatcacaa ggtgcgagat tgaatccgga gcagcaggat  3240
```

-continued

```
tcgagtgtaa tacaaggaac agcggtttac gaacccggtc tatcttccca tgaccagtca  3300
cagcattata accggaacta tattccggtt aaccttcttg aaccgaatct acatttctcc  3360
ggtcaagacc atcctcttcg ttttaaacat gaaaaaaaac acttgtttct tcccctcaaa  3420
acggttgttc agagaaagac actaagagta acttcttctc atgcatagtt ttttaggttc  3480
caataataat aacataaata aatcaagtgt tacaaagata caaacttaca aacatctatc  3540
ttctgatgtg tagctataac taaacaa                                      3567

SEQ ID NO: 305         moltype = AA  length = 189
FEATURE                Location/Qualifiers
source                 1..189
                       mol_type = protein
                       organism = synthetic construct
SEQUENCE: 305
MEEGGSSHDA ESNKKLVRGK IEIKRIENTT SRQVTFCKRR NGLLKKAYEL SVLCDAEVAL  60
VIFSTRGRLY EYANNSVKGT IERYKKACSD AVNPPSVTEA NTQYYQQEAS KLRRQIRDIQ  120
NSNRHIVGES LGSLNFKELK NLEGRLEKGI NRVRSKKNEL LMAEIEYMQK REMELQHDNI  180
ELRYHKVRD                                                          189

SEQ ID NO: 306         moltype = DNA  length = 6576
FEATURE                Location/Qualifiers
source                 1..6576
                       mol_type = other DNA
                       organism = synthetic construct
SEQUENCE: 306
aaatgcttac ctaatgtata tatgtgatgt attagagtaa atgcaattag taattacaag  60
gaaagtgatg gaggcatgag caaaaagagt ttctataatt tgtacacaaa tagttaatgt  120
gaactatgag aaaggtttgt gaatgattat gactatacgt atgattggtc accacttaat  180
ggattcctta atttcttgtt ccctcattaa gttgtcgtct catcatttct tttcatttct  240
agacccatgg tctcagattg gacttttaaa ggtagatttc aatatcaatg gtcgcacttt  300
tttagtccaa ttcattttca agttctcaaa caagtgtggt gattattttg cagttcttat  360
tcacacgtct aacttctatt atgtatgtca ttttctacgg ataagaagcg taagcgttgc  420
aaataatatt atctcgaatt aaatgggatt aattaggcca taatctagat tctatgtatc  480
ttttatatat ataaaaacaa aacatacgct caaatttagt tgcgtatttg agtagatatt  540
gtcttcatta cttgtaagaa aaaactcgtt ggactgcaca atagttttgt taacgtgtaa  600
ttaaatagcg tatttgtaag atttgagatt caaaatcgtc tttgacagct atgctcaaca  660
tgctttgaat cataagcact gtctagattc tcagcatgta acttatattt cagatcagat  720
tgactgcaaa acgaggtccc acgcaagaag gaaaagacaa gtatgatgtt cttggtctgg  780
agttctcagt cgagcatgtt attaaggggt gcaagagtgg atttccaaca aaaaacaagc  840
tttatgggac aaaaatcgaa gaaagaataa agatagaggg tgaaaacaca atatatgatt  900
tgttatcgcc tatttcccat aaaggattca gatactagga gaagttgatg ccaatttcac  960
atgcaagtct ctttcattac atctccatat tttaccgcac ctacgtctct atgtttacat  1020
tcttgtcatc gactttttca tgaataattt ttttttgcaa tttttatttc acttacaatt  1080
atgaatttct tatatatatt cttccaagtt gtaacgatca aataaatatg catgcattat  1140
gtcatatatg gctatacatc attttagatt attgattttt gcagtatctt atttgaaacc  1200
tttagttcta tctacggata tcaatgtcta aacttttgat tctttattta gattgtgttc  1260
ttcaatcaaa gattcccctc ataaattgtg tattctttgc aaaaaaagga gttcacttat  1320
ttcacttgtg attgtgaaca tattataaat tgtacttata aaaacattct gcagttaaaa  1380
gaaaattaaa catcaaagtt agaaaaatta actttatgaa aaaaatacct actagctagt  1440
tagtagtaag agcatcttca ttcatggttc ttaaaacaaa aaatacaagt agtttaatat  1500
aatttaaata aaaaaacgaa atttttattt tgaaataaga tttgaacaag ttgagaattg  1560
acaagtgttt attagggttt gaaaagttga tcaaatgtta tgattcatcg tcttctctct  1620
ctctctttac cttttctttg tttaatggtg agaactttct atgaaagtgt gtatttggtt  1680
acttgaacta atatttttat gactgacttt atgaaaacaa cacaatctac tagctacatg  1740
gactgtagaa tacaatttat attttagatt gctaagaagt tatcagttta tctacagttt  1800
ggttgaatta attcaactag gttatggacc ttatggttag acttggttag gttcaatatg  1860
aacacgtata gatacagaga ggagcatcta attaattgaa acgcagacgt gtttaaaaag  1920
aaagagagaa agattaccat aaaaagggag tttccaaaag atggttctga tgtgaaacag  1980
agccccatcc ctctcccttt ccctttctc gtgaaagata ttggatggtc ctccttcaat  2040
gtccaccacc tactactcat cttctctttt ttctttaatt agttttcaat ttcaatttca  2100
gtttaagttc ctataattta taaatatttc atatctattt atatgaaatg tgtagagaat  2160
aaaaagtgtg agtttatata tttgtcgagt atgtttgttt tgacaattgg tatataattt  2220
atctgcttat tatagatgta cgtataaata tatttcagct aagaaaaact tgtaaacttc  2280
tgtgtgttct gcaagtgggg tcttaatacc ttcaaaaaat agtccttcaa atgaaactga  2340
tcataaacca aatttgaaaa gagagagatg tatttttcaa aaacgacata attattagaa  2400
aagcagaaaa aaacagttaa gtgatactga gatcaataat aatatatagt atctcttcaa  2460
gaacaatatc tcattaccca cttctccttt gtgctgatct atcataaact ttaaacccca  2520
ggtaaggttc tgaatgttat acagtttata tagaataact ctaatatcaa atatttatat  2580
tcggagttct tttcatttct ttttcaattc aatatctgat cctttgttac ctagatttga  2640
tatgtttatt tattattgtt tatctgcaaa gagatttgat cattttaacc ctaaacctaa  2700
gtttcgtacc caaatcatac gatctatctt ttggttattc ttgatctgca aaatgattaa  2760
tttaatcatc aatcttaatt agcttctcta gagcaatatt tttttttctt aagctttgct  2820
ctagatcaat ctctctccct cttattatgt tattttattc atctggtgat atcacagaat  2880
caatggagga aggtgggagt agtcacgacg cagagagtag caagaagcta gtaagaggga  2940
agatagagat aaagaggata gagaacacaa caagtcgtca agtaactttc tgtaaacgac  3000
gcaatggtct tcttaagaaa gcttatgagc tttctgtctt gtgtgatgct gaagttgccc  3060
tcgtcatctt ctccactcgt ggccgtctct atgagtacgc caacaacagg tacgcttctc  3120
ctgcaccttt gatctttgct ttcttggttt actactacta ctacaagaaa atcttagtta  3180
aatgtatgga gaagtgactt gtagagtcaa gattagggtt tttgttaaat tacaatcctg  3240
ggtttttttcc catgccaaaa aaaaaaaatc ctgggttttt ttgttttttc taaattaaat  3300
```

-continued

```
atcgatctct ctagagctac cataactatg tgtgtgtgtg tgtttgtgta agcaagtaat  3360
gaagaaggaa gaaagctgtc ttgtcttctc aacttctagt tagccttctc gttagccttt  3420
tttggtgtca ctctttttct gcaaatcatt agaacctgat gcatgtcagc ttctccatga  3480
aatttcttta ttcaaattca aattagggtt tgatcagtaa acaagttggg tactttcttg  3540
gcacgaaata gcatgtatat tatataaata tgcaagactt atgttaccct ctgcctagtg  3600
taacttggga caaagcctaa tgaccatttg tcacttgtca ctagctaggg atccctataa  3660
ttatttaatc tagccaccaa aggcaaatga aaaccgaaaa tttcatattc ttgagttggt  3720
cttgagaaat ataatatgtg gctgaaataa aattgtcctg gtatgcaagt tcagaatttc  3780
aactctcttt ctaaaaaact gtaaatatat atacttctca tgtaaccgat tgtttacatt  3840
taatgtttaa ctttaccaaa gatgtagtta gagagcaaga tgtataacaa tataaatgca  3900
gtttttatgt ttctaatcta aaatgagttt tttcgatgta ataatctaaa atgagttgct  3960
accattatac tccctctgtt tccgaaagaa atattttcta gagtattcat gcatattaaa  4020
gaaacaatta atttttata attgaattta ttatttattt tactatacat tttccaataa  4080
atattaacca atagtattca accaattcaa atattttcaa ttaatgtttt ttaaaagtct  4140
acaactttc aacattaact actaaaagta ctttaaaatt ttagaaaatc tatcattttg  4200
gaacaaaaaa taaatctaga aaatcctact ttcaggaaca gaaggtgtat atatatatag  4260
cttttgttac aatagttgac gaagaacttc aaattaaaca ataaacacac atgagtttaa  4320
tttgtctaat attgaaatca ctcatcgact gttaaaaaaa acaatattca tattaatata  4380
taagccattg ctgaatttat acatatgtag tccttggata tattaatgag agggagataa  4440
ctcagagaag tgtcagaact cgaaatggta cgggccaatg agaagctctg gcattctgag  4500
ctctatttat ctgttattat tatctgtaaa aaattactga tcctttaagc atattgtgat  4560
gaaattgaat catataatat gcatggacgt tgttgtgttt accaatttga aatcatacta  4620
ctagtgtaat acttaattac ttatatcctt actttagtta actgcattga cagacattta  4680
ttatttgatg taaattacct tggaaaaata tggtttgatt gaaattatct cttcatactg  4740
gcaatcagaa actggtccaa acttcaaaac cacacattcc tttctggttg attttaaggt  4800
ttttggccgg gaaaataaac tttccaaaac cctaatcaaa atacagtacg tactatgttt  4860
aagagtttat atttattaaa ttaaatctaa taggttctcg aactgaactt tttagcgtga  4920
agggtacaat tgaaagatac aagaaagctt gttccgatgc cgttaaccct ccttctgtca  4980
ccgaagctaa tactcaggta ccattcttta gttttttttt tttagttctt ttggccggga  5040
aagctttttt gcgatttcga cagtgtttaa gctttgccta acgatagctg atctctttac  5100
cttttattta gccttaaatt gttcaccatg aattagttta agcctaatta accttgtgtt  5160
taaaaatctt tttatctttt tggggttatt agatagctca ttgctaagtc ttagcagttt  5220
taggccatga ttatcgctaa aactgtttc tgggtttttt aatttttttt ttgtttttc  5280
tgattaaaaa aggaaaaaat taaaaaaaag tcaatcgcgg gtcgtcacgt gtcagtgtag  5340
cccgtaaaaa gtacaagaaa caaactaaag ttgatccttc ttttgcgact ttagtaaccg  5400
ataatcgtgc tcttagattc aagtctttct tctatctcaa tgtcattttt acgaaatgaa  5460
ttcacatttt gtcaaaaaaa aaattagttc ttttattctt cccctctttt tttgtctttt  5520
tttttgtgat gaccaattaa cattacaaaa aaaataaaaa aaatttggat gggttcttga  5580
aacgttttgg tgtttatatg catggaactc tgaagtacta tcagcaagaa gcatctaagc  5640
ttcggaggca gattcgtgac attcagaatt ctaacaggta aataaggcag tcttaatgtt  5700
caaaaaaaat aaaaaataag acagtctttt ggtagtgttt caaaaaaaaa aaacgacagt  5760
cttttggttt gatcactact tctctattat agatgttgtt ttgattattt aatgttgtga  5820
cttgaaaggc atatagttgg ggaatcactt ggttccttga acttcaagga actcaaaaac  5880
ctcgaaggac gtcttgaaaa aggaatcagc cgtgtccgat ccaagaaggt acttacccta  5940
acgtctcttt gtctctctat aacttatatt gttttcttac tcttatatga aaatctcgca  6000
gaatgagctg ttaatggcag agatagagta tatgcagaag agggtaagta acgtttcttc  6060
catatctttc accgtctttt taggtttttg agttcctata aatcgtgtag gaaatggagt  6120
tgcaacacta aggttagtct aaatctctct tctttacatc atcgcctacc cgagaagata  6180
acgtgtgtaa caaaccaaac tttgatgttc ggtctttgca gatatcacaa ggtgcgagat  6240
tgaatccgga gcagcaggat tcgagtgtaa tacaaggaac agcggtttac gaatccggtt  6300
tatcttccca tgatcagtca cagcattata accggaacta tattccggtt aaccttcttg  6360
aaccgaatca acaattctcc ggtcaagacc aacctcctct cgttttaaac atgaaaaaaa  6420
aaacttgttt cttcccctca aaacgattgt tcagagaaag acactaaggg tatgactggt  6480
tttcccgcta ccacccgcaa acgcagcttt tgcggttggt agcggttgct ggcgttttgc  6540
aacaatcgct caaaccgctc taaaccgctc caaatc                             6576
```

```
SEQ ID NO: 307         moltype = AA  length = 177
FEATURE                Location/Qualifiers
source                 1..177
                       mol_type = protein
                       organism = synthetic construct
SEQUENCE: 307
MEEGGSSHDA ESSKKLVRGK IEIKRIENTT SRQVTFCKRR NGLLKKAYEL SVLCDAEVAL  60
VIFSTRGRLY EYANNSVKGT IERYKKACSD AVNPPSVTEA NTQYYQQEAS KLRRQIRDIQ  120
NSNRHIVGES LGSLNFKELK NLEGRLEKGI SRVRSKKNEL LMAEIEYMQK REMELQH     177
```

```
SEQ ID NO: 308         moltype = DNA  length = 3559
FEATURE                Location/Qualifiers
source                 1..3559
                       mol_type = other DNA
                       organism = synthetic construct
SEQUENCE: 308
cccacttctc ctttgtgctg atctatcata agctttaaac cccaggtacg gttctgaata  60
ttatacaatt tatatagaat aactctaata tacaagattt atattcagag ttcttttcat  120
tttcattttc aattcaatat ctgatccttt gttacctaga tttgatatgt ttatttatta  180
ttgtttacaa agagatttga tcattttaac cctaaaccta agttttgtac ccaaatcata  240
tgatctatct tttggttatt cttgatctgc aaaatgatta atttgatcat caatcttaat  300
tatattctct ataacaatct tttttttat taagctttgc tctgatcaat ctctctccct  360
cttattatgt tattttattc atctggtgat atcacagaat caatggagga aggtgggagt  420
```

-continued

```
agtcacgacg cagagagtaa caagaagcta gtaagaggga agatagagat aaagaggata  480
gagaacacaa caagtcgtca agtaactttc tgtaaacgac gcaatggtct tcttaagaaa  540
gcttatgagc tttctgtctt gtgtgatgct gaagttgccc tcgtcatctt ctcgactcgt  600
ggccgtctct atgagtacgc caacaacagg tacgcttctc ctgcaccttc ttgatctttg  660
ctttcttggt ttattactac tacaagaaaa tcttagttaa atgtatggag aagtgacttg  720
tcgagtcaag attagggttt ttgttaattt acaatcctgg gtttttttcc catgccaaaa  780
aacaaaatcc tgggtttttct tgttttccta aattaaatat ctctctagag ctaccataac  840
tatgtgtgtg tgtgtgtttg tgtaagcaaa taatgaagaa ggaagaaagc tgtcttgtct  900
tctcaacttc tagttagcct tctcgttagc ctttttttggt gtcactcttt ttctgcaaat  960
cattgaaacc tgatgcatgc cagcttctcc atgaaatttc tttactcaaa ttaatactag  1020
ggtttaatca gtaaacaagt tgggtacttt cttgacacga aatagcatgt atattatata  1080
aatatgcaag acttatgtaa ccctctgtct agtgtaactt gggacagagc ctaatgatca  1140
gttgtcacta gctagggatc cctataatta tttaatctag ccccccaaag gcaaatgaaa  1200
actgaaaatt tcatattctt gagttggtct tgagaaatat aatatgtggc tgaaataaaa  1260
ttgtcctggt atgcaagttc agaatttcaa ctctctttct aaaaaactgt atatatataa  1320
tatgtaaccg attgtttaca tttattttta actttaccaa agatgtagtt agagaggatt  1380
atgtataaca atataaatgc agtttttagg tttctaatct aaaatgagtt gctacaatct  1440
atatatattt gatctagaaa tgggatttgt aataaggttt aacatataat aatgggattt  1500
cttaatttct cttcacaagt cgcatatatc tttttgtctc atatatacat cttttgttac  1560
agtagttgac gaagaacttc aaattaaaca ataaacacac atgactttaa tttgtctaac  1620
attgaaatca ctcatcgtct gttgaaaaaa taatattgat attaatacat aagccattgc  1680
tgaatgtata catatgtagt ccttggatat attaatgaga gggagataac tcggagaagt  1740
gtcagaactc gaaattgtac gggccaatga gaagctctgg cattctgagc tccatttatt  1800
tgttattatc tctaaaaaaa ttactgatcc tttaagcata ttgtgatgaa attgaatcat  1860
ataaatatgca tggacgttgt tgtgtactcc tcctaattac caatttgaaa tcatactact  1920
agtgtaatac ttaattactt atatccttac tttttatttt gtctcaacgt caactatttc  1980
attaaccgat aaattagtac aaagtatttg accacaccaa tttgaccaca catgcaacaa  2040
tgcatcttag taacacactg gaacactcac taggtgattt cttactcgga accagcgcaa  2100
cctgagtaca ttgctgcatt tttcacactt atatccttac tttagttaac tgcattagca  2160
gccatttatt atttgatgta aattaccttg gaaaaatatg atacttcagc ctgacataat  2220
atgtttgatt gaaattctct tcatcatcct ggcaatcaga gactggtcca aacttcaaag  2280
ccacacattc ctttcttgtc gattttaagg tttttggccg ggaaaataaa ctttcaaaaa  2340
ccctaatcaa agtacagtac ttactatgtt taagagtatg tttattaaat taaatctaat  2400
aggttctcca actttttagc gtgaagggta caattgaaag atacaagaaa gcttgttccg  2460
atgccgttaa ccctccttct gtcaccgaag ctaatactca ggtaccgttc tttagttctt  2520
ttattccccc tctcttttttc tttttctcat ctttttttta tgatgaccaa ttaacgttac  2580
aaaaaaaatt aaaaaaattt ggatgggttc atgaaacgtt ttggtgtttg tatgcatgga  2640
actctgaagt actatcagca agaagcctct aagcttcgga ggcagattcg tgacattcaa  2700
aattctaaca ggtaaataag acggtctttt ggtttgatca ctacttctct attattgatg  2760
ttgttttgat tatttaatgt tgtgaaatga aaggcatata gttggggaat cacttggttc  2820
cttgaacttc aaggaactca aaaacctcga aggacgtctt gaaaaaggaa tcaaccgtgt  2880
ccgatccaag aaggtactta ccctaacgtc tctttgtctc tctataactt atatagtttt  2940
cttactctta taatgaaaat ctcgcagaat gagctgttaa tggcagagat agagtatatg  3000
cagaagaggg taagtaacgt ttcttccata tcttgcaccg tctttttagg tttttgagtt  3060
tcctataaat cgtgtaggaa atggagttgc aacacgataa catgtagcta aggttagtct  3120
aaatctctct tctttacatc atcgcctacc cgagaagata acgtgtgtaa caaaccaaac  3180
tttgatgttc ggtctttgca gatatcacaa ggtgcgagat tgaatccgga gcagcaggat  3240
tcgagtgtaa tacaaggaac agcggtttac gaacccggtc tatcttccca tgaccagtca  3300
cagcattata accggaacta tattccggtt aaccttcttg aaccgaatct acatttctcc  3360
ggtcaagacc aaccttaaac atgaaaaaaa acacttgttt cttcccctca aaacggttgt  3420
tcagagaaag acactaagag taacttcttc tcatgcatag ttttttaggt tccaataata  3480
ataacataaa taaatcaagt gttacaaaga tacaaactta caaacatcta tcttctgatg  3540
tgtagctata actaaacaa                                               3559
```

```
SEQ ID NO: 309          moltype = AA  length = 180
FEATURE                 Location/Qualifiers
source                  1..180
                        mol_type = protein
                        organism = synthetic construct
SEQUENCE: 309
MEEGGSSHDA ESNKKLVRGK IEIKRIENTT SRQVTFCKRR NGLLKKAYEL SVLCDAEVAL  60
VIFSTRGRLY EYANNSVKGT IERYKKACSD AVNPPSVTEA NTQYYQQEAS KLRRQIRDIQ  120
NSNRHIVGES LGSLNFKELK NLEGRLEKGI NRVRSKKNEL LMAEIEYMQK REMELQHDNM  180
```

```
SEQ ID NO: 310          moltype = DNA  length = 3397
FEATURE                 Location/Qualifiers
source                  1..3397
                        mol_type = other DNA
                        organism = synthetic construct
SEQUENCE: 310
cccacttctc ctttgtgctg atctatcata agctttaaac cccaggtacg gttctgaata  60
ttatacaatt tatatagaat aactctaata tacaagattt atattcagag ttcttttcat  120
tttcatttc aattcaatat ctgatccttt gttacctaga tttgatatgt ttatttatta  180
ttgtttacaa agagatttga tcattttaac cctaaaccta agttttgtac ccaaatcata  240
tgatctatct tttggttatt cttgatctgc aaaatgatta atttgatcat caatcttaat  300
tatattctct ataacaatct tttttttttat taagctttgc tctgatcaat ctctctccct  360
cttattatgt tattttattc atctggtgat atcacagaat caatggagga aggtgggagt  420
agtcacgacg cagagagtaa caagaagcta gtaagaggga agatagagat aaagaggata  480
gagaacacaa caagtcgtca agtaactttc tgtaaacgac gcaatggtct tcttaagaaa  540
```

-continued

```
gcttatgagc tttctgtctt gtgtgatgct gaagttgccc tcgtcatctt ctcgactcgt  600
ggccgtctct atgagtacgc caacaacagg tacgcttctc ctgcaccttc ttgatctttg  660
ctttcttggt ttattactac tacaagaaaa tcttagttaa atgtatggag aagtgacttg  720
tcgagtcaag attagggttt ttgttaattt acaatcctgg gttttttttcc catgccaaaa  780
aacaaaatcc tgggttttct tgttttccta aattaaatat ctctctagag ctaccataac  840
tatgtgtgtg tgtgtgtttg tgtaagcaaa taatgaagaa ggaagaaagc tgtcttgtct  900
tctcaacttc tagttagcct tctcgttagc cttttttggt gtcactcttt ttctgcaaat  960
cattgaaacc tgatgcatgc cagcttctcc atgaaatttc tttactcaaa ttaatactag  1020
ggtttaatca gtaaacaagt tgggtacttt cttgacacga aatagcatgt atattatata  1080
aatatgcaag acttatgtaa ccctctgtct agtgtaactt gggacagagc ctaatgatca  1140
gttgtcacta gctagggatc cctataatta tttaatctag ccccccaaag gcaaatgaaa  1200
actgaaaatt tcatattctt gagttggtct tgagaaatat aatatgtggc tgaaataaaa  1260
ttgtcctggt atgcaagttc agaatttcaa ctctctttct aaaaaactgt atatatataa  1320
tatgtaaccg attgtttaca tttattttta actttaccaa agatgtagtt agagaggatt  1380
atgtataaca atataaatgc agtttttagg tttctaatct aaaatgagtt gctacaatct  1440
atatatattt gatctagaaa tgggatttgt aataaggttt aacatataat aatgggattt  1500
cttaatttct cttcacaagt cgcatatatc ttttgtctc atatatacat cttttgttac  1560
agtagttgac gaagaacttc aaattaaaca ataaacacac atgactttaa tttgtctaac  1620
attgaaatca ctcatcgtct gttgaaaaaa taatattgat attaatacat aagccattgc  1680
tgaatgtata catatgtagt ccttggatat attaatgaga gggagataac tcggagaagt  1740
gtcagaactc gaaattgtac gggccaatga gaagctctgg cattctgagc tccatttatt  1800
tgttattatc tctaaaaaaa ttactgatcc tttaagcata ttgtgatgaa attgaatcat  1860
ataatatgca tggacgttgt tgtgtactcc tcctaattac caatttgaaa tcatactact  1920
agtgtaatac ttaattactt atatccttac tttttatttt gtctcaacgt caactatttc  1980
attaaccgat aaattagtac aaagtatttg accacaccaa tttgaccaca catgcaacaa  2040
tgcatcttag taacacactg gaacactcac taggtgattt cttactcgga accagcgcaa  2100
cctgagtaca ttgctgcatt tttcacactt atatccttac tttagttaac tgcattagca  2160
gccatttatt atttgatgta aattaccttg gaaaaatatg atacttcagc ctgacataat  2220
atgtttgatt gaaattctct tcatcatcct ggcaatcaga gactggtcca aacttcaaag  2280
ccacacattc ctttcttgtc gattttaagg tttttggccg ggaaaataaa ctttcaaaaa  2340
ccctaatcaa agtacagtac ttactatgtt taagagtatg tttattaaat taaatctaat  2400
aggttctcca actttttagc gtgaagggta caattgaaag atacaagaaa gcttgttccg  2460
atgccgttaa ccctccttct gtcaccgaag ctaatactca ggtaccgttc tttagttctt  2520
ttattccccc tctcttttc tttttctcat cttttttttta tgatgaccaa ttaacgttac  2580
aaaaaaaatt aaaaaaattt ggatgggttc atgaaacgtt ttggtgtttg tatgcatgga  2640
actctgaagt actatcagca agaagcctct aagcttcgga ggcagattcg tgacattcaa  2700
aattctaaca ggtaaataag acggtctttt ggtttgatca ctacttctct attattgatg  2760
ttgttttgat tatttaatgt tgtgaaatga aaggcatata gttggggaat cacttggttc  2820
cttgaacttc aaggaactca aaaacctcga aggacgtctt gaaaaaggaa tcaaccgtgt  2880
ccgatccaag aaggtactta ccctaacgtc tctttgtctc tctataactt atatagtttt  2940
cttactctta taatgaaaat ctcgcagaat gagctgttaa tggcagagat agagtatatg  3000
cagaagaggg taagtaacgt ttcttccata tcttgcaccg tctttttagg tttttgagtt  3060
tcctataaat cgtgtaggaa atggagttgc aacacgataa catgtacctg cgagctaagg  3120
ttagtctaaa tctctcttct ttacatcatc gcctacccga gaagataacg tgtgtaacaa  3180
accaaacttt gatgttcggt ctttgcagat atcacaaggt gcgagattga atccggagca  3240
gcaggattcg agtgtaatac aaggaacagc ggtttacgaa cccggtctat cttcccatga  3300
ccagtcacag cattataacc ggaactatat tccggttaac cttcttgaac cgaatctaca  3360
tttctccggt caagaccaac ctcctcctaa gttttaa                            3397
```

```
SEQ ID NO: 311          moltype = AA  length = 247
FEATURE                 Location/Qualifiers
source                  1..247
                        mol_type = protein
                        organism = synthetic construct
SEQUENCE: 311
MEEGGSSHDA ESNKKLVRGK IEIKRIENTT SRQVTFCKRR NGLLKKAYEL SVLCDAEVAL  60
VIFSTRGRLY EYANNSVKGT IERYKKACSD AVNPPSVTEA NTQYYQQEAS KLRRQIRDIQ  120
NSNRHIVGES LGSLNFKELK NLEGRLEKGI NRVRSKKNEL LMAEIEYMQK REMELQHDNM  180
YLRAKISQGA RLNPEQQDSS VIQGTAVYEP GLSSHDQSQH YNRNYIPVNL LEPNLHFSGQ  240
DQPPPKF                                                           247
```

```
SEQ ID NO: 312          moltype = DNA  length = 6354
FEATURE                 Location/Qualifiers
source                  1..6354
                        mol_type = other DNA
                        organism = synthetic construct
SEQUENCE: 312
atgattatga ctatacgtat gattggtcac cacttaatgg attccttaat ttcttgttcc  60
ctcattaagt tgtcgtctca tcatttcttt tcatttctag acccatggtc tcagattgga  120
cttttaaagg tagatttcaa tatcaatggt cgcacttttt tagtccaatt cattttcaag  180
ttctcaaaca agtgtggtga ttattttgca gttcttattc acacgtctaa cttctattat  240
gtatgtcatt ttctacggat aagaagcgta agcgttgcaa ataatattat ctcgaattaa  300
atgggattaa ttaggccata atctagattc tatgtatctt ttatatatat aaaaacaaaa  360
catacgctca aatttagttg cgtatttgag tagatattgt cttcattact tgtaagaaaa  420
aactcgttgg actgcacaat agttttgtta acgtgtaatt aaatagcgta tttgtaagat  480
ttgagattca aaatcgtctt tgacagctat gctcaacatg ctttgaatca taagcactgt  540
ctagattctc agcatgtaac ttatatttca gatcagattg actgcaaaac gaggtcccac  600
gcaagaagga aaagacaagt atgatgttct tggtctggag ttctcagtcg agcatgttat  660
taaggggtgc aagagtggat ttccaacaaa aaacaagctt tatgggacaa aaatcgaaga  720
```

-continued

```
aagaataaag atagagggtg aaaacacaat atatgatttg ttatcgccta tttcccataa  780
aggattcaga tactaggaga agttgatgcc aatttcacat gcaagtctct ttcattacat  840
ctccatattt taccgcacct acgtctctat gtttacattc ttgtcatcga ctttttcatg  900
aataattttt ttttgcaatt tttatttcac ttacaattat gaatttctta tatatattct  960
tccaagttgt aacgatcaaa taaatatgca tgcattatgt catatatggc tatacatcat  1020
tttagattat tgatttttgc agtatcttat ttgaaacctt tagttctatc tacggatatc  1080
aatgtctaaa cttttgattc tttatttaga ttgtgttctt caatcaaaga ttcccctcat  1140
aaattgtgta ttctttgcaa aaaaaggagt tcacttattt cacttgtgat tgtgaacata  1200
ttataaattg tacttataaa aacattctgc agttaaaaga aaattaaaca tcaaagttag  1260
aaaaattaac tttatgaaaa aaatacctac tagctagtta gtagtaagag catcttcatt  1320
catggttctt aaaacaaaaa atacaagtag tttaatataa tttaaataaa aaaacgaaat  1380
ttttattttg aaataagatt tgaacaagtt gagaattgac aagtgtttat tagggtttga  1440
aaagttgatc aaatgttatg attcatcgtc ttctctctct ctctttacct tttctttgtt  1500
taatggtgag aactttctat gaaagtgtgt atttggttac ttgaactaat atttttatga  1560
ctgactttat gaaaacaaca caatctacta gctacatgga ctgtagaata caatttatat  1620
tttagattgc taagaagtta tcagtttatc tacagtttgg ttgaattaat tcaactaggt  1680
tatggacctt atggttagac ttggttaggt tcaatatgaa cacgtataga tacagagagg  1740
agcatctaat taattgaaac gcagacgtgt ttaaaaagaa agagagaaag attaccataa  1800
aaagggagtt tccaaaagat ggttctgatg tgaaacagag ccccatccct ctccctttcc  1860
cttttctcgt gaaagatatt ggatggtcct ccttcaatgt ccaccaccta ctactcatct  1920
tctctttttt ctttaattag ttttcaattt caatttcagt ttaagttcct ataatttata  1980
aatatttcat atctatttat atgaaatgtg tagagaataa aaagtgtgag tttatatatt  2040
tgtcgagtat gtttgttttg acaattggta tataatttat ctgcttatta tagatgtacg  2100
tataaatata tttcagctaa gaaaaacttg taaacttctg tgtgttctgc aagtggggtc  2160
ttaatacctt caaaaaatag tccttcaaat gaaactgatc ataaaccaaa tttgaaaaga  2220
gagagatgta tttttcaaaa acgacataat tattagaaaa gcagaaaaaa acagttaagt  2280
gatactgaga tcaataataa tatatagtat ctcttcaaga acaatatctc attacccact  2340
tctcctttgt gctgatctat cataaacttt aaaccccagg taaggttctg aatgttatac  2400
agtttatata gaataactct aatatcaaat atttatattc ggagttcttt tcatttcttt  2460
ttcaattcaa tatctgatcc tttgttacct agatttgata tgtttattta ttattgttta  2520
tctgcaaaga gatttgatca ttttaaccct aaacctaagt ttcgtaccca aatcatacga  2580
tctatctttt ggttattctt gatctgcaaa atgattaatt taatcatcaa tcttaattag  2640
cttctctaga gcaatatttt tttttcttaa gctttgctct agatcaatct ctctccctct  2700
tattatgtta ttttattcat ctggtgatat cacagaatca atggaggaag gtgggagtag  2760
tcacgacgca gagagtagca agaagctagt aagagggaag atagagataa agaggataga  2820
gaacacaaca agtcgtcaag taactttctg taaacgacgc aatggtcttc ttaagaaagc  2880
ttatgagctt tctgtcttgt gtgatgctga agttgccctc gtcatcttct ccactcgtgg  2940
ccgtctctat gagtacgcca acaacaggta cgcttctcct gcacctttga tctttgcttt  3000
cttggtttac tactactact acaagaaaat cttagttaaa tgtatggaga agtgacttgt  3060
agagtcaaga ttagggtttt tgttaaatta caatcctggg tttttttccca tgccaaaaaa  3120
aaaaaatcct gggttttttt gtttttttcta aattaaatat cgatctctct agagctacca  3180
taactatgtg tgtgtgtgtg tttgtgtaag caagtaatga agaaggaaga aagctgtctt  3240
gtcttctcaa cttctagtta gccttctcgt tagccttttt tggtgtcact ctttttctgc  3300
aaatcattag aacctgatgc atgtcagctt ctccatgaaa tttctttatt caaattcaaa  3360
ttagggtttg atcagtaaac aagttgggta ctttcttggc acgaaatagc atgtatatta  3420
tataaatatg caagacttat gttaccctct gcctagtgta acttgggaca aagcctaatg  3480
accatttgtc acttgtcact agctagggat ccctataatt atttaatcta gccaccaaag  3540
gcaaatgaaa accgaaaatt tcatattctt gagttggtct tgagaaatat aatatgtggc  3600
tgaaataaaa ttgtcctggt atgcaagttc agaatttcaa ctctctttct aaaaaactgt  3660
aaatatatat acttctcatg taaccgattg tttacattta atgtttaact ttaccaaaga  3720
tgtagttaga gagcaagatg tataacaata taaatgcagt ttttatgttt ctaatctaaa  3780
atgagttttt tcgatgtaat aatctaaaat gagttgctac cattatactc cctctgtttc  3840
cgaaagaaat attttctaga gtattcatgc atattaaaga aacaattaat tttttataat  3900
tgaatttatt atttatttta ctatacattt tccaataaat attaaccaat agtattcaac  3960
caattcaaat attttcaatt aatgtttttt aaaagtctac aacttttcaa cattaactac  4020
taaaagtact ttaaaatttt agaaaatcta tcattttgga acaaaaaata aatctagaaa  4080
atcctacttt caggaacaga aggtgtatat atatatagct tttgttacaa tagttgacga  4140
agaacttcaa attaaacaat aaacacacat gagtttaatt tgtctaatat tgaaatcact  4200
catcgactgt taaaaaaaac aatattcata ttaatatata agccattgct gaatttatac  4260
atatgtagtc cttggatata ttaatgagag ggagataact cagagaagtg tcagaactcg  4320
aaatggtacg ggccaatgag aagctctggc attctgagct ctatttatct gttattatta  4380
tctgtaaaaa attactgatc ctttaagcat attgtgatga aattgaatca tataatatgc  4440
atggacgttg ttgtgtttac caatttgaaa tcatactact agtgtaatac ttaattactt  4500
atatccttac tttagttaac tgcattgaca gacatttatt atttgatgta aattaccttg  4560
gaaaaatatg gtttgattga aattatctct tcatactggc aatcagaaac tggtccaaac  4620
ttcaaaacca cacattcctt tctggttgat tttaaggttt ttggccggga aaataaactt  4680
tccaaaaccc taatcaaaat acagtacgta ctatgtttaa gagtttatat ttattaaatt  4740
aaatctaata ggttctcgaa ctgaactttt tagcgtgaag ggtacaattg aaagatacaa  4800
gaaagcttgt tccgatgccg ttaaccctcc ttctgtcacc gaagctaata ctcaggtacc  4860
attctttagt tttttttttt tagttctttt ggccgggaaa gctttttttgc gatttcgaca  4920
gtgtttaagc tttgcctaac gatagctgat ctctttacct tttatttagc cttaaattgt  4980
tcaccatgaa ttagtttaag cctaattaac cttgtgttta aaaatctttt tatctttttg  5040
gggttattag atagctcatt gctaagtctt agcagtttta ggccatgatt atcgctaaaa  5100
ctgttttctg ggttttttaa tttttttttt gtttttctg attaaaaaag gaaaaaatta  5160
aaaaaaagtc aatcgcgggt cgtcacgtgt cagtgtagcc cgtaaaaagt acaagaaaca  5220
aactaaagtt gatccttctt ttgcgacttt agtaaccgat aatcgtgctc ttagattcaa  5280
gtctttcttc tatctcaatg tcatttttac gaaatgaatt cacattttgt caaaaaaaaa  5340
attagttctt ttattcttcc cctctttttt tgtctttttt tttgtgatga ccaattaaca  5400
ttacaaaaaa aataaaaaaa atttggatgg gttcttgaaa cgttttggtg tttatatgca  5460
```

```
tggaactctg aagtactatc agcaagaagc atctaagctt cggaggcaga ttcgtgacat  5520
tcagaattct aacaggtaaa taaggcagtc ttaatgttca aaaaaaaataa aaaataagac  5580
agtcttttgg tagtgtttca aaaaaaaaaa acgacagtct tttggtttga tcactacttc  5640
tctattatag atgttgtttt gattatttaa tgttgtgact tgaaaggcat atagttgggg  5700
aatcacttgg ttccttgaac ttcaaggaac tcaaaaacct cgaaggacgt cttgaaaaag  5760
gaatcagccg tgtccgatcc aagaaggtac ttaccctaac gtctctttgt ctctctataa  5820
cttatattgt tttcttactc ttatatgaaa atctcgcaga atgagctgtt aatggcagag  5880
atagagtata tgcagaagag ggtaagtaac gtttcttcca tatctttcac cgtcttttta  5940
ggtttttgag ttcctataaa tcgtgtagga aatggagttg caacacgata acatgtacct  6000
gcgagctaag gttagtctaa atctctcttc tttacatcat cgcctacccg agaagataac  6060
gtgtgtaaca aaccaaactt tgatgttcgg tctttgcaga tatcacaagg tgcgagattg  6120
aatccggagc agcaggattc gagtgtaata caaggaacag cggtttacga atccggttta  6180
tcttcccatg atcagtcaca gcattataac cggaactata ttccggttaa ccttcttgaa  6240
ccgaatcaac aattctccgg tcaagaccaa cctcctctca gttttaaaca tgaaaaaaaa  6300
aacttgtttc ttcccctcaa aacgattgtt cagagaaaga cactaagggt atga        6354

SEQ ID NO: 313          moltype = AA  length = 369
FEATURE                 Location/Qualifiers
source                  1..369
                        mol_type = protein
                        organism = synthetic construct
SEQUENCE: 313
MIMTIRMIGH HLMDSLISCS LIKLSSHHFF SFLDPWSQIG LLKIRLTAKR GPTQEGKDKY  60
DVLGLEFSVE HVIKGCKSGF PTKNKLYGTK IEERIKIEES MEEGGSSHDA ESSKKLVRGK  120
IEIKRIENTT SRQVTFCKRR NGLLKKAYEL SVLCDAEVAL VIFSTRGRLY EYANNSVKGT  180
IERYKKACSD AVNPPSVTEA NTQYYQQEAS KLRRQIRDIQ NSNRHIVGES LGSLNFKELK  240
NLEGRLEKGI SRVRSKKNEL LMAEIEYMQK REMELQHDNM YLRAKISQGA RLNPEQQDSS  300
VIQGTAVYES GLSSHDQSQH YNRNYIPVNL LEPNQQFSGQ DQPPLSFKHE KKNLFLPLKT  360
IVQRKTLRV                                                         369

SEQ ID NO: 314          moltype = DNA  length = 6345
FEATURE                 Location/Qualifiers
source                  1..6345
                        mol_type = other DNA
                        organism = synthetic construct
SEQUENCE: 314
atgattatga ctatacgtat gattggtcac cacttaatgg attccttaat ttcttgttcc  60
ctcattaagt tgtcgtctca tcatttcttt tcatttctag acccatggtc tcagattgga  120
cttttaaagg tagatttcaa tatcaatggt cgcacttttt tagtccaatt catttttcaag  180
ttctcaaaca agtgtggtga ttattttgca gttcttattc acacgtctaa cttctattat  240
gtatgtcatt ttctacggat aagaagcgta agcgttgcaa ataatattat ctcgaattaa  300
atgggattaa ttaggccata atctagattc tatgtatctt ttatatatat aaaaacaaaa  360
catacgctca aatttagttg cgtatttgag tagatattgt cttcattact tgtaagaaaa  420
aactcgttgg actgcacaat agttttgtta acgtgtaatt aaatagcgta tttgtaagat  480
ttgagattca aaatcgtctt tgacagctat gctcaacatg ctttgaatca taagcactgt  540
ctagattctc agcatgtaac ttatatttca gatcagattg actgcaaaac gaggtcccac  600
gcaagaagga aaagacaagt atgatgttct tggtctggag ttctcagtcg agcatgttat  660
taaggggtgc aagagtggat ttccaacaaa aaacaagctt tatgggacaa aaatcgaaga  720
aagaataaag atagagggtg aaaacacaat atatgatttg ttatcgccta tttcccataa  780
aggattcaga tactaggaga agttgatgcc aatttcacat gcaagtctct ttcattacat  840
ctccatattt taccgcacct acgtctctat gtttacattc ttgtcatcga ctttttcatg  900
aataattttt ttttgcaatt tttatttcac ttacaattat gaatttctta tatatattct  960
tccaagttgt aacgatcaaa taaatatgca tgcattatgt catatatggc tatacatcat  1020
tttagattat tgatttttgc agtatcttat ttgaaacctt tagttctatc tacggatatc  1080
aatgtctaaa cttttgattc tttatttaga ttgtgttctt caatcaaaga ttcccctcat  1140
aaattgtgta ttctttgcaa aaaaaggagt tcacttattt cacttgtgat tgtgaacata  1200
ttataaattg tacttataaa aacattctgc agttaaaaga aaattaaaca tcaaagttag  1260
aaaaattaac tttatgaaaa aaatacctac tagctagtta gtagtaagag catcttcatt  1320
catggttctt aaaacaaaaa atacaagtag tttaatataa tttaaataaa aaaacgaaat  1380
ttttatttttg aaataagatt tgaacaagtt gagaattgac aagtgtttat tagggtttga  1440
aaagttgatc aaatgttatg attcatcgtc ttctctctct ctctttacct tttctttgtt  1500
taatggtgag aactttctat gaaagtgtgt atttggttac ttgaactaat atttttatga  1560
ctgactttat gaaaacaaca caatctacta gctacatgga ctgtagaata caatttatat  1620
tttagattgc taagaagtta tcagtttatc tacagtttgg ttgaattaat tcaactaggt  1680
tatggacctt atggttagac ttggttaggt tcaatatgaa cacgtataga tacagagagg  1740
agcatctaat taattgaaac gcagacgtgt ttaaaaagaa agagagaaag attaccataa  1800
aaagggagtt tccaaaagat ggttctgatg tgaaacagag ccccatccct ctccctttcc  1860
cttttctcgt gaaagatatt ggatggtcct ccttcaatgt ccaccaccta ctactcatct  1920
tctctttttt ctttaattag ttttcaattt caatttcagt ttaagttcct ataatttata  1980
aatatttcat atctatttat atgaaatgtg tagagaataa aaagtgtgag tttatatatt  2040
tgtcgagtat gtttgttttg acaattggta tataatttat ctgcttatta tagatgtacg  2100
tataaatata tttcagctaa gaaaaacttg taaacttctg tgtgttctgc aagtggggtc  2160
ttaatacctt caaaaaatag tccttcaaat gaaactgatc ataaaccaaa tttgaaaaga  2220
gagagatgta tttttcaaaa acgacataat tattagaaaa gcagaaaaaa acagttaagt  2280
gatactgaga tcaataataa tatatagtat ctcttcaaga acaatatctc attacccact  2340
tctcctttgt gctgatctat cataaacttt aaaccccagg taaggttctg aatgttatac  2400
agtttatata gaataactct aatatcaaat atttatattc ggagttcttt tcatttcttt  2460
ttcaattcaa tatctgatcc tttgttacct agatttgata tgtttattta ttattgttta  2520
tctgcaaaga gatttgatca ttttaaccct aaacctaagt ttcgtaccca aatcatacga  2580
```

-continued

```
tctatctttt ggttattctt gatctgcaaa atgattaatt taatcatcaa tcttaattag  2640
cttctctaga gcaatatttt tttttcttaa gctttgctct agatcaatct ctctccctct  2700
tattatgtta ttttattcat ctggtgatat cacagaatca atggaggaag gtgggagtag  2760
tcacgacgca gagagtagca agaagctagt aagagggaag atagagataa agaggataga  2820
gaacacaaca agtcgtcaag taactttctg taaacgacgc aatggtcttc ttaagaaagc  2880
ttatgagctt tctgtcttgt gtgatgctga agttgccctc gtcatcttct ccactcgtgg  2940
ccgtctctat gagtacgcca acaacaggta cgcttctcct gcacctttga tctttgcttt  3000
cttggtttac tactactact acaagaaaat cttagttaaa tgtatggaga agtgacttgt  3060
agagtcaaga ttagggtttt tgttaaatta caatcctggg ttttttccca tgccaaaaaa  3120
aaaaaatcct gggttttttt gtttttteta aattaaatat cgatctctct agagctacca  3180
taactatgtg tgtgtgtgtg tttgtgtaag caagtaatga agaaggaaga aagctgtctt  3240
gtcttctcaa cttctagtta gccttctcgt tagccttttt tggtgtcact ctttttctgc  3300
aaatcattag aacctgatgc atgtcagctt ctccatgaaa tttctttatt caaattcaaa  3360
ttagggtttg atcagtaaac aagttgggta ctttcttggc acgaaatagc atgtatatta  3420
tataaatatg caagacttat gttaccctct gcctagtgta acttgggaca aagcctaatg  3480
accatttgtc acttgtcact agctagggat ccctataatt atttaatcta gccaccaaag  3540
gcaaatgaaa accgaaaatt tcatattctt gagttggtct tgagaaatat aatatgtggc  3600
tgaaataaaa ttgtcctggt atgcaagttc agaatttcaa ctctctttct aaaaaactgt  3660
aaatatatat acttctcatg taaccgattg tttacattta atgtttaact ttaccaaaga  3720
tgtagttaga gagcaagatg tataacaata taaatgcagt ttttatgttt ctaatctaaa  3780
atgagttttt tcgatgtaat aatctaaaat gagttgctac cattatactc cctctgtttc  3840
cgaaagaaat attttctaga gtattcatgc atattaaaga aacaattaat tttttataat  3900
tgaatttatt atttatttta ctatacattt tccaataaat attaaccaat agtattcaac  3960
caattcaaat attttcaatt aatgtttttt aaaagtctac aacttttcaa cattaactac  4020
taaaagtact ttaaaatttt agaaaatcta tcattttgga acaaaaaata aatctagaaa  4080
atcctacttt caggaacaga aggtgtatat atatatagct tttgttacaa tagttgacga  4140
agaacttcaa attaaacaat aaacacacat gagtttaatt tgtctaatat tgaaatcact  4200
catcgactgt taaaaaaaac aatattcata ttaatatata agccattgct gaatttatac  4260
atatgtagtc cttggatata ttaatgagag ggagataact cagagaagtg tcagaactcg  4320
aaatggtacg ggccaatgag aagctctggc attctgagct ctatttatct gttattatta  4380
tctgtaaaaa attactgatc ctttaagcat attgtgatga aattgaatca tataatatgc  4440
atggacgttg ttgtgtttac caatttgaaa tcatactact agtgtaatac ttaattactt  4500
atatccttac tttagttaac tgcattgaca gacatttatt atttgatgta aattaccttg  4560
gaaaaatatg gtttgattga aattatctct tcatactggc aatcagaaac tggtccaaac  4620
ttcaaaacca cacattcctt tctggttgat tttaaggttt ttggccggga aaataaactt  4680
tccaaaaccc taatcaaaat acagtacgta ctatgtttaa gagtttatat ttattaaatt  4740
aaatctaata ggttctcgaa ctgaactttt tagcgtgaag ggtacaattg aaagatacaa  4800
gaaagcttgt tccgatgccg ttaaccctcc ttctgtcacc gaagctaata ctcaggtacc  4860
attctttagt tttttttttt tagttctttt ggccgggaaa gctttttgc gatttcgaca  4920
gtgtttaagc tttgcctaac gatagctgat ctctttacct tttatttagc cttaaattgt  4980
tcaccatgaa ttagtttaag cctaattaac cttgtgttta aaaatctttt tatctttttg  5040
gggttattag atagctcatt gctaagtctt agcagtttta ggccatgatt atcgctaaaa  5100
ctgttttctg ggttttttaa tttttttttt gtttttttctg attaaaaaag gaaaaaatta  5160
aaaaaaagtc aatcgcgggt cgtcacgtgt cagtgtagcc cgtaaaaagt acaagaaaca  5220
aactaaagtt gatccttctt ttgcgacttt agtaaccgat aatcgtgctc ttagattcaa  5280
gtctttcttc tatctcaatg tcatttttac gaaatgaatt cacattttgt caaaaaaaaa  5340
attagttctt ttattcttcc cctctttttt tgtctttttt tttgtgatga ccaattaaca  5400
ttacaaaaaa aataaaaaaa atttggatgg gttcttgaaa cgttttggtg tttatatgca  5460
tggaactctg aagtactatc agcaagaagc atctaagctt cggaggcaga ttcgtgacat  5520
tcagaattct aacaggtaaa taaggcagtc ttaatgttca aaaaaaataa aaaataagac  5580
agtcttttgg tagtgtttca aaaaaaaaaa acgacagtct tttggtttga tcactacttc  5640
tctattatag atgttgtttt gattatttaa tgttgtgact tgaaaggcat atagttgggg  5700
aatcacttgg ttccttgaac ttcaaggaac tcaaaaacct cgaaggacgt cttgaaaaag  5760
gaatcagccg tgtccgatcc aagaaggtac ttaccctaac gtctctttgt ctctctataa  5820
cttatattgt tttcttactc ttatatgaaa atctcgcaga atgagctgtt aatggcagag  5880
atagagtata tgcagaagag ggtaagtaac gtttcttcca tatctttcac cgtcttttta  5940
ggtttttgag ttcctataaa tcgtgtagga aatggagttg caacacgata acatgtacct  6000
gcgagctaag gttagtctaa atctctcttc tttacatcat cgcctacccg agaagataac  6060
gtgtgtaaca aaccaaactt tgatgttcgg tctttgcaga tatcacaagg tgcgagattg  6120
aatccggagc agcaggattc gagtgtaata caaggaacag cggtttacga atccggttta  6180
tcttcccatg atcagtcaca gcattataac cggaactata ttccggttaa ccttcttgaa  6240
ccgaatcaac aattctccgg tcaagaccaa cctcctctcc ttttaaacat gaaaaaaaaa  6300
acttgtttct tcccctcaaa acgattgttc agagaaagac actaa                  6345
```

```
SEQ ID NO: 315          moltype = AA  length = 366
FEATURE                 Location/Qualifiers
source                  1..366
                        mol_type = protein
                        organism = synthetic construct
SEQUENCE: 315
MIMTIRMIGH HLMDSLISCS LIKLSSHHFF SFLDPWSQIG LLKIRLTAKR GPTQEGKDKY  60
DVLGLEFSVE HVIKGCKSGF PTKNKLYGTK IEERIKIEES MEEGGSSHDA ESSKKLVRGK  120
IEIKRIENTT SRQVTFCKRR NGLLKKAYEL SVLCDAEVAL VIFSTRGRLY EYANNSVKGT  180
IERYKKACSD AVNPPSVTEA NTQYYQQEAS KLRRQIRDIQ NSNRHIVGES LGSLNFKELK  240
NLEGRLEKGI SRVRSKKNEL LMAEIEYMQK REMELQHDNM YLRAKISQGA RLNPEQQDSS  300
VIQGTAVYES GLSSHDQSQH YNRNYIPVNL LEPNQQFSGQ DQPPLLLNMK KKTCFFPSKR  360
LFRERH                                                             366
```

```
SEQ ID NO: 316          moltype = DNA  length = 3386
```

-continued

```
FEATURE               Location/Qualifiers
source                1..3386
                      mol_type = other DNA
                      organism = synthetic construct
SEQUENCE: 316
cccacttctc ctttgtgctg atctatcata agctttaaac cccaggtacg gttctgaata  60
ttatacaatt tatatagaat aactctaata tacaagattt atattcagag ttcttttcat  120
tttcattttc aattcaatat ctgatccttt gttacctaga tttgatatgt ttatttatta  180
ttgtttacaa agagatttga tcattttaac cctaaaccta agttttgtac ccaaatcata  240
tgatctatct tttggttatt cttgatctgc aaaatgatta atttgatcat caatcttaat  300
tatattctct ataacaatct ttttttttat taagctttgc tctgatcaat ctctctccct  360
cttattatgt tattttattc atctggtgat atcacagaat caatggagga aggtgggagt  420
agtcacgacg cagagagtaa caagaagcta gtaagaggga agatagagat aaagaggata  480
gagaacacaa caagtcgtca agtaactttc tgtaaacgac gcaatggtct tcttaagaaa  540
gcttatgagc tttctgtctt gtgtgatgct gaagttgccc tcgtcatctt ctcgactcgt  600
ggccgtctct atgagtacgc caacaacagg tacgcttctc ctgcaccttc ttgatctttg  660
ctttcttggt ttattactac tacaagaaaa tcttagttaa atgtatggag aagtgacttg  720
tcgagtcaag attagggttt ttgttaattt acaatcctgg gttttttttcc catgccaaaa  780
aacaaaatcc tgggttttct tgttttccta aattaaatat ctctctagag ctaccataac  840
tatgtgtgtg tgtgtgtttg tgtaagcaaa taatgaagaa ggaagaaagc tgtcttgtct  900
tctcaacttc tagttagcct tctcgttagc cttttttggt gtcactcttt ttctgcaaat  960
cattgaaacc tgatgcatgc cagcttctcc atgaaatttc tttactcaaa ttaatactag  1020
ggtttaatca gtaaacaagt tgggtacttt cttgacacga aatagcatgt atattatata  1080
aatatgcaag acttatgtaa ccctctgtct agtgtaactt gggacagagc ctaatgatca  1140
gttgtcacta gctagggatc cctataatta tttaatctag ccccccaaag gcaaatgaaa  1200
actgaaaatt tcatattctt gagttggtct tgagaaatat aatatgtggc tgaaataaaa  1260
ttgtcctggt atgcaagttc agaatttcaa ctctctttct aaaaaactgt atatatataa  1320
tatgtaaccg attgtttaca tttattttta actttaccaa agatgtagtt agagaggatt  1380
atgtataaca atataaatgc agtttttagg tttctaatct aaaatgagtt gctacaatct  1440
atatatattt gatctagaaa tgggatttgt aataaggttt aacatataat aatgggattt  1500
cttaatttct cttcacaagt cgcatatatc tttttgtctc atatatacat cttttgttac  1560
agtagttgac gaagaacttc aaattaaaca ataaacacac atgactttaa tttgtctaac  1620
attgaaatca ctcatcgtct gttgaaaaaa taatattgat attaatacat aagccattgc  1680
tgaatgtata catatgtagt ccttggatat attaatgaga gggagataac tcggagaagt  1740
gtcagaactc gaaattgtac gggccaatga gaagctctgg cattctgagc tccatttatt  1800
tgttattatc tctaaaaaaa ttactgatcc tttaagcata ttgtgatgaa attgaatcat  1860
ataatatgca tggacgttgt tgtgtactcc tcctaattac caatttgaaa tcatactact  1920
agtgtaatac ttaattactt atatccttac tttttatttt gtctcaacgt caactatttc  1980
attaaccgat aaattagtac aaagtatttg accacaccaa tttgaccaca catgcaacaa  2040
tgcatcttag taacacactg gaacactcac taggtgattt cttactcgga accagcgcaa  2100
cctgagtaca ttgctgcatt tttcacactt atatccttac tttagttaac tgcattagca  2160
gccatttatt atttgatgta aattaccttg gaaaaatatg atacttcagc ctgacataat  2220
atgtttgatt gaaattctct tcatcatcct ggcaatcaga gactggtcca aacttcaaag  2280
ccacacattc ctttcttgtc gattttaagg tttttggccg ggaaaataaa ctttcaaaaa  2340
ccctaatcaa agtacagtac ttactatgtt taagagtatg tttattaaat taaatctaat  2400
aggttctcca actttttagc gtgaagggta caattgaaag atacaagaaa gcttgttccg  2460
atgccgttaa ccctccttct gtcaccgaag ctaatactca ggtaccgttc tttagttctt  2520
ttattccccc tctcttttttc tttttctcat cttttttttta tgatgaccaa ttaacgttac  2580
aaaaaaaatt aaaaaaattt ggatgggttc atgaaacgtt ttggtgtttg tatgcatgga  2640
actctgaagt actatcagca agaagcctct aagcttcgga ggcagattcg tgacattcaa  2700
aattctaaca ggtaaataag acggtctttt ggtttgatca ctacttctct attattgatg  2760
ttgttttgat tatttaatgt tgtgaaatga aaggcatata gttggggaat cacttggttc  2820
cttgaacttc aaggaactca aaaacctcga aggacgtctt gaaaaaggaa tcaaccgtgt  2880
ccgatccaag aaggtactta ccctaacgtc tctttgtctc tctataactt atatagtttt  2940
cttactctta taatgaaaat ctcgcagaat gagctgttaa tggcagagat agagtatatg  3000
cagaagaggg taagtaacgt ttcttccata tcttgcaccg tctttttagg tttttgagtt  3060
tcctataaat cgtgtaggaa atggagttgc aacacgataa catgagctaa ggttagtcta  3120
aatctctctt ctttacatca tcgcctaccc gagaagataa cgtgtgtaac aaaccaaact  3180
ttgatgttcg gtctttgcag atatcacaag gtgcgagatt gaatccggag cagcaggatt  3240
cgagtgtaat acaaggaaca gcggtttacg aacccggtct atcttcccat gaccagtcac  3300
agcattataa ccggaactat attccggtta accttcttga accgaatcta catttctccg  3360
gtcaagacca acctcaactt gtctaa                                      3386

SEQ ID NO: 317        moltype = AA  length = 181
FEATURE               Location/Qualifiers
source                1..181
                      mol_type = protein
                      organism = synthetic construct
SEQUENCE: 317
MEEGGSSHDA ESNKKLVRGK IEIKRIENTT SRQVTFCKRR NGLLKKAYEL SVLCDAEVAL  60
VIFSTRGRLY EYANNSVKGT IERYKKACSD AVNPPSVTEA NTQYYQQEAS KLRRQIRDIQ  120
NSNRHIVGES LGSLNFKELK NLEGRLEKGI NRVRSKKNEL LMAEIEYMQK REMELQHDNM  180
S                                                                 181

SEQ ID NO: 318        moltype = DNA  length = 5189
FEATURE               Location/Qualifiers
source                1..5189
                      mol_type = other DNA
                      organism = synthetic construct
```

SEQUENCE: 318
cctcaacaaa caccagttat ttactgtgac aacatgggtg ccacatactt aacagccaac 60
ccggttttcc attcaagaat gaagcactta gccctcgact accacttcgt acgacaacag 120
gttcaaaacc ggacagttcg agtctcccat gtttccactc atgatcaact agcagacgtg 180
ttaaccaaac ctctttcaag accgcgtttt gaaggcttcc ttatcaagat tggtctttcc 240
tccggtggtc catcttgagg gggtgtatta gcttatatag aaagtctata caagtagccg 300
ttagtatctc cttgattact ctctaatcat tattgtatat tctctgtata ttacattcct 360
tgtattactc tttctctgta tatataaaca gagcaccaat actcaataat aatcatccaa 420
ttacgtatct caataattaa tattttagaa tgctagaagt tatcagttta tctacagttt 480
ggttgaatta attcaactag gttatggtta gacttggtta ggttcaatat gcacacagat 540
agatacggag aggagcatct aattaattga accgcagacg tgtttaaaaa gaaagagaga 600
aagattacca taaaaaggga gtttccaaaa gatggttctg atgtgaaaca gagccccatc 660
cctctccttt tccctttttct catgaaatat attggatggt cctccttcaa tgtccaccac 720
ctactactca tcttctcttt tttctttagt tagttttcaa tttcaatttc agtttcagtt 780
cctataattt ataaatattc atatctattt atatgcatgt atagagaata aaaagtgtga 840
gttatatagc tgtcgagtat ttccgttttg acaattggta gataatttat ctgtttttta 900
tatatgtata aatatatttc agctaagaaa aacttgtaaa cttctgtgtt tctgcaagtg 960
gggtcttaat accttcaaaa aatagtcctt caaatgaaac tgatcataaa ccaaatttga 1020
aagagagatg tatttttcaa aaacgacaat tattagaaaa gcagaaaaaa agcagttaag 1080
tgatactgag atcaataata atatatagta tctcttcaag aacaatatct cattacccac 1140
ttctcctttg tgctgatcta tcataagctt taaaccccag gtacggttct gaatattata 1200
caatttatat agaataactc taatatacaa gatttatatt cagagttctt ttcattttca 1260
ttttcaattc aatatctgat cctttgttac ctagatttga tatgtttatt tattattgtt 1320
tacaaagaga tttgatcatt ttaaccctaa acctaagttt tgtacccaaa tcatatgatc 1380
tatcttttgg ttattcttga tctgcaaaat gattaatttg atcatcaatc ttaattatat 1440
tctctataac aatctttttt tttattaagc tttgctctga tcaatctctc tccctcttat 1500
tatgttattt tattcatctg gtgatatcac agaatcaatg gaggaaggtg ggagtagtca 1560
cgacgcagag agtaacaaga agctagtaag agggaagata gagataaaga ggatagagaa 1620
cacaacaagt cgtcaagtaa ctttctgtaa acgacgcaat ggtcttctta agaaagctta 1680
tgagctttct gtcttgtgtg atgctgaagt tgccctcgtc atcttctcga ctcgtggccg 1740
tctctatgag tacgccaaca acaggtacgc ttctcctgca ccttcttgat ctttgctttc 1800
ttggtttatt actactacaa gaaaatctta gttaaatgta tggagaagtg acttgtcgag 1860
tcaagattag ggtttttgtt aatttacaat cctgggtttt tttcccatgc caaaaaacaa 1920
aatcctgggt tttcttgttt tcctaaatta aatatctctc tagagctacc ataactatgt 1980
gtgtgtgtgt gtttgtgtaa gcaaataatg aagaaggaag aaagctgtct tgtcttctca 2040
acttctagtt agccttctcg ttagcctttt ttggtgtcac tctttttctg caaatcattg 2100
aaacctgatg catgccagct tctccatgaa atttctttac tcaaattaat actagggttt 2160
aatcagtaaa caagttgggt actttcttga cacgaaatag catgtatatt atataaatat 2220
gcaagactta tgtaaccctc tgtctagtgt aacttgggac agagcctaat gatcagttgt 2280
cactagctag ggatccctat aattatttaa tctagccccc caaaggcaaa tgaaaactga 2340
aaatttcata ttcttgagtt ggtcttgaga aatataatat gtggctgaaa taaaattgtc 2400
ctggtatgca agttcagaat ttcaactctc tttctaaaaa actgtatata tataatatgt 2460
aaccgattgt ttacatttat ttttaacttt accaaagatg tagttagaga ggattatgta 2520
taacaatata aatgcagttt ttaggtttct aatctaaaat gagttgctac aatctatata 2580
tatttgatct agaaatggga tttgtaataa ggtttaacat ataataatgg gatttcttaa 2640
tttctcttca caagtcgcat atatcttttt gtctcatata tacatctttt gttacagtag 2700
ttgacgaaga acttcaaatt aaacaataaa cacacatgac tttaatttgt ctaacattga 2760
aatcactcat cgtctgttga aaaaataata ttgatattaa tacataagcc attgctgaat 2820
gtatacatat gtagtccttg gatatattaa tgagagggag ataactcgga gaagtgtcag 2880
aactcgaaat tgtacgggcc aatgagaagc tctggcattc tgagctccat ttatttgtta 2940
ttatctctaa aaaaattact gatcctttaa gcatattgtg atgaaattga atcatataat 3000
atgcatggac gttgttgtgt actcctccta attaccaatt tgaaatcata ctactagtgt 3060
aatacttaat tacttatatc cttacttttt attttgtctc aacgtcaact atttcattaa 3120
ccgataaatt agtacaaagt atttgaccac accaatttga ccacacatgc aacaatgcat 3180
cttagtaaca cactggaaca ctcactaggt gatttcttac tcggaaccag cgcaacctga 3240
gtacattgct gcattttca cacttatatc cttactttag ttaactgcat tagcagccat 3300
ttattatttg atgtaaatta ccttggaaaa atatgatact tcagcctgac ataatatgtt 3360
tgattgaaat tctcttcatc atcctggcaa tcagagactg gtccaaactt caaagccaca 3420
cattcctttc ttgtcgattt taaggttttt ggccgggaaa ataaactttc aaaaacccta 3480
atcaaagtac agtacttact atgtttaaga gtatgtttat taaattaaat ctaataggtt 3540
ctccaacttt ttagcgtgaa gggtacaatt gaaagataca agaaagcttg ttccgatgcc 3600
gttaaccctc cttctgtcac cgaagctaat actcaggtac cgttctttag ttcttttatt 3660
ccccctctct ttttcttttt ctcatctttt ttttatgatg accaattaac gttacaaaaa 3720
aaattaaaaa aatttggatg ggttcatgaa acgttttggt gtttgtatgc atggaactct 3780
gaagtactat cagcaagaag cctctaagct tcggaggcag attcgtgaca ttcaaaattc 3840
taacaggtaa ataagacggt cttttggttt gatcactact tctctattat tgatgttgtt 3900
ttgattattt aatgttgtga aatgaaaggc atatagttgg ggaatcactt ggttccttga 3960
acttcaagga actcaaaaac ctcgaaggac gtcttgaaaa aggaatcaac cgtgtccgat 4020
ccaagaaggt acttacccta acgtctcttt gtctctctat aacttatata gttttcttac 4080
tcttataatg aaaatctcgc agaatgagct gttaatggca gagatagagt atatgcagaa 4140
gagggtaagt aacgtttctt ccatatcttg caccgtcttt ttaggttttt gagtttccta 4200
taaatcgtgt aggaaatgga gttgcaacac gataacatgt acctgcgagc taaggttagt 4260
ctaaatctct cttctttaca tcatcgccta cccgagaaga taacgtgtgt aacaaaccaa 4320
actttgatgt tcggtctttg cagatatcac aaggtgcgag attgaatccg gagcagcagg 4380
attcgagtgt aatacaagga acagcggttt acgaacccgg tctatcttcc catgaccagt 4440
cacagcatta taaccggaac tatattccgg ttaaccttct tgaaccgaat ctacatttct 4500
ctcatacagc tcctagtatt gccttttatc gcccgtttct tttttcatca gttcatgatt 4560
ttacatttc taaccaagat gttggaagag ttaacgtatc tataccagag agatcgcacc 4620
acagggttgc taatctctag ccacggttta gctggaccgc tgaaatgtaa aaccgcagca 4680

```
gatttcagaa tctcttcagg ggacttaaag gatcgagatc ctagtccagc tacgtgccat  4740
gatgggtcaa gagactgtgt gagtcctttg aaagcaagta gggttggtgg taaagctcct  4800
ggttgccata actgtagtcc agagctaaca ctctgtaatc aaatcaagat ttgtgtaacc  4860
aagttgaagt gtagctaata tgatgaagag aaatgagatt gatgtacata tatatatact  4920
cacgagtctt aaccatgagg agtaagcttc tgtgatattg gtttgtctcc aagctttgag  4980
atcaaagaca ttcataccag aaagccaagc gcagtcatct tgacgtaagt ttgatgagat  5040
cagaggatgc gagaagttga aatagtcttt gttttttctt ccagggcaac agttatttcc  5100
gcaccatgaa tcaaaaactg caccaacaac gttaccgttg agatccgttt cccataaaga  5160
caaaaggtca cgttgtacta ctacatcat                                    5189

SEQ ID NO: 319         moltype = DNA  length = 5539
FEATURE                Location/Qualifiers
source                 1..5539
                       mol_type = other DNA
                       organism = synthetic construct
SEQUENCE: 319
cctcaacaaa caccagttat ttactgtgac aacatgggtg ccacatactt aacagccaac  60
ccggttttcc attcaagaat gaagcactta gccctcgact accacttcgt acgacaacag  120
gttcaaaacc ggacagttcg agtctcccat gtttccactc atgatcaact agcagacgtg  180
ttaaccaaac ctctttcaag accgcgtttt gaaggcttcc ttatcaagat tggtctttcc  240
tccggtggtc catcttgagg gggtgtatta gcttatatag aaagtctata caagtagccg  300
ttagtatctc cttgattact ctctaatcat tattgtatat tctctgtata ttacattcct  360
tgtattactc tttctctgta tatataaaca gagcaccaat actcaataat aatcatccaa  420
ttacgtatct caataattaa tattttagaa tgctagaagt tatcagttta tctacagttt  480
ggttgaatta attcaactag gttatggtta gacttggtta ggttcaatat gcacacagat  540
agatacggag aggagcatct aattaattga accgcagacg tgtttaaaaa gaaagagaga  600
aagattacca taaaaaggga gtttccaaaa gatggttctg atgtgaaaca gagccccatc  660
cctctccttt tcccttttct catgaaatat attggatggt cctccttcaa tgtccaccac  720
ctactactca tcttctcttt tttctttagt tagttttcaa tttcaatttc agtttcagtt  780
cctataattt ataaatattc atatctattt atatgcatgt atagagaata aaaagtgtga  840
gttatatagc tgtcgagtat ttccgttttg acaattggta gataatttat ctgtttttta  900
tatatgtata aatatatttc agctaagaaa aacttgtaaa cttctgtgtt tctgcaagtg  960
gggtcttaat accttcaaaa aatagtcctt caaatgaaac tgatcataaa ccaaatttga  1020
aagagagatg tatttttcaa aaacgacaat tattagaaaa gcagaaaaaa agcagttaag  1080
tgatactgag atcaataata atatatagta tctcttcaag aacaatatct cattacccac  1140
ttctcctttg tgctgatcta tcataagctt taaaccccag gtacggttct gaatattata  1200
caatttatat agaataactc taatatacaa gatttatatt cagagttctt ttcattttca  1260
ttttcaattc aatatctgat cctttgttac ctagatttga tatgtttatt tattattgtt  1320
tacaaagaga tttgatcatt ttaaccctaa acctaagttt tgtacccaaa tcatatgatc  1380
tatcttttgg ttattcttga tctgcaaaat gattaatttg atcatcaatc ttaattatat  1440
tctctataac aatctttttt tttattaagc tttgctctga tcaatctctc tccctcttat  1500
tatgttattt tattcatctg gtgatatcac agaatcaatg gaggaaggtg ggagtagtca  1560
cgacgcagag agtaacaaga agctagtaag agggaagata gagataaaga ggatagagaa  1620
cacaacaagt cgtcaagtaa ctttctgtaa acgacgcaat ggtcttctta agaaagctta  1680
tgagctttct gtcttgtgtg atgctgaagt tgccctcgtc atcttctcga ctcgtggccg  1740
tctctatgag tacgccaaca acaggtacgc ttctcctgca ccttcttgat ctttgctttc  1800
ttggtttatt actactacaa gaaaatctta gttaaatgta tggagaagtg acttgtcgag  1860
tcaagattag ggtttttgtt aatttacaat cctgggtttt tttcccatgc caaaaaaacaa  1920
aatcctgggt tttcttgttt tcctaaatta aatatctctc tagagctacc ataactatgt  1980
gtgtgtgtgt gtttgtgtaa gcaaataatg aagaaggaag aaagctgtct tgtcttctca  2040
acttctagtt agccttctcg ttagcctttt ttggtgtcac tctttttctg caaatcattg  2100
aaacctgatg catgccagct tctccatgaa atttctttac tcaaattaat actagggttt  2160
aatcagtaaa caagttgggt actttcttga cacgaaatag catgtatatt atataaatat  2220
gcaagactta tgtaaccctc tgtctagtgt aacttgggac agagcctaat gatcagttgt  2280
cactagctag ggatccctat aattatttaa tctagccccc caaaggcaaa tgaaaactga  2340
aaatttcata ttcttgagtt ggtcttgaga aatataaatat gtggctgaaa taaaattgtc  2400
ctggtatgca agttcagaat ttcaactctc tttctaaaaa actgtatata tataatatgt  2460
aaccgattgt ttacatttat ttttaacttt accaaagatg tagttagaga ggattatgta  2520
taacaatata aatgcagttt ttaggtttct aatctaaaat gagttgctac aatctatata  2580
tatttgatct agaaatggga tttgtaataa ggtttaacat ataataatgg gatttcttaa  2640
tttctcttca caagtcgcat atatcttttt gtctcatata tacatctttt gttacagtag  2700
ttgacgaaga acttcaaatt aaacaataaa cacacatgac tttaatttgt ctaacattga  2760
aatcactcat cgtctgttga aaaaataata ttgatattaa tacataagcc attgctgaat  2820
gtatacatat gtagtccttg gatatattaa tgagagggag ataactcgga gaagtgtcag  2880
aactcgaaat tgtacgggcc aatgagaagc tctggcattc tgagctccat ttatttgtta  2940
ttatctctaa aaaaattact gatcctttaa gcatattgtg atgaaattga atcatataat  3000
atgcatggac gttgttgtgt actcctccta attaccaatt tgaaatcata ctactagtgt  3060
aatacttaat tacttatatc cttacttttt attttgtctc aacgtcaact atttcattaa  3120
ccgataaatt agtacaaagt atttgaccac accaatttga ccacacatgc aacaatgcat  3180
cttagtaaca cactggaaca ctcactaggt gatttcttac tcggaaccag cgcaacctga  3240
gtacattgct gcatttttca cacttatatc cttactttag ttaactgcat tagcagccat  3300
ttattatttg atgtaaatta ccttggaaaa atatgatact tcagcctgac ataatatgtt  3360
tgattgaaat tctcttcatc atcctggcaa tcagagactg gtccaaactt caaagccaca  3420
cattcctttc ttgtcgattt taaggttttt ggccgggaaa ataaactttc aaaaacccta  3480
atcaaagtac agtacttact atgtttaaga gtatgtttat taaattaaat ctaataggtt  3540
ctccaacttt ttagcgtgaa gggtacaatt gaaagataca agaaagcttg ttccgatgcc  3600
gttaaccctc cttctgtcac cgaagctaat actcaggtac cgttctttag ttcttttatt  3660
ccccctctct ttttcttttt ctcatctttt ttttatgatg accaattaac gttacaaaaa  3720
aaattaaaaa aatttggatg ggttcatgaa acgttttggt gtttgtatgc atggaactct  3780
```

```
gaagtactat cagcaagaag cctctaagct tcggaggcag attcgtgaca ttcaaaattc  3840
taacaggtaa ataagacggt cttttggttt gatcactact tctctattat tgatgttgtt  3900
ttgattattt aatgttgtga aatgaaaggc atatagttgg ggaatcactt ggttccttga  3960
acttcaagga actcaaaaac ctcgaaggac gtcttgaaaa aggaatcaac cgtgtccgat  4020
ccaagaaggt acttacccta acgtctcttt gtctctctat aacttatata gttttcttac  4080
tcttataatg aaaatctcgc agaatgagct gttaatggca gagatagagt atatgcagaa  4140
gagggtaagt aacgtttctt ccatatcttg caccgtcttt ttaggttttt gagtttccta  4200
taaatcgtgt aggaaatgga gttgcaacac gataacatgt acctgcgagc taaggttagt  4260
ctaaatctct cttctttaca tcatcgccta cccgagaaga taacgtgtgt aacaaaccaa  4320
actttgatgt tcggtctttg cagatatcac aaggtgcgag attgaatccg gagcagcagg  4380
attcgagtgt aatacaagga acagcggttt acgaacccgg tctatcttcc catgaccagt  4440
cacagcatta taaccggaac tatattccgg ttaaccttct tgaaccgaat ctacatttct  4500
ccggtcaaga ccaacctcct cttcacacta agagtaactt cttctcatgc atagtttttt  4560
aggttccaat aataataaca taaataaatc aagtgttaca aagatacaaa cttacaaaca  4620
tctatcttct gatgtgtagc tataactaaa caaaatacat tatactattt gagatcacaa  4680
aaaaaactac attttttttt aattatagag gggtatactg gccccacaga ataaactaga  4740
tattcataaa gtctagttta atgtccttat tctatattac tctttagtat atatggacat  4800
gagagaacta tgagcagagg ctgaaggcta aacctacttc cctctgttct ctcatacagc  4860
tcctagtatt gccttttatc gcccgtttct tttttcatca gttcatgatt ttacattttc  4920
taaccaagat gttggaagag ttaacgtatc tataccagag agatcgcacc acagggttgc  4980
taatctctag ccacggttta gctggaccgc tgaaatgtaa aaccgcagca gatttcagaa  5040
tctcttcagg ggacttaaag gatcgagatc ctagtccagc tacgtgccat gatgggtcaa  5100
gagactgtgt gagtcctttg aaagcaagta gggttggtgg taaagctcct ggttgccata  5160
actgtagtcc agagctaaca ctctgtaatc aaatcaagat ttgtgtaacc aagttgaagt  5220
gtagctaata tgatgaagag aaatgagatt gatgtacata tatatatact cacgagtctt  5280
aaccatgagg agtaagcttc tgtgatattg gtttgtctcc aagctttgag atcaaagaca  5340
ttcataccag aaagccaagc gcagtcatct tgacgtaagt ttgatgagat cagaggatgc  5400
gagaagttga aatagtcttt gttttttctt ccagggcaac agttatttcc gcaccatgaa  5460
tcaaaaactg caccaacaac gttaccgttg agatccgttt cccataaaga caaaaggtca  5520
cgttgtacta ctacatcat                                                5539

SEQ ID NO: 320          moltype = DNA  length = 70
FEATURE                 Location/Qualifiers
source                  1..70
                        mol_type = other DNA
                        organism = synthetic construct
SEQUENCE: 320
acttgtctaa gttttaaaca tgaaaaaaaa cacttgtttc ttcccctcaa aacggttgtt  60
cagagaaaga                                                          70

SEQ ID NO: 321          moltype = DNA  length = 6602
FEATURE                 Location/Qualifiers
source                  1..6602
                        mol_type = other DNA
                        organism = synthetic construct
SEQUENCE: 321
aaatgcttac ctaatgtata tatgtgatgt attagagtaa atgcaattag taattacaag  60
gaaagtgatg gaggcatgag caaaaagagt ttctataatt tgtacacaaa tagttaatgt  120
gaactatgag aaaggtttgt gaatgattat gactatacgt atgattggtc accacttaat  180
ggattcctta atttcttgtt ccctcattaa gttgtcgtct catcatttct tttcatttct  240
agacccatgg tctcagattg gacttttaaa ggtagatttc aatatcaatg gtcgcacttt  300
tttagtccaa ttcattttca agttctcaaa caagtgtggt gattattttg cagttcttat  360
tcacacgtct aacttctatt atgtatgtca ttttctacgg ataagaagcg taagcgttgc  420
aaataatatt atctcgaatt aaatgggatt aattaggcca taatctagat tctatgtatc  480
ttttatatat ataaaaacaa aacatacgct caaatttagt tgcgtatttg agtagatatt  540
gtcttcatta cttgtaagaa aaaactcgtt ggactgcaca atagttttgt taacgtgtaa  600
ttaaatagcg tatttgtaag atttgagatt caaaatcgtc tttgacagct atgctcaaca  660
tgctttgaat cataagcact gtctagattc tcagcatgta acttatattt cagatcagat  720
tgactgcaaa acgaggtccc acgcaagaag gaaaagacaa gtatgatgtt cttggtctgg  780
agttctcagt cgagcatgtt attaaggggt gcaagagtgg atttccaaca aaaaacaagc  840
tttatgggac aaaaatcgaa gaaagaataa agatagaggg tgaaaacaca atatatgatt  900
tgttatcgcc tatttcccat aaaggattca gatactagga gaagttgatg ccaatttcac  960
atgcaagtct ctttcattac atctccatat tttaccgcac ctacgtctct atgtttacat  1020
tcttgtcatc gactttttca tgaataattt ttttttgcaa tttttatttc acttacaatt  1080
atgaatttct tatatatatt cttccaagtt gtaacgatca aataaaatatg catgcattat  1140
gtcatatatg gctatacatc attttagatt attgattttt gcagtatctt atttgaaacc  1200
tttagttcta tctacggata tcaatgtcta aacttttgat tctttattta gattgtgttc  1260
ttcaatcaaa gattcccctc ataaattgtg tattctttgc aaaaaaagga gttcacttat  1320
ttcacttgtg attgtgaaca tattataaat tgtacttata aaaacattct gcagttaaaa  1380
gaaaattaaa catcaaagtt agaaaaatta actttatgaa aaaaatacct actagctagt  1440
tagtagtaag agcatcttca ttcatggttc ttaaaacaaa aaatacaagt agtttaatat  1500
aatttaaata aaaaaacgaa atttttattt tgaaataaga tttgaacaag ttgagaattg  1560
acaagtgttt attagggttt gaaaagttga tcaaatgtta tgattcatcg tcttctctct  1620
ctctctttac cttttctttg tttaatggtg agaactttct atgaaagtgt gtatttggtt  1680
acttgaacta atatttttat gactgacttt atgaaaacaa cacaatctac tagctacatg  1740
gactgtagaa tacaatttat attttagatt gctaagaagt tatcagttta tctacagttt  1800
ggttgaatta attcaactag gttatggacc ttatggttag acttggttag gttcaatatg  1860
aacacgtata gatacagaga ggagcatcta attaattgaa acgcagacgt gtttaaaaag  1920
aaagagagaa agattaccat aaaaagggag tttccaaaag atggttctga tgtgaaacag  1980
```

```
agccccatcc ctctcccttt cccttttctc gtgaaagata ttggatggtc ctccttcaat  2040
gtccaccacc tactactcat cttctctttt ttctttaatt agttttcaat ttcaatttca  2100
gtttaagttc ctataattta taaatatttc atatctattt atatgaaatg tgtagagaat  2160
aaaaagtgtg agtttatata tttgtcgagt atgtttgttt tgacaattgg tatataattt  2220
atctgcttat tatagatgta cgtataaata tatttcagct aagaaaaact tgtaaacttc  2280
tgtgtgttct gcaagtgggg tcttaatacc ttcaaaaaat agtccttcaa atgaaactga  2340
tcataaacca aatttgaaaa gagagagatg tatttttcaa aaacgacata attattagaa  2400
aagcagaaaa aaacagttaa gtgatactga gatcaataat aatatatagt atctcttcaa  2460
gaacaatatc tcattaccca cttctccttt gtgctgatct atcataaact ttaaacccca  2520
ggtaaggttc tgaatgttat acagtttata tagaataact ctaatatcaa atatttatat  2580
tcggagttct tttcatttct ttttcaattc aatatctgat cctttgttac ctagatttga  2640
tatgtttatt tattattgtt tatctgcaaa gagatttgat cattttaacc ctaaacctaa  2700
gtttcgtacc caaatcatac gatctatctt ttggttattc ttgatctgca aaatgattaa  2760
tttaatcatc aatcttaatt agcttctcta gagcaatatt tttttttctt aagctttgct  2820
ctagatcaat ctctctccct cttattatgt tattttattc atctggtgat atcacagaat  2880
caatggagga aggtgggagt agtcacgacg cagagagtag caagaagcta gtaagaggga  2940
agatagagat aaagaggata gagaacacaa caagtcgtca agtaactttc tgtaaacgac  3000
gcaatggtct tcttaagaaa gcttatgagc tttctgtctt gtgtgatgct gaagttgccc  3060
tcgtcatctt ctccactcgt ggccgtctct atgagtacgc caacaacagg tacgcttctc  3120
ctgcaccttt gatctttgct ttcttggttt actactacta ctacaagaaa atcttagtta  3180
aatgtatgga gaagtgactt gtagagtcaa gattagggtt tttgttaaat tacaatcctg  3240
ggttttttcc catgccaaaa aaaaaaaatc ctgggttttt ttgttttttc taaattaaat  3300
atcgatctct ctagagctac cataactatg tgtgtgtgtg tgtttgtgta agcaagtaat  3360
gaagaaggaa gaaagctgtc ttgtcttctc aacttctagt tagccttctc gttagccttt  3420
tttggtgtca ctctttttct gcaaatcatt agaacctgat gcatgtcagc ttctccatga  3480
aatttcttta ttcaaattca aattagggtt tgatcagtaa acaagttggg tactttcttg  3540
gcacgaaata gcatgtatat tatataaata tgcaagactt atgttaccct ctgcctagtg  3600
taacttggga caaagcctaa tgaccatttg tcacttgtca ctagctaggg atccctataa  3660
ttatttaatc tagccaccaa aggcaaatga aaaccgaaaa tttcatattc ttgagttggt  3720
cttgagaaat ataatatgtg gctgaaataa aattgtcctg gtatgcaagt tcagaatttc  3780
aactctcttt ctaaaaaact gtaaatatat atacttctca tgtaaccgat tgtttacatt  3840
taatgtttaa ctttaccaaa gatgtagtta gagagcaaga tgtataacaa tataaatgca  3900
gtttttatgt ttctaatcta aaatgagttt tttcgatgta ataatctaaa atgagttgct  3960
accattatac tccctctgtt tccgaaagaa atattttcta gagtattcat gcatattaaa  4020
gaaacaatta atttttata attgaattta ttatttattt tactatacat tttccaataa  4080
atattaacca atagtattca accaattcaa atattttcaa ttaatgtttt ttaaaagtct  4140
acaactttc aacattaact actaaaagta ctttaaaatt ttagaaaatc tatcattttg  4200
gaacaaaaaa taaatctaga aaatcctact ttcaggaaca gaaggtgtat atatatatag  4260
cttttgttac aatagttgac gaagaacttc aaattaaaca ataaacacac atgagtttaa  4320
tttgtctaat attgaaatca ctcatcgact gttaaaaaaa acaatattca tattaatata  4380
taagccattg ctgaatttat acatatgtag tccttggata tattaatgag agggagataa  4440
ctcagagaag tgtcagaact cgaaatggta cgggccaatg agaagctctg gcattctgag  4500
ctctatttat ctgttattat tatctgtaaa aaattactga tcctttaagc atattgtgat  4560
gaaattgaat catataatat gcatggacgt tgttgtgttt accaatttga aatcatacta  4620
ctagtgtaat acttaattac ttatatcctt actttagtta actgcattga cagacattta  4680
ttatttgatg taaattacct tggaaaaata tggtttgatt gaaattatct cttcatactg  4740
gcaatcagaa actggtccaa acttcaaaac cacacattcc tttctggttg attttaaggt  4800
ttttggccgg gaaaataaac tttccaaaac cctaatcaaa atacagtacg tactatgttt  4860
aagagtttat atttattaaa ttaaatctaa taggttctcg aactgaactt tttagcgtga  4920
agggtacaat tgaaagatac aagaaagctt gttccgatgc cgttaaccct ccttctgtca  4980
ccgaagctaa tactcaggta ccattcttta gtttttttt tttagttctt ttggccggga  5040
aagcttttt gcgatttcga cagtgtttaa gctttgccta acgatagctg atctctttac  5100
cttttattta gccttaaatt gttcaccatg aattagttta agcctaatta accttgtgtt  5160
taaaaatctt tttatctttt tggggttatt agatagctca ttgctaagtc ttagcagttt  5220
taggccatga ttatcgctaa aactgttttc tgggtttttt aatttttttt ttgtttttc  5280
tgattaaaaa aggaaaaaat taaaaaaaag tcaatcgcgg gtcgtcacgt gtcagtgtag  5340
cccgtaaaaa gtacaagaaa caaactaaag ttgatccttc ttttgcgact ttagtaaccg  5400
ataatcgtgc tcttagattc aagtctttct tctatctcaa tgtcattttt acgaaatgaa  5460
ttcacatttt gtcaaaaaaa aaattagttc ttttattctt cccctctttt tttgtctttt  5520
tttttgtgat gaccaattaa cattacaaaa aaaataaaaa aaatttggat gggttcttga  5580
aacgttttgg tgtttatatg catggaactc tgaagtacta tcagcaagaa gcatctaagc  5640
ttcggaggca gattcgtgac attcagaatt ctaacaggta aataaggcag tcttaatgtt  5700
caaaaaaaat aaaaaataag acagtctttt ggtagtgttt caaaaaaaaa aaacgacagt  5760
cttttggttt gatcactact tctctattat agatgttgtt ttgattattt aatgttgtga  5820
cttgaaaggc atatagttgg ggaatcactt ggttccttga acttcaagga actcaaaaac  5880
ctcgaaggac gtcttgaaaa aggaatcagc cgtgtccgat ccaagaaggt acttacccta  5940
acgtctcttt gtctctctat aacttatatt gttttcttac tcttatatga aaatctcgca  6000
gaatgagctg ttaatggcag agatagagta tatgcagaag agggtaagta acgtttcttc  6060
catatctttc accgtctttt taggtttttg agttcctata aatcgtgtag gaaatggagt  6120
tgcaacacga taacatgtac ctgcgagcta aggttagtct aaatctctct tctttacatc  6180
atcgcctacc cgagaagata acgtgtgtaa caaaccaaac tttgatgttc ggtctttgca  6240
caaggtgcga gattgaatcc ggagcagcag gattcgagtg taatacaagg aacagcggtt  6300
tacgaatccg gtttatcttc ccatgatcag tcacagcatt ataaccggaa ctatattccg  6360
gttaaccttc ttgaaccgaa tcaacaattc tccggtcaag accaacctcc tctccaactt  6420
gtctaagttt taaacatgaa aaaaaaaact tgtttcttcc cctcaaaacg attgttcaga  6480
gaaagacact aagggtatga ctggttttcc cgctaccacc cgcaaacgca gcttttgcgg  6540
ttggtagcgg ttgctggcgt tttgcaacaa tcgctcaaac cgctctaaac cgctccaaat  6600
cg                                                                 6602
```

-continued

```
SEQ ID NO: 322          moltype = DNA  length = 4144
FEATURE                 Location/Qualifiers
source                  1..4144
                        mol_type = other DNA
                        organism = synthetic construct
SEQUENCE: 322
cttttctccc ttgagatcga tcttagaacc tagatagtag ctagctatag tagatggagt  60
ccaaaaagat tttatttgat ctctctcagc ttgtgtgtag tgtttgaccg tgtttggttt  120
atctttaagc tatagggttg atataaatgg agggtggtgc gagtgatgaa gtagcagaga  180
gcagcaagaa gatagggaga gggaagatag agataaagag gatagagaac accacgaatc  240
gccaagtcac tttctgcaaa agacgcaatg gtctgctcaa gaaagcttat gagctctctg  300
tcttgtgtga cgctgaggtt gctcttgtca tcttctccac tcgcggtcgt ctctacgagt  360
acgccaacaa caggtaagat aagcatctat taacttcttt tagatcttga ttgtttgttt  420
tctctgggtt ttgaatcttt atgggttttc tctttgtggt ttcttttctc ttcttttaaa  480
gtttctctga gtctcaactc tttgctgaaa actttgattt atatgtgtgt accaaaatta  540
gggtttgtac ccaagaaccc tagttttgct ttggggaaaa ctctaatcta tttgcttctc  600
tctcttgaaa aagctgtgag gtcttctatg ataataatta attagcatct ccataccttg  660
taccagtcac tttttttttc ttttactaga tctttatagt acagcctatc tgtatctatc  720
tatgtatgtc agttctacat gacatttcga taaatttgat gacccatcag gtttatttct  780
gcagattgat cataattagg attccatcat agtagtgaaa aaagtagggt tcttgacaaa  840
atataatatt atatatcata taatggctat ataaagctaa gtagattcct taaaaaaatg  900
atacactagc taggggggaga cgggtgtttt gtcttctgac acttctctat aaaaccagtg  960
atttgatctg ttaaatcaag aaatgtttag gggacaaagc ttgtggttgt gtcactaatt  1020
aattaatcat caatcaatca aaaaataaaa ataaacagaa aatttgactt ttgttattag  1080
tttccccact ccaagttggg gactagtcat ttccatttct atcaaagttt ccagctatta  1140
acagctcatg ttcctttcta cattttgatt gttttagaaa agattaatct gttgattttt  1200
ggttggttga taccacagat aagttgagga tctataatct aattttctta aagtcaagtc  1260
tcatatcatg gatttaagac ttaactagaa aatttgtagt tacaatgtag acttcacacg  1320
actaaagaat attttcatta tttaccaacg tgtaaagatt ctacatatag taaatgtgta  1380
tgtgacatca cgattttata aaagtaggtt tagttgaata cccaactaat ctgattaaca  1440
aaagaggaat gcattaggtc tagctagtag gtaggtatgt agaaatttgc aatttctagg  1500
tttctatttt caaatgcgta gctaaaattt acactatctt tcttatttca aacgtcctca  1560
tgctttaatg ccttttgaca tttctcaacc tcaacttgtc atcatacatc acaaattaaa  1620
tagtgaaaat gataacgtta tatgtgtttc aaaaaaaaaa aaaaaagata acgttatata  1680
caaatatgtc tagctttttt ctcaaattta aggatctagg aatttcactt ccttggttaa  1740
aacagtaatc gctcccaatt aattctattc atttacacat gttgtagtac taactaaaac  1800
tctaattcag gtatgatatg tattatatat atctttttt attttatttt attttgaaac  1860
acttttatta tagccaaaaa tacatgttat aagggaaatc tcaagtctag tagtgttttc  1920
gaacctataa ggaaatttgg attttgtatt atatgaaaat ttggacacgt tagaaaattt  1980
ccattcctaa gaagcttata ataaggtttc atattgatgt atttttattt ttacctacca  2040
caaaaataaa tcaacaaaat gaaattagac atctatacat tagtacccat atagtaatgt  2100
cactcttata atgaacttgg ttataacata tcaaacgatt cataatgaaa tatttttggt  2160
caaatcgatc actgaataga ttaaccatgc gtagaagtcg ataaagatgt aatttatata  2220
taggatatgt acaatatgtc tttgcttata gccttctaat ttactaactc ttgtatttta  2280
tttttgtgga tgttggcgaa atcgtacaac taatcaaaag tgtaagagga acgatcgaaa  2340
ggtacaagaa agcttgctcc gacgctgtta atcctccttc cgtcaccgaa gctaatactc  2400
aagtaagctt ccgtaattag ttactttacc actacgtttc ttcttgtttc agtttctgac  2460
tttactgaat cctttgtggg gtcgaacact tgatgaagta ctatcagcaa gagtcatcta  2520
agctacggag acagatccgg gacattcaga atctgaacag acacattctt ggtgaatctc  2580
tcggttcctt gaacctcaag gaactcaaga acctcgaagg taggcttgaa aaaggcatcg  2640
gtcgtgtccg ctccaagaag gttaataact ttcaattcct tcaatccctt tatatgcttc  2700
gacttgatct gattcttgac ccttacgttt tattcttcgc ccagcatgag atgctagttg  2760
cagagataga gtacatgcaa aaaagggtaa aaaacatatc ttcctcaaca agtaacccta  2820
ctttctataa caatcttctc tttcataata tagctcccgt ttctgttcat gtaggagatc  2880
gagcttcaaa acgataacat gtatctccga tccaaggtct tatcaatact ctctcttttt  2940
cagaaatata aatattttta taatacattt atttattaaa atatactatt ggtataaaat  3000
tattggaagt tgataagtac gaaaatacaa tacatttatt tattaaaatt taatatattt  3060
ttaatacgta tcaaagcata gacatatatc ttttacaaac atagctaggg agtatatgct  3120
ttttgtttgc attttgattt ttttttcaat atatatacaa tttatctctt cgatgagcaa  3180
gttaatttta tataattcta cagattaatg aaagagcggg aatgcagcag caggaagcga  3240
gtgtgataca tcaacaaggg acggtttacg agtcatcttc tcatcagtcg gagcagtaca  3300
accggaacta tattccggtt aaccttcttg aaccaaatca gaactcctcc gaccaaaacc  3360
aaccacctct ccaacttgtt taagtaaagt ctaatcaaca aaataaagctc cttatgcatt  3420
tgtctattca tgttacaatt atggttaaac aacttaaaat aaagacgggt aacgatttga  3480
gagggaccta agttatatgt accttgatta tttatatgta atgtattgtg tacgttccag  3540
ctagtaactt taagacaaga gacttaacta aatttctagt ttctaataaa gctaatacat  3600
aatttacacc agagagaacg tagatagtac ctcatgatta ctaattgtag acaagaccac  3660
tgaaacacaa aagggtttgt ggatttctcg agtcttgcac gccaagtaac ttcagtgaaa  3720
caggatctta aatcgagcga catgtcatca aggaacaaaa ggatgcgtta aggtctttga  3780
cagcgagtta ctaaagctgg tggtagaagc tagcaatcct cagattaaca ctgtgcagta  3840
tatgagaatc tgttagttca atgagactta gaaaggtctc ttgaattagt gaggagtata  3900
tatagcaggg gaatgagatt gatactcacg gtgcttgaag aaatgtatac ctgaaaatta  3960
aagcgcagcg atgaggaaag aagcttgaaa tgagaaactg atgatattac aaatgatgca  4020
tctctcacac catggtttta tatagtaaac caagattcca ctgttacaaa gcaaggacac  4080
atgaaagacc taacttttac tgcagcagag cagccaaaag gagcgacatg tcttatcatg  4140
agca                                                               4144

SEQ ID NO: 323          moltype = DNA  length = 4310
FEATURE                 Location/Qualifiers
```

-continued

```
source                  1..4310
                        mol_type = other DNA
                        organism = synthetic construct
SEQUENCE: 323
gaggttcttc cttttttct tcatccaatc cttgaatctt ggagtgtttt tcatttcatc  60
tcttgctttt ctcccttgag atcgatctta gaacctagat agtagctagc tatagtagat  120
ggagtccaaa aagattttat ttgatctctc tcagcttgtg tgtagtgttt gaccgtgttt  180
ggtttatctt taagctatag ggttgatata aatggagggt ggtgcgagtg atgaagtagc  240
agagagcagc aagaagatag ggagagggaa gatagagata aagaggatag agaacaccac  300
gaatcgccaa gtcactttct gcaaaagacg caatggtctg ctcaagaaag cttatgagct  360
ctctgtcttg tgtgacgctg aggttgctct tgtcatcttc tccactcgcg gtcgtctcta  420
cgagtacgcc aacaacaggt aagataagca tctattaact tcttttagat cttgattgtt  480
tgttttctct gggttttgaa tctttatggg ttttctcttt gtggtttctt ttctcttctt  540
ttaaagtttc tctgagtctc aactctttgc tgaaaacttt gatttatatg tgtgtaccaa  600
aattagggtt tgtacccaag aaccctagtt ttgctttggg gaaaactcta atctatttgc  660
ttctctctct tgaaaaagct gtgaggtctt ctatgataat aattaattag catctccata  720
ccttgtacca gtcacttttt ttttctttta ctagatcttt atagtacagc ctatctgtat  780
ctatctatgt atgtcagttc tacatgacat ttcgataaat ttgatgaccc atcaggttta  840
tttctgcaga ttgatcataa ttaggattcc atcatagtag tgaaaaaagt agggttcttg  900
acaaaatata atattatata tcatataatg gctatataaa gctaagtaga ttccttaaaa  960
aaatgataca ctagctaggg ggagacgggt gttttgtctt ctgacacttc tctataaaac  1020
cagtgatttg atctgttaaa tcaagaaatg tttaggggac aaagcttgtg gttgtgtcac  1080
taattaatta atcatcaatc aatcaaaaaa taaaaataaa cagaaaattt gacttttgtt  1140
attagtttcc ccactccaag ttggggacta gtcatttcca tttctatcaa agtttccagc  1200
tattaacagc tcatgttcct ttctacattt tgattgtttt agaaaagatt aatctgttga  1260
tttttggttg gttgatacca cagataagtt gaggatctat aatctaattt tcttaaagtc  1320
aagtctcata tcatggattt aagacttaac tagaaaattt gtagttacaa tgtagacttc  1380
acacgactaa agaatatttt cattatttac caacgtgtaa agattctaca tatagtaaat  1440
gtgtatgtga catcacgatt ttataaaagt aggtttagtt gaatacccaa ctaatctgat  1500
taacaaaaga ggaatgcatt aggtctagct agtaggtagg tatgtagaaa tttgcaattt  1560
ctaggtttct attttcaaat gcgtagctaa aatttacact atctttctta tttcaaacgt  1620
cctcatgctt taatgccttt tgacatttct caacctcaac ttgtcatcat acatcacaaa  1680
ttaaatagtg aaaatgataa cgttatatgt gtttcaaaaa aaaaaaaaaa agataacgtt  1740
atatacaaat atgtctagct tttttctcaa atttaaggat ctaggaattt cacttccttg  1800
gttaaaacag taatcgctcc caattaattc tattcattta cacatgttgt agtactaact  1860
aaaactctaa ttcaggtatg atatgtatta tatatatctt tttttatttt attttatttt  1920
gaaacacttt tattatagcc aaaaatacat gttataaggg aaatctcaag tctagtagtg  1980
ttttcgaacc tataaggaaa tttggatttt gtattatatg aaaatttgga cacgttagaa  2040
aatttccatt cctaagaagc ttataataag gtttcatatt gatgtatttt tatttttacc  2100
taccacaaaa ataaatcaac aaaatgaaat tagacatcta tacattagta cccatatagt  2160
aatgtcactc ttataatgaa cttggttata acatatcaaa cgattcataa tgaaatattt  2220
ttggtcaaat cgatcactga atagattaac catgcgtaga agtcgataaa gatgtaattt  2280
atatatagga tatgtacaat atgtctttgc ttatagcctt ctaatttact aactcttgta  2340
ttttattttt gtggatgttg gcgaaatcgt acaactaatc aaaagtgtaa gaggaacgat  2400
cgaaaggtac aagaaagctt gctccgacgc tgttaatcct ccttccgtca ccgaagctaa  2460
tactcaagta agcttccgta attagttact ttaccactac gtttcttctt gtttcagttt  2520
ctgactttac tgaatccttt gtggggtcga acacttgatg aagtactatc agcaagagtc  2580
atctaagcta cggagacaga tccgggacat tcagaatctg aacagacaca ttcttggtga  2640
atctctcggt tccttgaacc tcaaggaact caagaacctc gaaggtaggc ttgaaaaagg  2700
catcggtcgt gtccgctcca agaaggttaa taactttcaa ttccttcaat ccctttatat  2760
gcttcgactt gatctgattc ttgaccctta cgttttattc ttcgcccagc atgagatgct  2820
agttgcagag atagagtaca tgcaaaaaag ggtaaaaaac atatcttcct caacaagtaa  2880
ccctactttc tataacaatc ttctctttca taatatagct cccgtttctg ttcatgtagg  2940
agatcgagct tcaaaacgat aacatgtatc tccgatccaa ggtcttatca atactctctc  3000
tttttcagaa atataaatat ttttataata catttattta ttaaaatata ctattggtat  3060
aaaattattg gaagttgata agtacgaaaa tacaatacat ttatttatta aaatttaata  3120
tatttttaat acgtatcaaa gcatagacat atatctttta caaacatagc tagggagtat  3180
atgctttttg tttgcatttt gatttttttt tcaatatata tacaatttat ctcttcgatg  3240
agcaagttaa ttttatataa ttctacagat taatgaaaga gcgggaatgc agcagcagga  3300
agcgagtgtg atacatcaac aagggacggt ttacgagtca tcttctcatc agtcggagca  3360
gtacaaccgg aactatattc cggttaacct tcttgaacca aatcagaact cctccgacca  3420
aaaccaacca cctctccaac ttgtttaagt aaagtctaat caacaaaata agctccttat  3480
gcatttgttg ttacaattat ggttaaacaa cttaaaataa agacgggtaa cgatttgaga  3540
gggacctaag ttacatatgt accttgatta tttatatgta atgtattgtg tacgttccag  3600
ctagtaactt taagacaaga gacttaacta aatttctagt ttctaataaa gctaatacat  3660
aatttacacc agagagaacg tagatagtac ctcatgatta ctaattgtag acaagaccac  3720
tgaaacacaa aagggtttgt ggatttctcg agtcttgcac gccaagtaac ttcagtgaaa  3780
caggatctta aatcgagcga catgtcatca aggaacaaaa ggatgcgtta aggtctttga  3840
cagcgagtta ctaaagctgg tggtagaagc tagcaatcct cagattaaca ctgtgcagta  3900
tatgagaatc tgttagttca atgagactta gaaaggtctc ttgaattagt gaggagtata  3960
tatagcaggg gaatgagatt gatactcacg gtgcttgaag aaatgtatac ctgaaaatta  4020
aagcgcagcg atgaggaaag aagcttgaaa tgagaaactg atgatattac aaatgatgca  4080
tctctcacac catggtttta tatagtaaac caagattcca ctgttacaaa gcaaggacac  4140
atgaaagacc taacttttac tgcagcagag cagccaaaag gagcgacatg tcttatcatg  4200
agcagtcaaa tgagaatgaa agcctcttat agctaaactg ttgtctgttt cttctataca  4260
tgtgttttgg catctgtctt agtctgtgga tattgttttc tataataatt             4310

SEQ ID NO: 324          moltype = DNA  length = 143
FEATURE                 Location/Qualifiers
```

```
source                  1..143
                        mol_type = other DNA
                        organism = Brassica napus
SEQUENCE: 324
attttgattt ttttttcaat atatatacaa tttatctctt cgatgagcaa gttaatttta  60
tataattcta cagattaatg aaagagcggg aatgcagcag caggaagcga gtgtgataca  120
tcaacaaggg acggtttacg agt                                          143

SEQ ID NO: 325          moltype = DNA  length = 103
FEATURE                 Location/Qualifiers
source                  1..103
                        mol_type = other DNA
                        organism = Brassica napus
SEQUENCE: 325
atatatacaa tttatctctt cgatgagcaa gttaatttta tataattcta cagattaatg  60
aaagagcggg aatgcagcag caggaagcga gtgtgataca tca                    103

SEQ ID NO: 326          moltype = DNA  length = 63
FEATURE                 Location/Qualifiers
source                  1..63
                        mol_type = other DNA
                        organism = Brassica napus
SEQUENCE: 326
cgatgagcaa gttaatttta tataattcta cagattaatg aaagagcggg aatgcagcag  60
cag                                                                63

SEQ ID NO: 327          moltype = DNA  length = 143
FEATURE                 Location/Qualifiers
source                  1..143
                        mol_type = other DNA
                        organism = Brassica napus
SEQUENCE: 327
tgaaagagcg ggaatgcagc agcaggaagc gagtgtgata catcaacaag ggacggttta  60
cgagtcatct tctcatcagt cggagcagta caaccggaac tatattccgg ttaaccttct  120
tgaaccaaat cagaactcct ccg                                          143

SEQ ID NO: 328          moltype = DNA  length = 103
FEATURE                 Location/Qualifiers
source                  1..103
                        mol_type = other DNA
                        organism = Brassica napus
SEQUENCE: 328
agcaggaagc gagtgtgata catcaacaag ggacggttta cgagtcatct tctcatcagt  60
cggagcagta caaccggaac tatattccgg ttaaccttct tga                    103

SEQ ID NO: 329          moltype = DNA  length = 63
FEATURE                 Location/Qualifiers
source                  1..63
                        mol_type = other DNA
                        organism = Brassica napus
SEQUENCE: 329
catcaacaag ggacggttta cgagtcatct tctcatcagt cggagcagta caaccggaac  60
tat                                                                63

SEQ ID NO: 330          moltype = DNA  length = 143
FEATURE                 Location/Qualifiers
source                  1..143
                        mol_type = other DNA
                        organism = Brassica napus
SEQUENCE: 330
ccggaactat attccggtta accttcttga accaaatcag aactcctccg accaaaacca  60
accacctctc caacttgttt aagtaaagtc taatcaacaa aataagctcc ttatgcattt  120
gtctattcat gttacaatta tgg                                          143

SEQ ID NO: 331          moltype = DNA  length = 103
FEATURE                 Location/Qualifiers
source                  1..103
                        mol_type = other DNA
                        organism = Brassica napus
SEQUENCE: 331
accttcttga accaaatcag aactcctccg accaaaacca accacctctc caacttgttt  60
aagtaaagtc taatcaacaa aataagctcc ttatgcattt gtc                    103

SEQ ID NO: 332          moltype = DNA  length = 63
FEATURE                 Location/Qualifiers
source                  1..63
                        mol_type = other DNA
                        organism = Brassica napus
```

```
SEQUENCE: 332
aactcctccg accaaaacca accacctctc caacttgttt aagtaaagtc taatcaacaa  60
aat                                                                63

SEQ ID NO: 333         moltype = DNA  length = 143
FEATURE                Location/Qualifiers
source                 1..143
                       mol_type = other DNA
                       organism = Brassica napus
SEQUENCE: 333
ccacctctcc aacttgttta agtaaagtct aatcaacaaa ataagctcct tatgcatttg  60
tctattcatg ttacaattat ggttaaacaa cttaaaataa agacgggtaa cgatttgaga  120
gggacctaag ttacatatgt acc                                          143

SEQ ID NO: 334         moltype = DNA  length = 103
FEATURE                Location/Qualifiers
source                 1..103
                       mol_type = other DNA
                       organism = Brassica napus
SEQUENCE: 334
agtaaagtct aatcaacaaa ataagctcct tatgcatttg tctattcatg ttacaattat  60
ggttaaacaa cttaaaataa agacgggtaa cgatttgaga ggg                    103

SEQ ID NO: 335         moltype = DNA  length = 63
FEATURE                Location/Qualifiers
source                 1..63
                       mol_type = other DNA
                       organism = Brassica napus
SEQUENCE: 335
ataagctcct tatgcatttg tctattcatg ttacaattat ggttaaacaa cttaaaataa  60
aga                                                                63

SEQ ID NO: 336         moltype = DNA  length = 143
FEATURE                Location/Qualifiers
source                 1..143
                       mol_type = other DNA
                       organism = Brassica napus
SEQUENCE: 336
ttgtctattc atgttacaat tatggttaaa caacttaaaa taaagacggg taacgatttg  60
agagggacct aagttacata tgtaccttga ttatttatat gtaatgtatt gtgtacgttc  120
cagctagtaa ctttaagaca aga                                          143

SEQ ID NO: 337         moltype = DNA  length = 103
FEATURE                Location/Qualifiers
source                 1..103
                       mol_type = other DNA
                       organism = Brassica napus
SEQUENCE: 337
tatggttaaa caacttaaaa taaagacggg taacgatttg agagggacct aagttacata  60
tgtaccttga ttatttatat gtaatgtatt gtgtacgttc cag                    103

SEQ ID NO: 338         moltype = DNA  length = 63
FEATURE                Location/Qualifiers
source                 1..63
                       mol_type = other DNA
                       organism = Brassica napus
SEQUENCE: 338
taaagacggg taacgatttg agagggacct aagttacata tgtaccttga ttatttatat  60
gta                                                                63

SEQ ID NO: 339         moltype = DNA  length = 11
FEATURE                Location/Qualifiers
source                 1..11
                       mol_type = other DNA
                       organism = Brassica napus
SEQUENCE: 339
caacttgtct a                                                       11

SEQ ID NO: 340         moltype = DNA  length = 12
FEATURE                Location/Qualifiers
source                 1..12
                       mol_type = other DNA
                       organism = Brassica napus
SEQUENCE: 340
aacttgtcta ag                                                      12

SEQ ID NO: 341         moltype = DNA  length = 10
FEATURE                Location/Qualifiers
```

-continued

```
source                 1..10
                       mol_type = other DNA
                       organism = Brassica napus
SEQUENCE: 341
ttcaacttgt                                                              10

SEQ ID NO: 342         moltype = DNA  length = 23
FEATURE                Location/Qualifiers
source                 1..23
                       mol_type = other DNA
                       organism = synthetic construct
SEQUENCE: 342
tataattcta cagattaatg aaa                                               23

SEQ ID NO: 343         moltype = DNA  length = 23
FEATURE                Location/Qualifiers
source                 1..23
                       mol_type = other DNA
                       organism = synthetic construct
SEQUENCE: 343
cgagtcatct tctcatcagt cgg                                               23

SEQ ID NO: 344         moltype = DNA  length = 23
FEATURE                Location/Qualifiers
source                 1..23
                       mol_type = other DNA
                       organism = synthetic construct
SEQUENCE: 344
cttaaacaag ttggagaggt ggt                                               23

SEQ ID NO: 345         moltype = DNA  length = 23
FEATURE                Location/Qualifiers
source                 1..23
                       mol_type = other DNA
                       organism = synthetic construct
SEQUENCE: 345
accataattg taacatgaat aga                                               23

SEQ ID NO: 346         moltype = DNA  length = 23
FEATURE                Location/Qualifiers
source                 1..23
                       mol_type = other DNA
                       organism = synthetic construct
SEQUENCE: 346
agagggacct aagttacata tgt                                               23
```